United States Patent
Mazitschek et al.

(10) Patent No.: US 12,134,721 B2
(45) Date of Patent: Nov. 5, 2024

(54) COMPLEXES AND LIGANDS

(71) Applicant: The General Hospital Corporation, Boston, MA (US)

(72) Inventors: Ralph Mazitschek, Belmont, MA (US); N. Connor Payne, Cambridge, MA (US); Alena Kalyakina, Karlsruhe (DE)

(73) Assignee: The General Hospital Corporation, Boston, MA (US)

( * ) Notice: Subject to any disclaimer, the term of this patent is extended or adjusted under 35 U.S.C. 154(b) by 769 days.

(21) Appl. No.: 17/287,236

(22) PCT Filed: Oct. 22, 2019

(86) PCT No.: PCT/US2019/057501
§ 371 (c)(1),
(2) Date: Apr. 21, 2021

(87) PCT Pub. No.: WO2020/086629
PCT Pub. Date: Apr. 30, 2020

(65) Prior Publication Data
US 2022/0025254 A1    Jan. 27, 2022

Related U.S. Application Data

(60) Provisional application No. 62/748,965, filed on Oct. 22, 2018.

(51) Int. Cl.
| | | |
|---|---|---|
| *C09K 11/06* | (2006.01) |
| *C07D 487/18* | (2006.01) |
| *C07D 519/00* | (2006.01) |
| *C07F 5/00* | (2006.01) |
| *G01N 21/64* | (2006.01) |
| *G01N 33/58* | (2006.01) |

(52) U.S. Cl.
CPC ............ *C09K 11/06* (2013.01); *C07D 487/18* (2013.01); *C07D 519/00* (2013.01); *C07F 5/00* (2013.01); *G01N 21/6428* (2013.01); *G01N 33/582* (2013.01); *C09K 2211/182* (2013.01); *G01N 2021/6439* (2013.01)

(58) Field of Classification Search
CPC ..................................................... C09K 11/06
USPC ......................................................... 540/460
See application file for complete search history.

(56) References Cited

U.S. PATENT DOCUMENTS

| | | |
|---|---|---|
| 8,697,372 B2 | 4/2014 | Trinquet et al. |
| 2010/0167289 A1 | 1/2010 | Butlin et al. |
| 2011/0189088 A1 | 8/2011 | Xu et al. |
| 2016/0221971 A1 | 8/2016 | Magda et al. |

FOREIGN PATENT DOCUMENTS

| | | | |
|---|---|---|---|
| WO | 2008/063721 | * | 5/2008 |
| WO | WO 2010/051544 | | 5/2010 |

OTHER PUBLICATIONS

Algar et al., "FRET as a biomolecular research tool—understanding its potential while avoiding pitfalls, " Nat. Methods, Sep. 2019, 16(9):815-829.
Asawa et al., "A comparative study of target engagement assays for HDAC1 Inhibitor profiling," SLAS Discov., Mar. 2020, 25(3):253-264.
Ash et al., "Effect of wavelength and beam width on penetration in light-tissue interaction using computational methods," Lasers Med. Sci., Nov. 2017, 32(8):1909-1918.
Badr et al., "Obtusaquinone: a cysteine-modifying compound that targets Keap1 for degradation," ACS Chem. Biol., 2020, 15(6):1445-1454, 25 pages.
Banks et al., "Differential HDAC1/2 network analysis reveals a role for prefoldin/CCT in HDAC1/2 complex assembly," Sci. Rep., Sep. 2018, 8:13712, 13 pages.
Beeby et al., "Non-radiative deactivation of the excited states of europium, terbium and ytterbium complexes by proximate energy-matched Oh, NH and CH oscillators: an improved luminescence method for establishing solution hydration states," J. Chem. Soc. Perkin Trans., 1999, 2(3):493-503.
Blay et al., "High-throughput screening: today's biochemical and cell-based approaches," Drug Discov. Today, Oct. 2020, 25(10):1807-1821.
Bradner et al., "Chemical phylogenetics of histone deacetylases," Nat. Chem. Biol., Mar. 2010, 6(3):238-243.
Bünzli, "Lanthanide luminescence for biomedical analyses and imaging," Chem. Rev., May 2010, 110(5):2729-2755.
Busby et al., "Advancements in assay technologies and strategies to enable drug discovery," ACS Chem. Biol., Sep. 2020, 15:2636-2648, 20 pages.
Cardoso Dos Santos et al., "Time-gated FRET nanoprobes for autofluorescence-free long-term in vivo imaging of developing zebrafish," Adv. Mater., 2020, 32(39):e2003912, 7 pages.
Chen et al., "Single-chain lanthanide luminescence biosensors for cell-based imaging and screening of protein-protein interactions," iScience, Sep. 2020, 23(9):101533, 26 pages.
Cheng & Prusoff, "Relationship between the inhibition constant (Ki) and the concentration of inhibitor which causes 50 per cent inhibition (I50) of an enzymatic reaction," Biochem. Pharmacol., Dec. 1973, 22(23):3099-3108.
Cho et al., "Lanthanide-based optical probes of biological systems," Cell Chem. Biol., Aug. 2020, 27(8):921-936, 16 pages.
Cho et al., "Ultrasensitive optical imaging with lanthanide lumiphores," Nature Chemical Biology, Nov. 2017, 14:15-21, 12 pages.
Cleasby et al., "Structure of the BTB domain of Keap1 and its interaction with the triterpenoid antagonist CDDO," PLoS One, Jun. 2014, 9(6):e98896, 10 pages.
Cuadrado et al., "Therapeutic targeting of the NRF2 and KEAP1 partnership in chronic diseases," Nat. Rev. Drug Discov., Apr. 2019, 18(4):295-317, 23 pages.

(Continued)

*Primary Examiner* — Niloofar Rahmani
(74) *Attorney, Agent, or Firm* — Fish & Richardson P.C.

(57) ABSTRACT

The present application provides ligands and fluorescent or luminescent complexes comprising these ligands.

20 Claims, 63 Drawing Sheets

(56) References Cited

OTHER PUBLICATIONS

Dai et al., "Horizontal cell biology: monitoring global changes of protein interaction states with the proteome-wide cellular thermal shift assay (CETSA)," Annu. Rev. Biochem., 2019, 88:383-408.

Davies et al., "Monoacidic inhibitors of the kelch-like ECH-associated protein 1: nuclear factor erythroid 2-related factor 2 (KEAP1:NRF2) protein-protein interaction with high cell potency identified by fragment-based discovery," J. Med. Chem., Apr. 2016, 59(8):3991-4006, 69 pages.

Dayalan Naidu et al., "C151 in KEAP1 is the main cysteine sensor for the cyanoenone class of NRF2 activators, irrespective of molecular size or shape," Sci. Rep., May 2018, 8:8037, 12 pages.

Degorce et al., "HTRF: a technology tailored for drug discovery—a review of theoretical aspects and recent applications," Curr. Chem. Genomics, May 2009, 3:22-32.

Dubach et al., "In vivo imaging of specific drug-target binding at subcellular resolution," Nat. Commun., May 2014, 5:3946, 9 pages.

England et al., "NanoLuc: a small luciferase is brightening up the field of bioluminescence," Bioconjug. Chem., 2016, 27(5):1175-1187, 29 pages.

Ergin et al., "Time-resolved fluorescence resonance energy transfer [TR-FRET] assays for biochemical processes, " Curr. Pharm. Biotechnol., 2016, 17:1222-1230.

Fang et al., "Recent Advances in Design of Fluorescence-Based Assays for High-Throughput Screening," Analytical Chemistry, 2019, 91:482-504.

Francés-Soriano et al., "In situ rolling circle amplification Förster resonance energy transfer (RCA-FRET) for washing-free real-time single-protein imaging," Anal. Chem., 2021, 93(3):1842-1850.

Fuller et al., "CoREST complex-selective histone deacetylase inhibitors show prosynaptic effects and an improved safety profile to enable treatment of synaptopathies," ACS Chem. Neurosci., Mar. 2019, 10(3):1729-1743.

Hildebrandt et al., "Luminescent terbium complexes: superior Förster resonance energy transfer donors for flexible and sensitive multiplexed biosensing," Coord. Chem. Rev., Aug. 2014, 273-274:125-138, 14 pages.

Horrocks et al., "Lanthanide ion probes of structure in biology. Laser-induced luminescence decay constants provide a direct measure of the number of metal-coordinated water molecules," J. Am. Chem. Soc., Jan. 1979, 101(2):334-340.

Hulme et al., "Ligand binding assays at equilibrium: validation and interpretation," Br. J. Pharmacol., Nov. 2010, 161(6):1219-1237.

International Preliminary Report on Patentability in International Appln. No. PCT/US2019/057501, dated Apr. 27, 2021, 7 pages.

International Search Report and Written Opinion in International Appln. No. PCT/US2019/057501, dated Feb. 14, 2020, 15 pages.

Jarmoskaite et al., "How to measure and evaluate binding affinities," eLife, Aug. 2020, 9:e57264, 34 pages.

Johnson et al., "Using the golden triangle to optimize clearance and oral absorption," Bioorg. Med. Chem. Lett., Oct. 2009, 19(19):5560-5564.

Juillerat et al., "Directed evolution of O6-alkylguanine-DNA alkyltransferase for efficient labeling of fusion proteins with small molecules in vivo," Chem. Biol., Apr. 2003, 10(4):313-317, 5 pages.

Latva et al., "Correlation between the lowest triplet state energy level of the ligand and lanthanide(III) luminescence quantum yield," J. Lumin., Sep. 1997, 75(2):149-169.

Lee et al., "Development of a homogeneous time-resolved fluorescence resonance energy transfer (TR-FRET) assay for the inhibition of Keap1-Nrf2 protein-protein interaction," SLAS Discovery, 2020, 26(1):100-112, 13 pages.

Liu et al., "Treatment of obesity with celastrol," Cell, 2015, 161(5):999-1011.

Los et al., "HaloTag: a novel protein labeling technology for cell imaging and protein analysis," ACS Chemical Biology, Jun. 2008, 3(6):373-382.

Lu et al., "Discovery of a Keap1-dependent peptide PROTAC to knockdown Tau by ubiquitination-proteasome degradation pathway," Eur. J. Med. Chem., Feb. 2018, 146:251-259.

Marks et al., "A substrate-independent TR-FRET histone deacetylase inhibitor assay," J. Biomol. Screening, Sep. 2011, 16(10):1247-1253.

Mathis et al., "Stable luminescent chelates and macrocyclic compounds," Lanthanide Luminescence: Photophysical, Analytical and Biological Aspects, Jul. 2010, 47-88.

Mazitschek et al., "Development of a fluorescence polarization based assay for histone deacetylase ligand discovery," Bioorganic & Medicinal Chemistry Letters, May 2008, 18(9):2809-2812.

Methot et al., "Exploration of the internal cavity of histone deacetylase (HDAC) with selective HDAC1/HDAC2 inhibitors (SHI-1:2)," Bioorg. Med. Chem. Lett., Mar. 2008, 18(3):973-978.

Mohandessi et al., "Cell-penetrating peptides as delivery vehicles for a protein-targeted terbium complex," Chem. A Eur. J., 2012 18(35):10825-10829, 6 pages.

Moore et al., "From antenna to assay: lessons learned in lanthanide luminescence," Acc. Chem. Res., Apr. 2009, 42(4):542-552.

Neklesa et al., "Small-molecule hydrophobic tagging-induced degradation of HaloTag fusion proteins," Nat. Chem. Biol., Jul. 2011, 7:538-543.

Payne et al., "Bright and stable luminescent probes for target engagement profiling in live cells," Nat Chem Biol, Oct. 2021, 17:1168-1177, 28 pages.

Payne et al., "Supplementary information—Bright and stable luminescent probes for target engagement profiling in live cells," Nat Chem Biol, Oct. 2021, 17: 162 pages.

PCT Invitation to Pay Additional Fees And, Where Applicable, Protest Fee in International Appln. No. PCT/US2019/057501, dated Dec. 26, 2019, 2 pages.

Peterson and Kwon, "The HaloTag: improving soluble expression and applications in protein functional analysis," Curr. Chem. Genomics, Sep. 2012, 6:8-17.

Poore et al., "Development of a high-throughput Cul3-Keap1 time-resolved fluorescence resonance energy transfer (TR-FRET) assay for identifying Nrf2 activators," SLAS Discov., 2019, 24(2):175-189.

Rajendran et al., "Lanthanide-Based Imaging of Protein-Protein Interactions in Live Cells," Inorg. Chem., 2014, 53(4):1839-1853, 15 pages.

Reis et al., "Light-controlled modulation of gene expression by chemical optoepigenetic probes," Nat Chem Biol, Mar. 2016, 12(5):317-323, 10 pages.

Reviews in Fluorescence 2016, 1st ed., Geddes (ed)., 2017, Chapter 3, 27 pages.

Robers et al., "Target engagement and drug residence time can be observed in living cells with BRET," Nat. Commun., Dec. 2015, 6:10091, 10 pages.

Rodenko et al., "340-nm pulsed UV LED system for europium-based time-resolved fluorescence detection of immunoassays," Opt. Express, Sep. 2016, 24(19):22135-22143.

Sanderson et al., "Fluorescence microscopy," Cold Spring Harbor Protoc., Oct. 2014, 1042-1065, 25 pages.

Seashore-Ludlow et al., "Perspective on CETSA literature: toward more quantitative data interpretation," SLAS Discov., Feb. 2020, 25(2):118-126.

Selvin, "Principles and biophysical applications of lanthanide-based probes," Annu. Rev. Biophys. Biomol. Struct., 2002, 31:275-302.

Sy et al., "Lanthanide-based luminescence biolabelling," Chem. Commun., Feb. 2016, 52(29):5080-5095, 17 pages.

Tong et al., "Bardoxolone conjugation enables targeted protein degradation of BRD4," Sci. Rep., Sep. 2020, 10:15543, 8 pages.

Tran et al., "A comparative assessment study of known small-molecule Keap1-Nrf2 protein-protein interaction inhibitors: chemical synthesis, binding properties and cellular activity," J. Med. Chem., Aug. 2019, 62(17):8028-8052, 25 pages.

Vinegoni et al., "Fluorescence anisotropy imaging in drug discovery," Adv. Drug Delivery Rev., 2019, 151-152:262-288, 69 pages.

Vinegoni et al., "Measurement of drug—target engagement in live cells by two-photon fluorescence anisotropy imaging," Nat. Protoc., Jun. 2017, 12(7):1472-1497.

Wegner et al., "Quantum-dot-based Förster resonance energy transfer immunoassay for sensitive clinical diagnostics of low-volume serum samples," ACS Nano, Aug. 2013, 7(8):7411-7419, 9 pages.

(56) References Cited

OTHER PUBLICATIONS

Wilson and Soh, "Re-evaluating the conventional wisdom about binding assays," Trends Biochem. Sci., May 2020, 45(8):639-649, 11 pages.

Wu et al., "Quantum dot-based FRET immunoassay for HER2 using ultrasmall affinity proteins,," Small, 2019, 14:1802266, 5 pages.

Xu et al., "Octadentate Cages of TB(III) 2-Hydroxyisophthalamides: A New Standard for Luminescent Lanthanide Labels," Journal of the American Chemical Society, Oct. 2011, 133:19900-19910.

Yanagisawa et al., "Seven-Coordinate Luminophores: Brilliant Luminescence of Lanthanide Complexes with C3v Geometrical Structures," European Journal of Inogranic Chemistry, Sep. 2015, 28:4769-4774.

Zhu et al., "A click chemistry approach for the synthesis of macrocycles from aryl amide-based precursors directed by hydrogen bonding," Organic & Biomolecular Chemistry, Jun. 2009, 7(16):3243-3250, 9 pages.

Zwier et al., "A fluorescent ligand-binding alternative using tag-lite® technology," J. Biomol. Screening, Oct. 2010, 15:1248-1259.

Office Action in European Appln. No. 19875601.7, dated Mar. 17, 2023, 8 pages.

Extended European Search Report in European Appln. No. 19875601.7, dated Jun. 22, 2022, 9 pages.

\* cited by examiner

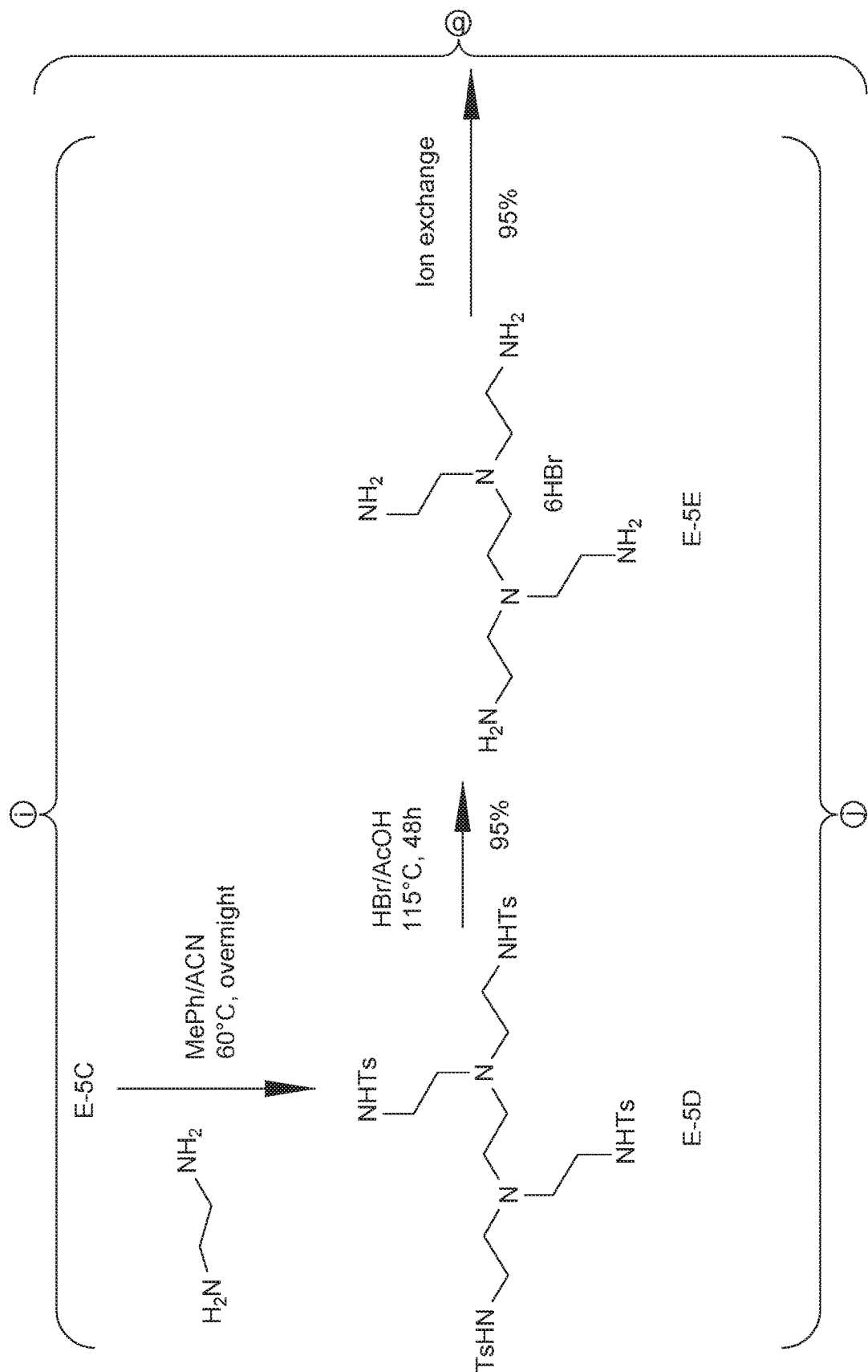
FIG. 10 (Continue)

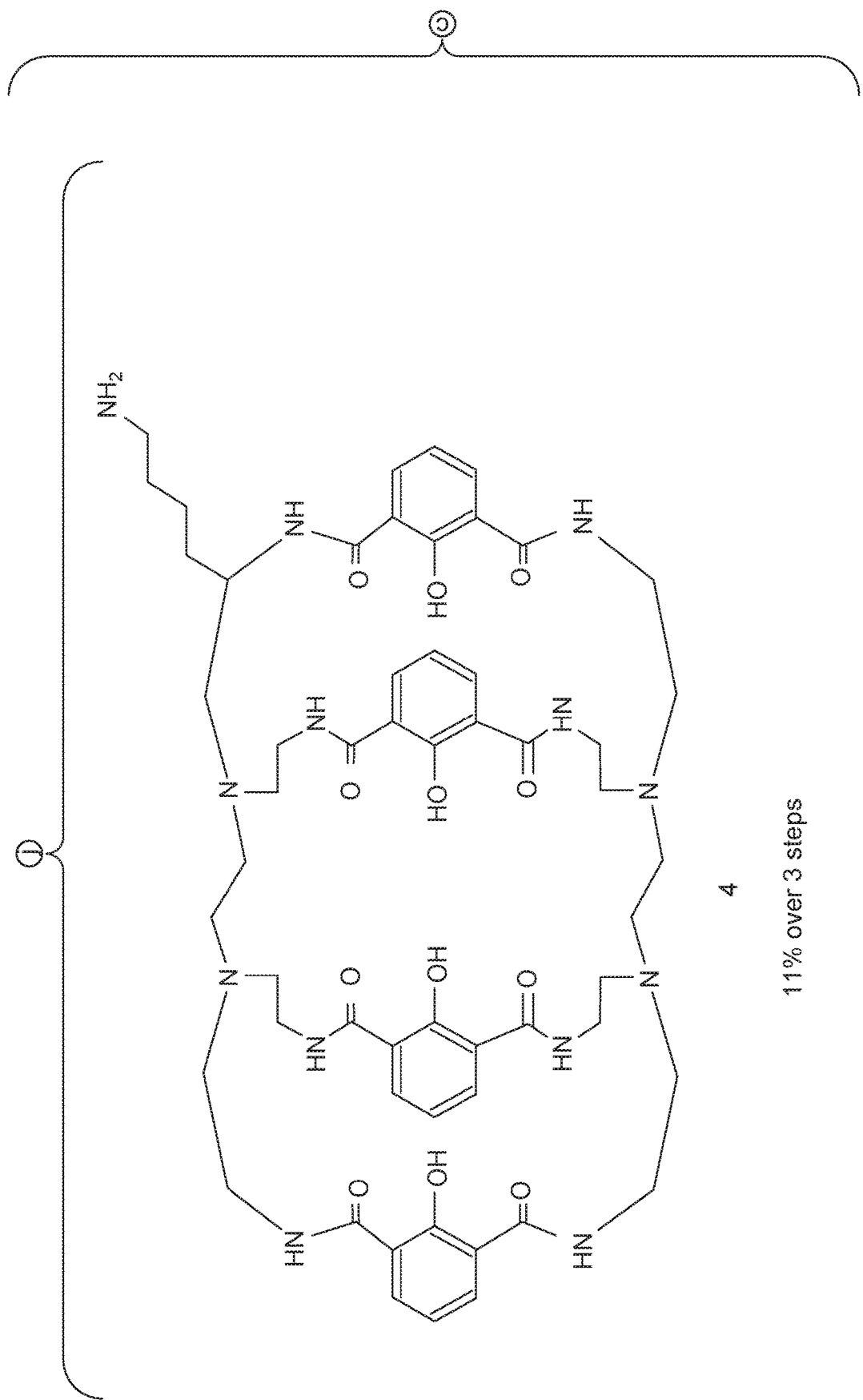
FIG. 10 (Continue)

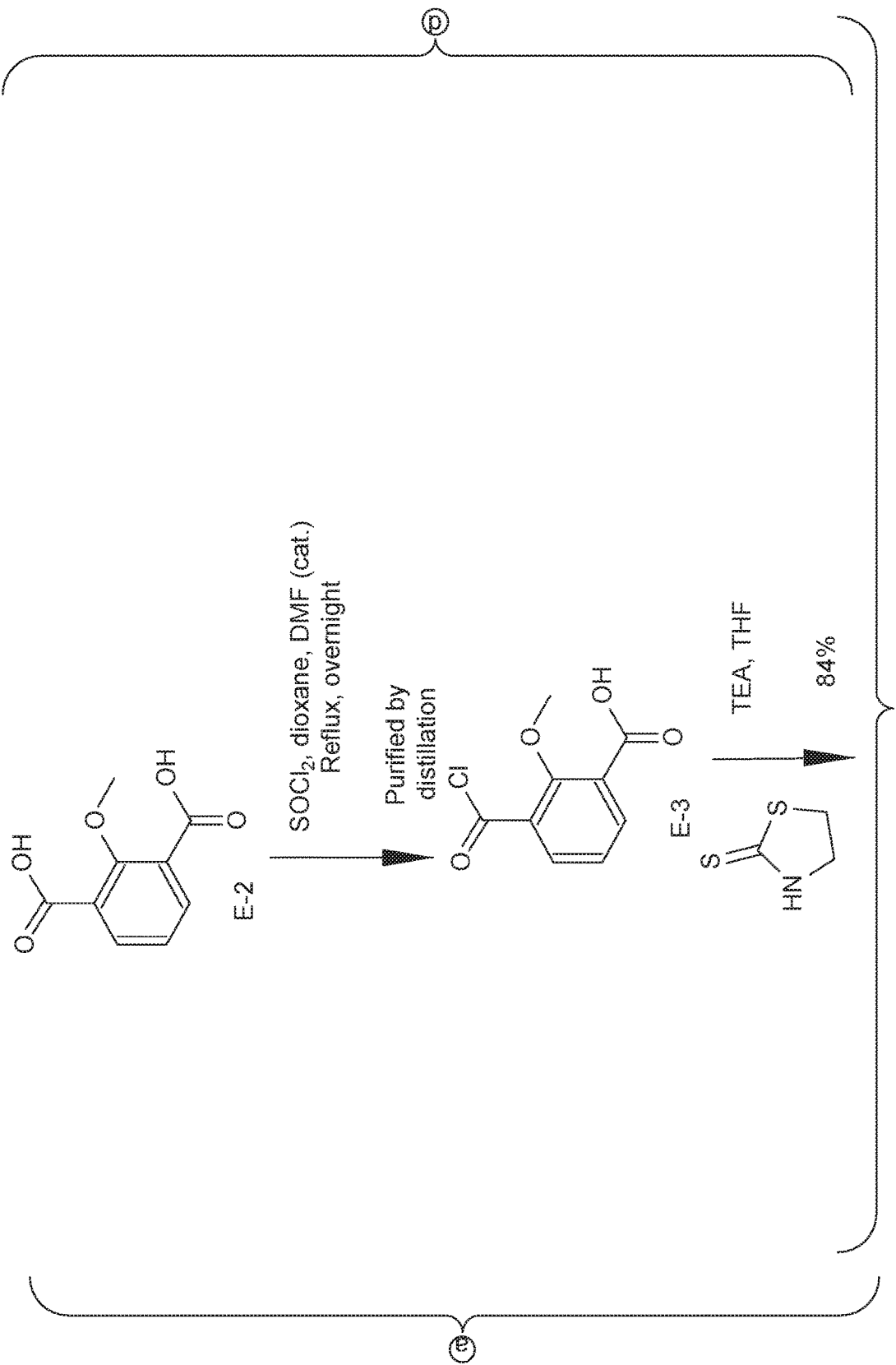
FIG. 10 (Continue)

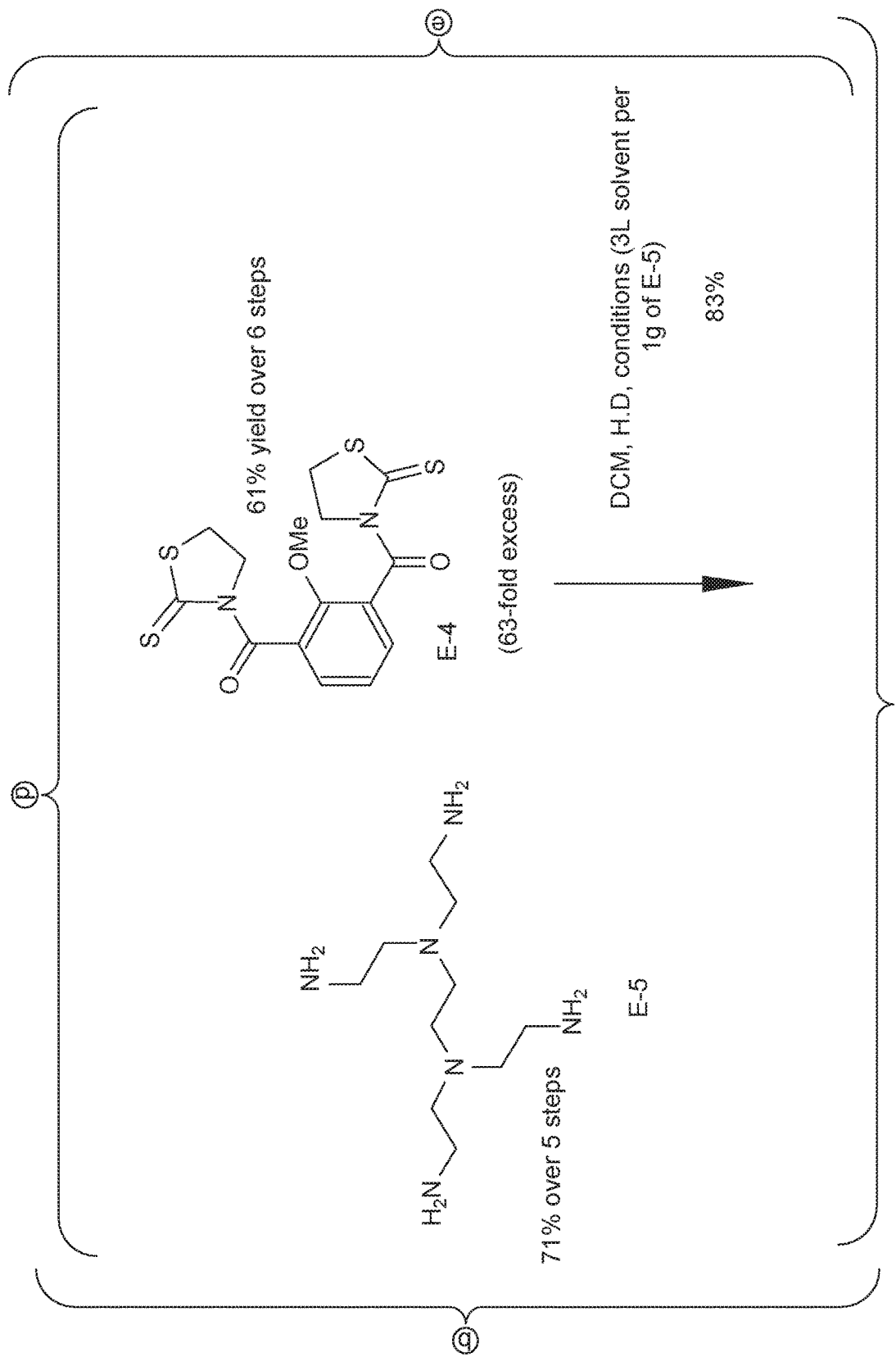
FIG. 10 (Continue)

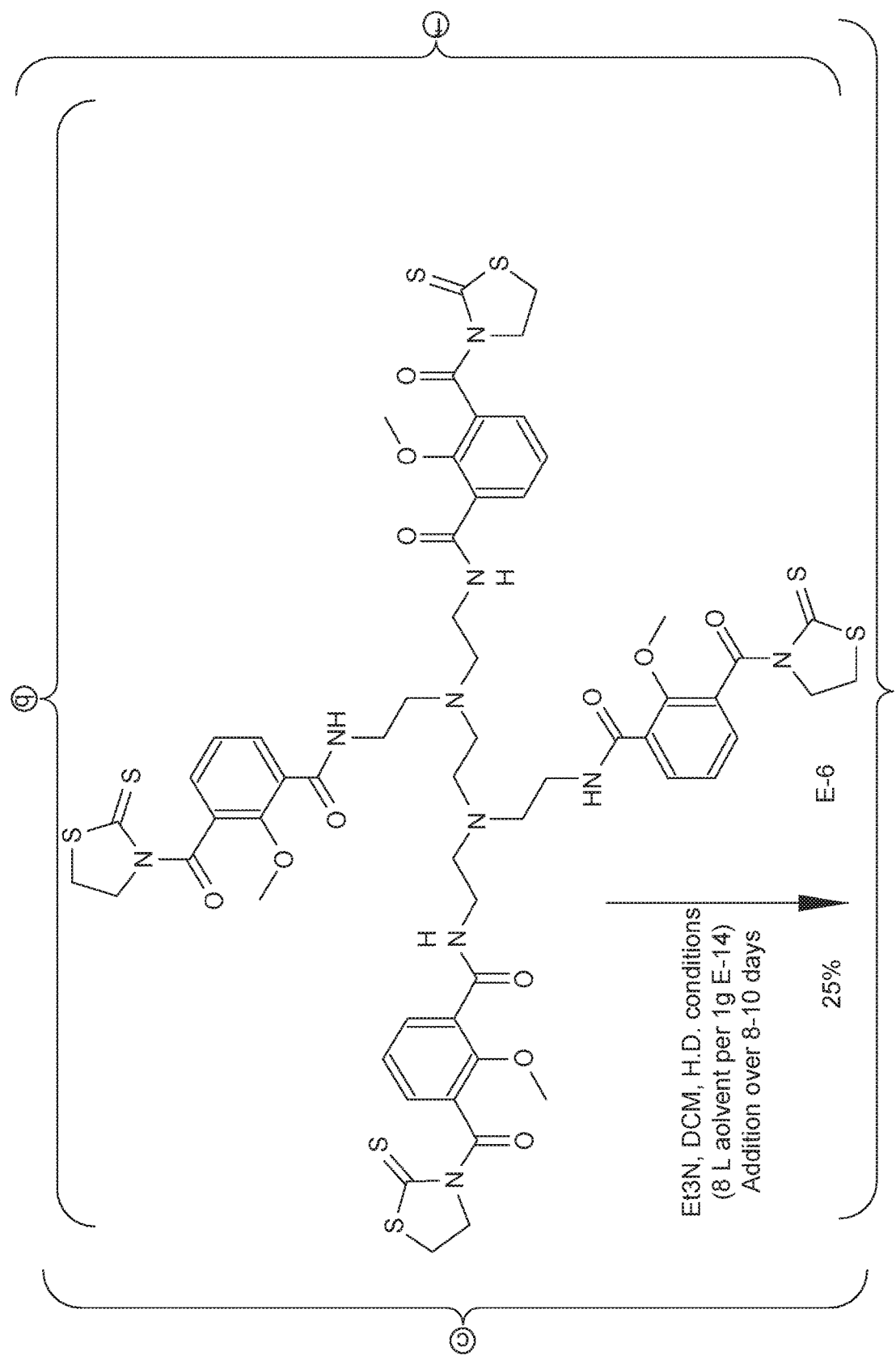
FIG. 10 (Continue)

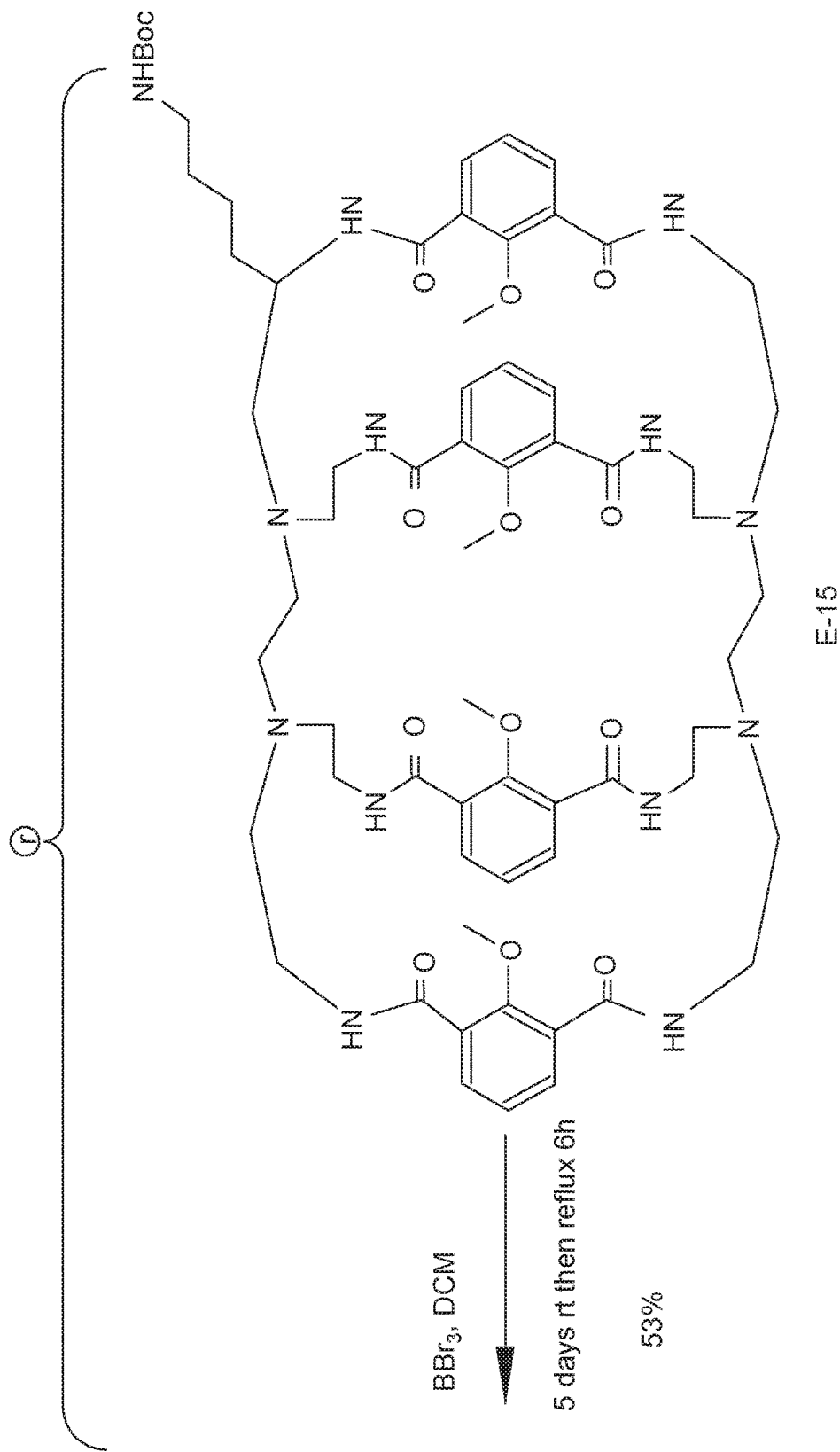
FIG. 10 (Continue)

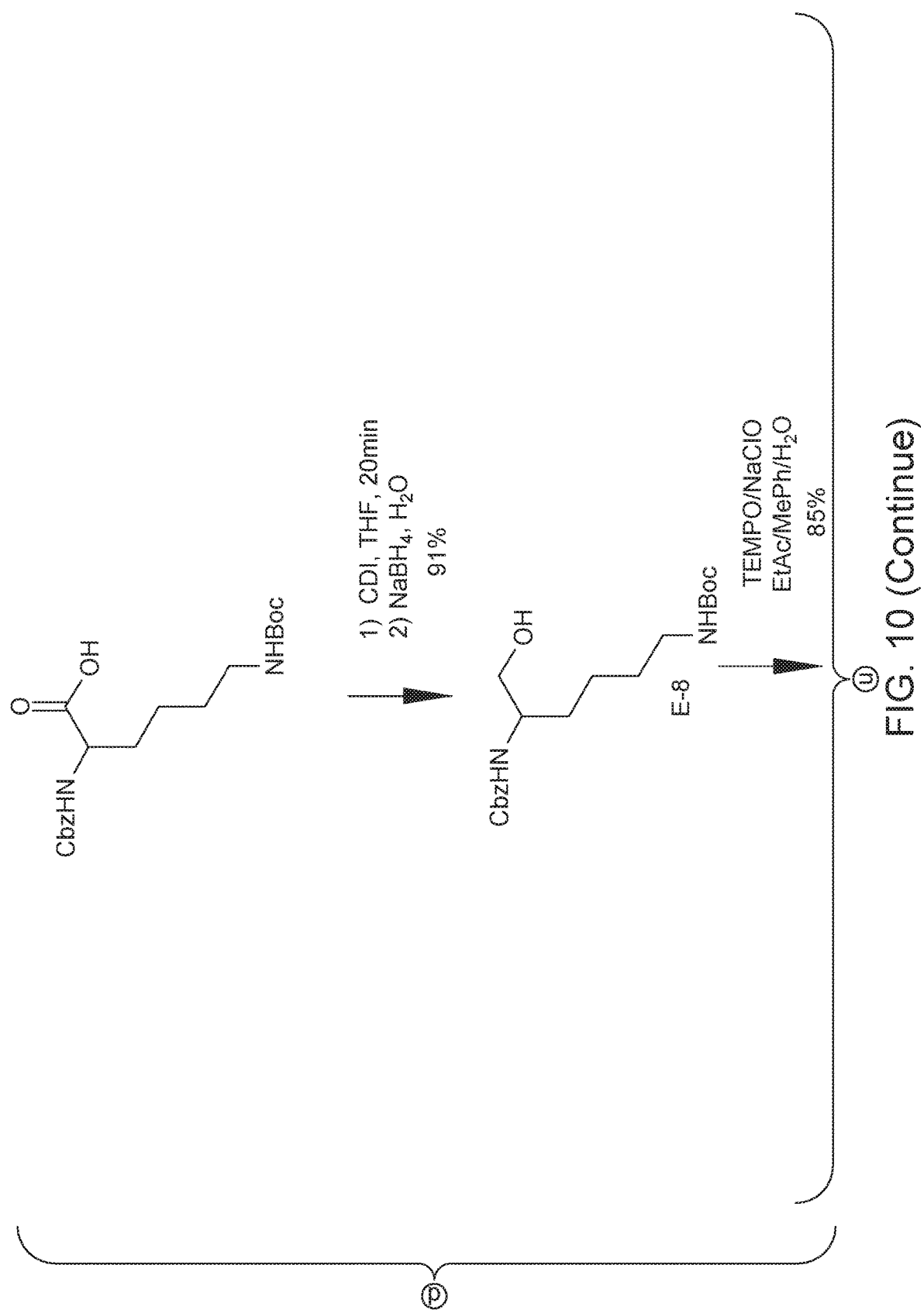
FIG. 10 (Continue)

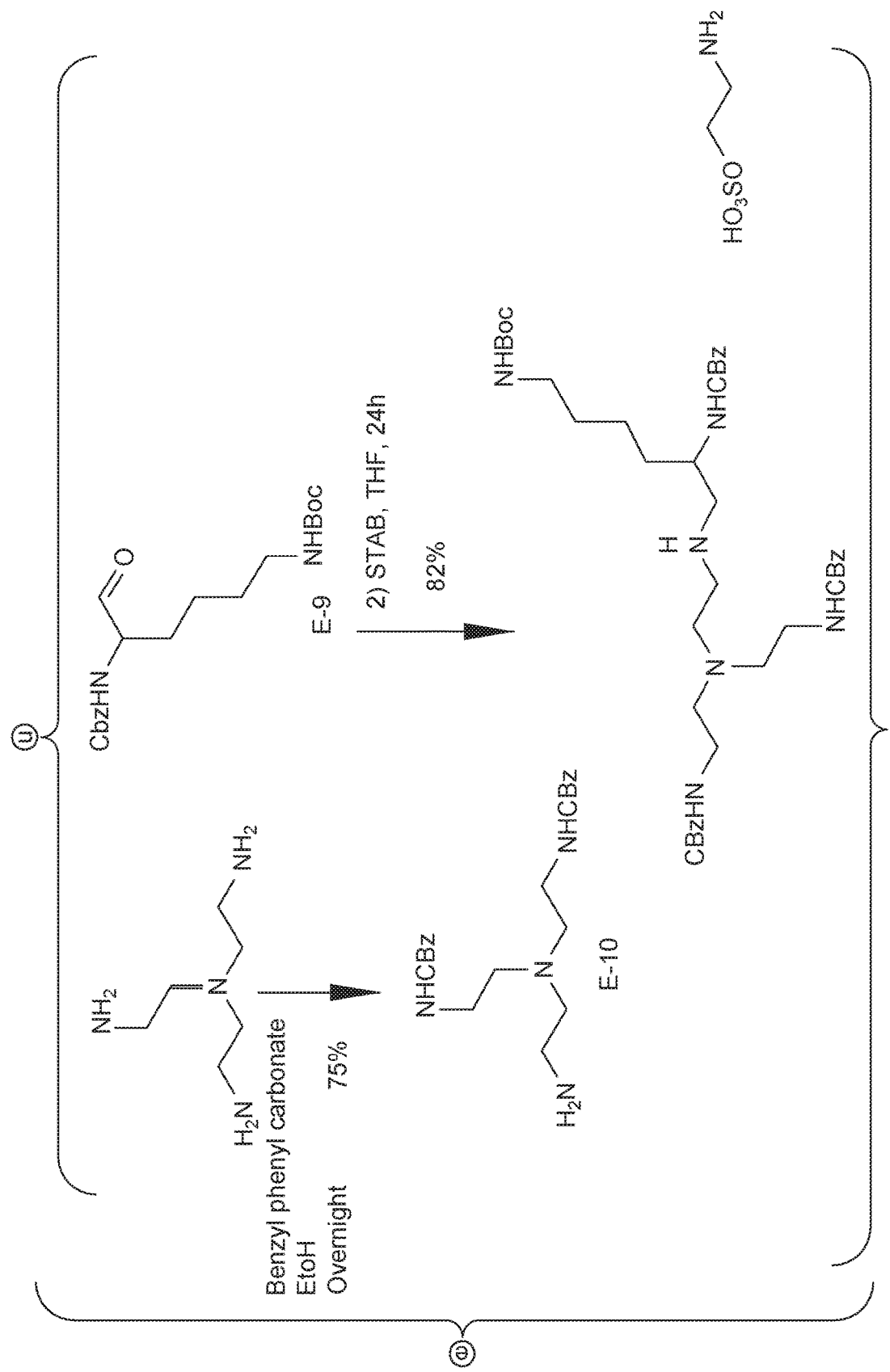
FIG. 10 (Continue)

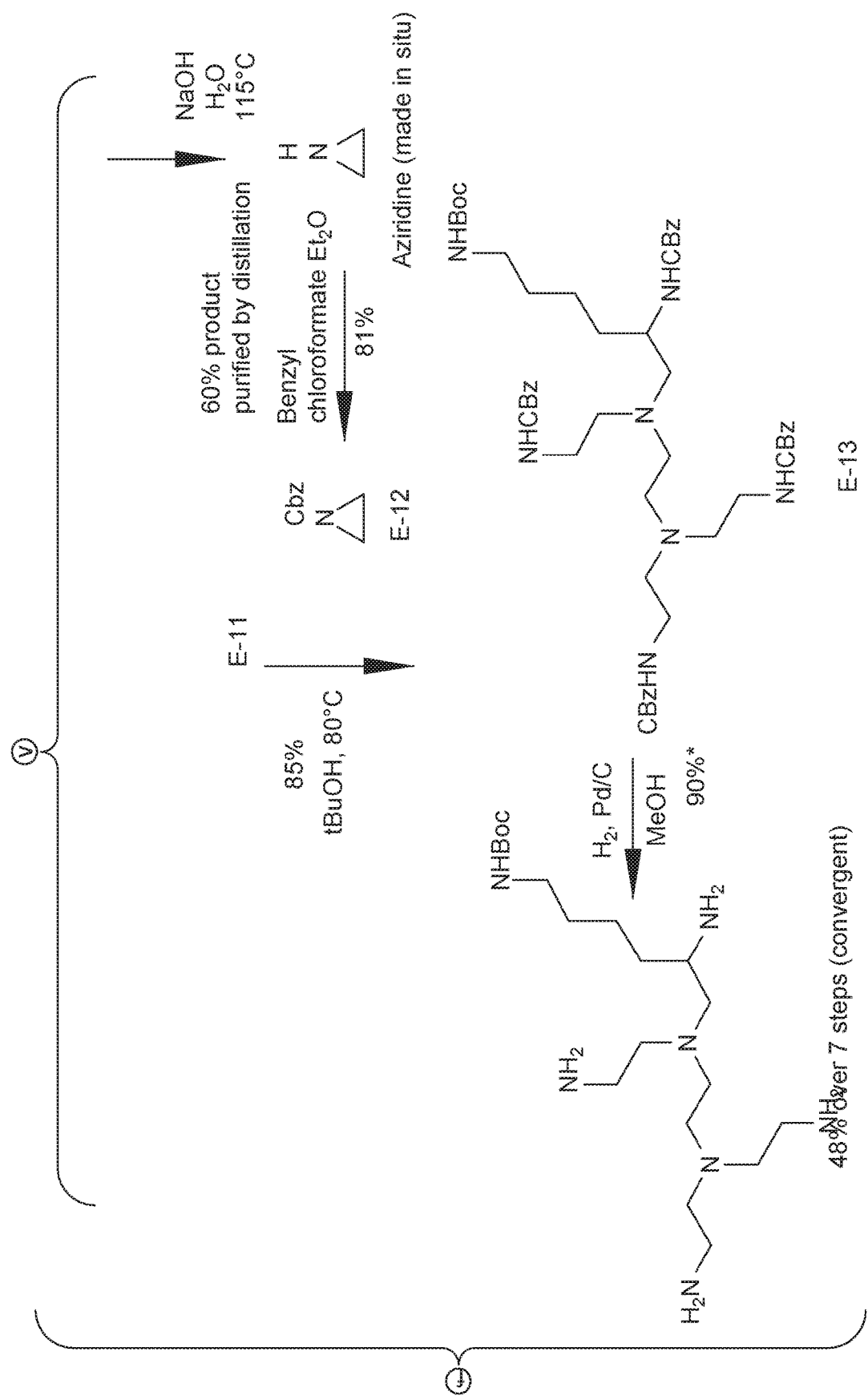
FIG. 10 (Continue)

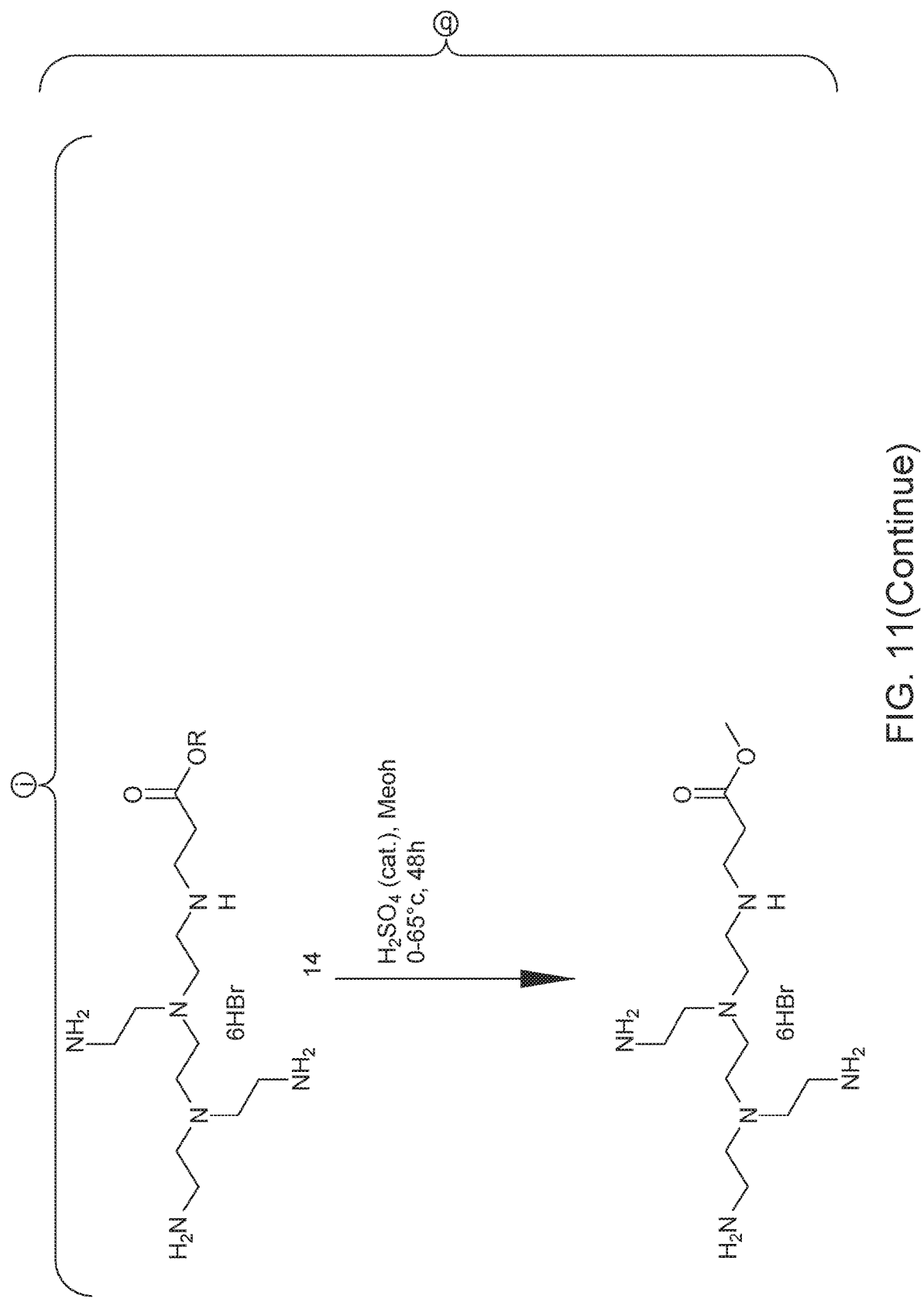
FIG. 11(Continue)

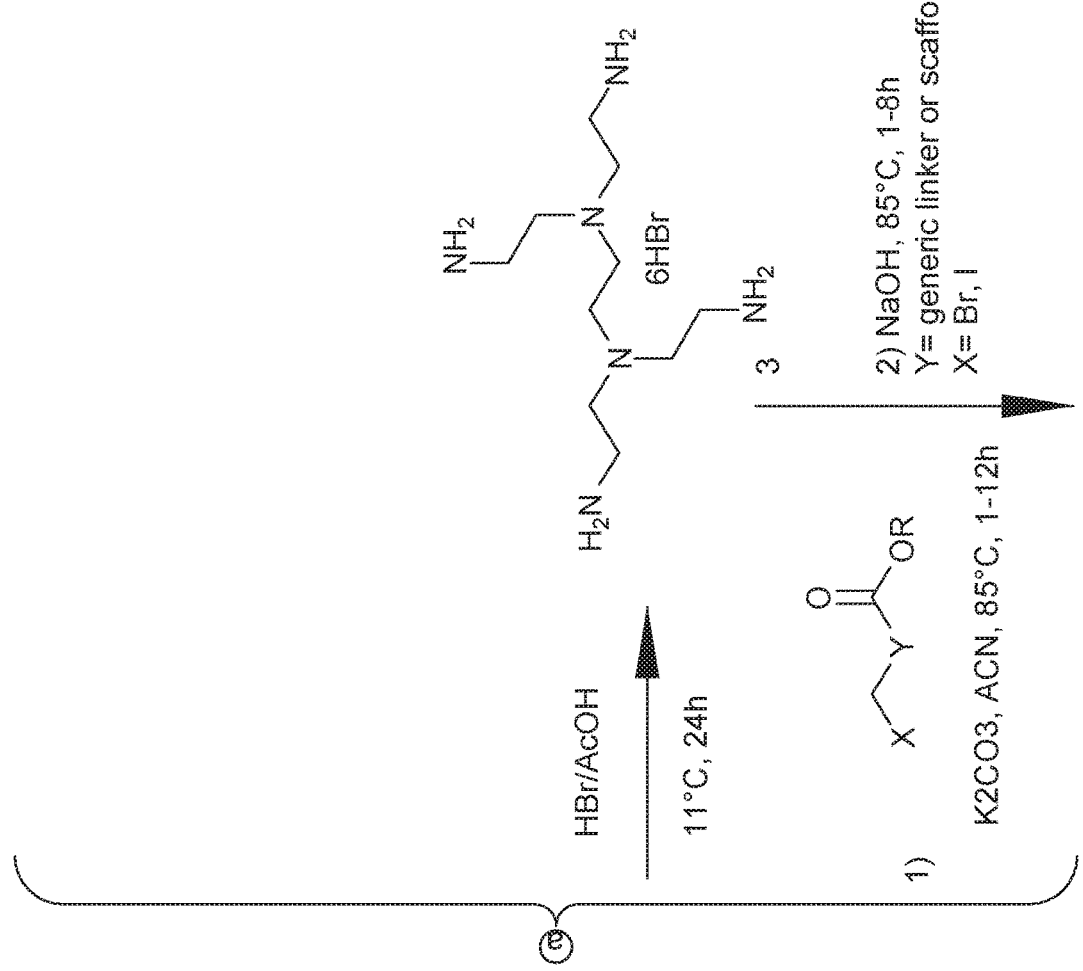
FIG. 11 (Continue)

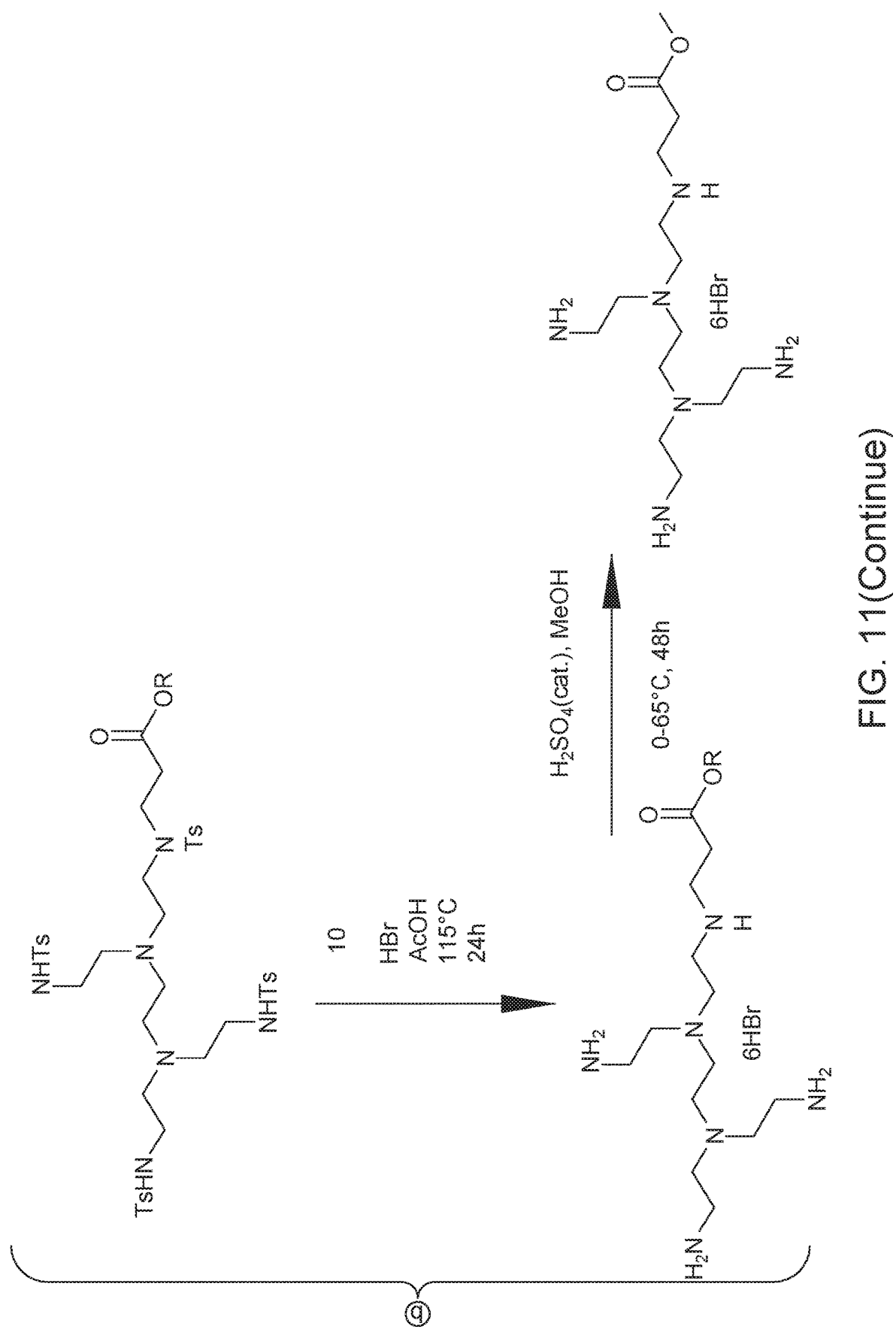
FIG. 11 (Continue)

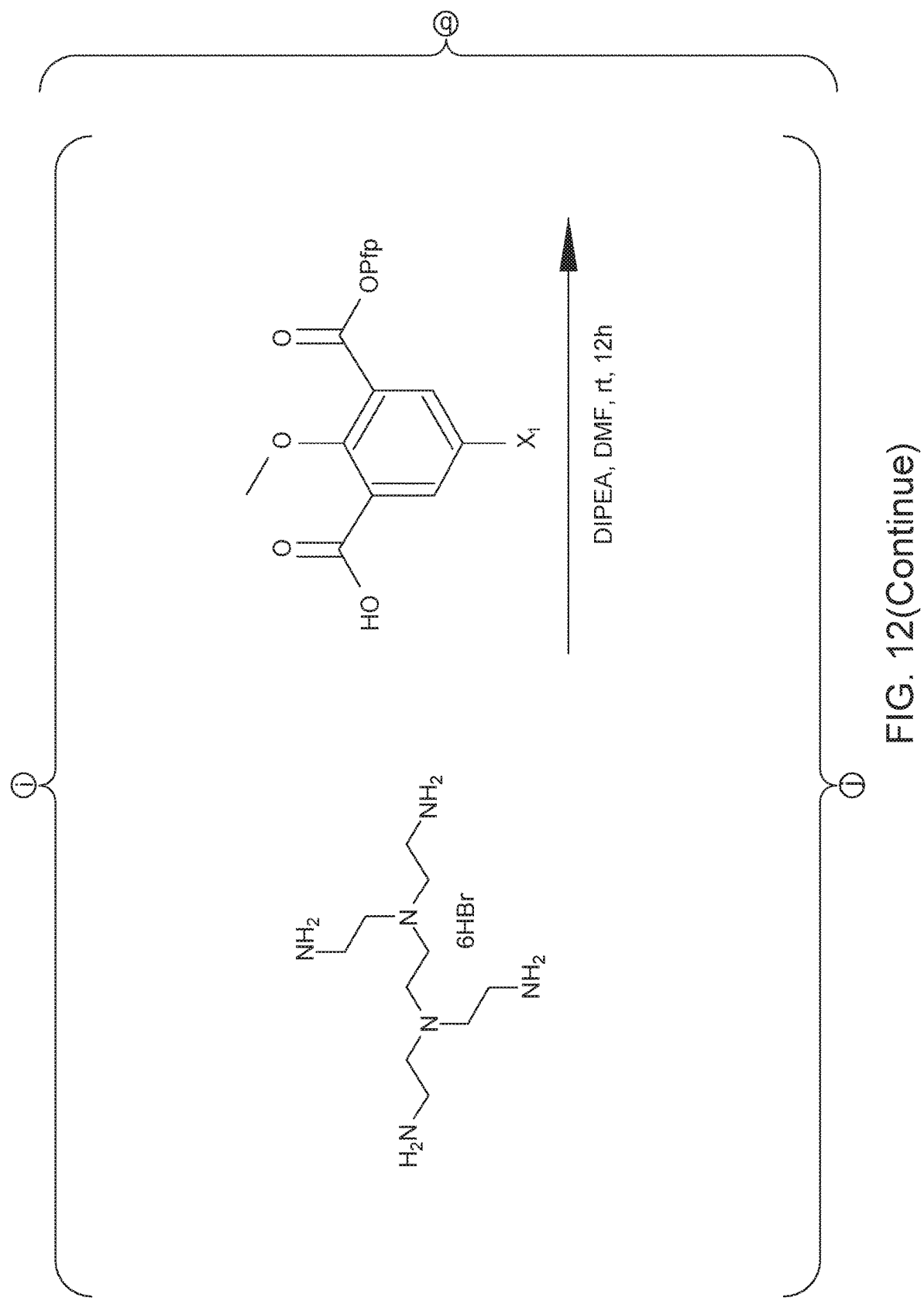
FIG. 12(Continue)

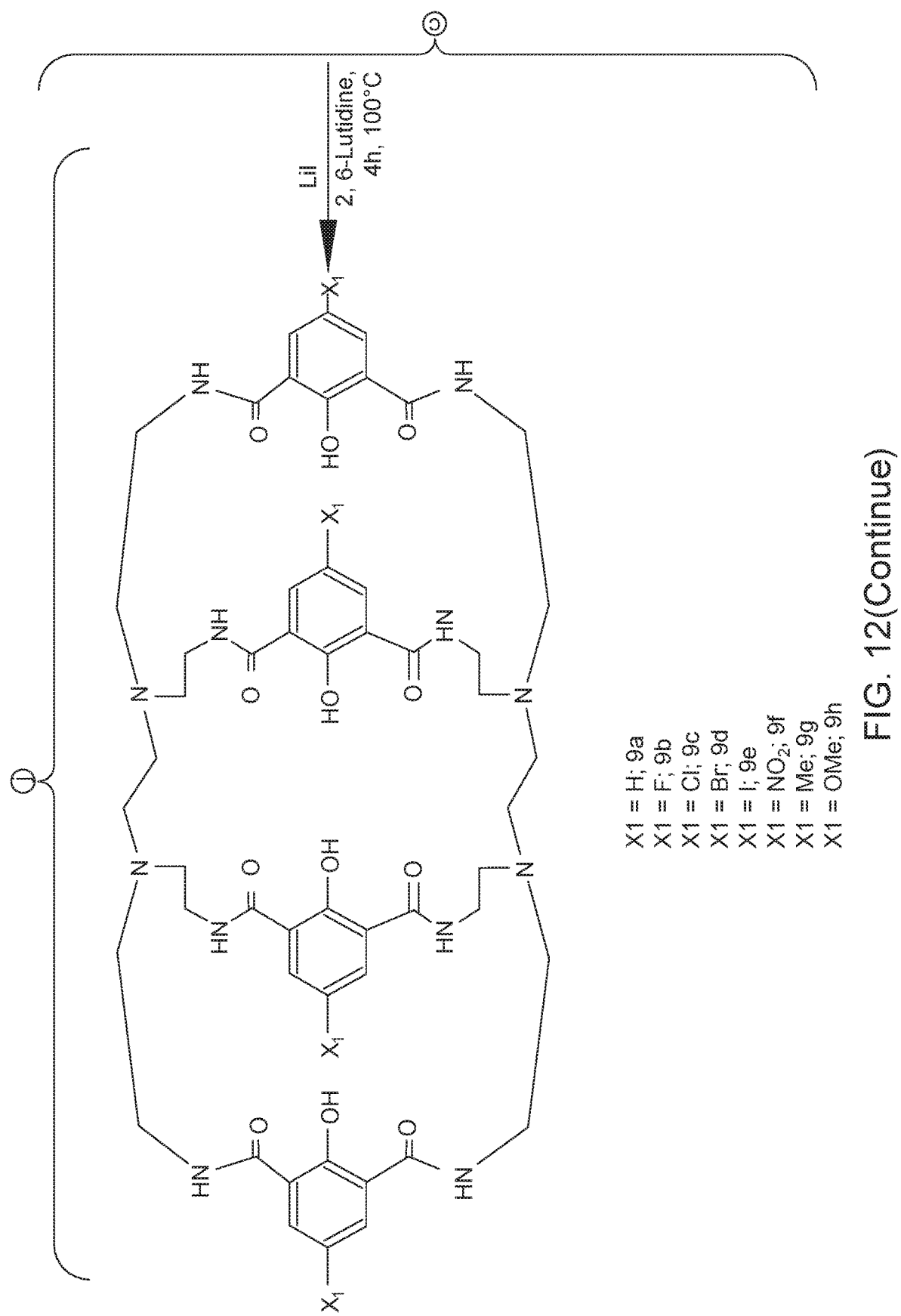
FIG. 12(Continue)

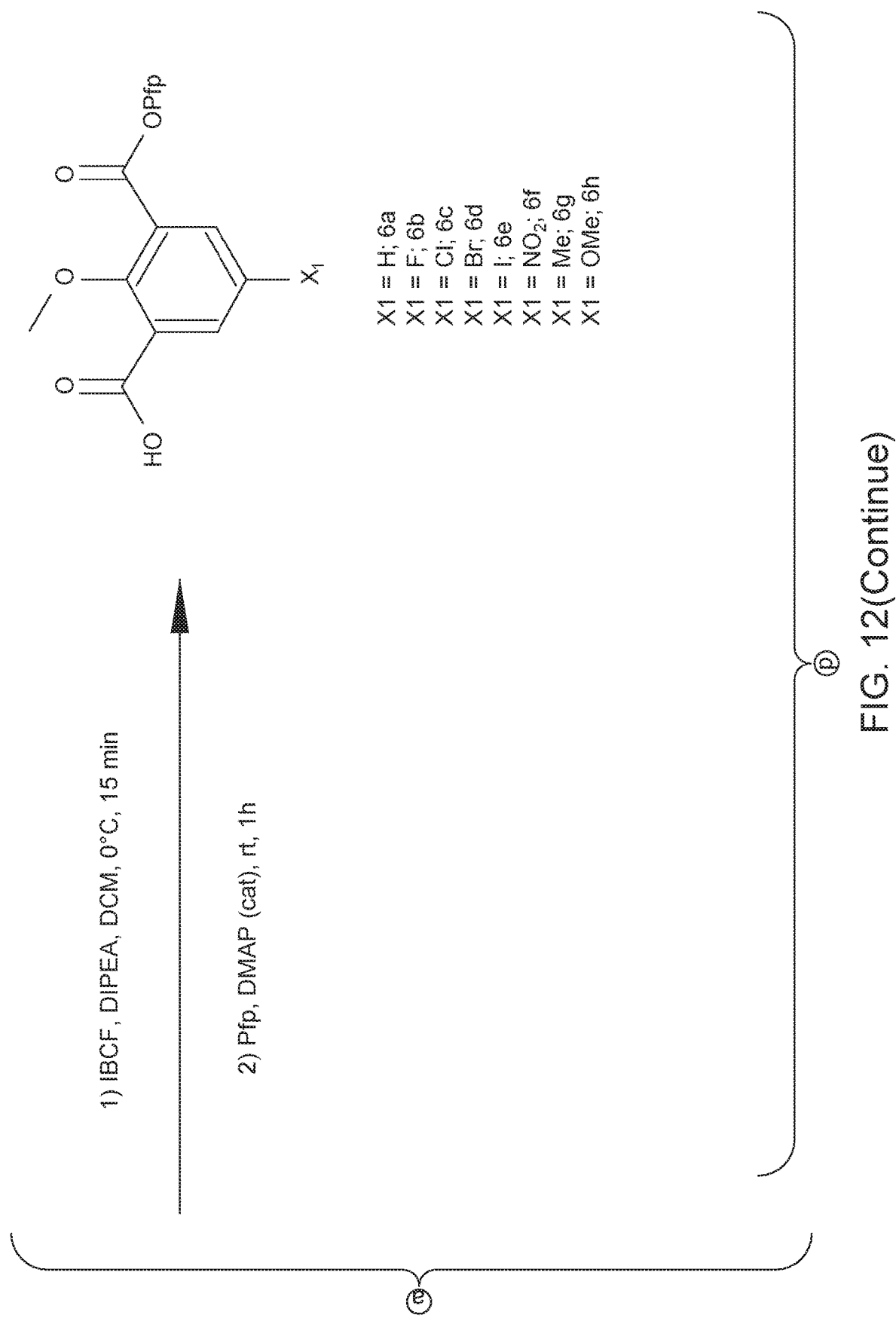
FIG. 12 (Continue)

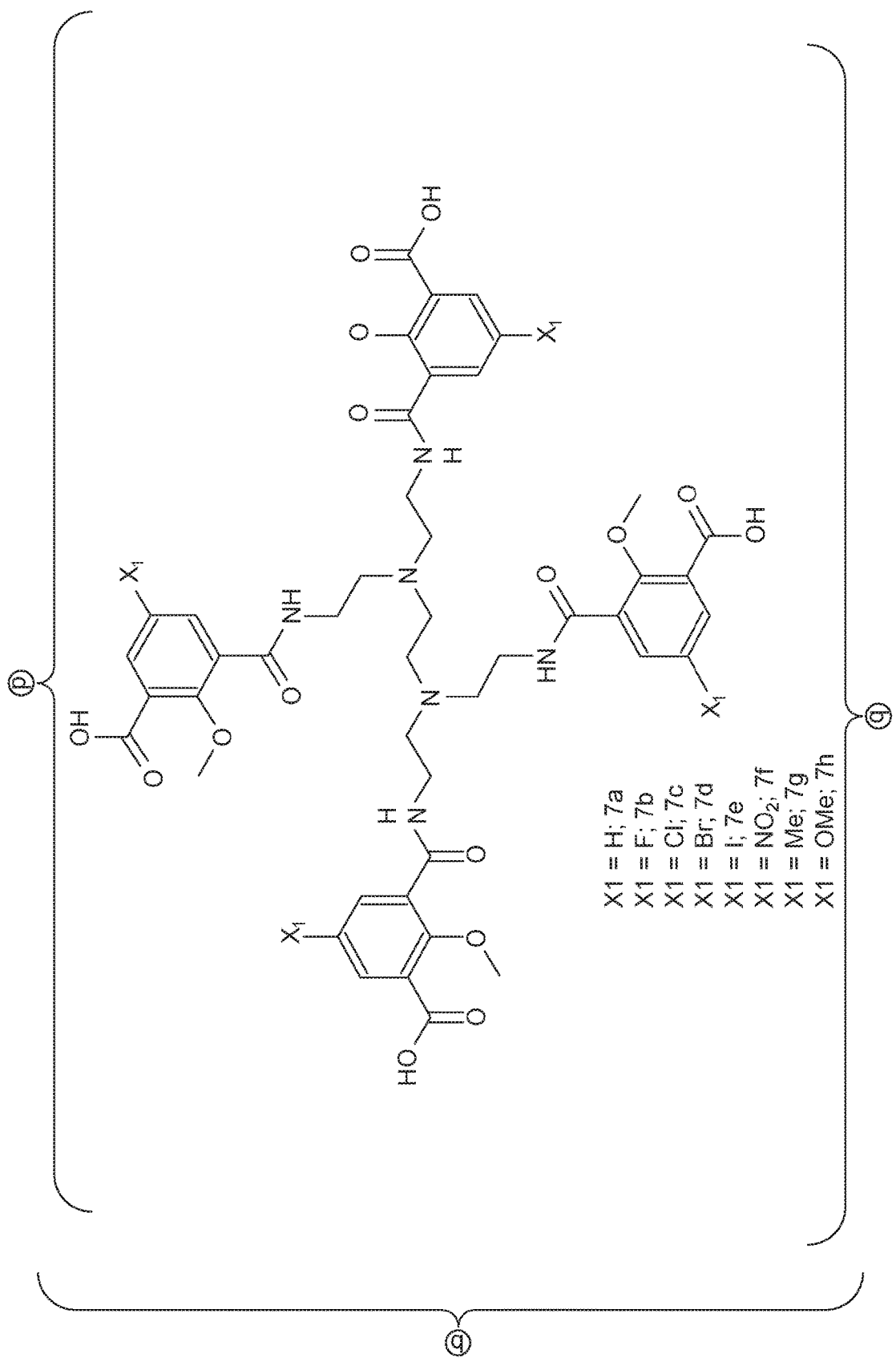
FIG. 12(Continue)

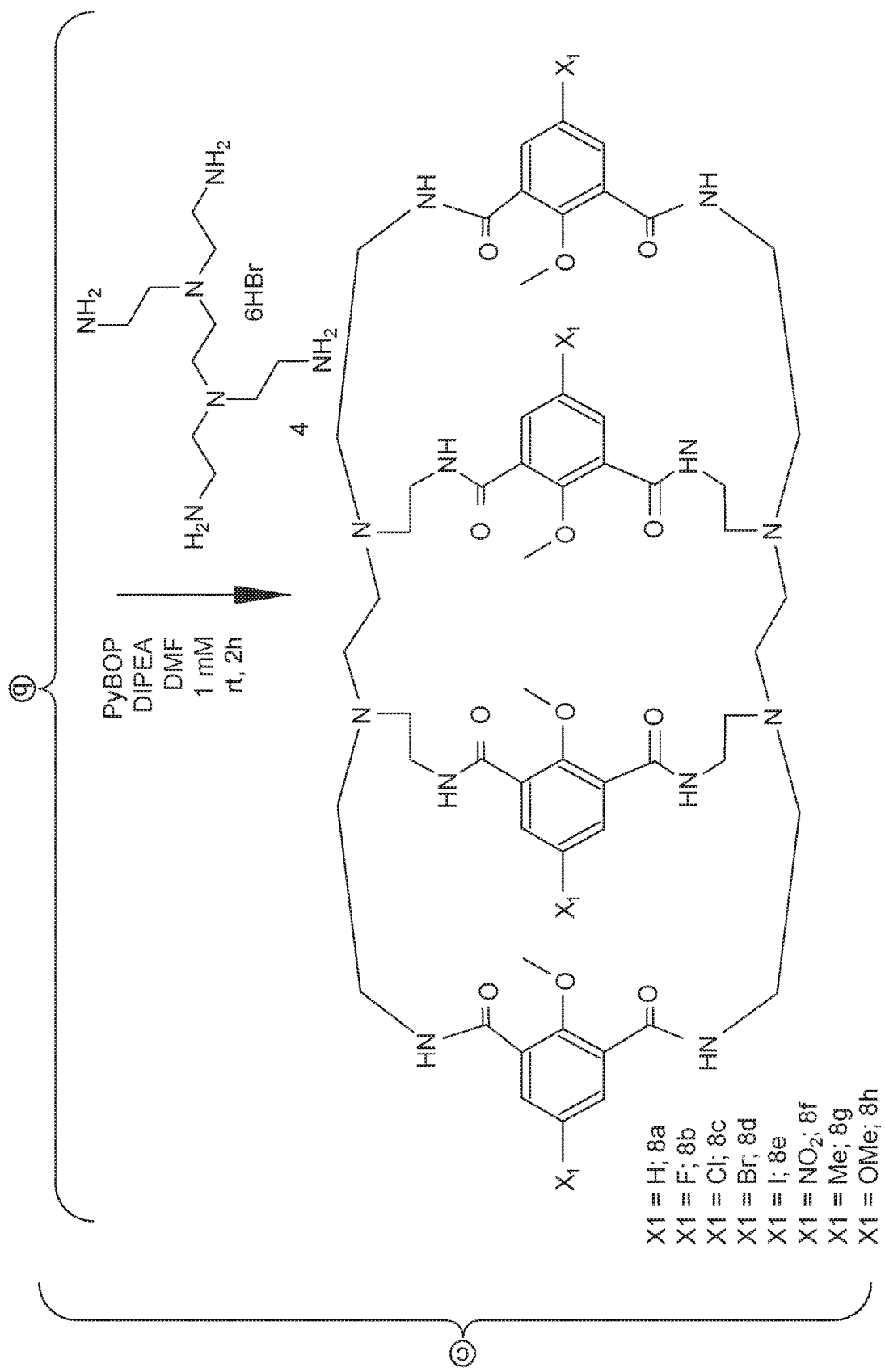
FIG. 12(Continue)

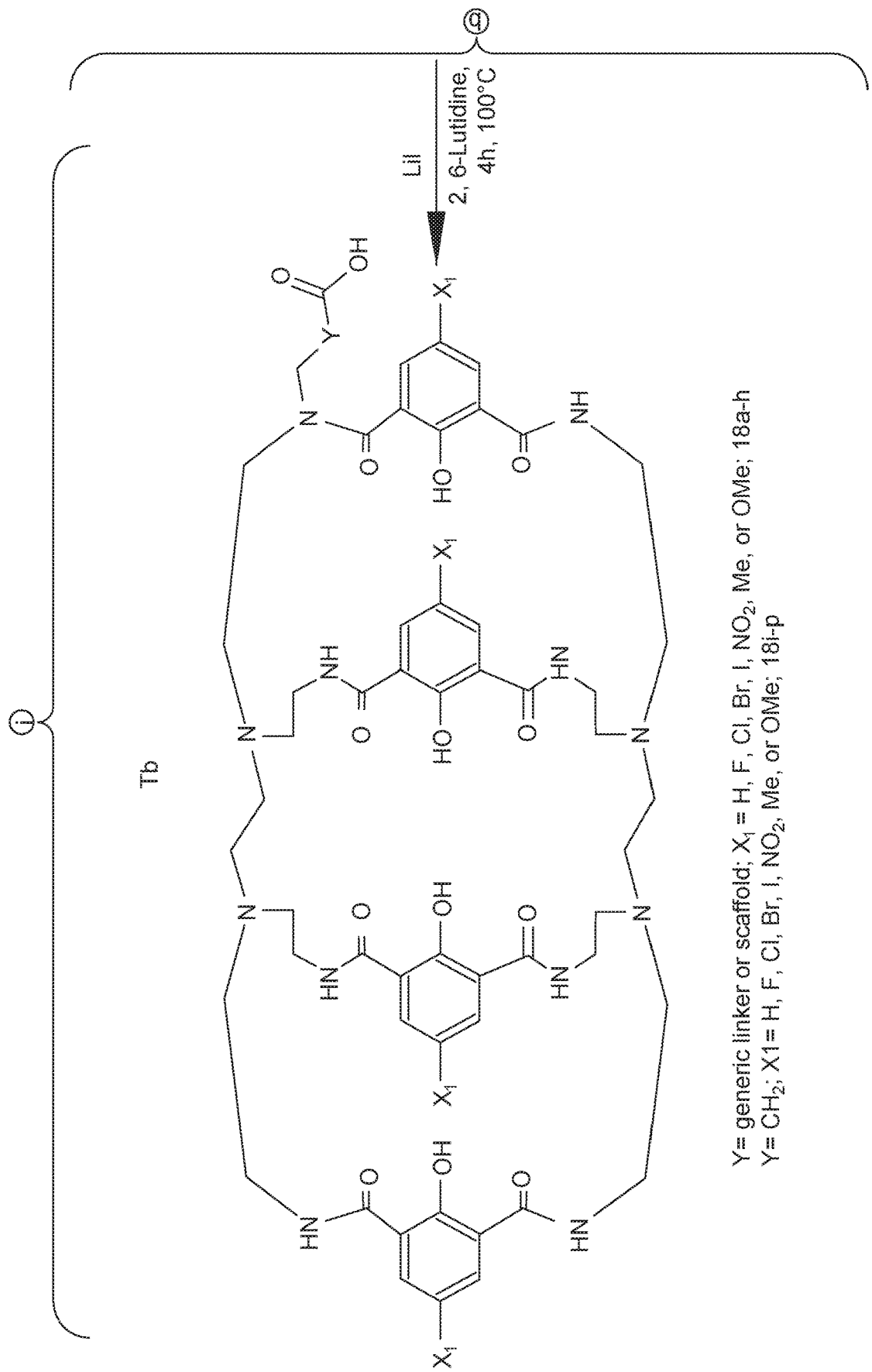
FIG. 13 (Continue)

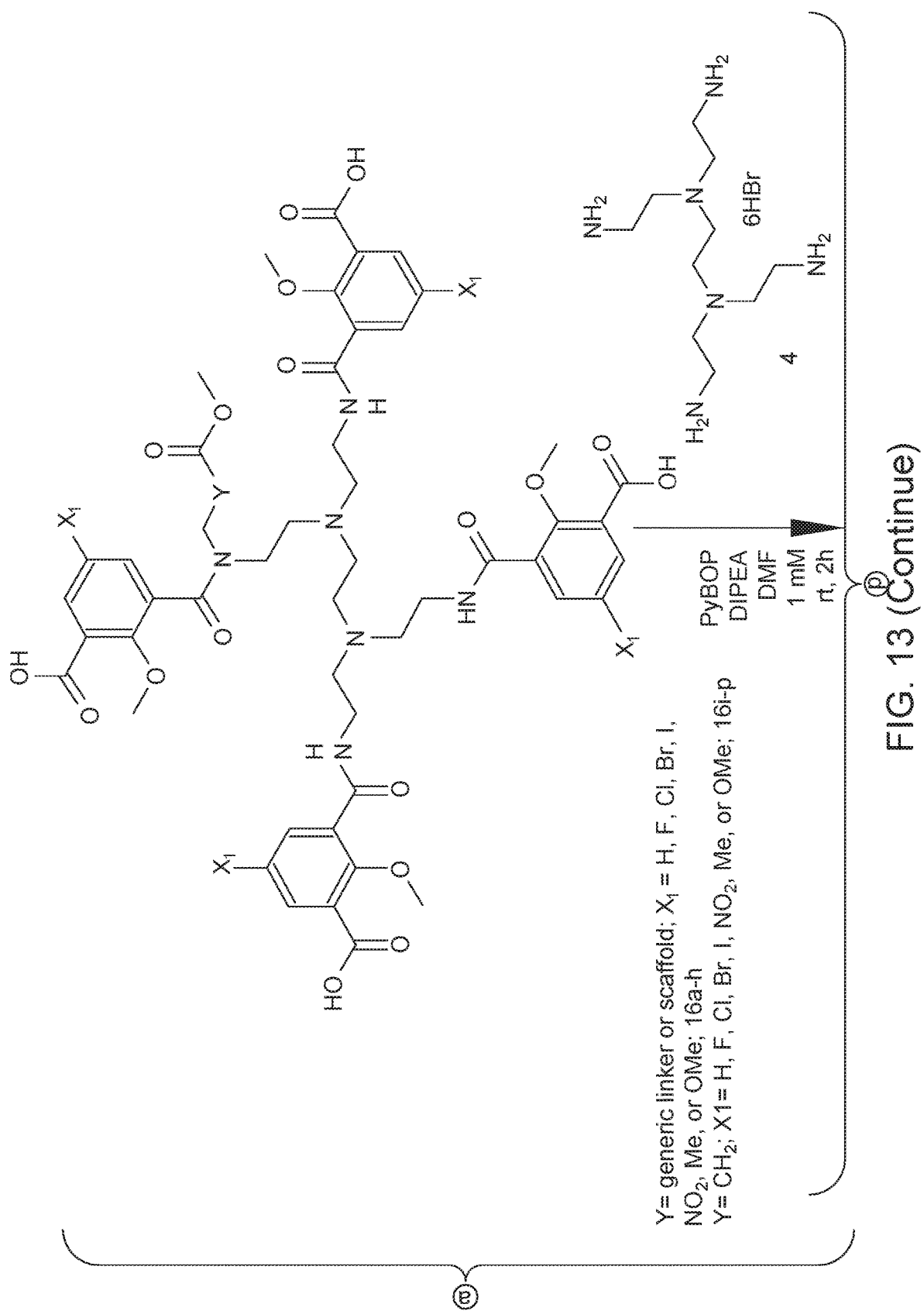
FIG. 13 (Continue)

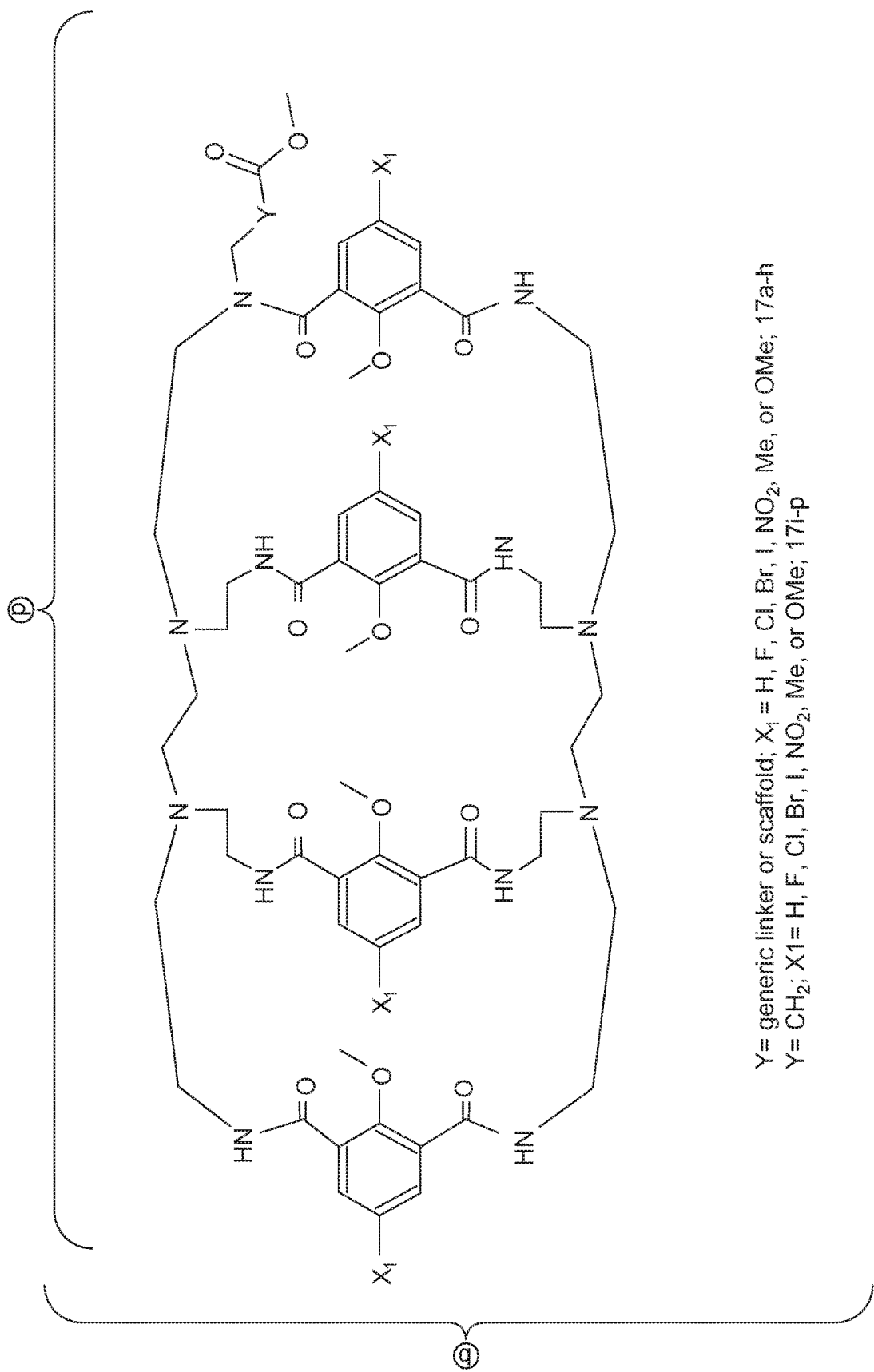
FIG. 13 (Continue)

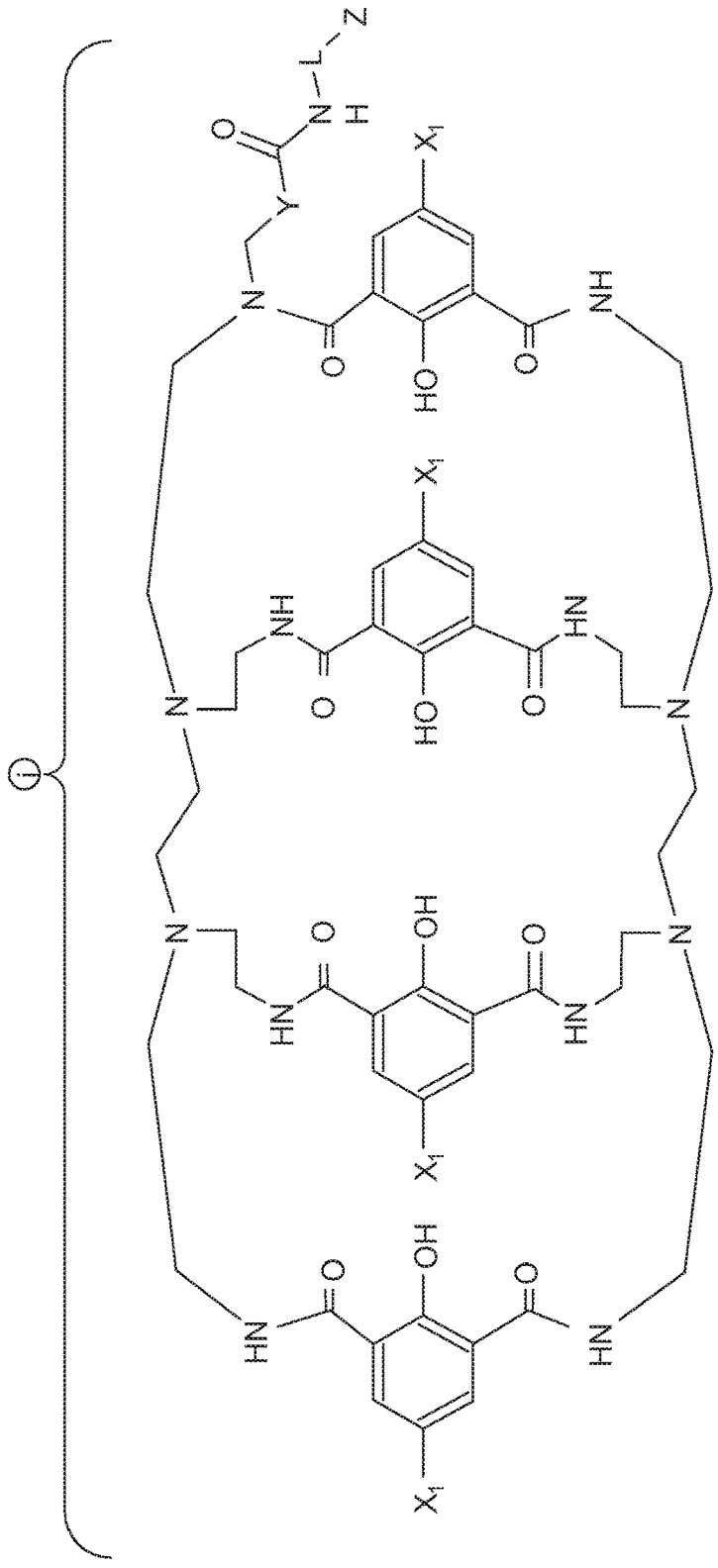

FIG. 14(Continue)

Y= generic linker or scaffold; $X_1$ = H, F, Cl, Br, I, $NO_2$, Me, or OMe; L = generic linker or scaffold; Z= fluorophore/antenna/turn-on probe/fluorescent quencher or protein tag substrate; 19a-h
Y= generic linker or scaffold; $X_1$ = H, F, Cl, Br, I, $NO_2$, Me, or OMe; L = generic linker or scaffold; Z= fluorophore/antenna/turn-on probe/fluorescent quencher or protein tag substrate; 19i-p

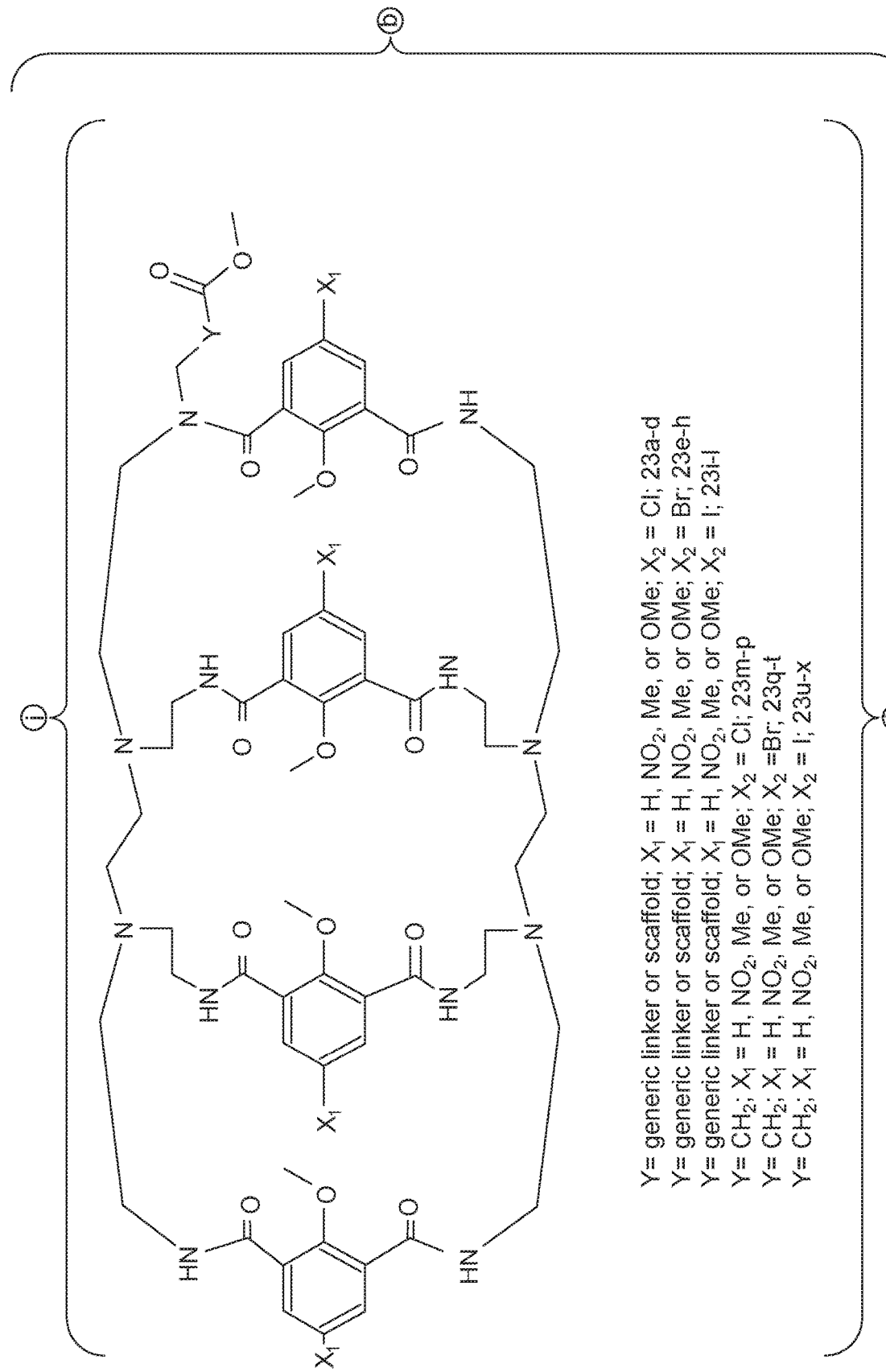
FIG. 15(Continue)

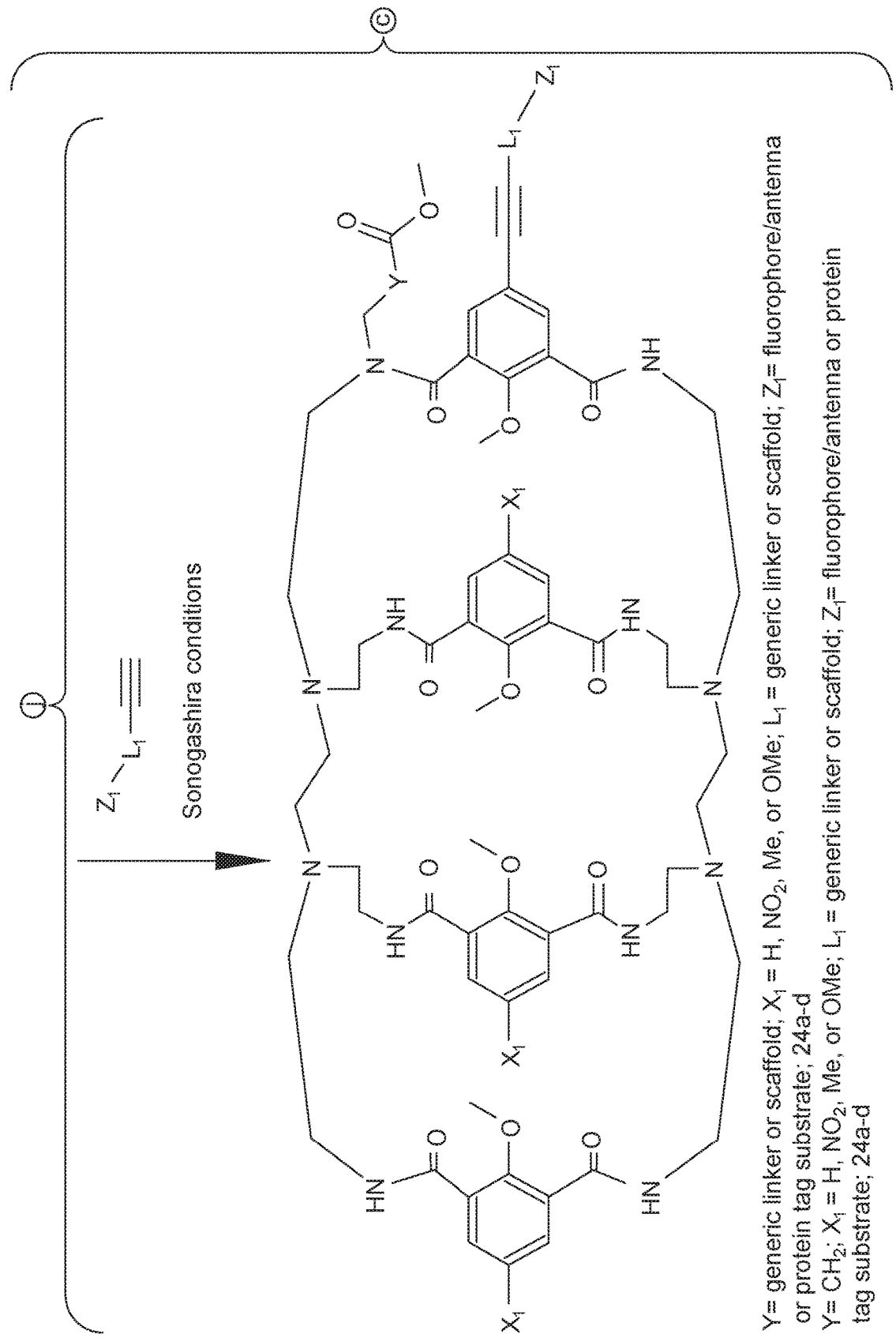
FIG. 15(Continue)

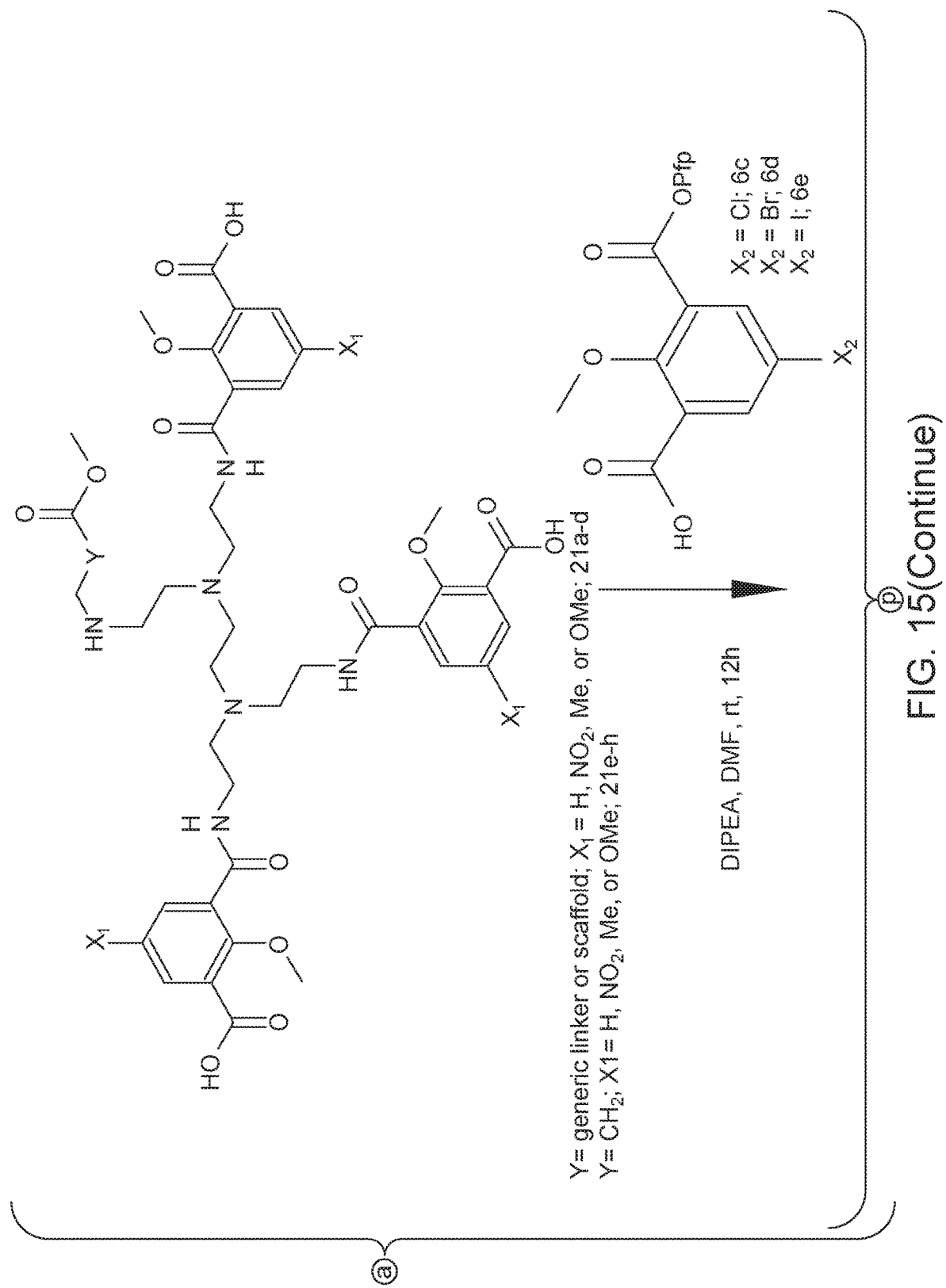
FIG. 15(Continue)

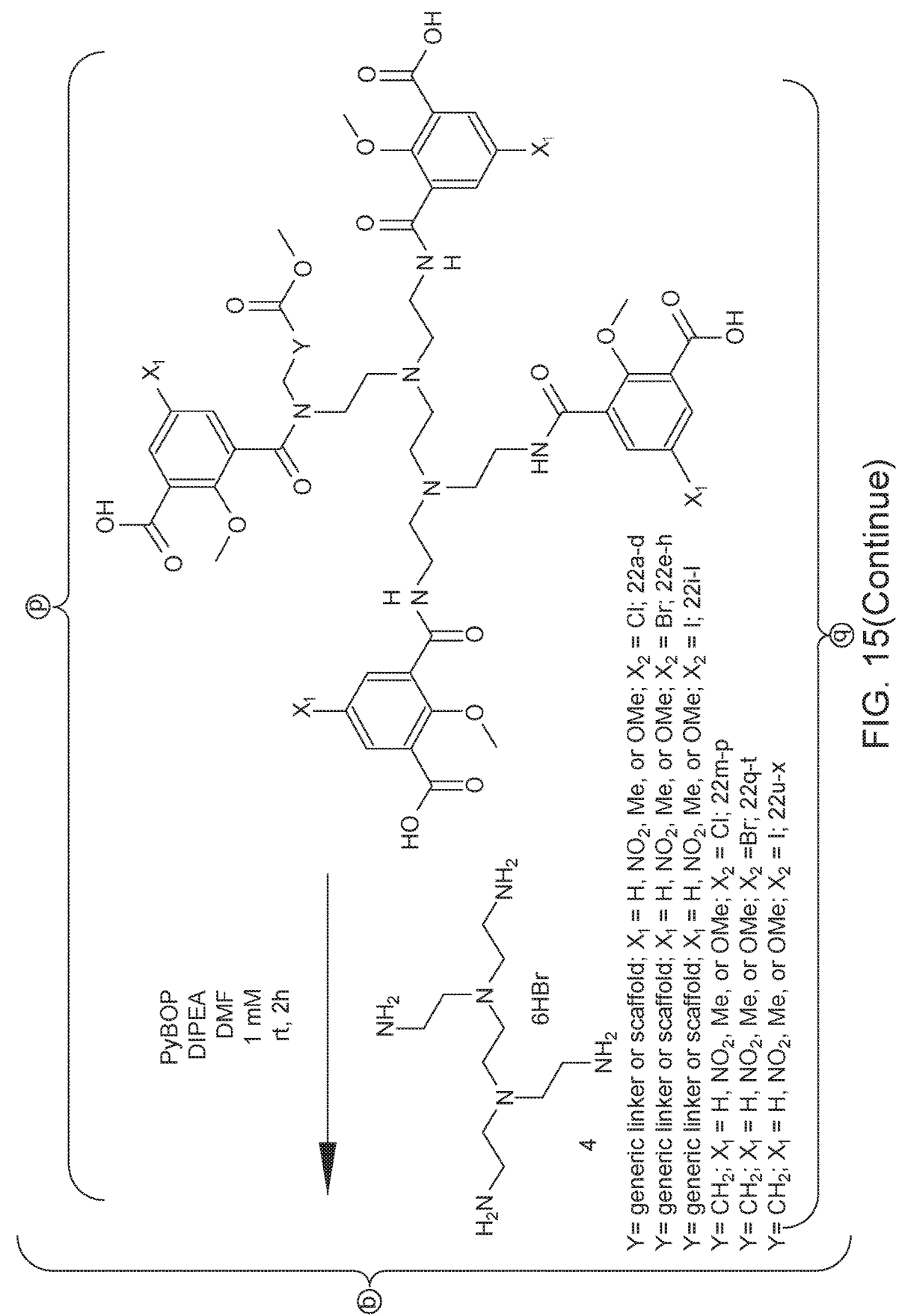
FIG. 15 (Continue)

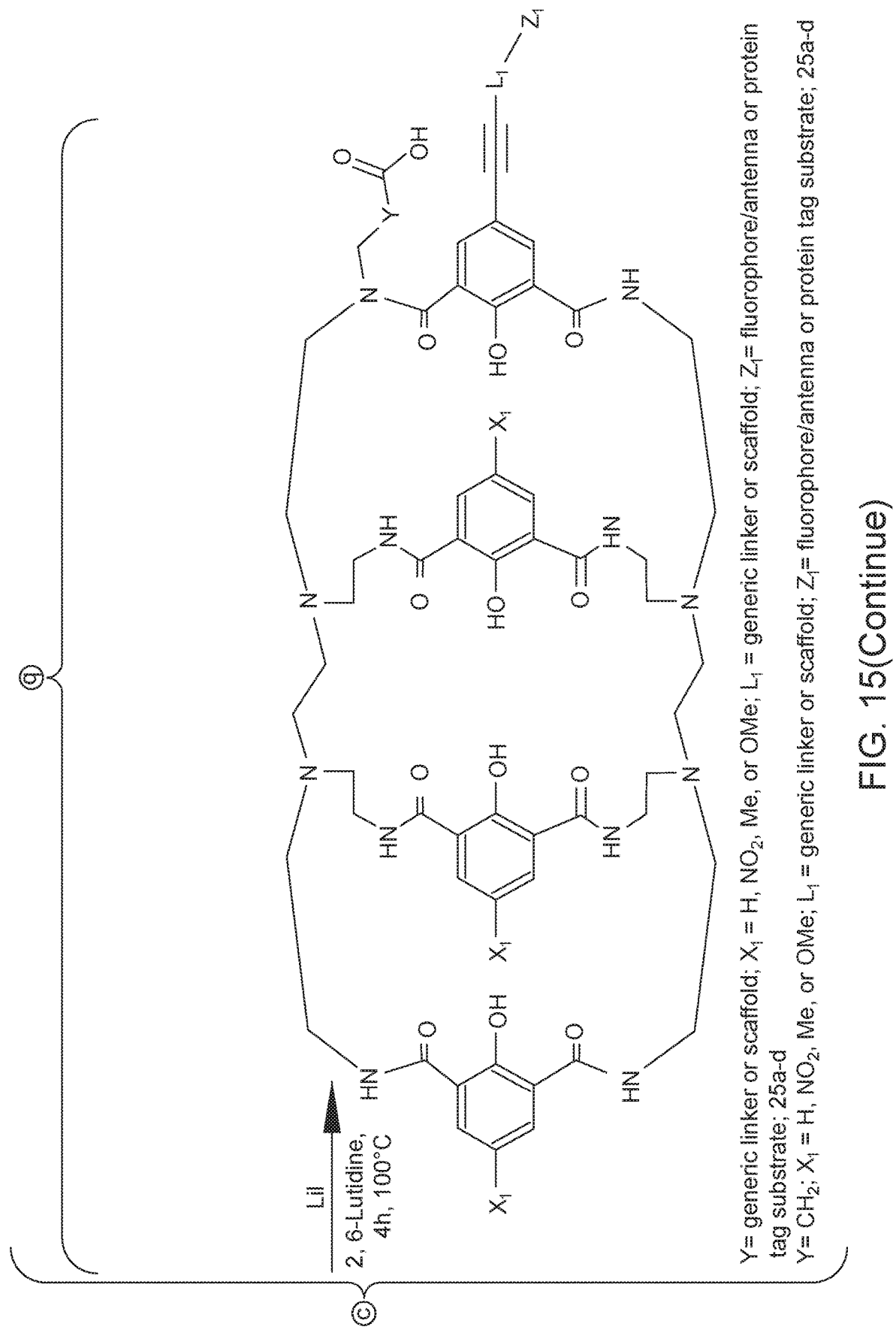
FIG. 15(Continue)

Y= generic linker or scaffold; $X_1$ = H, $NO_2$, Me, or OMe; $L_1$ = generic linker or scaffold; $Z_1$= fluorophore/antenna or protein tag substrate; 25a-d
Y= $CH_2$; $X_1$ = H, $NO_2$, Me, or OMe; $L_1$ = generic linker or scaffold; $Z_1$= fluorophore/antenna or protein tag substrate; 25a-d $Z_2$-$L_2$-$NH_2$, PyBOP, DIPEA
DMF, rt, 1h

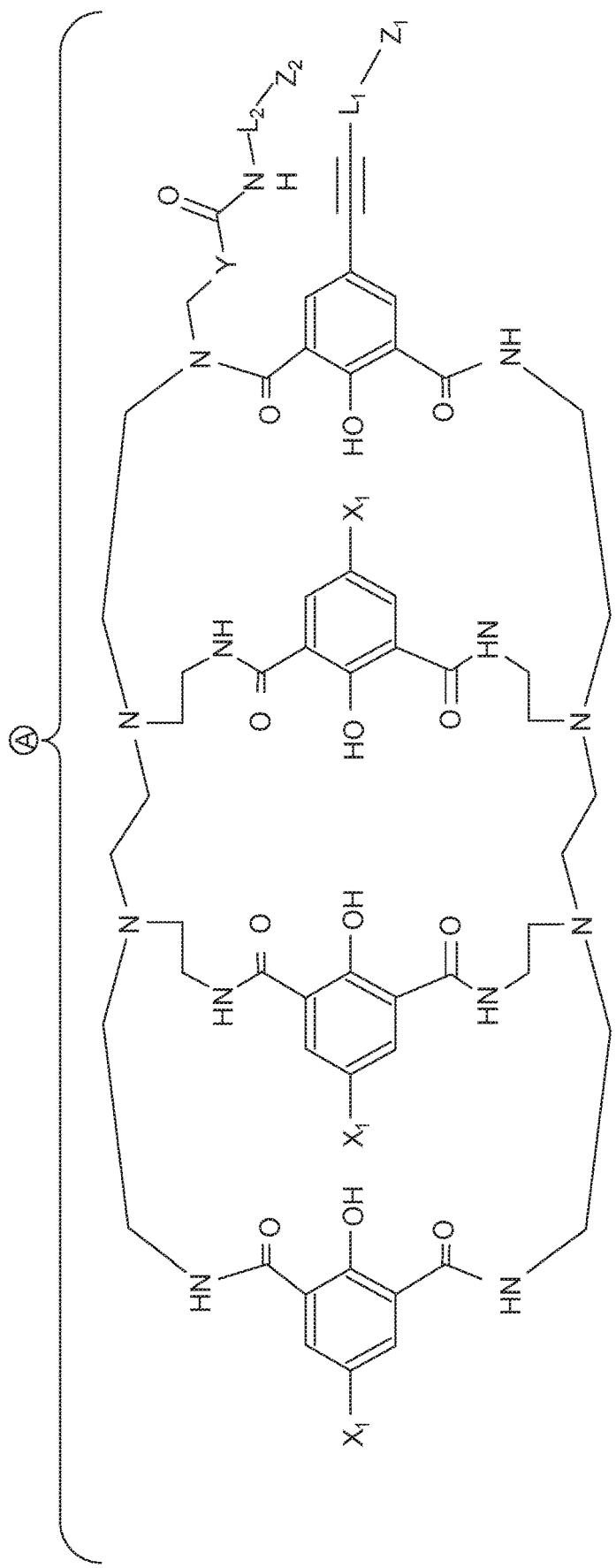

Y= generic linker or scaffold; $X_1$ = H, $NO_2$, Me, or OMe; $L_1$ = generic linker or scaffold; $Z_1$= fluorophore/antenna/turn-on probe/fluorescent quencher or protein tag substrate;
$L_2$ = generic linker or scaffold; $Z_2$ = orthogonal protein tag substrate or turn-on probe; 26a-d
Y= $CH_2$; $X_1$ = H, $NO_2$, Me, or OMe; $L_1$ = generic linker or scaffold; $Z_1$= fluorophore/antenna/turn-on probe/fluorescent quencher or protein tag substrate;
$L_2$ = generic linker or scaffold; $Z_2$ = orthogonal protein tag substrate or turn-on probe; 26a-d

FIG. 16(Continue)

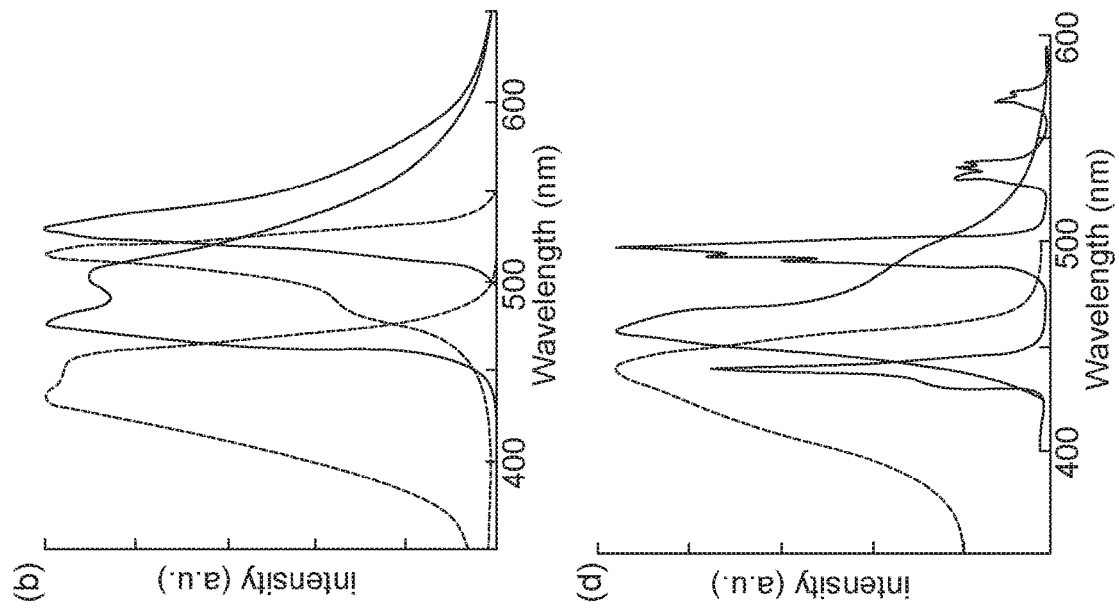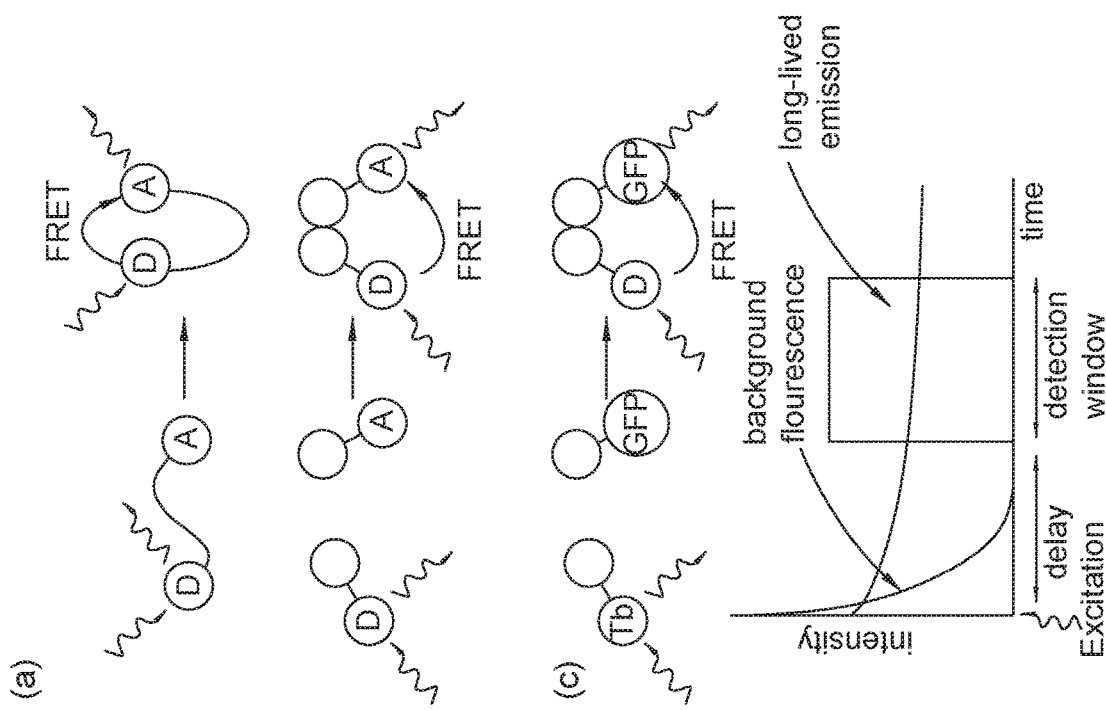
FIG. 18

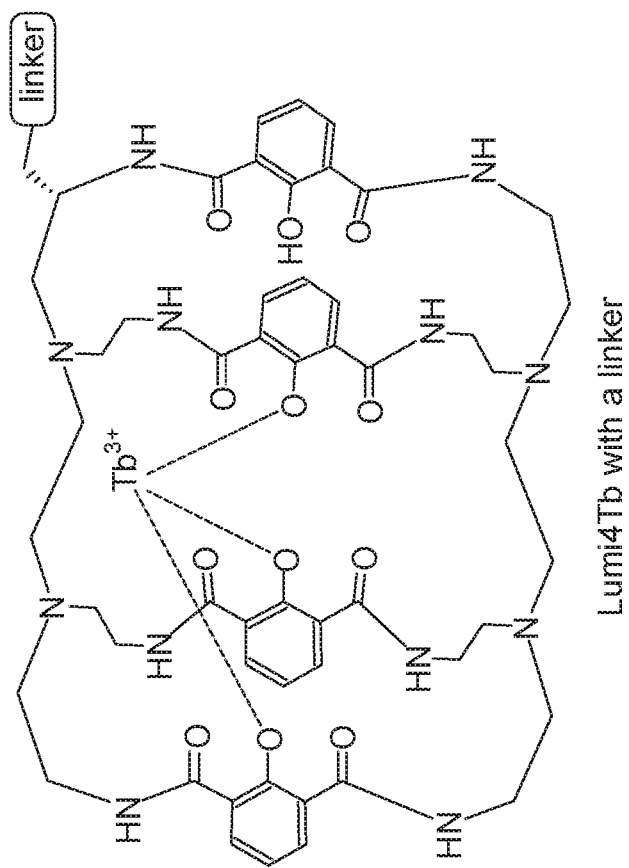
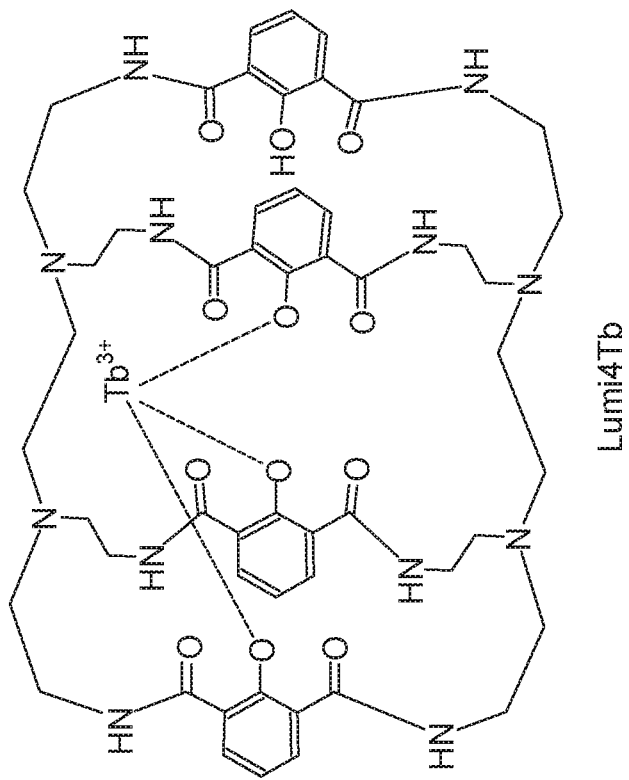
FIG. 19

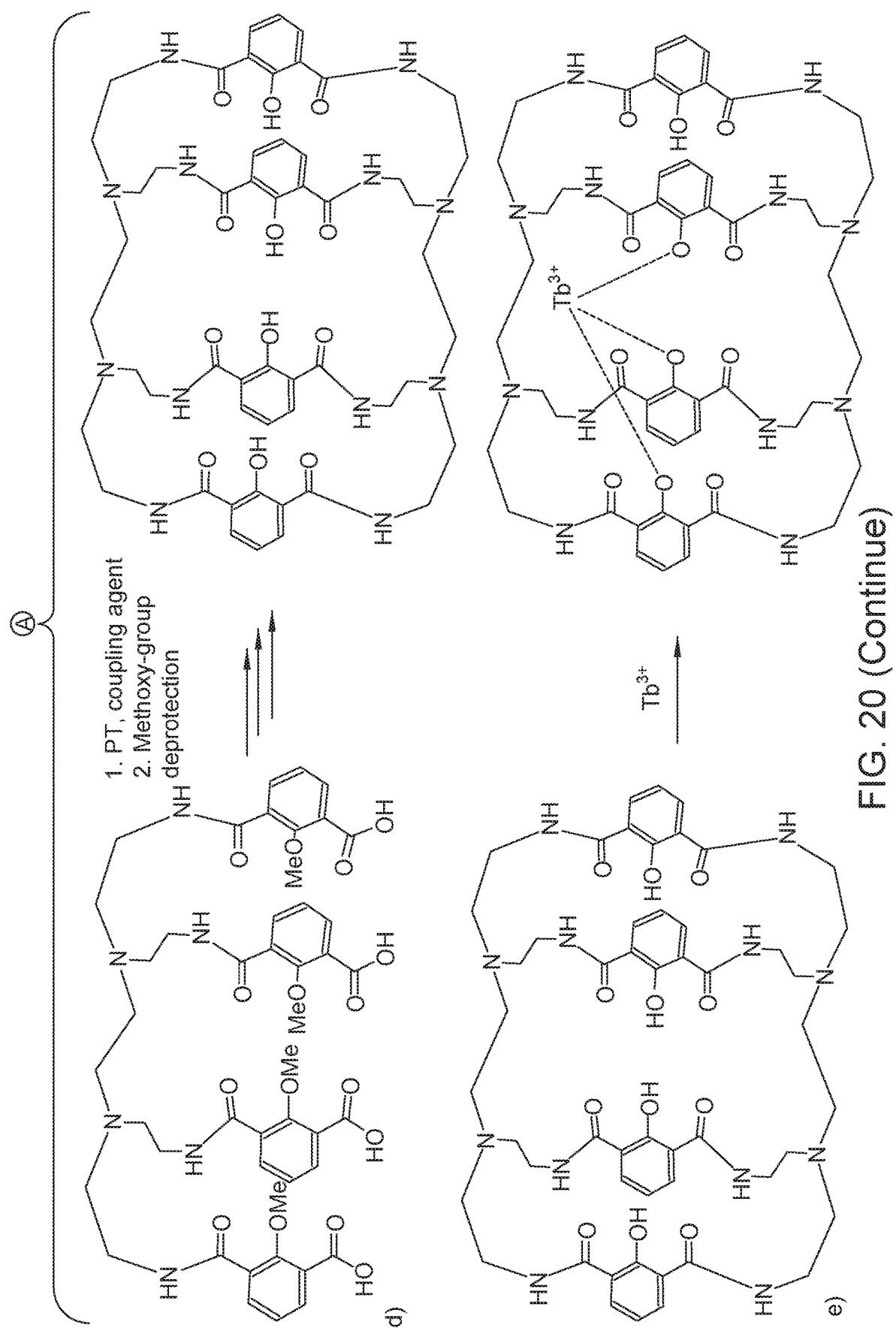
FIG. 20 (Continue)

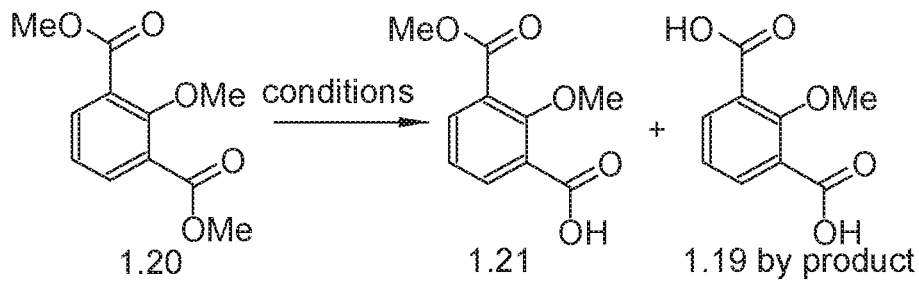

| Entry | Base | Solvent | Time | T | P(1.21)/SM(1.20)/BP(1.19) ratio, % |
|---|---|---|---|---|---|
| 1 | LiOH | MeOH/H$_2$O | 2h | rt | 20/60/20 |
| 2 | LiOH | MeOH | 2h | rt | 30/45/25 |
| 3 | LiOH[a] | MeOH | 2h | reflux | -/-/30[b] |
| 4 | NaOH | MeOH/H$_2$O | 2h | rt | 20/70/10 |
| 5 | NaOH | MeOH/H$_2$O | 4h | rt | 25/50/25 |
| 6 | NaOH | MeOH/H$_2$O | 1.5h | reflux | -/60/40 |
| 7 | KOH | MeOH/H$_2$O | 2h | rt | -/100/- |
| 8 | KOH | MeOH/H$_2$O | 2h | rt | -/100/- |
| 9 | KOH | MeOH/H$_2$O | 8h | rt | 10/90/- |
| 10 | KOH | MeOH/H$_2$O | 24h | rt | 10/70/20 |
| 11 | KOH | MeOH/H$_2$O | 4h | 50°C | 40/40/20 |
| 12 | KOH | MeOH | 2h | 50°C | 45/40/15 |
| 13 | KOH | MeOH | 4h | 50°C | 55/25/20 |
| 14 | KOH | MeOH | 5h | 50°C | 45/20/35 |
| 15 | KOH | CH$_3$CN | 10 min | rt | 20/60/20 |
| 16 | KOH | THF | 15 min | rt | 30/40/30 |

[a]4 equiv. [b]2-hydroxyisophthalate 1.23 was obtained

FIG. 25

| Entry | Conditions | Time | Conversion[a] [%] |
|---|---|---|---|
| 1 | BBr₃, anhydrous DCM, 0°C-rt | 2 d | 18 |
| 2 | BBr₃, anhydrous DCM, 0°C-40°C | 3 d | 26 |
| 3 | NaN₃, DMF, 80°C | 2 h | 40 |
| 4 | NaN₃, DMF, 80°C | 4 h | [b] |
| 5 | LiOH, MeOH, reflux | 8 h | [c] |
| 6 | LiI, 2,6-lutidine, reflux | 4 h | 100 |

[a] calculated based on LC-MS results; [b] product was not isolated, SM was lost [c] SM was recovered.

FIG. 29 (Continue)

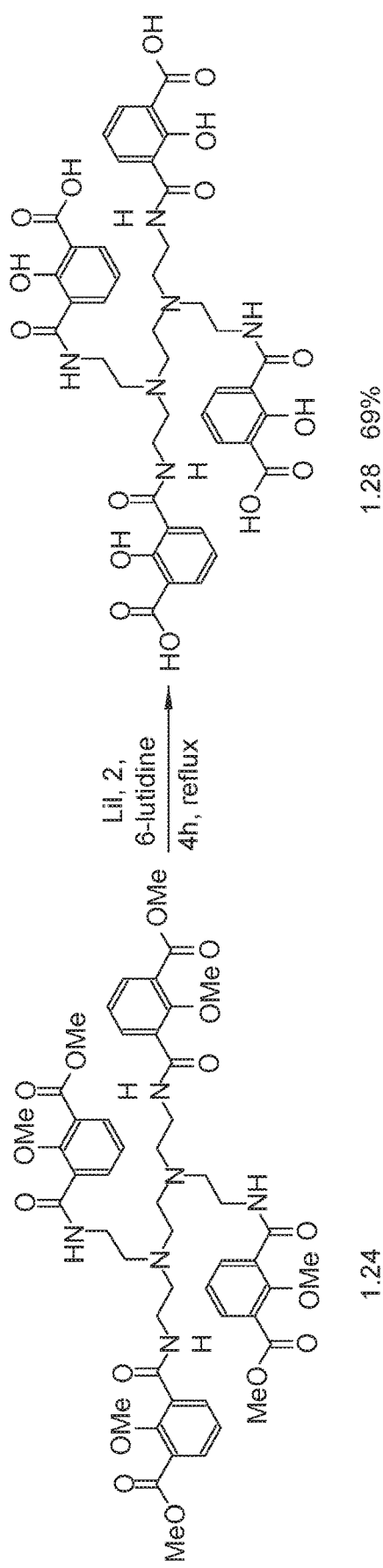
FIG. 30
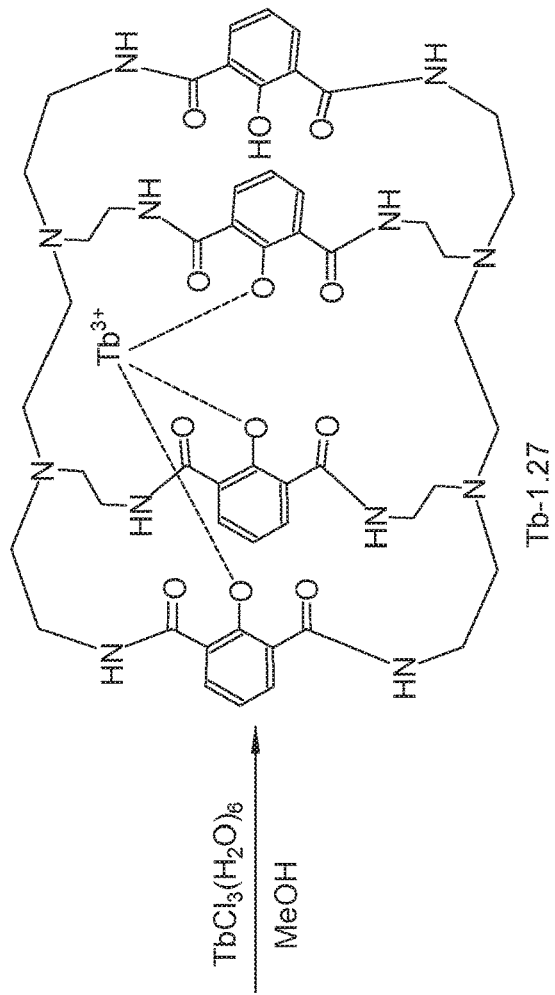
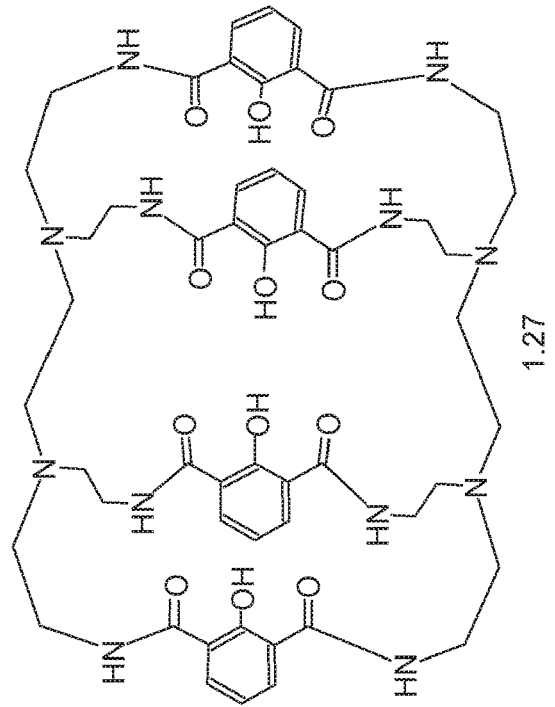
FIG. 31

| Entry | Reagents | Solvent | T, °C | P/SM/BO[a] ratio, % |
|---|---|---|---|---|
| 1 | DIAD | THF | 0° C | -/100/- |
| 2 | DIAD | THF | rt | 10/40/10 |
| 3 | DIAD | THF | reflux | -/25/25 |
| 4 | DEAD | THF | rt | 10/35/10 |
| 5 | DEAD | THF | reflux | -/25/30 |
| 6 | DIAD | DMSO | rt | 10/50/- |
| 7 | DIAD | DMSO | reflux | 15/45/10 |
| 8 | DEAD | DMSO | rt | 10/55/- |
| 9 | DEAD | DMSO | reflux | 15/45/15 |

[a] schematic representation of the double substituted product. The exact geometry of the product is not considered.

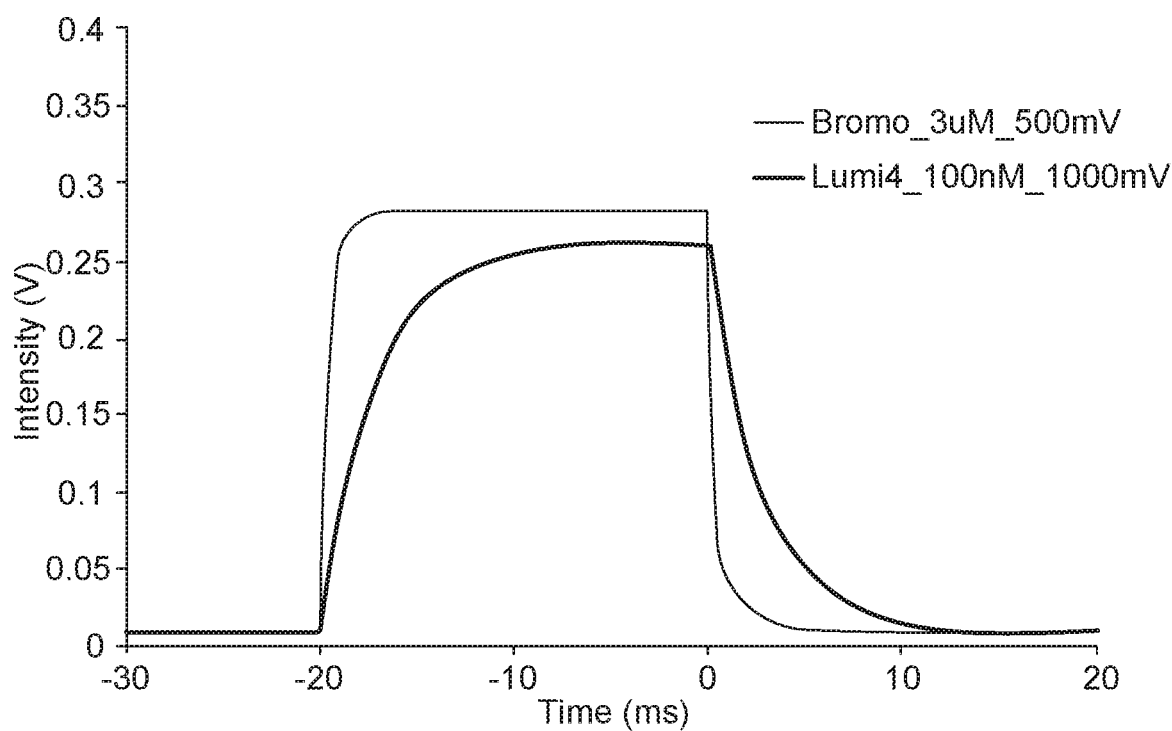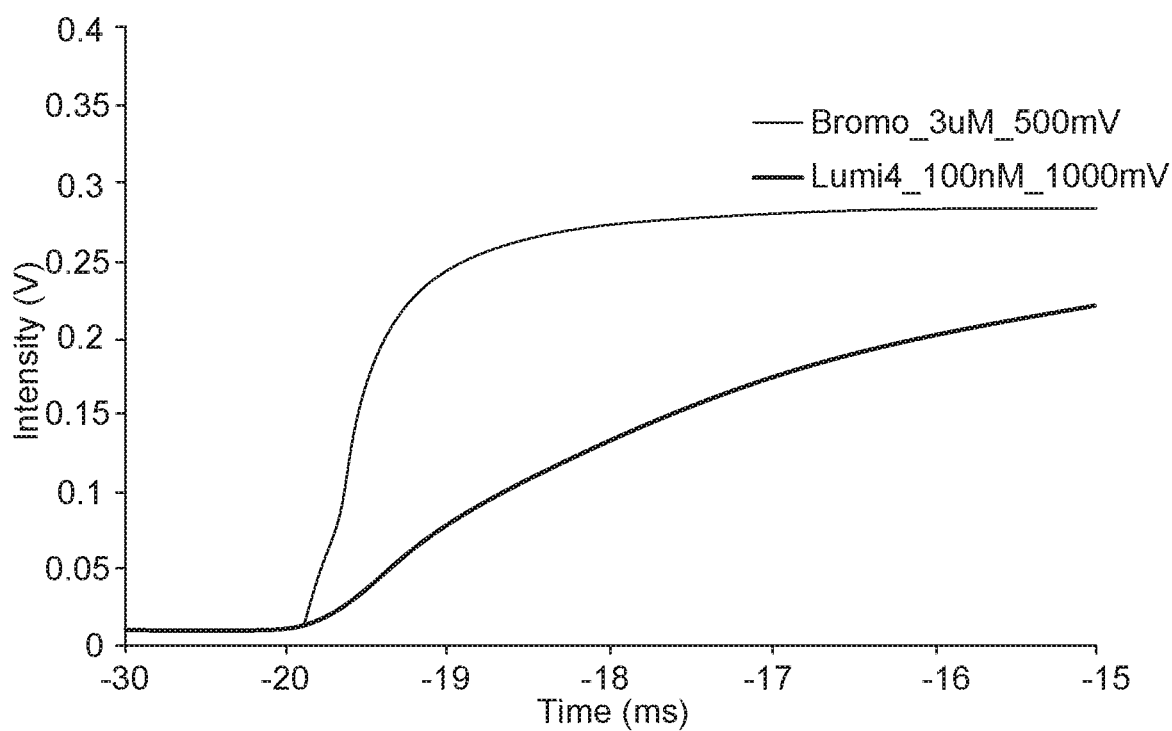
FIG. 41

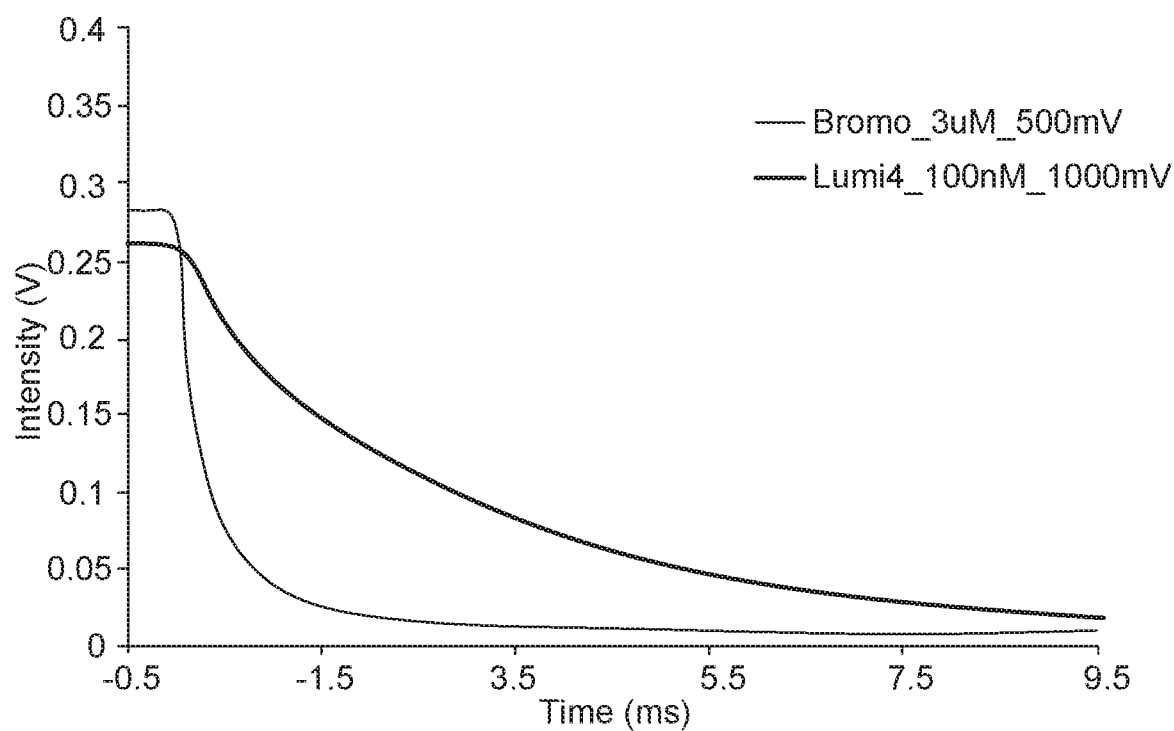
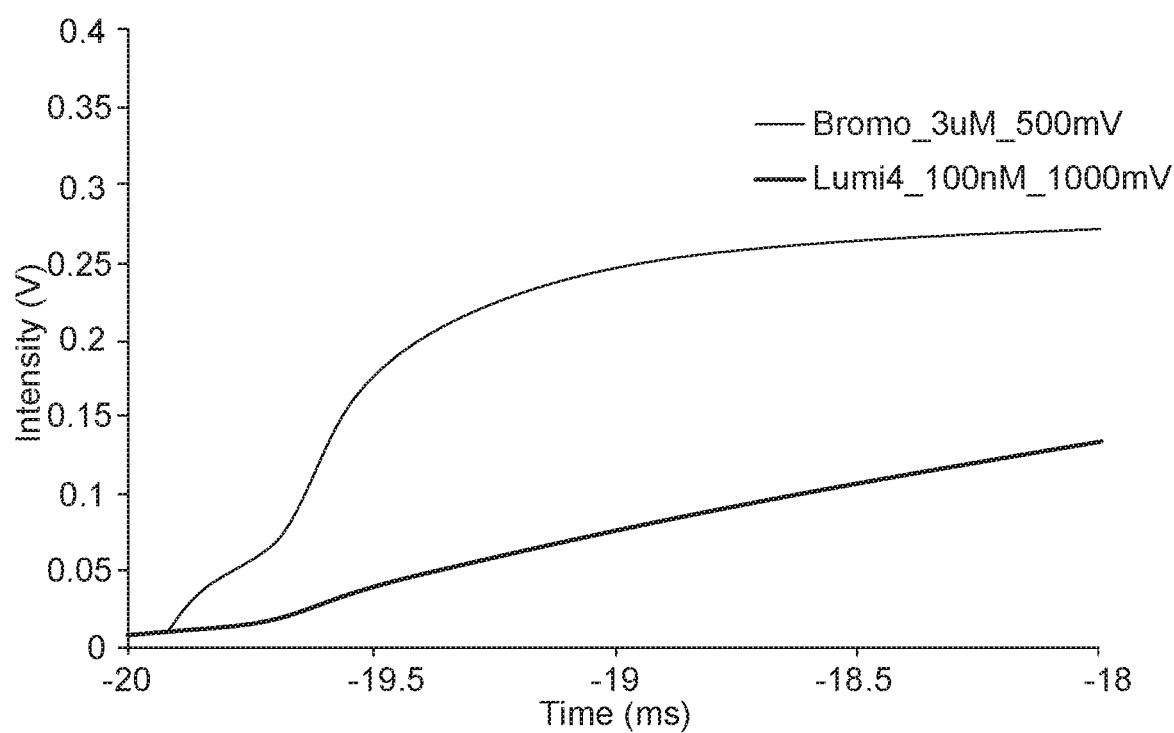
FIG. 42

COMPLEXES AND LIGANDS

CLAIM OF PRIORITY

This application claims the benefit of U.S. Provisional Application No. 62/748,965, filed Oct. 22, 2018. The entire contents of the foregoing are hereby incorporated by reference.

STATEMENT OF FEDERALLY SPONSORED RESEARCH

This invention was made with government support under Grant No. AI132981 awarded by the National Institutes of Health. The government has certain rights in the invention.

TECHNICAL FIELD

This invention relates to fluorescent and luminescent ligands and complexes, and well as method of making and using these ligands and complexes.

BACKGROUND

Fluorescence based technologies are critical for life-science research and clinical diagnostics. Most high-throughput assays are based on various modes of fluorescence detection due to the high sensitivity, large-dynamic range, signal stability, variety of readily accessible fluorophores and ease of operation. Similarly, fluorescence-based microscopy techniques comprise arguably the most important imaging technology currently employed in biomedical research. In recent years the application of time resolved (TR) fluorescence measurements has greatly improved the sensitivity of homogenous biochemical assays and high-resolution microscopy. In particular the combination of TR readouts with Förster resonance energy transfer (FRET) has been widely adapted in high-throughput screening. In TR-FRET based assays, a signal is generated through fluorescent resonance energy transfer between a donor with a long luminescence lifetime and an acceptor fluorophore when in close proximity to each other. The time gated measurement allows to virtually eliminate non-specific background signals originating from autofluorescence of screening compounds, buffer reagents and assay plates, while the FRET component limits the readout to acceptor molecules that are in immediate proximity of the donor. This approach therefore enables the quantitative measurement of the interaction of biomolecules and/or small molecule ligands with superior sensitivity.

SUMMARY

In some embodiments, the present application provides a compound of Formula (I):

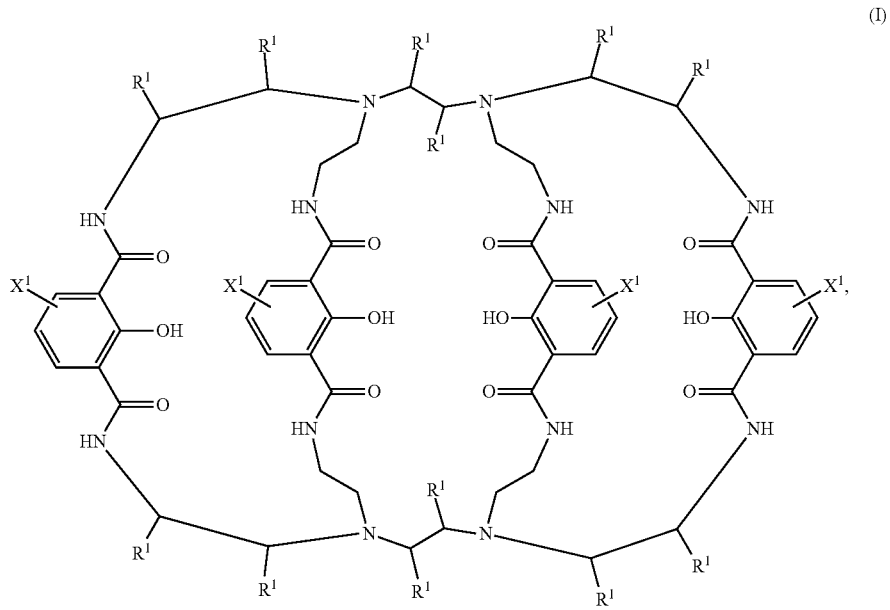

or a pharmaceutically acceptable salt thereof, wherein $X^1$ and $R^1$ are as described herein.

In some embodiments, the present application provides a method of making a compound of Formula (II):

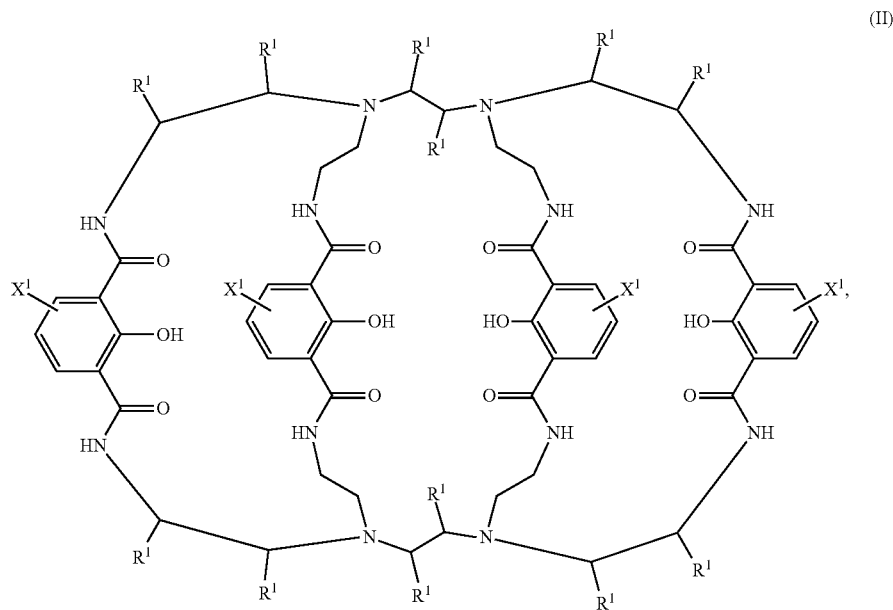

(II)

or a pharmaceutically acceptable salt thereof, wherein: $R^1$ and $X^1$ are as described herein.

In some embodiments, the present application provides a compound of Formula (III):

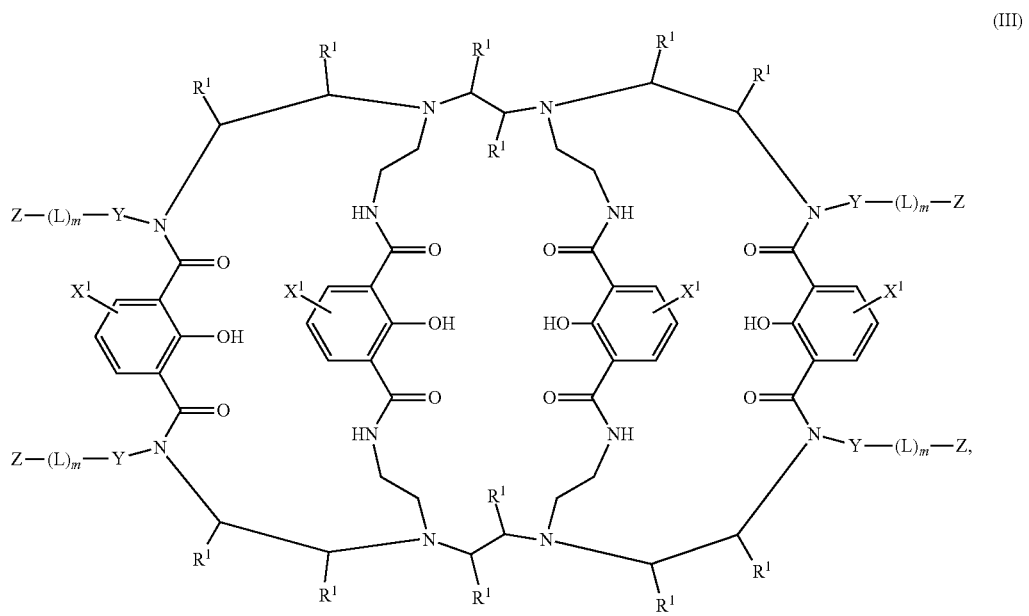

(III)

or a pharmaceutically acceptable salt thereof, wherein $R^1$, $X^1$, Y, L, m, and Z are as described herein.

In some embodiments, the present application provides a method of method of making a compound of Formula (IIIc):

(IIIc)

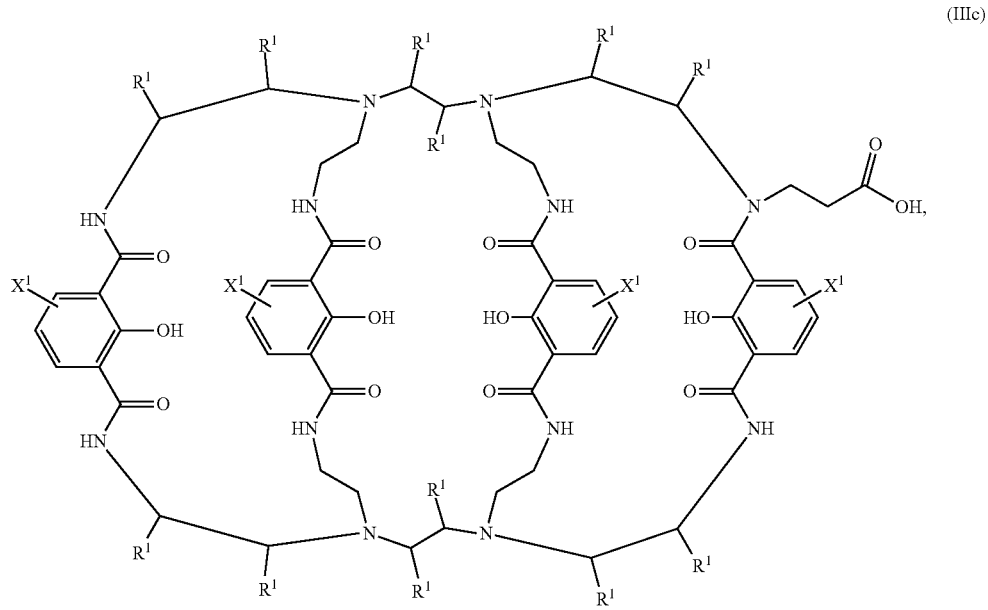

or a pharmaceutically acceptable salt thereof, wherein R and X are as described herein.

In some embodiments, the present application provides a method of making a compound of Formula III(f):

(IIIf)

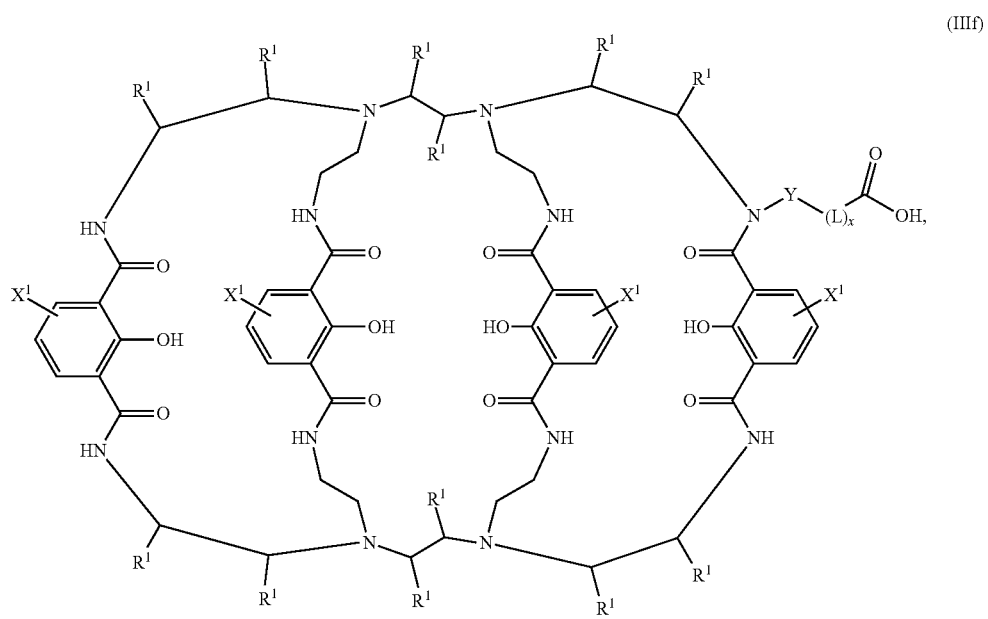

or a pharmaceutically acceptable salt thereof, wherein $R^1$, $X^1$, Y, L, and x are as described herein.

In some embodiments, the present application provides a method of making a compound of Formula (IIIi):

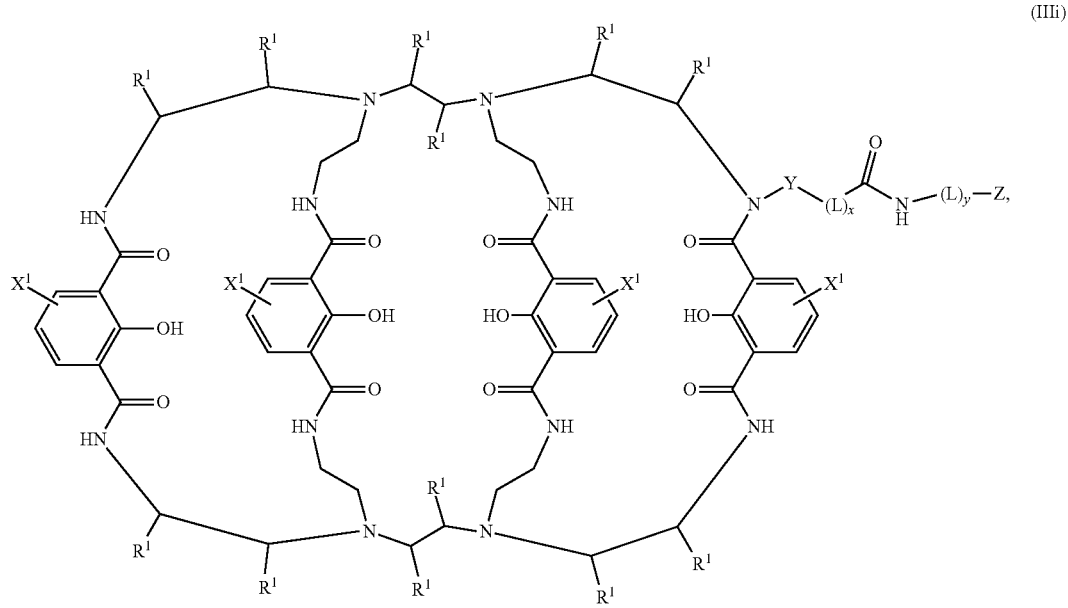

(IIIi)

or a pharmaceutically acceptable salt thereof, wherein $R^1$, $X^1$, Y, L, x, y, and Z are as described herein.

In some embodiments, the present application provides a compound of Formula (IV):

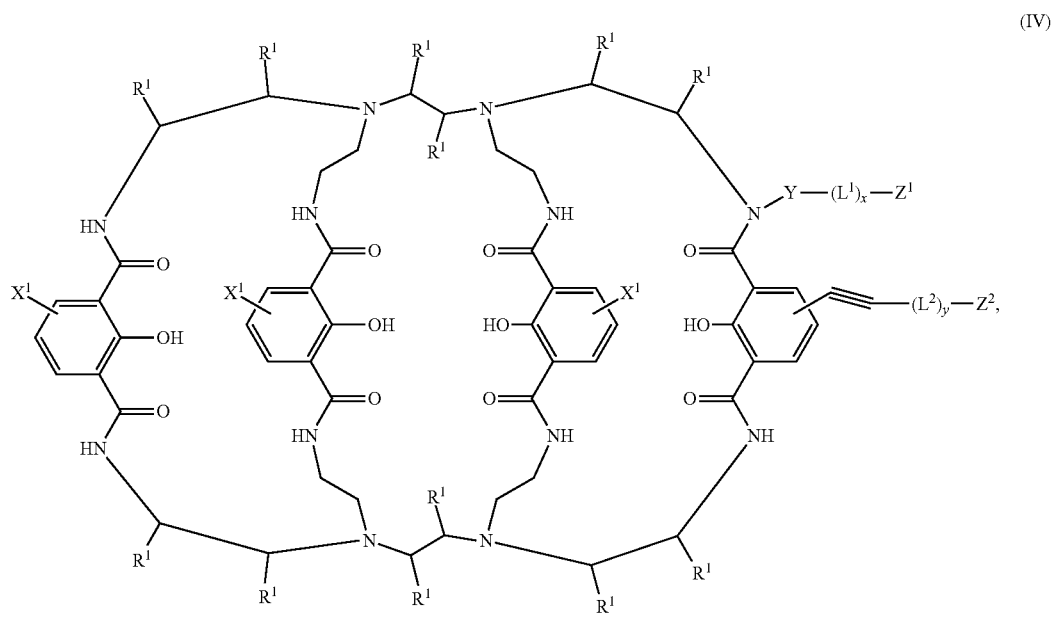

(IV)

or a pharmaceutically acceptable salt thereof, wherein $R^1$, $X^1$, y, $L^1$, $L^2$, $Z^1$, and $Z^2$ are as described herein.

In some embodiments, the present application provides a method of making a compound of Formula (IVc):

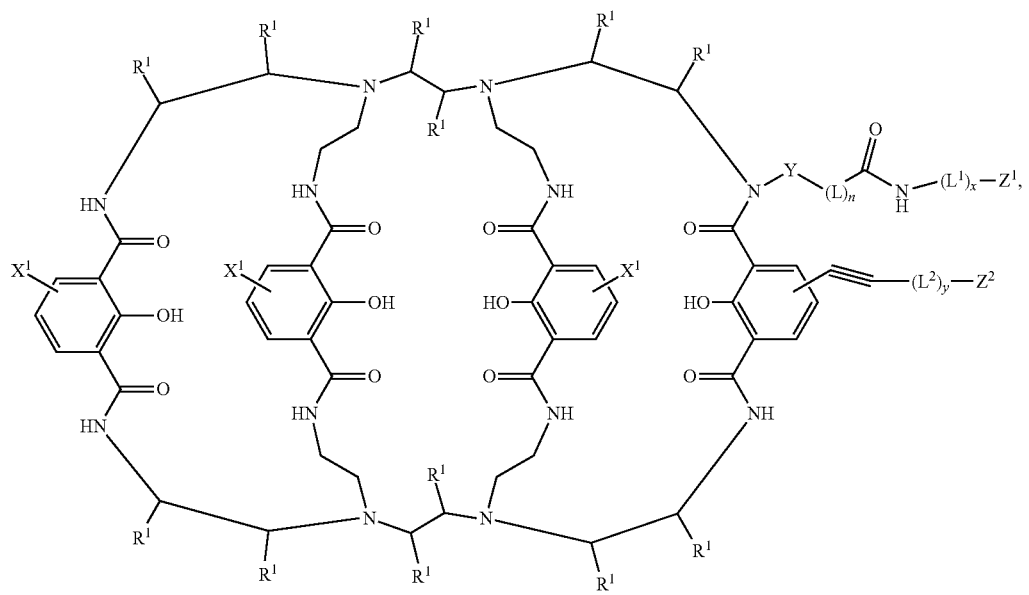

(IVc)

or a pharmaceutically acceptable salt thereof, wherein $R^1$, $X^1$, Y, L, n, $L^1$, $L^2$, x, y, $Z^1$, and $Z^2$ are as described herein.

In some embodiments, the present application provides a compound of Formula (V):

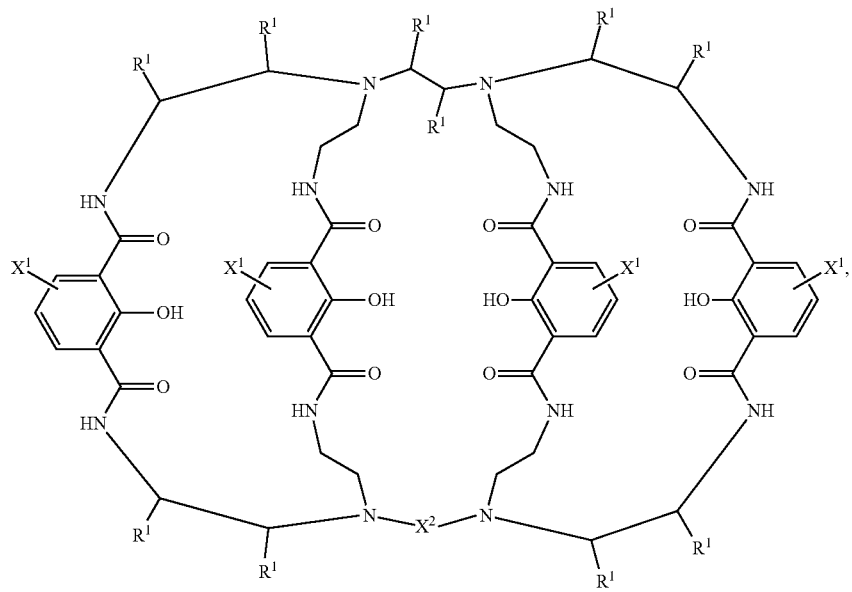

(V)

or a pharmaceutically acceptable salt thereof, wherein $R^1$, $X^1$, and $X^2$ are as described herein.

In some embodiments, the present application provides a compound of Formula (VI):

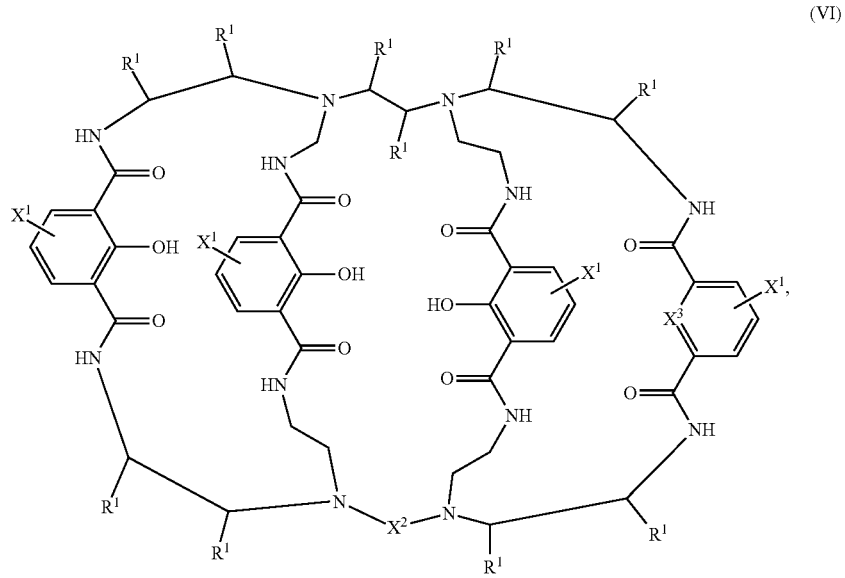

(VI)

or a pharmaceutically acceptable salt thereof, wherein $R^1$, $X^1$, $X^2$, and $X^3$ are as described herein.

In some embodiments, the present application provides a compound of Formula (VII):

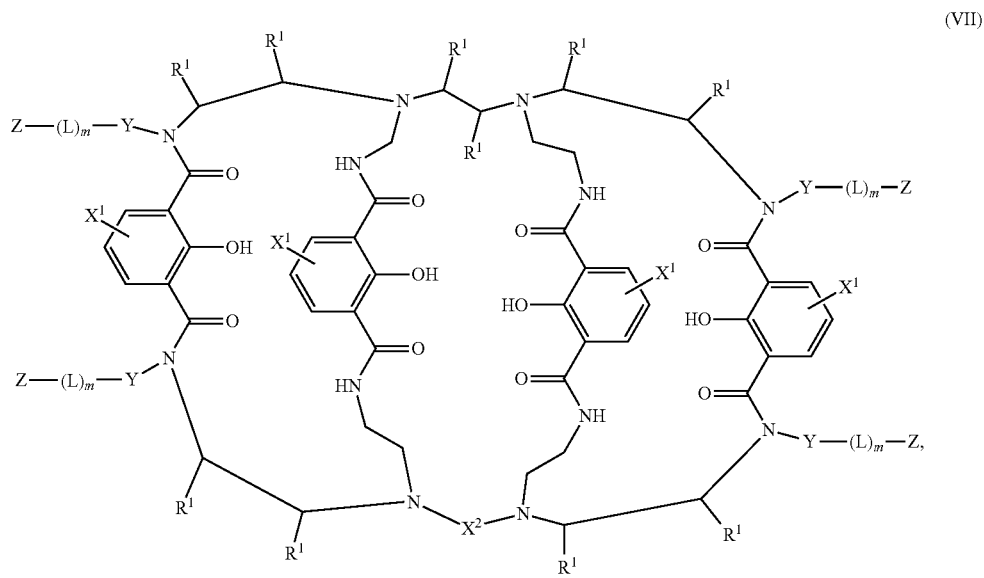

(VII)

or a pharmaceutically acceptable salt thereof, wherein $R^1$, $X^2$, $X^2$, Y, L, m, and Z are as described herein.

In some embodiments, the present application provides a compound of Formula (VIII):

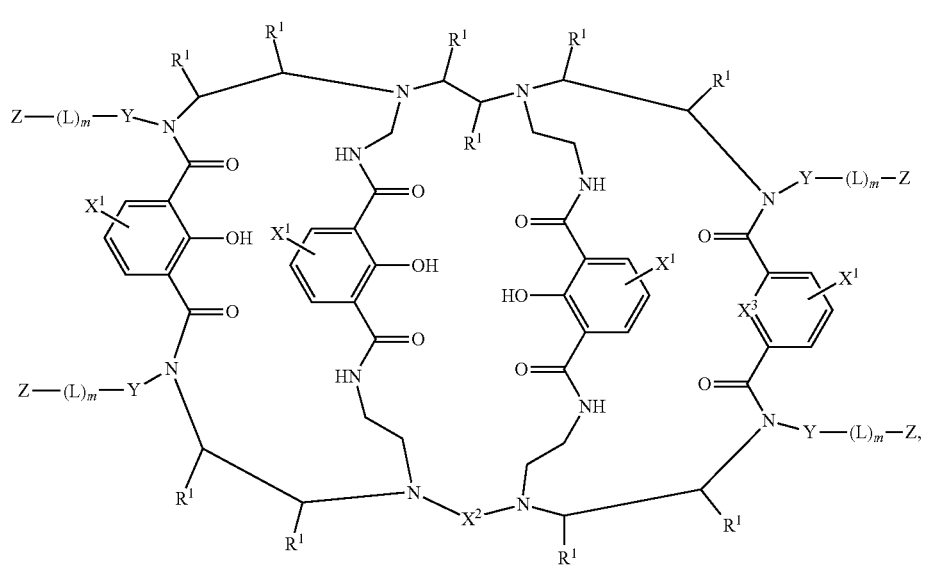

(VIII)

or a pharmaceutically acceptable salt thereof, wherein $R^1$, $X^1$, $X^2$, $X^3$, Y, L, m, and Z are as described herein.

In some embodiments, the present application provides a fluorescent or luminescent complex comprising any one of the compounds described herein, or a pharmaceutically acceptable salt thereof, and a lanthanide metal.

In some embodiments, the present application provides a fluorescent or luminescent complex comprising a compound of formula:

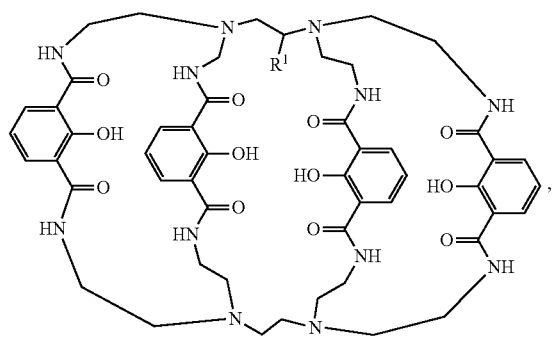

or a pharmaceutically acceptable salt thereof, and a lanthanide metal selected from Eu (europium), Sm (samarium), and Dy (dysprosium).

In some embodiments, the present application provides a method of using the fluorescent or luminescent complex as described herein as a fluorescent or luminescent donor in a Förster resonance energy transfer (FRET)-based biomedical assay. In some aspects of these embodiments, the fluorescent or luminescent complex comprises a fluorescence or luminescence quencher capable of modulating a lifetime of the complex.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the present application will be apparent from the following detailed description and figures, and from the claims.

DESCRIPTION OF DRAWINGS

FIG. 18 shows FRET-based biosensors and effects of donor and acceptor photophysics on detection. (a) Conformational changes of a single-chain biosensor (top) or interaction of dual-chain biosensor (bottom) components that bring donor (D) and acceptor (A) fluorophores within the FRET distance (<10 nm). (b) Excitation (dotted) and emission (solid) spectra of CFP (cyan) and YFP (yellow), a common donor-acceptor pair for live-cell FRET imaging. Overlap of CFP emission and YFP excitation spectra (green) allows sensitized YFP emission (yellow band) to be detected upon the excitation of CFP (cyan band). Crosstalk, or direct excitation of YFP in the CFP band (blue) and bleed-through of CFP emission into the YFP band (orange), obscures the true FRET signals, necessitating multiple measurements with different filter sets. (c) With a long-lifetime Tb(III) donor and short-lifetime GFP acceptor, Tb(III) and Tb(III)-sensitized GFP emission can be separated using narrow-pass emission filters, eliminating bleed-through. Crosstalk is eliminated by time-gated detection (TGD) of long-lifetime Tb(III)-to-GFP FRET. (d) Excitation (dotted) and emission (solid) spectra of Tb(III) as a FRET donor to GFP along with time-gated detection (TGD), also showing that Tb(III) can sensitize the emission of two or more differently colored acceptors. With a long-lifetime Tb(III) donor and short-lifetime GFP acceptor, Tb(III) and Tb(III)-sensitized GFP emission can be separated using narrow-pass emission filters, eliminating bleed-through. Crosstalk is eliminated by time-gated detection (TGD) of long-lifetime Tb(III)-to-GFP FRET.

FIG. 19 shows Structural formulae of the compound Lumi4Tb® and its analog with the linker.

FIG. 25 contains Summary of tested saponification reactions with dimethyl 1,2-methoxyisophthalate (1.20), the amount of the base is 1.00 equiv, unless otherwise stated.

FIG. 30 shows Deprotection of ester and ether groups using LuI in 2,6-luthidine.

FIG. 31 shows The synthesis of the Tb(III) complex Tb-1.27 with the bicapped ligand 1.27.

FIG. 41 contains line plots comparing Lumi4 and the symmetric tetrabromo derivative of Lumi4.

FIG. 42 contains line plots comparing Lumi4 and the symmetric tetrabromo derivative of Lumi4.

DETAILED DESCRIPTION

Figure 1:
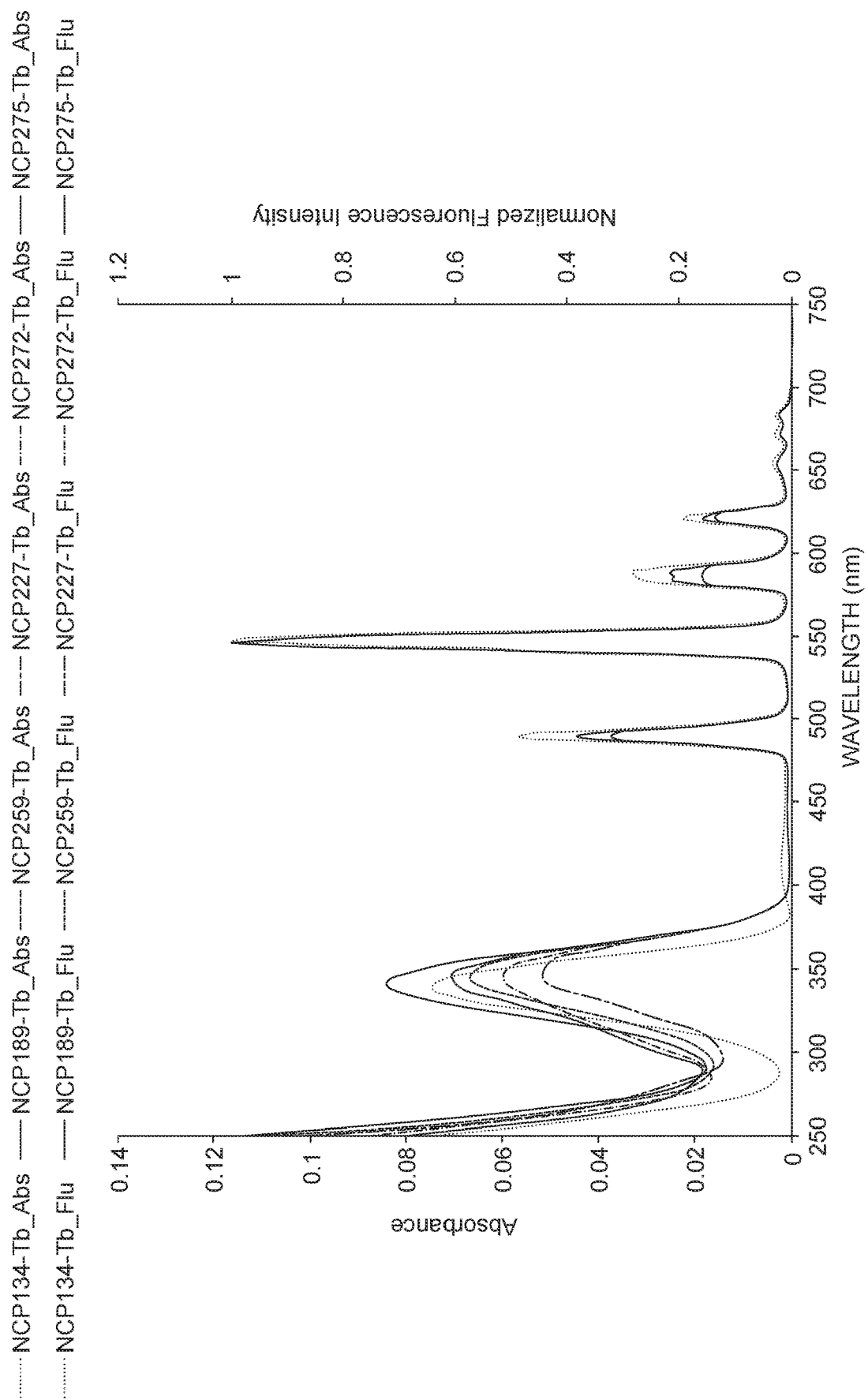
FIG. 1 shows Absorbance and normalized fluorescence spectra of representative Tb complexes.
Figure 2:
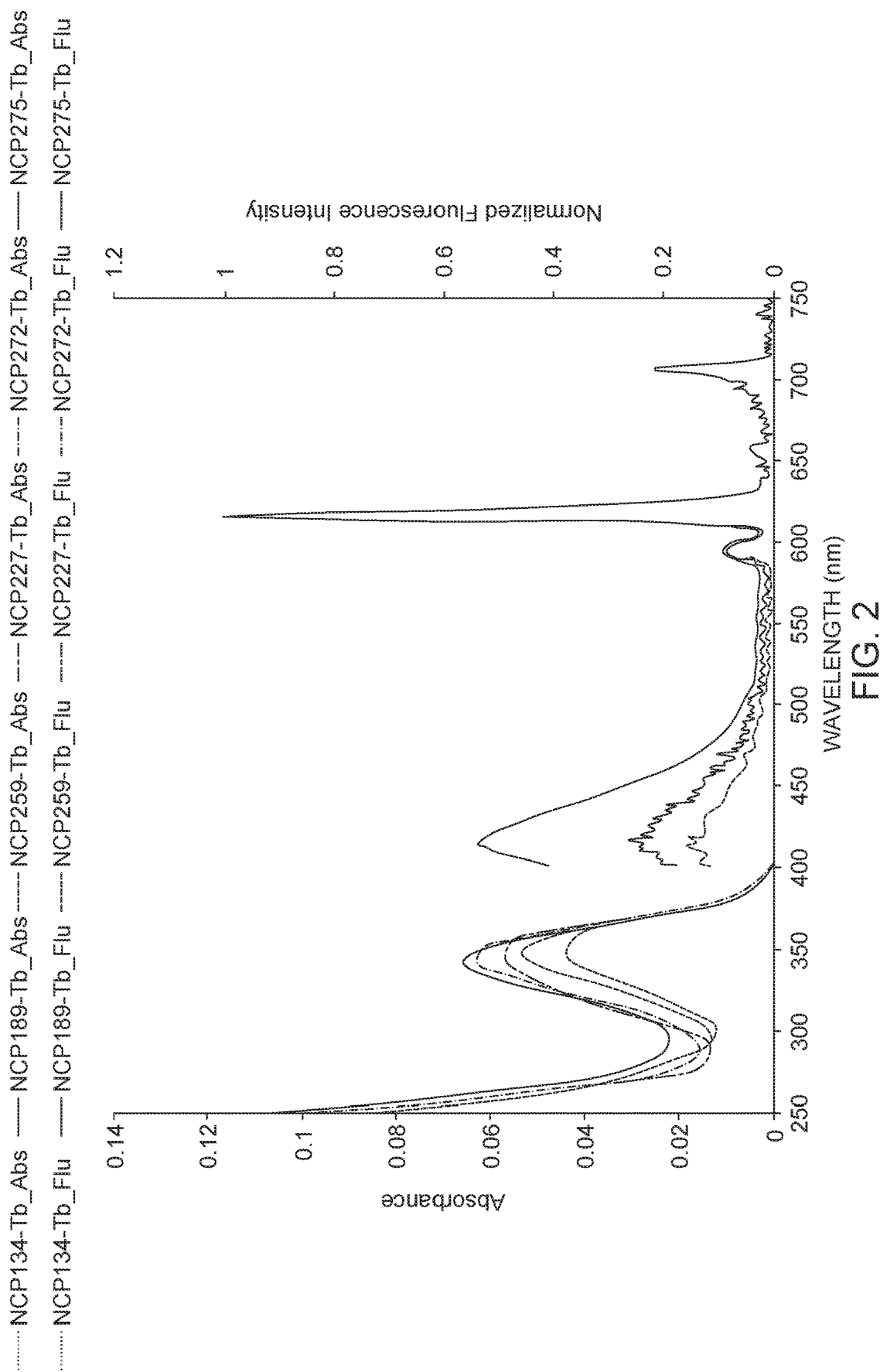
FIG. 2 shows Absorbance and normalized fluorescence spectra of representative Eu complexes.
Figure 3:
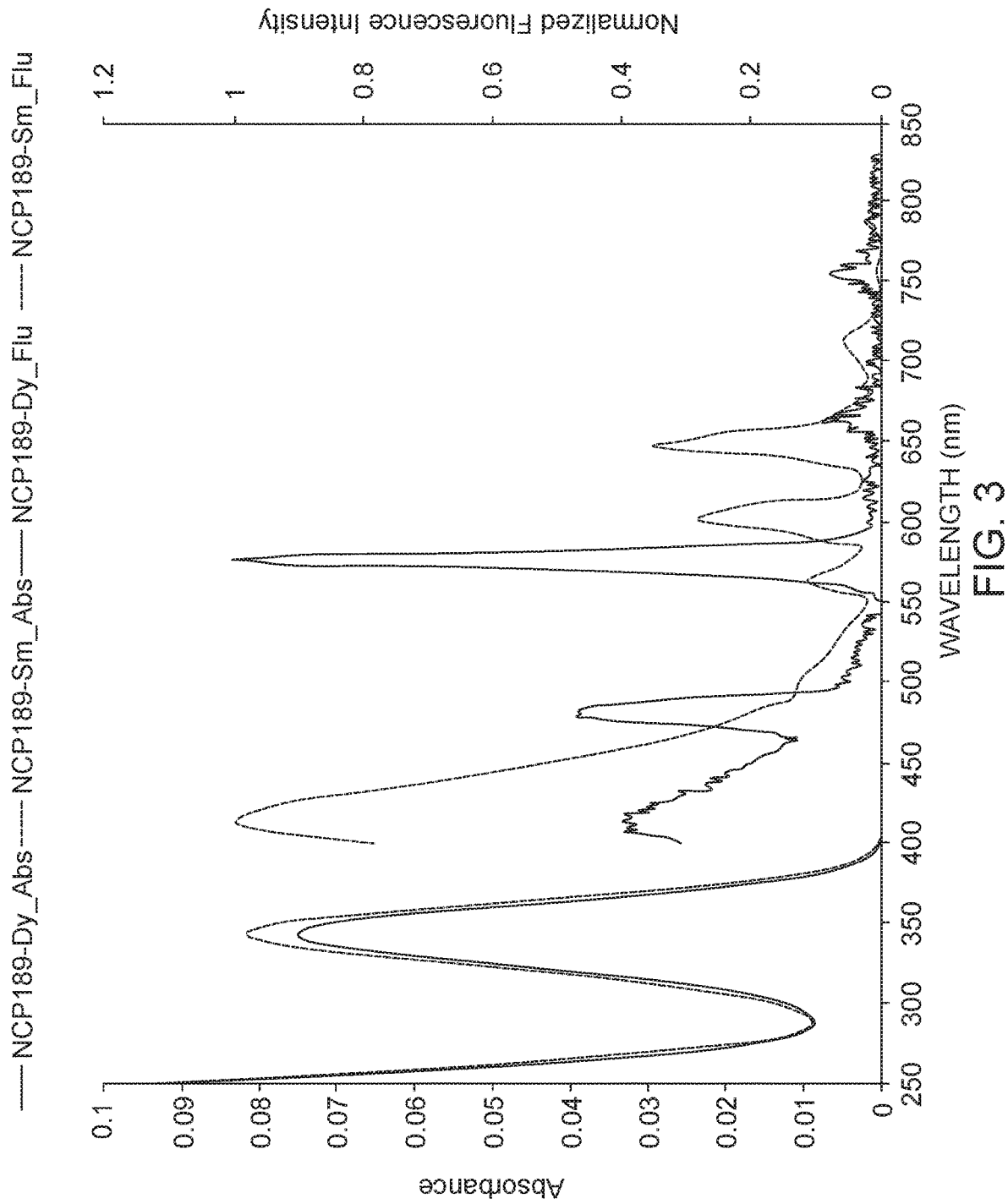
FIG. 3 shows Absorbance and normalized fluorescence spectra of NCP189-Dy and NCP189-Sm complexes.

Important for the development of sensitive and robust TR-FRET based assays is the availability of fluorescent donors that satisfy following criteria: 1) stable in biological buffers, 2) luminescence lifetime is sufficiently long compared to that of autofluorescence generated from biological samples, 3) good quantum yield and brightness, 4) insensitive to assay environment. In addition, for cell-based assays the donors must not impact cell viability or physiology, efficiently diffuse through cellular membranes and distribute equally within cellular compartments.

For example, the favorable luminescent properties of Lanthanide (Ln)-based emitters (long lifetimes, narrow luminescent bands, large effective STOKES' shifts) make them uniquely attractive as FRET-donors for a variety of biomedical applications. Of particular interest in this context are complexes containing Tb (terbium) or Eu (europium), and also Sm (samarium) or Dy (dysprosium). In particular, highly coordinated cryptate complexes of these metals have been recognized for their desirable properties.

While hundreds of luminescent Ln-complexes have been reported, only a small number satisfy the characteristics required for biological assay and imaging applications. Only few of these reagents are commercially available and the market shares are largely divided between two PerkinElmer and CisBio. The precise chemical structures of some of the commercial reagents are not disclosed and published structures generally require a lengthy and difficult synthesis, which limits accessibility to these reagents. Commercially available products are priced at a premium.

Lumi4Tb® is the most popular FRET-donor, which incorporates all aforementioned properties and is therefore widely used in many biomedical assays. However, the high costs (priced on the order of $500-$1000 per microgram) significantly limit access, in particular for experiments that require milligram quantities for further functionalization of the ligand.

Given the cost-prohibitive nature of these reagents, described herein are novel cryptate ligands and their complexes with lanthanide metals such as Tb. The synthetic methodology is shorter and more efficient when compared with the existing synthetic routes for such reagents, and therefore allows for greater variability in structural modifications. The optical properties of Tb-complexes described here are superior to the published and commercialized products.

EXEMPLARY EMBODIMENTS

In some embodiments, the present application provides a compound of Formula (I):

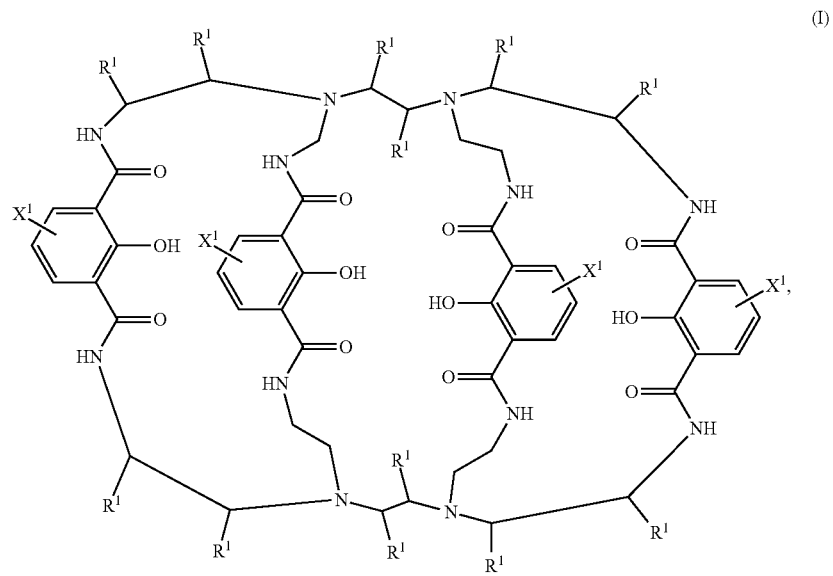

or a pharmaceutically acceptable salt thereof, wherein:
each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and
each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, the compound of Formula (I) has Formula (Ia):

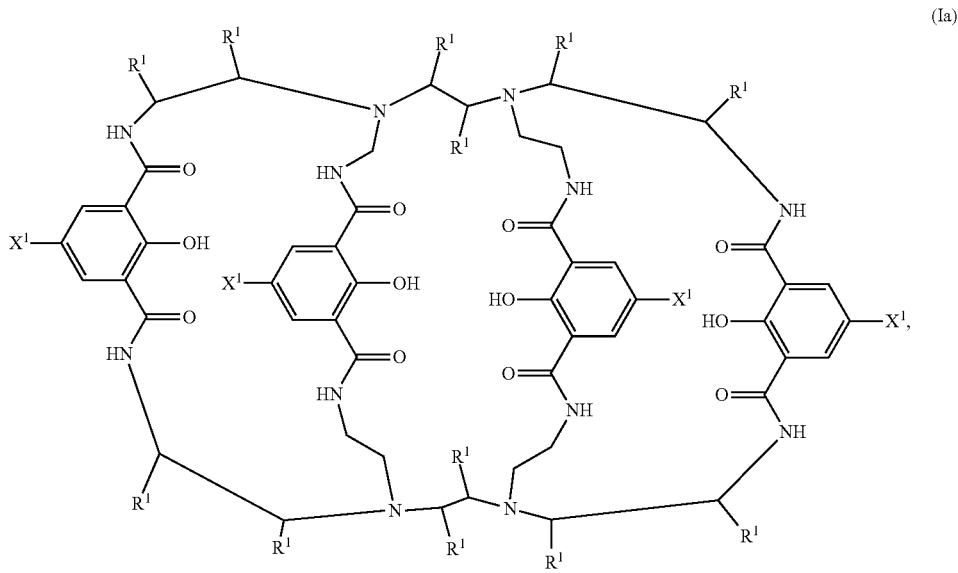

(Ia)

or a pharmaceutically acceptable salt thereof.

In some embodiments, each $X^1$ is independently selected from halo, $NO_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present application provides a method of making a compound of Formula (II):

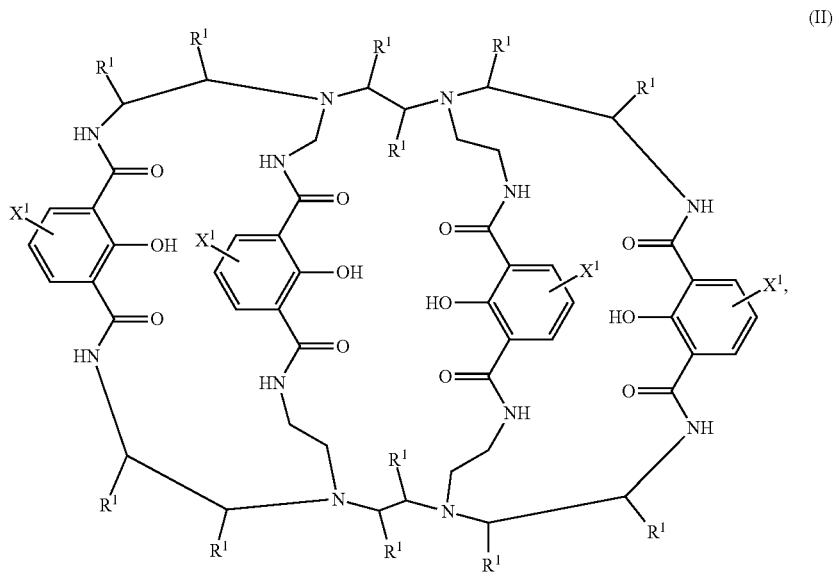

(II)

or a pharmaceutically acceptable salt thereof, wherein:

each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$, the method comprising deprotecting a compound of Formula (IIa):

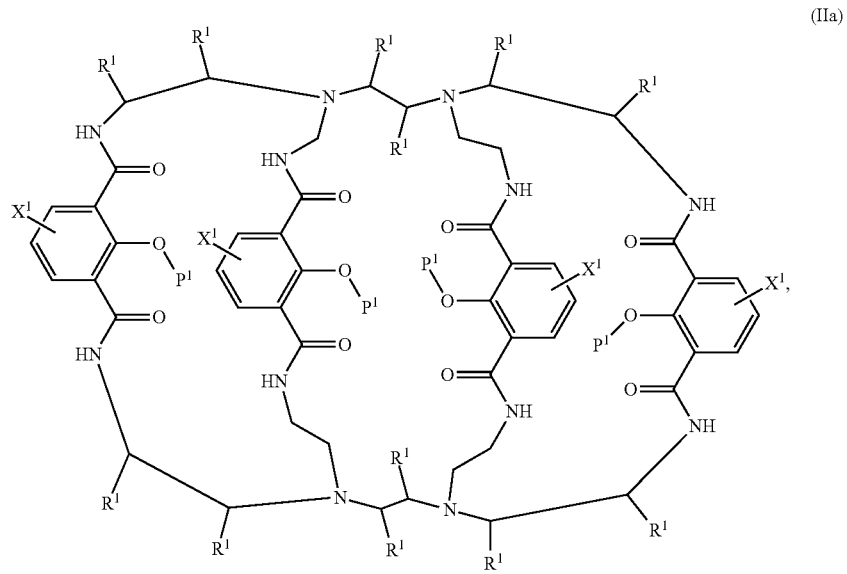

(IIa)

or a salt thereof, wherein each $P^1$ is independently a protecting group,
to obtain the compound of Formula (II).

In some embodiments, the compound of Formula (IIa) is prepared by a method comprising coupling a compound of Formula (IIb):

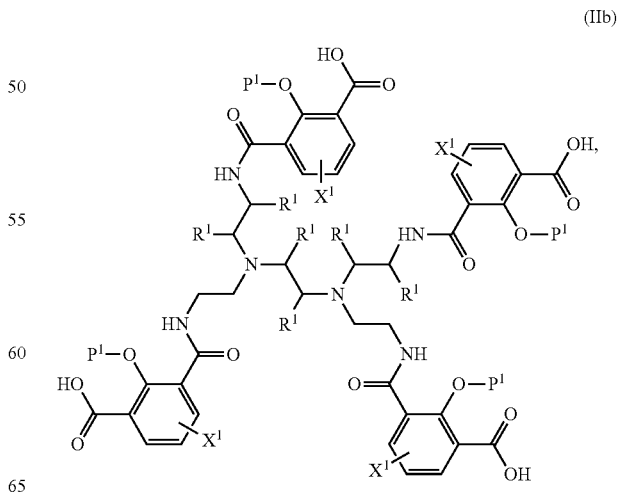

(IIb)

or a salt thereof, with a compound of formula (1):

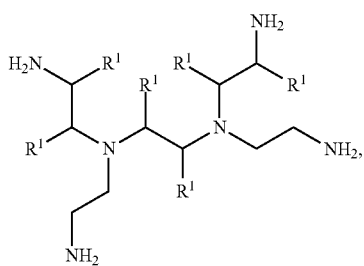
(1)

or a salt thereof, to obtain the compound of Formula (IIa).

In some embodiments, the coupling is conducted in the presence of a coupling reagent that promotes a reaction between a carboxylic acid and an amine to form an amide.

In some embodiments, the coupling reagent is PyBOP.

In some embodiments, the compound of Formula (IIb) is prepared by a method comprising coupling a compound of formula (1), or a salt thereof, with a compound of formula (2):

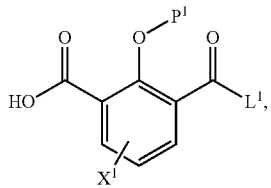
(2)

or a salt thereof, wherein $L^1$ is a leaving group, to obtain the compound of Formula (IIb).

In some embodiments, $L^1$ is an activated ester.

In some embodiments, $L^1$ is selected from: N-hydroxysuccinimide, sulfo-N-hydroxysuccinimide, tetrafluorophenoxy, pentafluorophenoxy, and p-nitophenoxy.

In some embodiments, the compound of formula (2) is prepared by a method comprising reacting a compound of formula (3):

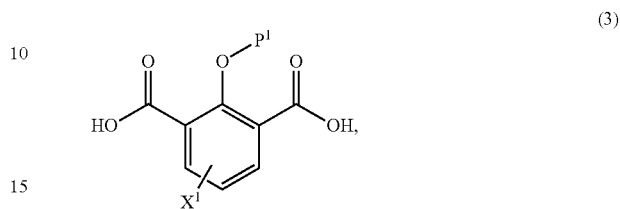
(3)

or a salt thereof, with $L^1H$, to obtain the compound of formula (2).

In some embodiments, the compound of formula (3) is prepared by a method comprising oxidizing a compound of formula (4):

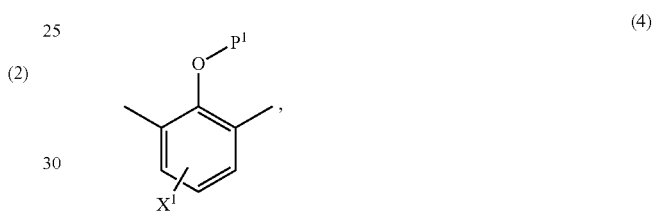
(4)

or a salt thereof, to obtain the compound of formula (3).

In some embodiments, the oxidizing is conducted in the presence of potassium permanganate.

In some embodiments:
the compound of Formula (II) has formula:

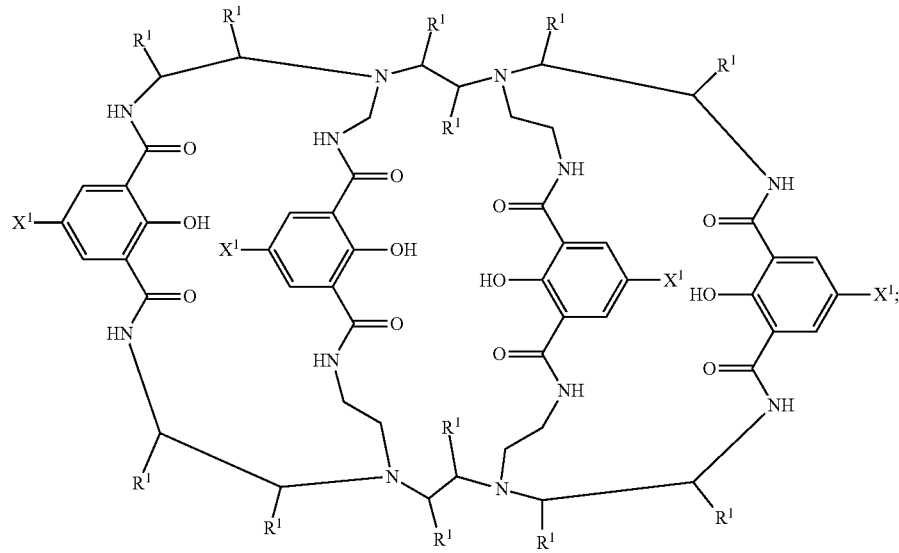

or a salt thereof, the compound of Formula (IIa) has formula:

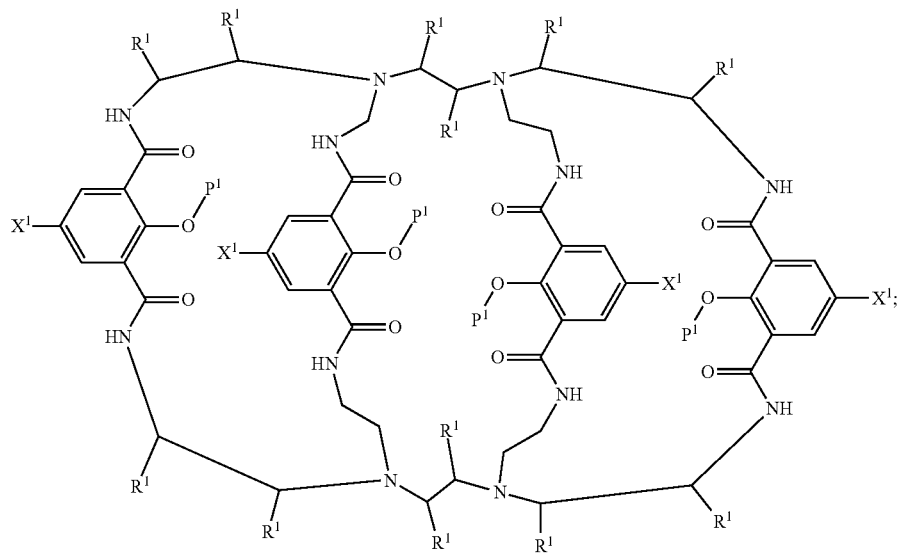

or a salt thereof, the compound of Formula (IIb) has formula:

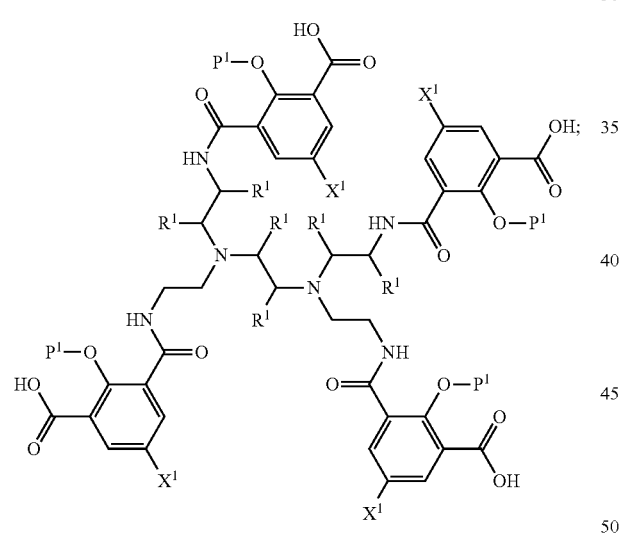

or a salt thereof, the compound of formula (2) has formula:

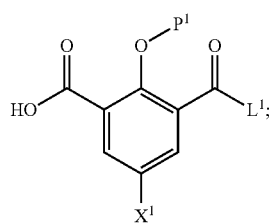

or a salt thereof, the compound of formula (3) has formula:

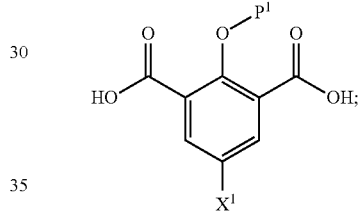

or a salt thereof, and the compound of formula (4) has formula:

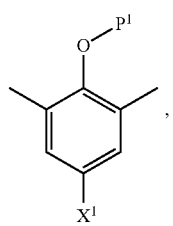

or a salt thereof.

In some embodiments, each $P^1$ is a methyl group.

In some embodiments, the deprotecting of the compound of Formula (IIa) comprises treating the compound of Formula (IIa) with a lithium halide or a boron halide.

In some embodiments, the deprotecting of the compound of Formula (IIa) comprises treating the compound of Formula (IIa) with LiI or BBr$_3$.

In some embodiments, each $X^1$ is independently selected from H, halo, NO$_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is H.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present application provides a compound of Formula (III):

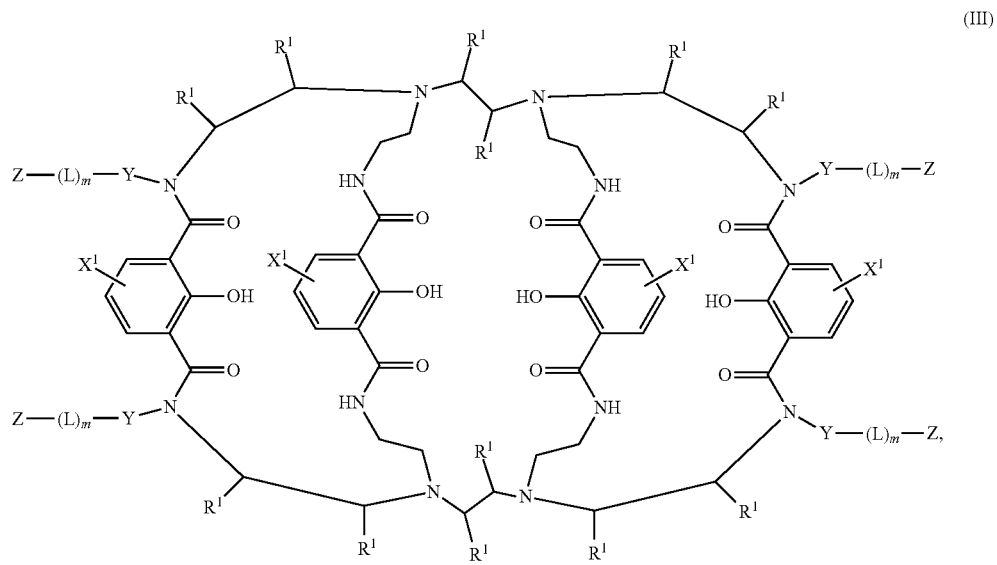

(III)

or a pharmaceutically acceptable salt thereof, wherein:
each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each m is an integer from 0 to 100; wherein if m is 0 then L is a bond; and each Z is selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

wherein:
if Y is a bond and m is 0, then Z is H or $C_{1-3}$ alkyl; and
at least one m is greater than 0.

In some embodiments, the compound of Formula (III) has Formula (IIIb):

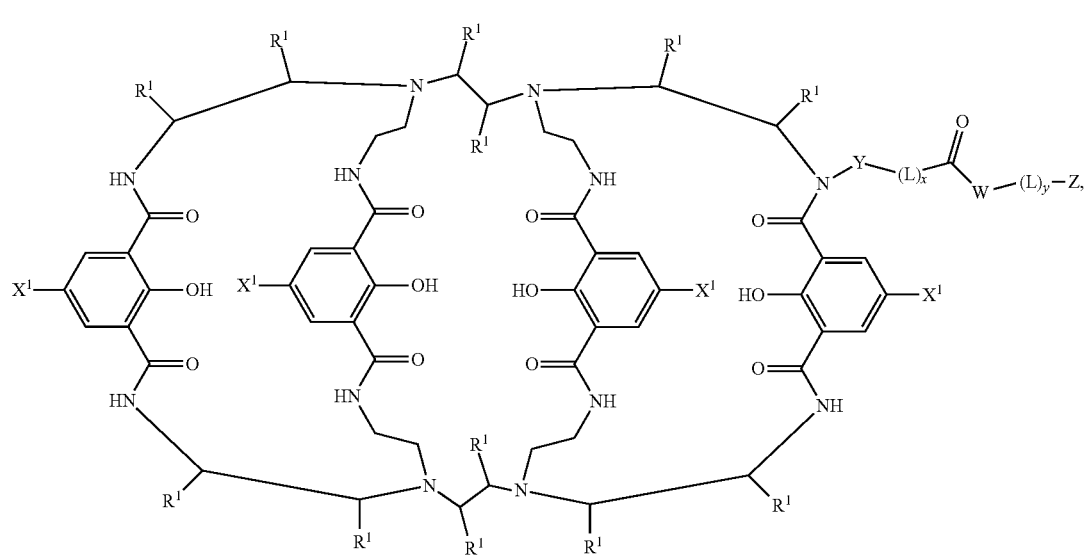

(IIIb)

or a pharmaceutically acceptable salt thereof, wherein:

W is selected from NH and O;

the sum of x and y is m, if x is 0 then L is a bond; and if y is 0 then L is a bond and Z is H or $C_{1-3}$ alkyl.

In some embodiments, Z is an activated ester selected from N-hydroxysuccinimide, sulfo-N-hydroxysuccinimide, tetrafluorophenoxy, pentafluorophenoxy, and p-nitophenoxy.

In some embodiments, Z is a maleimide.

In some embodiments, Z is a biorthogonal functional group selected from $N_3$, $C_{2-6}$ alkynyl, a cyclooctynyl, a tetrazine, a transcyclooctene, a oxanorbornadiene, a norbomene, a nitrile oxide, an isocyanide, and a tetrazole.

In some embodiments, Z is a chemical substrate tag selected from: HaloTag, a SNAPTag, and a CLIPTag.

In some embodiments, Z is selected from any one of the following groups:

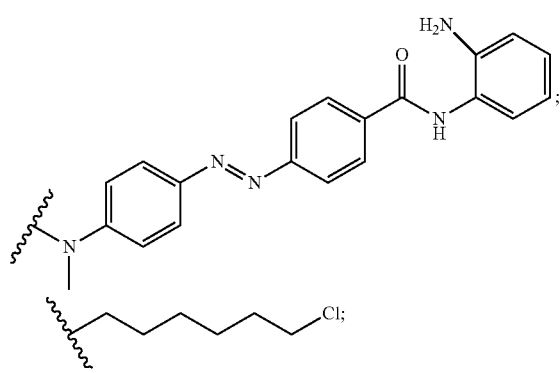

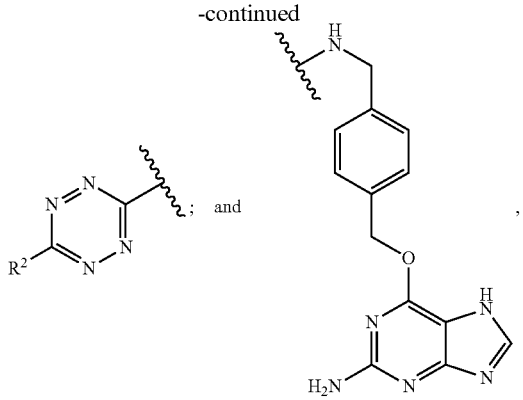

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, Z is a biomolecule selected from a protein, a peptide, a lipid, a nucleic acid, and a saccharide.

In some embodiments, Z is a photocrosslinking label selected from an azide, a benzophenone, and an aziridine.

In some embodiments, m is an integer from 0 to 50.

In some embodiments, m is an integer from 0 to 30.

In some embodiments, Y is methylene or ethylene.

In some embodiments, at least one L is C(O)NH.

In some embodiments, at least one L is $CH_2CH_2$—O— or —O—$CH_2CH_2$.

In some embodiments, each $X^1$ is independently selected from H, halo, $NO_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is H.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present application provides a method of making a compound of Formula (IIIc):

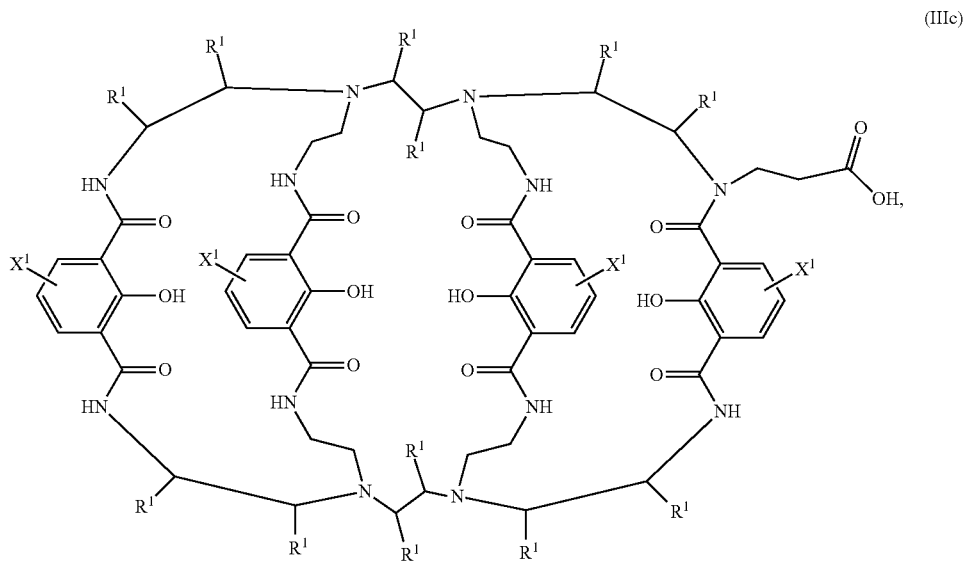

(IIIc)

or a pharmaceutically acceptable salt thereof, wherein:

each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

the method comprising deprotecting a compound of Formula (IIId):

(IIId)

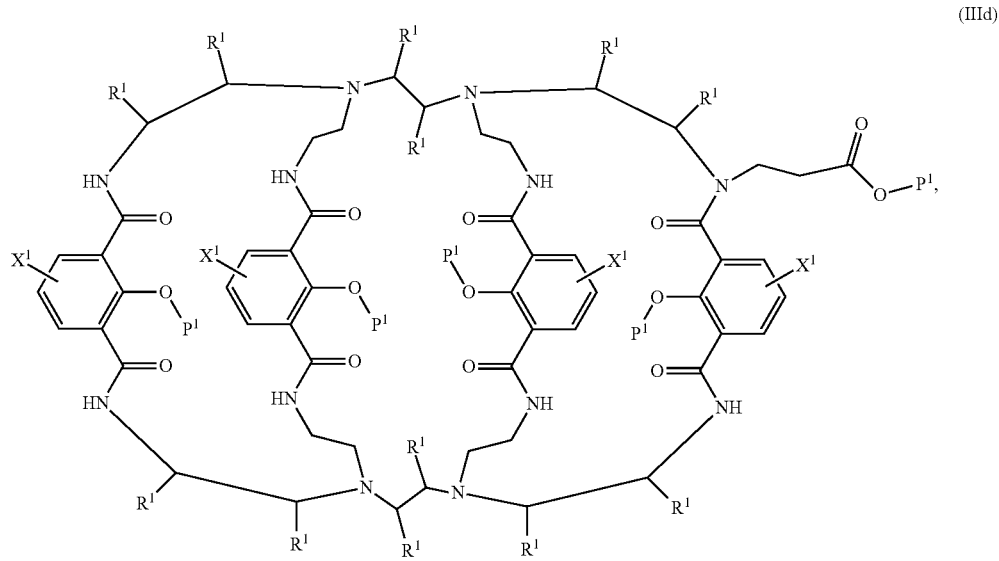

wherein each P¹ is independently a protecting group, to obtain the compound of Formula (IIIc).

In some embodiments, the compound of Formula (IIId) is prepared by a method comprising coupling a compound of Formula (IIIe):

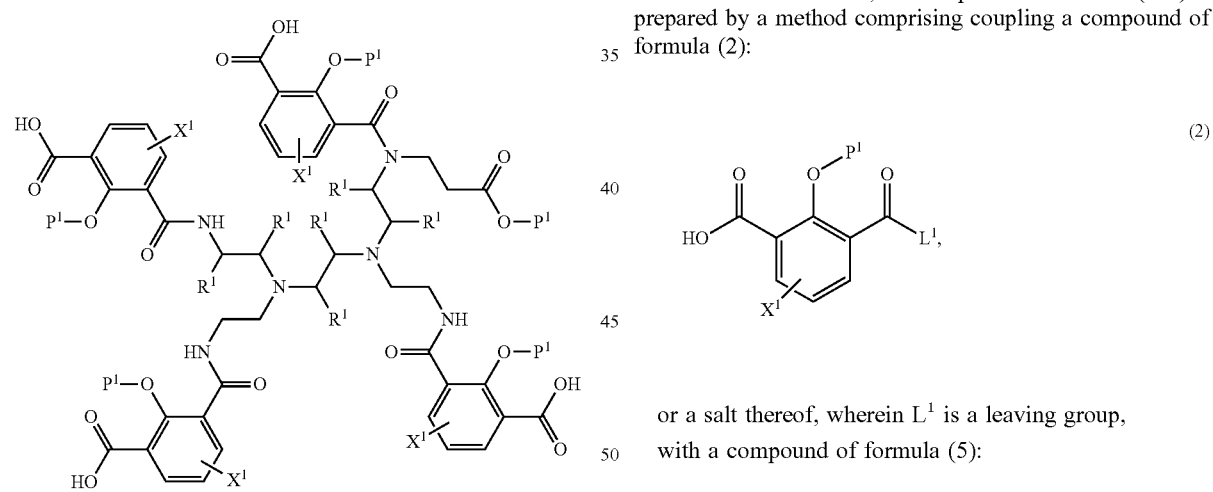

(IIIe)

or a salt thereof, with a compound of formula (1):

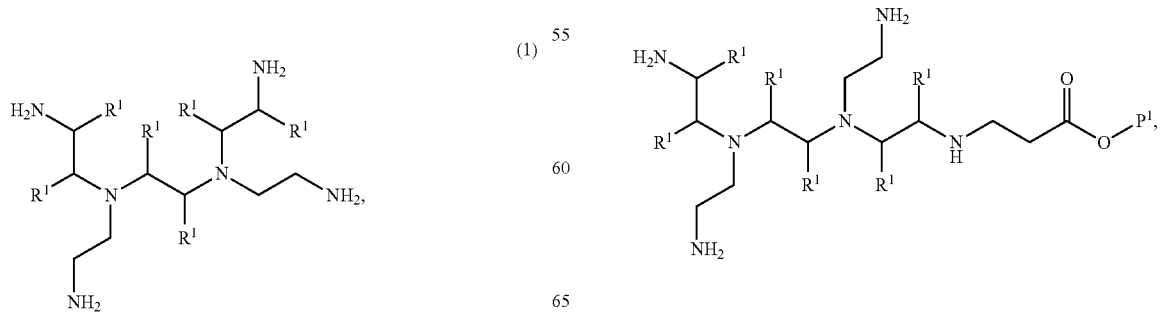

(1)

or a salt thereof, to obtain the compound of Formula (IIId).

In some embodiments, the coupling is conducted in the presence of a coupling reagent that promotes a reaction between a carboxylic acid and an amine to form an amide.

In some embodiments, the coupling reagent is PyBOP.

In some embodiments, the compound of Formula (IIIe) is prepared by a method comprising coupling a compound of formula (2):

(2)

or a salt thereof, wherein $L^1$ is a leaving group, with a compound of formula (5):

(5)

or a salt thereof, to obtain the compound of Formula (IIIe).

In some embodiments:
the compound of Formula (IIIc) has formula:
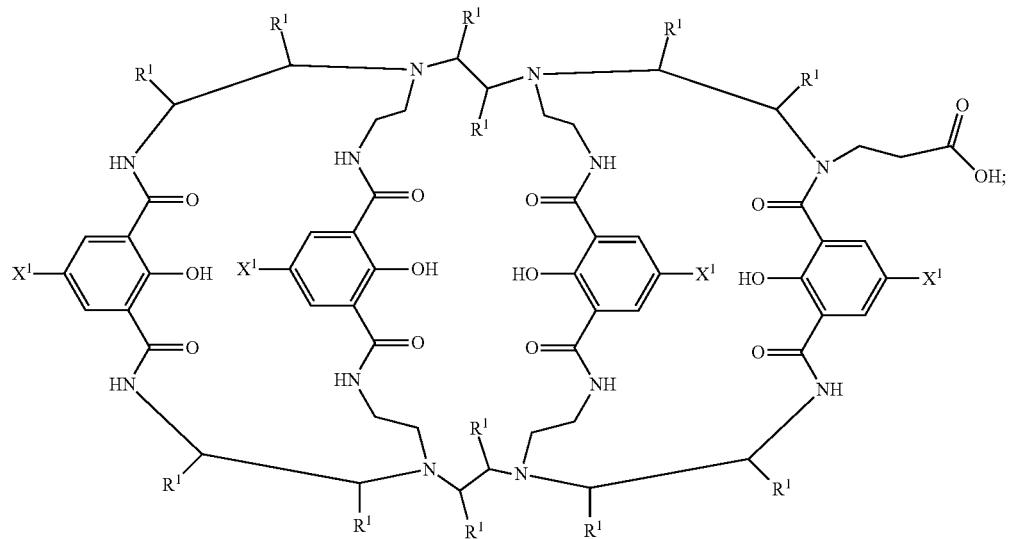
or a salt thereof, the compound of Formula (IIId) has formula:
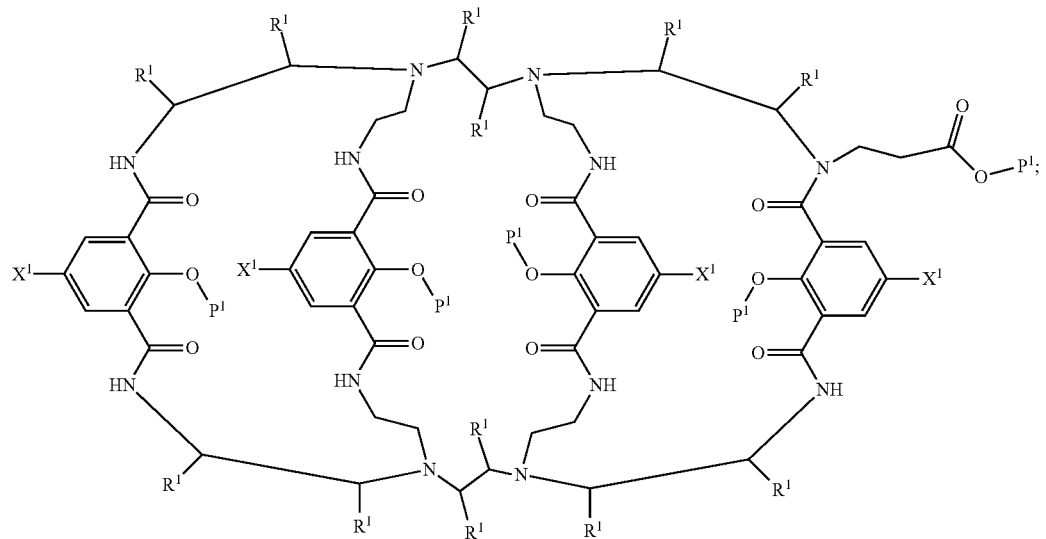
or a salt thereof, the compound of Formula (IIIe) has formula:

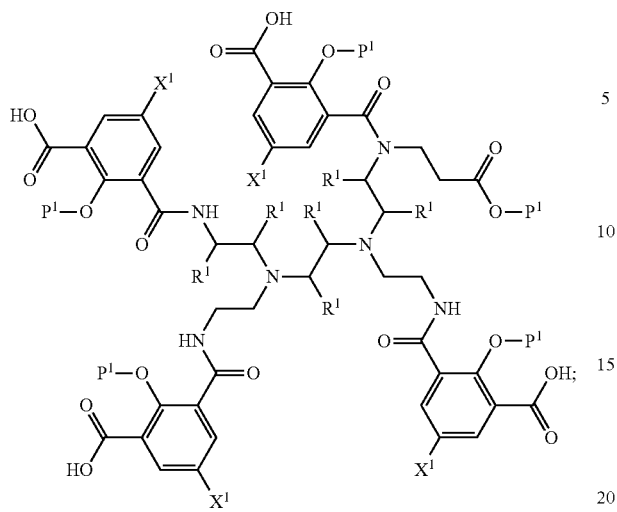

or a salt thereof, and the compound of formula (2) has formula:

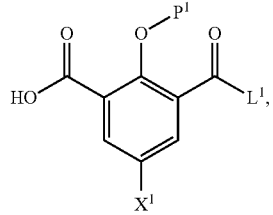

or a salt thereof.

In some embodiments, $L^1$ is an activated ester.

In some embodiments, $L^1$ is selected from: N-hydroxysuccinimide, sulfo-N-hydroxysuccinimide, tetrafluorophenoxy, pentafluorophenoxy, and p-nitrophenoxy.

In some embodiments, the compound of formula (5) is prepared by a method comprising reacting the compound of formula (6):

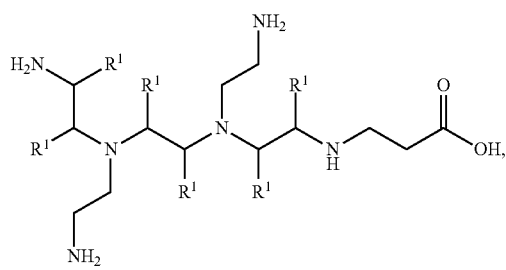

or a salt thereof, with $P^1$-$L^2$, or a salt thereof, wherein $L^2$ is a leaving group, to obtain the compound of formula (5).

In some embodiments, the compound of formula (6) is prepared by a method comprising deprotecting a compound of formula (7):

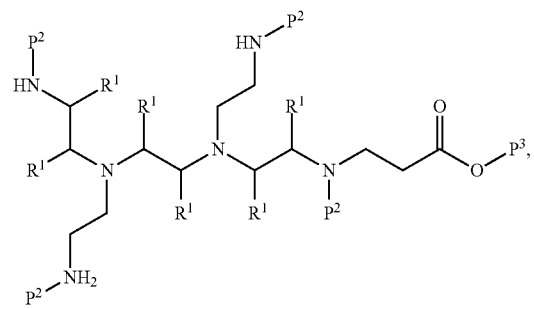

or a salt thereof, wherein:
each $P^2$ is independently a protecting group; and
$P^3$ is a protecting group,
to obtain the compound of formula (6).

In some embodiments, each $P^2$ is tosyl.

In some embodiments, $P^3$ is t-butyl.

In some embodiments, the deprotecting comprises treating the compound of formula (7), or a salt thereof, with an acid.

In some embodiments, the deprotecting comprises removing both $P^2$ and $P^3$ protecting groups from the compound of formula (7) to yield the compound of formula (6).

In some embodiments, the compound of formula (7) is prepared by a method comprising reacting a compound of formula (8):

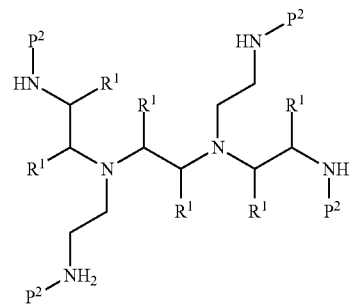

or a salt thereof, with a compound of formula (9):

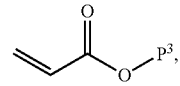

or a salt thereof, to obtain the compound of formula (7).

In some embodiments, the compound of formula (8) is prepared by a method comprising reacting a compound of formula (10):

or a salt thereof, with ethylenediamine, or a salt thereof, to obtain the compound of formula (8).

In some embodiments, each $P^1$ is a methyl group.

In some embodiments, the deprotecting comprises treating the compound of Formula (IIId) with a lithium halide or a boron halide.

In some embodiments, the deprotecting comprises treating the compound of Formula (IIId) with LiI or BBr$_3$.

In some embodiments, each $X^1$ is independently selected from H, halo, NO$_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is H.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$; and the remaining $R^1$ groups are all H.

In some embodiments, the present application provides a method of making a compound of Formula III(f):

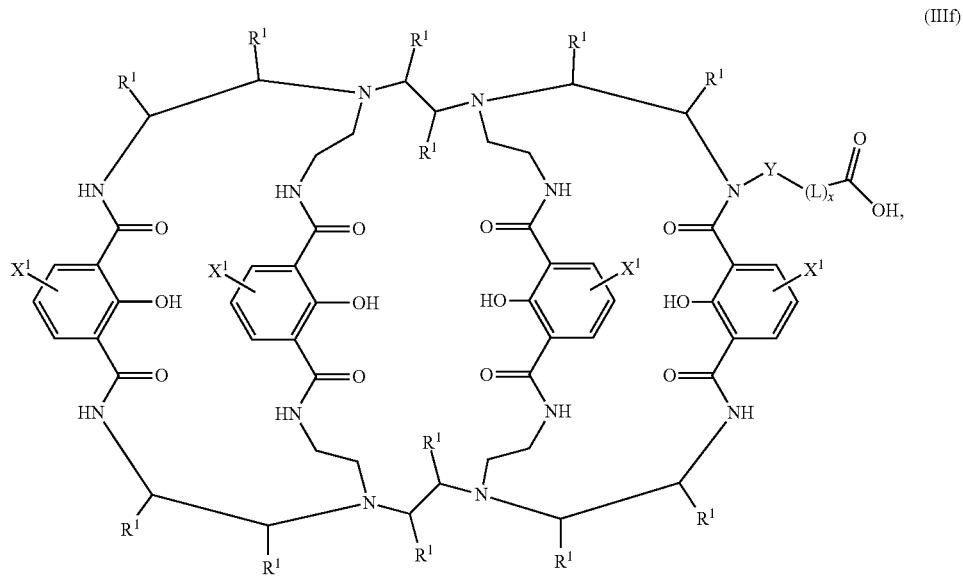

(IIIf)

or a pharmaceutically acceptable salt thereof, wherein:

Y is selected from $C_{1-6}$ alkylene, $C_{2-6}$ alkenylene, and $C_{2-6}$ alkynylene;

x is an integer from 0 to 100; wherein if x is 0 then L is a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each $X^1$ is independently selected from halo, NO$_2$, CN, N$_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$;

the method comprising deprotecting a compound of Formula (IIIg):

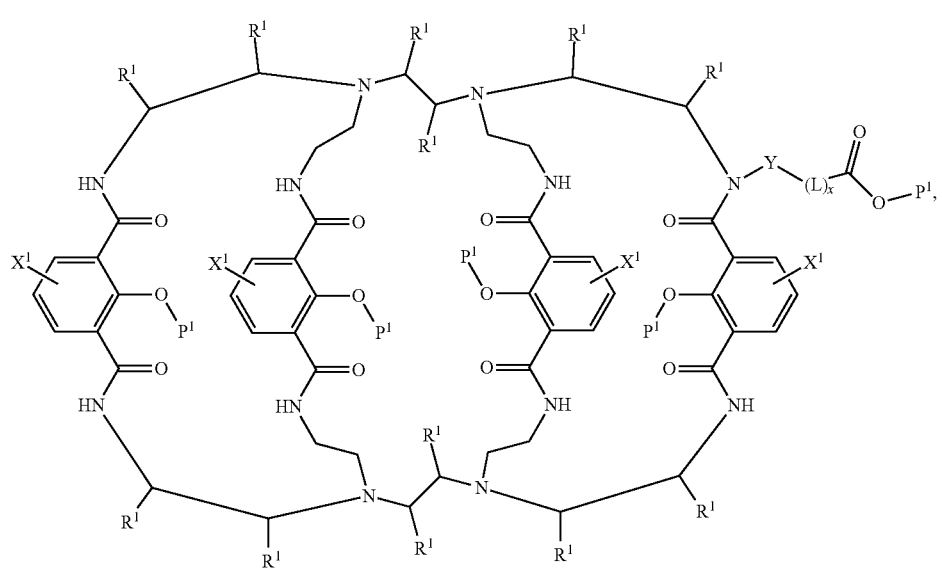

(IIIg)

or a salt thereof, wherein each $P^1$ is independently a protecting group, to obtain the compound of Formula (IIIf).

In some embodiments, each $P^1$ is a methyl group.

In some embodiments, the deprotecting comprises treating the compound of Formula (IIIg) with a lithium halide or a boron halide.

In some embodiments, the deprotecting comprises treating the compound of Formula (IIIg) with LiI or $BBr_3$.

In some embodiments, the compound of Formula (IIIg) is prepared by a method comprising coupling a compound of Formula (IIIh):

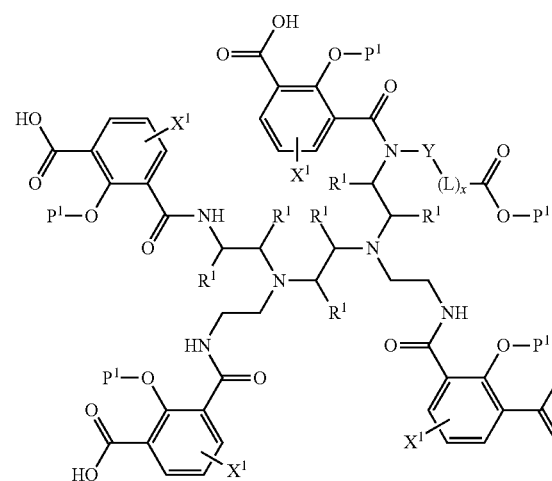

(IIIh)

or a salt thereof, with a compound of formula (1):

(1)

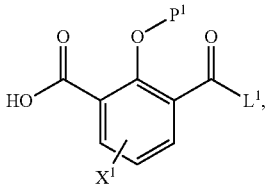

or a salt thereof, to obtain the compound of Formula (IIIg).

In some embodiments, the coupling is conducted in the presence of a coupling reagent that promotes a reaction between a carboxylic acid and an amine to form an amide.

In some embodiments, the coupling reagent is PyBOP.

In some embodiments, the compound of Formula (IIIh) is prepared by a method comprising coupling a compound of formula (2):

(2)

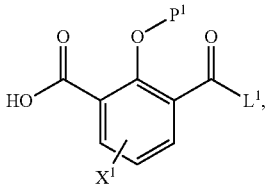

or a salt thereof, wherein $L^1$ is a leaving group, with a compound of formula (11):

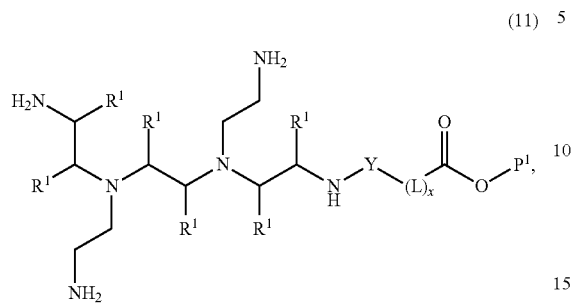

or a salt thereof, to obtain the compound of Formula (IIIh).

In some embodiments, $L^1$ is an activated ester.

In some embodiments, $L^1$ is selected from: N-hydroxysuccinimide, sulfo-N-hydroxysuccinimide, tetrafluorophenoxy, pentafluorophenoxy, and p-nitrophenoxy.

In some embodiments:
the compound of Formula (IIIf) has formula:

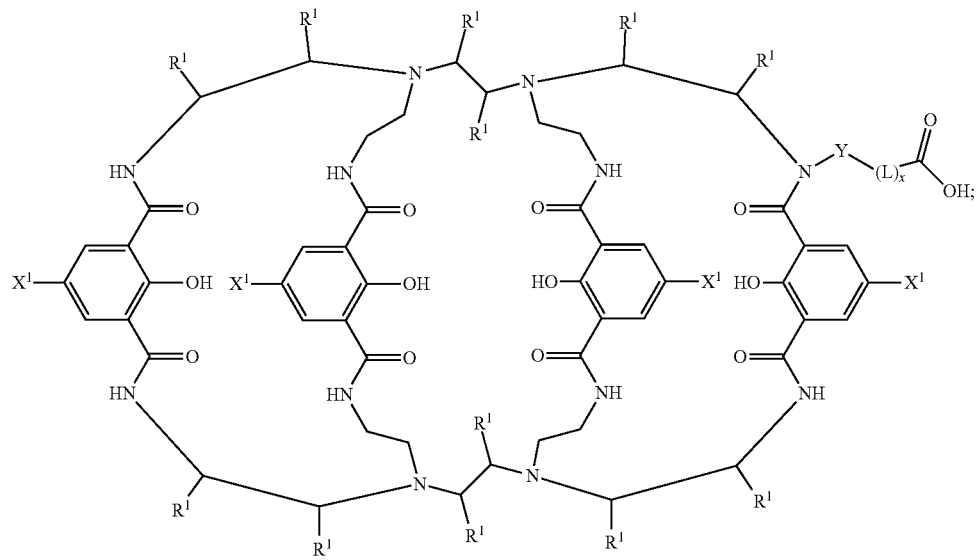

or a salt thereof, the compound of Formula (IIIg) has formula:

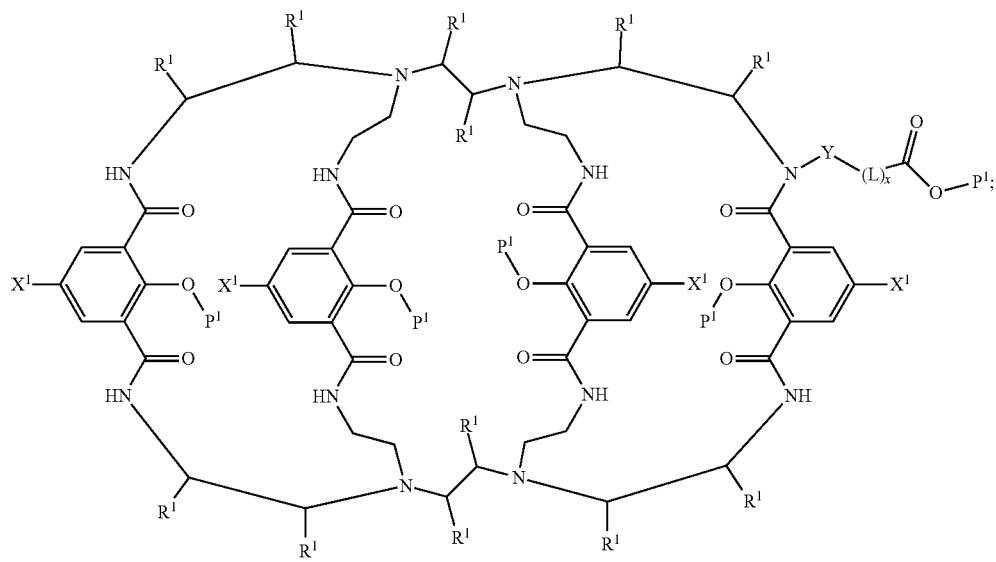

or a salt thereof, the compound of Formula (IIIh) has formula:

(12)

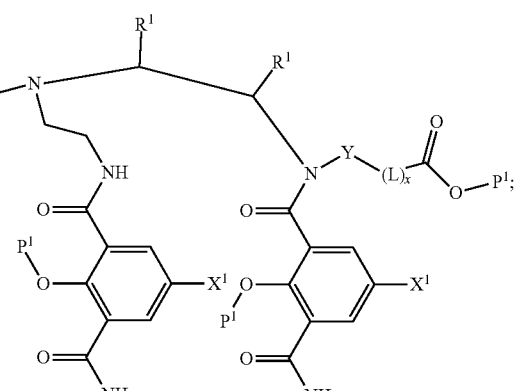

or a salt thereof, with $P^1$-$L^2$, or a salt thereof, wherein $L^2$ is a leaving group,
to obtain the compound of formula (11).

In some embodiments, the compound of formula (12) is prepared by a method comprising deprotecting a compound of formula (13):

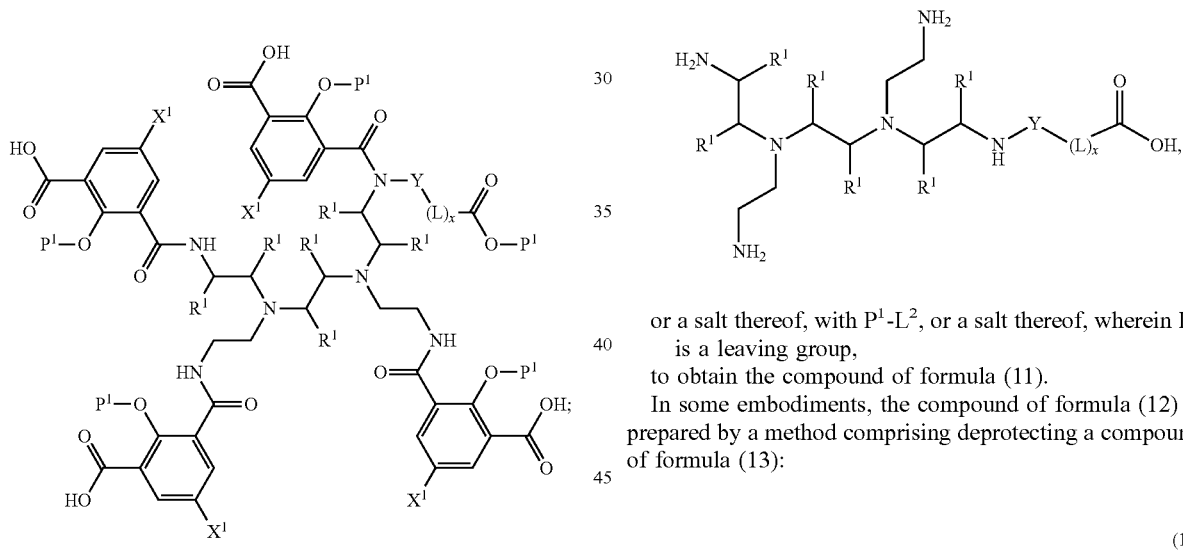

or a salt thereof, and the compound of formula (2) has formula:

(13)

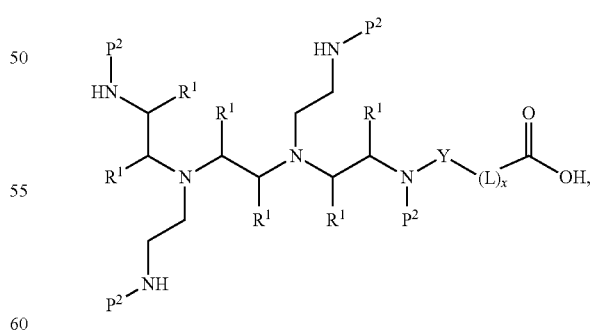

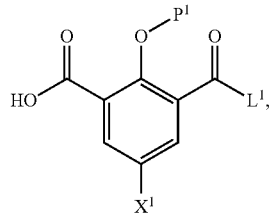

or a salt thereof.

In some embodiments, the compound of formula (11) is prepared by a method comprising reacting the compound of formula (12):

or a salt thereof, wherein each $P^2$ is independently a protecting group;
to obtain the compound of formula (12).

In some embodiments, $P^2$ is tosyl.

In some embodiments, the deprotecting comprises treating the compound of formula (13) with an acid.

In some embodiments, the compound of formula (13) is prepared by a method comprising reacting a compound of formula (8):

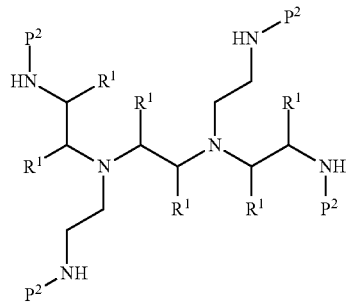

(8)

or a salt thereof, with a compound of formula (14):

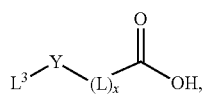

(14)

or salt thereof, wherein L is a leaving group, to obtain the compound of formula (13).

In some embodiments, $L^3$ is a halo.

In some embodiments, the halo is Br or I.

In some embodiments, Y is $C_{1-6}$ alkyl, x is an integer from 1 to 30, and each L is —O—CH$_2$CH$_2$.

In some embodiments, Y is $C_{1-6}$ alkyl, x is 0, and L is a bond.

In some embodiments, each $X^1$ is independently selected from H, halo, NO$_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is H.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$; and the remaining $R^1$ groups are all H.

In some embodiments, the present application provides a method of making a compound of Formula (IIIi):

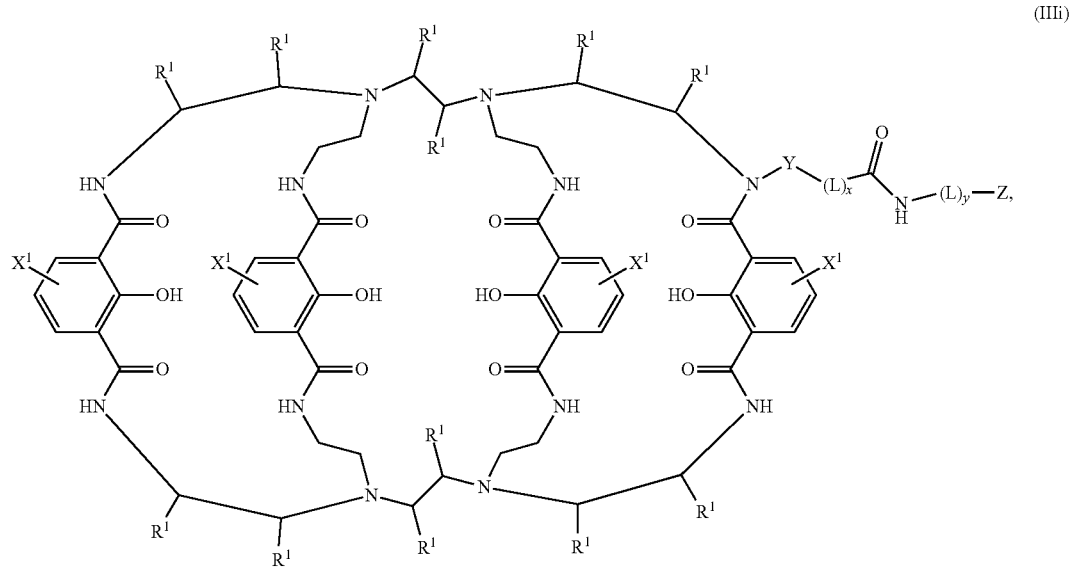

(IIIi)

or a pharmaceutically acceptable salt thereof, wherein:

Y is selected from $C_{1-6}$ alkylene, $C_{2-6}$ alkenylene, and $C_{2-6}$ alkynylene;

x is an integer from 0 to 100; wherein if x is 0 then L is a bond;

y is an integer from 0 to 100, wherein if y is 0 then L is a bond and Z is H or $C_{1-3}$ alkyl;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each $X^1$ is independently selected from halo, NO$_2$, CN, N$_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, NH$_2$, $C_{1-3}$ alkylamino, di($C_{1-3}$ alkyl)amino, NO$_2$, CN, C(O)OH, $C_{1-3}$ alkoxy, $C_{1-3}$ haloalkoxy, and N$_3$;

each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each Z is selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

the method comprising coupling a compound of Formula (IIIf):

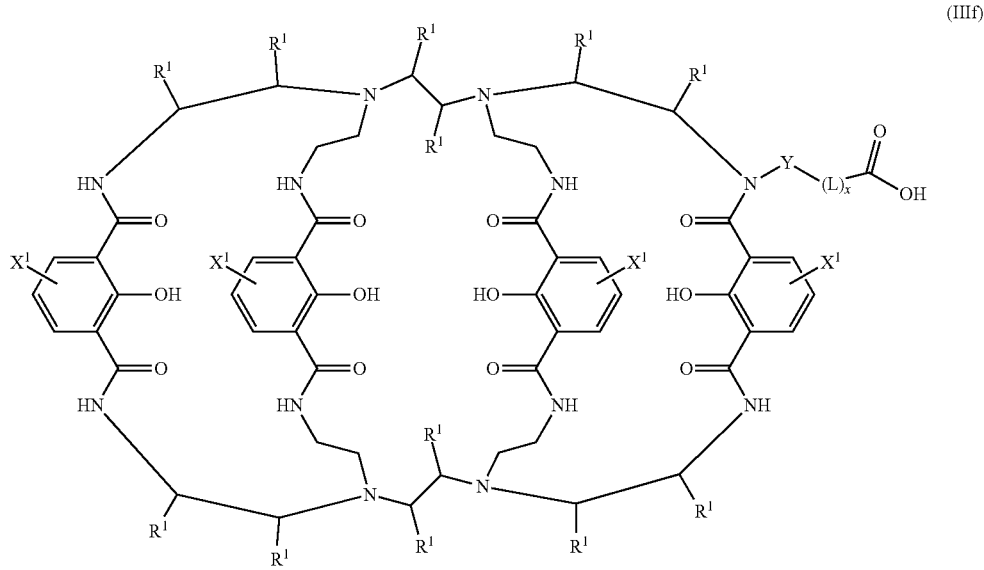

(IIIf)

or a salt thereof, with a compound of formula (15):

$$H_2N\text{-}(L)_y\text{-}Z \qquad (15),$$

or a salt thereof, to obtain the compound of Formula (IIIi).

In some embodiments, the coupling is conducted in the presence of a coupling reagent that promotes a reaction between a carboxylic acid and an amine to form an amide.

In some embodiments, the coupling reagent is PyBOP.

In some embodiments:

the compound of Formula (IIIi) has formula:

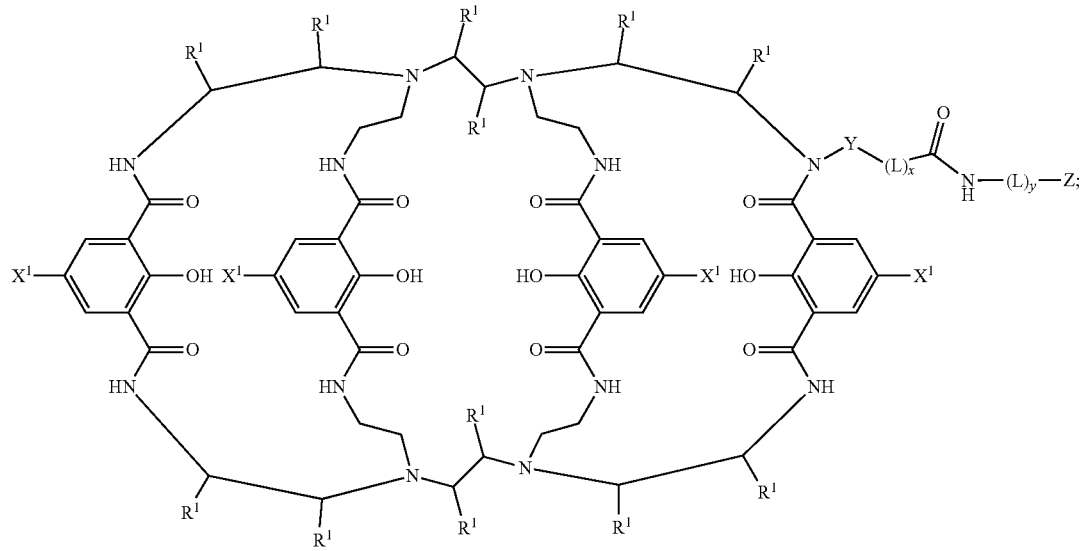

or a salt thereof, and the compound of Formula (IIIf) has formula:

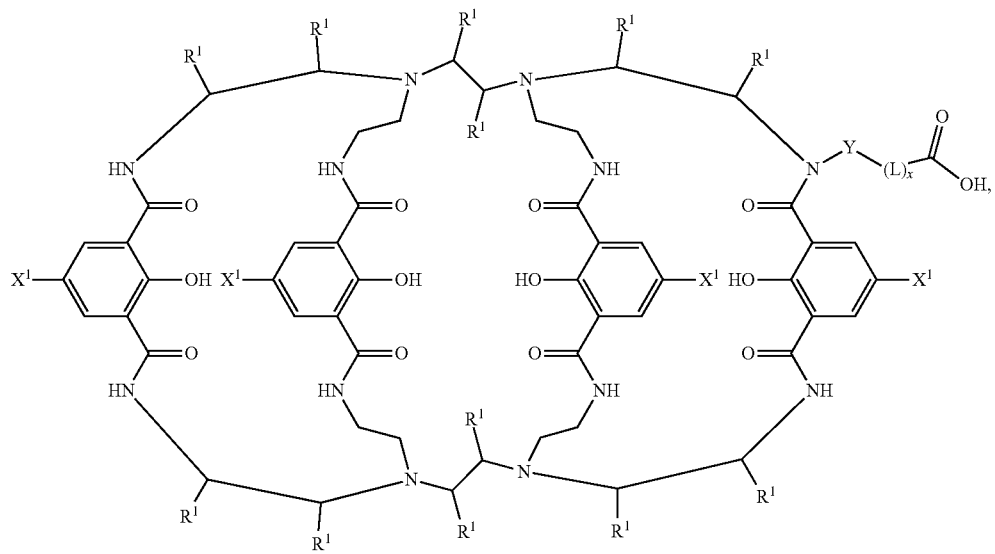

or a salt thereof.

In some embodiments, each $X^1$ is independently selected from H, halo, $NO_2$, methyl, and methoxy.

In some embodiments, each $X^1$ is independently a halo.

In some embodiments, each halo is independently selected from Br, Cl, F, and I.

In some embodiments, each $X^1$ is the same.

In some embodiments, each $X^1$ is H.

In some embodiments, each $X^1$ is Br.

In some embodiments, Y is $C_{1-6}$ alkylene.

In some embodiments, at least one L is $CH_2CH_2$—O— or —O—$CH_2CH_2$—.

In some embodiments, Z is an activated ester selected from N-hydroxysuccinimide, sulfo-N-hydroxysuccinimide, tetrafluorophenoxy, pentafluorophenoxy, and p-nitrophenoxy.

In some embodiments, Z is a maleimide.

In some embodiments, Z is a biorthogonal functional group selected from $N_3$, $C_{2-6}$ alkynyl, a cyclooctynyl, a tetrazine, a transcyclooctene, a oxanorbornadiene, a norbornene, a nitrile oxide, an isocyanide, and a tetrazole.

In some embodiments, Z is a chemical substrate tag selected from: HaloTag, a SNAPTag, and a CLIPTag.

In some embodiments, Z is selected from any one of the following groups:

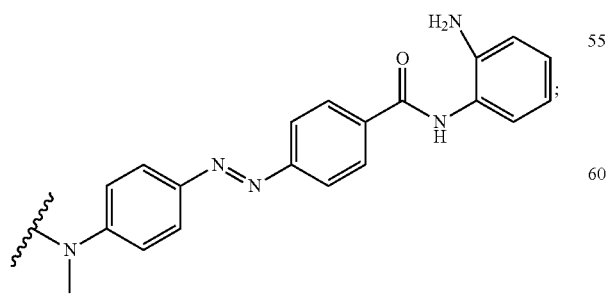

-continued

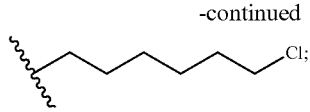

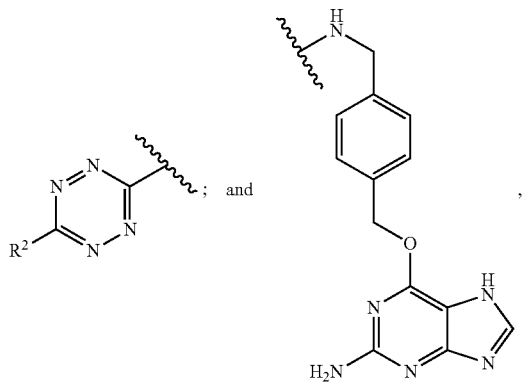

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, Z is a biomolecule selected from a protein, a peptide, a lipid, a nucleic acid, and a saccharide.

In some embodiments, Z is a photocrosslinking label selected from an azide, a benzophenone, and an aziridine.

In some embodiments, the present application provides a compound of Formula (IV).

(IV)

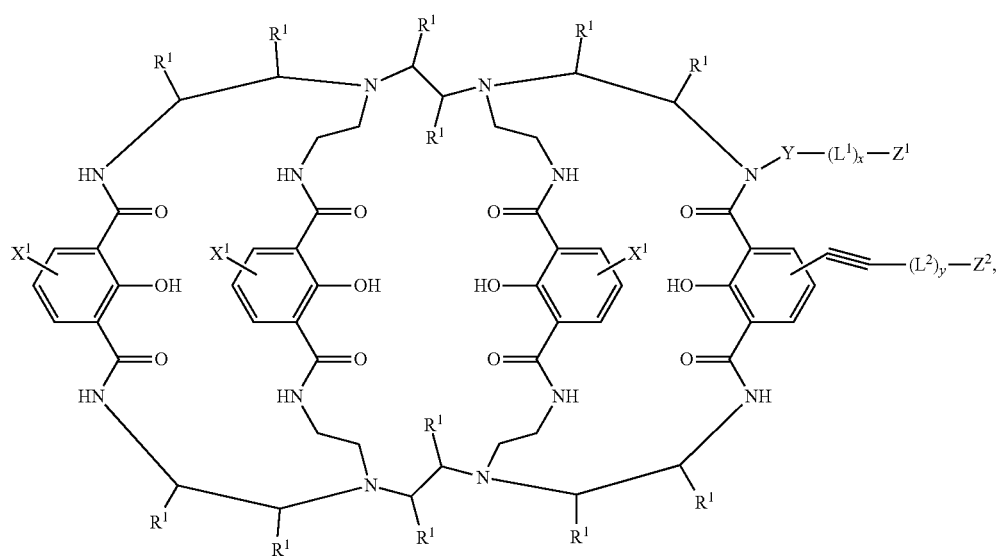

or a pharmaceutically acceptable salt thereof, wherein:
Y is selected from $C_{1-6}$ alkylene, $C_{2-6}$ alkenylene, $C_{2-6}$ alkynylene, and a bond;
each $L^1$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;
each $L^2$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;
each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;
x is an integer from 0 to 100; wherein if x is 0 then $L^1$ is a bond and $Z^1$ is H or $C_{1-3}$ alkyl;
y is an integer from 0 to 100; wherein if y is 0 then $L^2$ is a bond and $Z^2$ is H or $C_{1-3}$ alkyl;
$Z^1$ and $Z^2$ are each independently selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter.

In some embodiments, the compound of Formula (IV) has Formula (IVa):

(IVa)

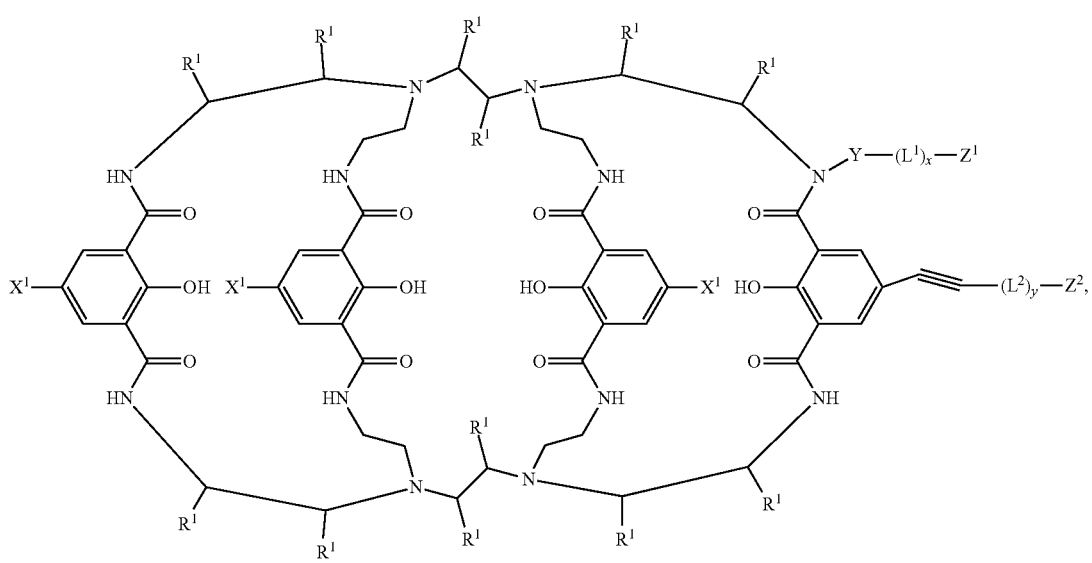

or a pharmaceutically acceptable salt thereof.

In some embodiments, each $Z^1$ or $Z^2$ is independently an activated ester selected from N-hydroxysuccinimide, sulfo-N-hydroxysuccinimide, tetrafluorophenoxy, pentafluorophenoxy, and p-nitrophenoxy.

In some embodiments, each $Z^1$ or $Z^2$ is independently a maleimide.

In some embodiments, each $Z^1$ or $Z^2$ is independently a biorthogonal functional group selected from $N_3$, $C_{2-6}$ alkynyl, a cyclooctynyl, a tetrazine, a transcyclooctene, a oxanorbornadiene, a norbornene, a nitrile oxide, an isocyanide, and a tetrazole.

In some embodiments, each $Z^1$ or $Z^2$ is independently a chemical substrate tag selected from: HaloTag, a SNAPTag, and a CLIPTag.

In some embodiments, each $Z^1$ or $Z^2$ is independently selected from any one of the following groups:

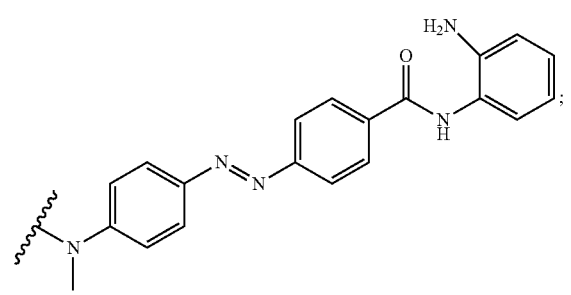

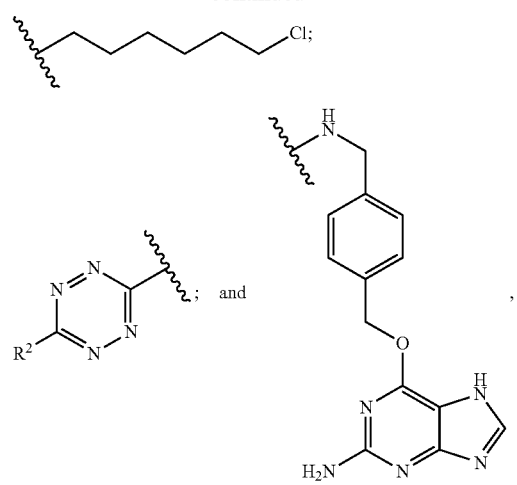

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, each $Z^1$ or $Z^2$ is independently a biomolecule selected from a protein, a peptide, a lipid, a nucleic acid, and a saccharide.

In some embodiments, each $Z^1$ or $Z^2$ is independently a photocrosslinking label selected from an azide, a benzophenone, and an aziridine.

In some embodiments, at least one of $L^1$ or $L^2$ is $CH_2CH_2$—O— or —O—$CH_2CH_2$.

In some embodiments, the compound of Formula (IV) has Formula (IVb):

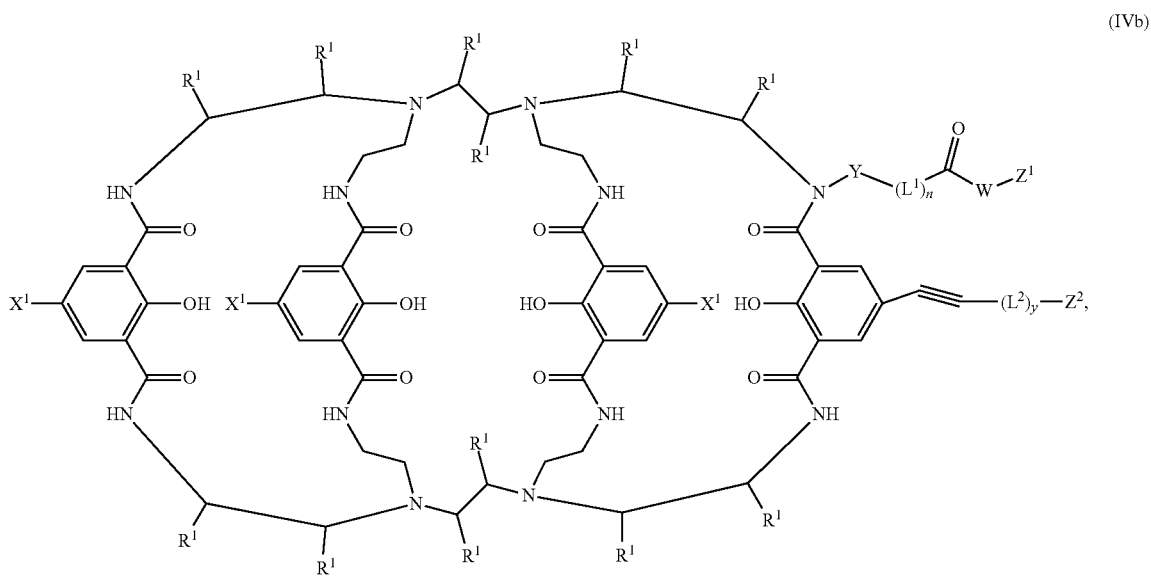

(IVb)

or a pharmaceutically acceptable salt thereof, wherein:
$Z^1$ is selected from H and $C_{1-3}$ alkyl;
W is selected from O and NH; and
n is an integer from 0 to 100.

In some embodiments, W is O.
In some embodiments, W is NH.
In some embodiments, Y is $C_{1-3}$ alkylene.
In some embodiments, the $C_{1-3}$ alkylene is methylene.
In some embodiments, at least one of $L^1$ and $L^2$ is $CH_2CH_2$—O— or —O—$CH_2CH_2$.
In some embodiments, each $X^1$ is independently selected from H, halo, $NO_2$, methyl, and methoxy.
In some embodiments, each $X^1$ is independently a halo.
In some embodiments, each halo is independently selected from Br, Cl, F, and I.
In some embodiments, each $X^1$ is the same.
In some embodiments, each $X^1$ is H.
In some embodiments, each $X^1$ is Br.
In some embodiments, each $R^1$ is H.
In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.
In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present application provides a method of making a compound of Formula (IVc):

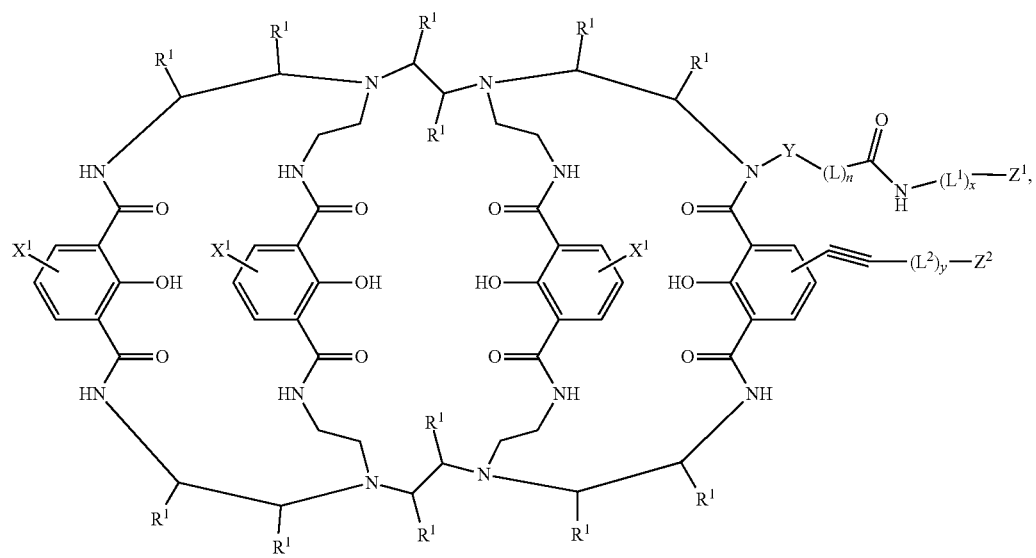

(IVc)

or a pharmaceutically acceptable salt thereof, wherein:
Y is selected from $C_{1-6}$ alkylene, $C_{2-6}$ alkenylene, $C_{2-6}$ alkynylene, and a bond;
each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;
each $L^1$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;
each $L^2$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;
each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and
each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;
x is an integer from 0 to 100; wherein if x is 0 then $L^1$ is a bond and $Z^1$ is H or $C_{1-3}$ alkyl;
y is an integer from 0 to 100; wherein if y is 0 then $L^2$ is a bond and $Z^2$ is H or $C_{1-3}$ alkyl;
n is an integer from 0 to 100, wherein if n is o then L is a bond; and
$Z^1$ and $Z^2$ are each independently selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;
the method comprising coupling a compound of Formula (IVd):

(IVd)

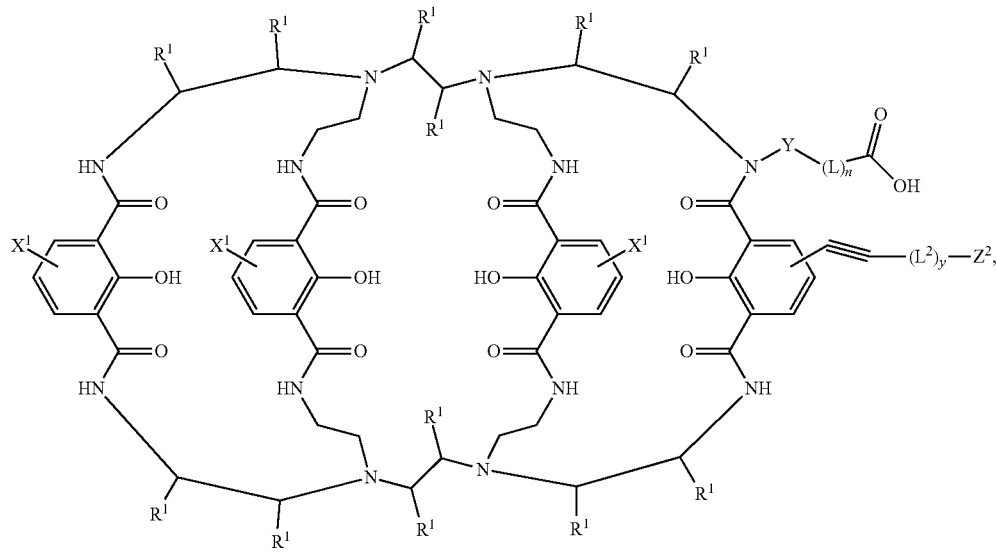

or a salt thereof, with a compound of formula (16):

or a salt thereof, to obtain the compound of Formula (IVc).

In some embodiments, the coupling is conducted in the presence of a coupling reagent that promotes a reaction between a carboxylic acid and an amine to form an amide.

In some embodiments, the coupling reagent is PyBOP.

In some embodiments, the compound of Formula (IVd) is prepared by a method comprising deprotecting a compound of Formula (IVe)

or a salt thereof, wherein each $P^1$ is independently a protecting group, to obtain the compound of Formula (IVd).

In some embodiments, $P^1$ is a methyl group.

In some embodiments, deprotecting the compound of Formula (IVe) comprises treating the compound with a lithium halide or a boron halide.

In some embodiments, deprotecting the compound of Formula (IVe) comprises treating the compound with LiI or $BBr_3$.

In some embodiments, the compound of Formula (IVe) is prepared by a method comprising coupling a compound of Formula (IVf):

(IVe)

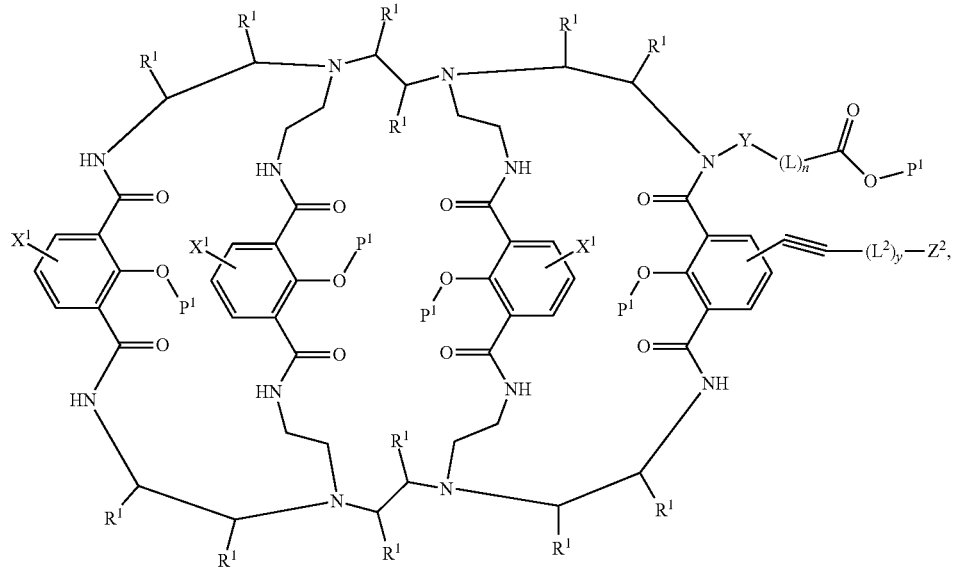

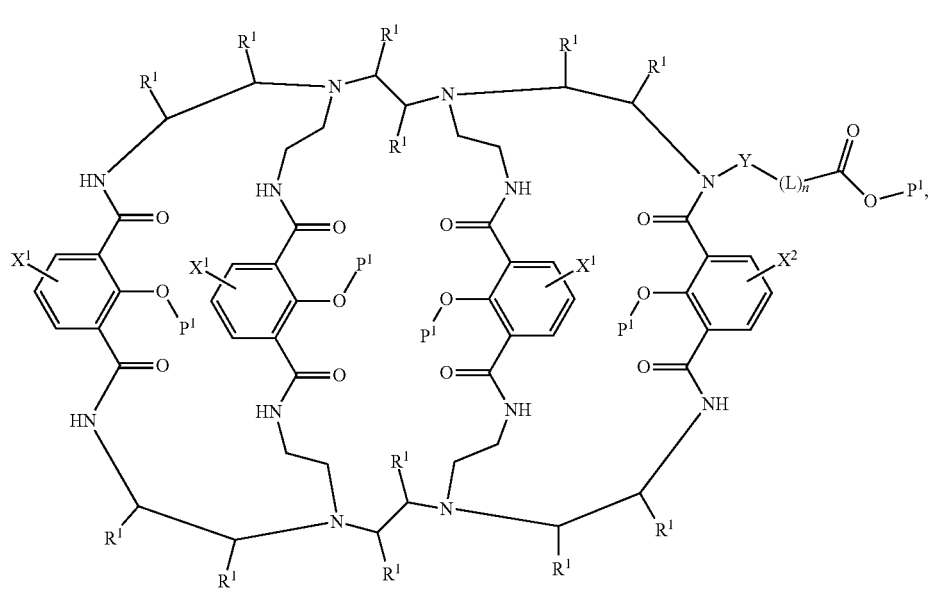

or a pharmaceutically acceptable salt thereof, wherein $X^2$ is halo,
with a compound of formula (17):

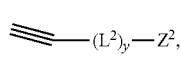

or a salt thereof, to obtain the compound of Formula (IVe).

In some embodiments, the halo is selected from Cl, Br and I.

In some embodiments, the coupling is conducted in the presence of a transition metal catalyst.

In some embodiments, the transition metal catalyst is Pd catalyst.

In some embodiments, the compound of Formula (IVf) is prepared by a method comprising coupling a compound of Formula (IVg):

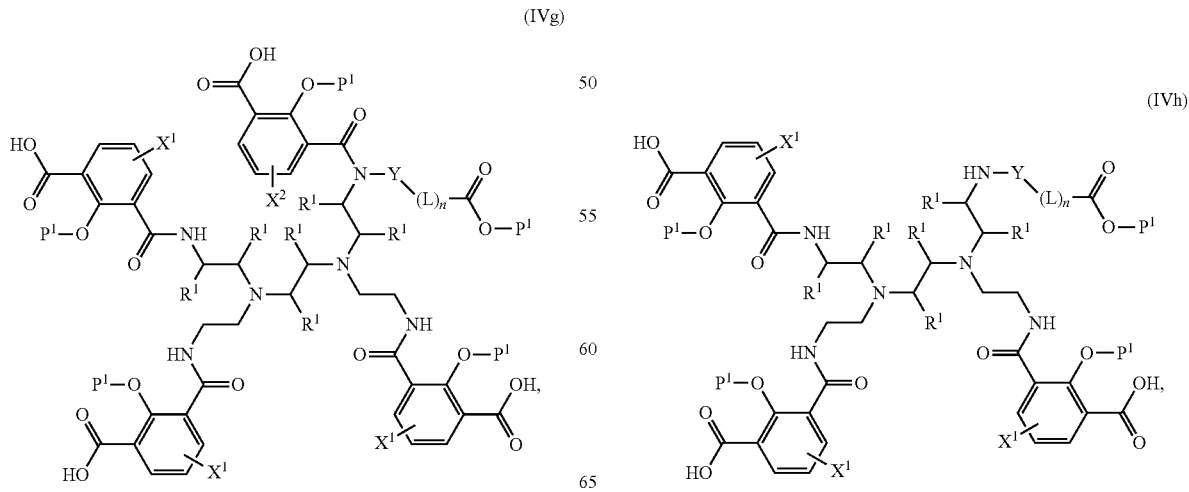

or a salt thereof, with a compound of formula (1):

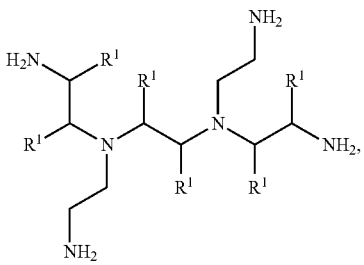

or a salt thereof, to obtain the compound of Formula (IVf).

In some embodiments, the compound of Formula (IVg) is prepared by a method comprising reacting a compound of Formula (IVh):

or a salt thereof, with a compound of formula (18):

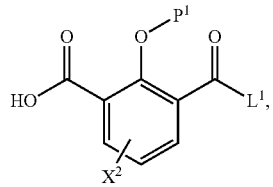
(18)

or a salt thereof, wherein L¹ is a leaving group,
to obtain the compound of Formula (IVg).

In some embodiments, L¹ is an activated ester.

In some embodiments, L¹ is selected from: N-hydroxysuccinimide, sulfo-N-hydroxysuccinimide, tetrafluorophenoxy, pentafluorophenoxy, and p-nitophenoxy.

In some embodiments, the compound of Formula (IVh) is prepared by a method comprising reacting a compound of formula (11):

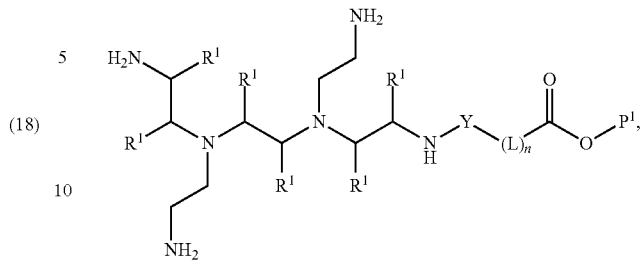
(11)

or a salt thereof, with a compound of formula (2):

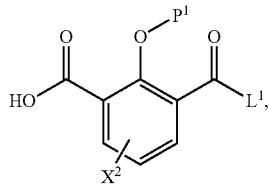
(2)

or a salt thereof, to obtain the compound of Formula (IVh).

In some embodiments:
the compound of Formula (IVc) has formula:

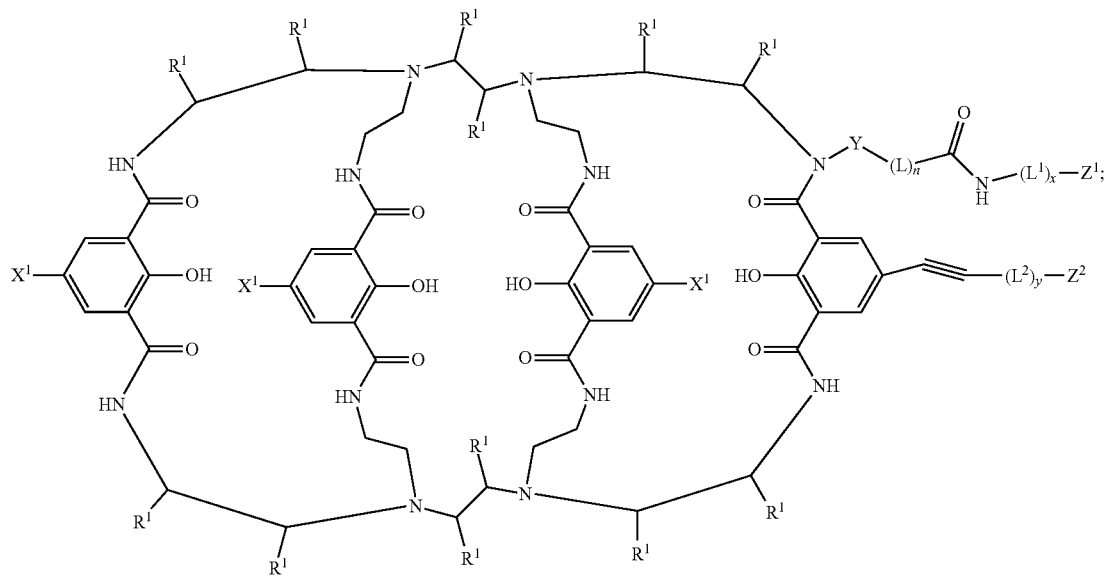

or a salt thereof, the compound of Formula (IVd) has formula:

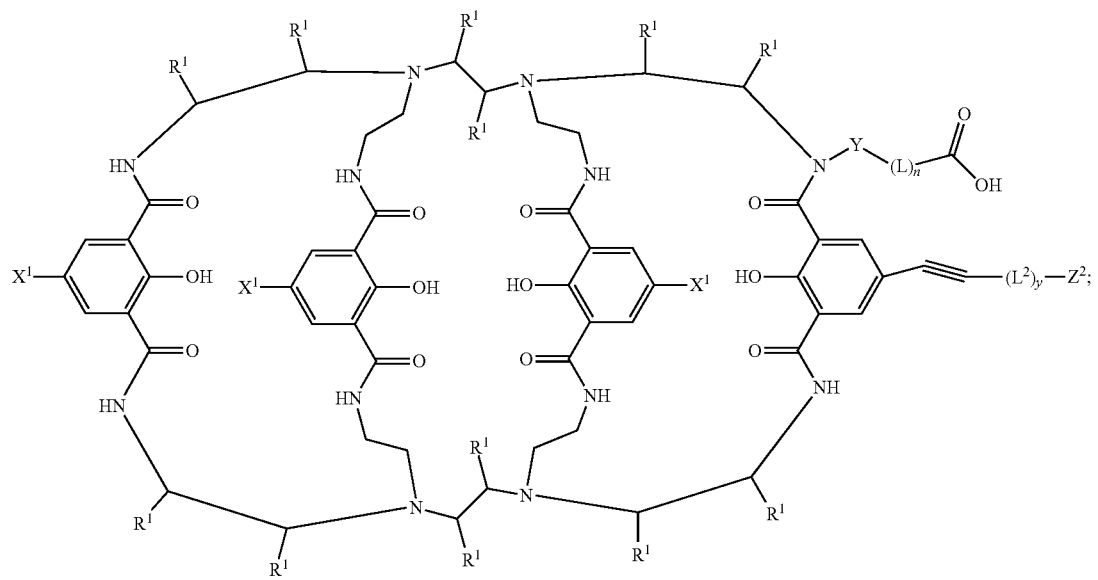
or a salt thereof, the compound of Formula (IVe) has formula:
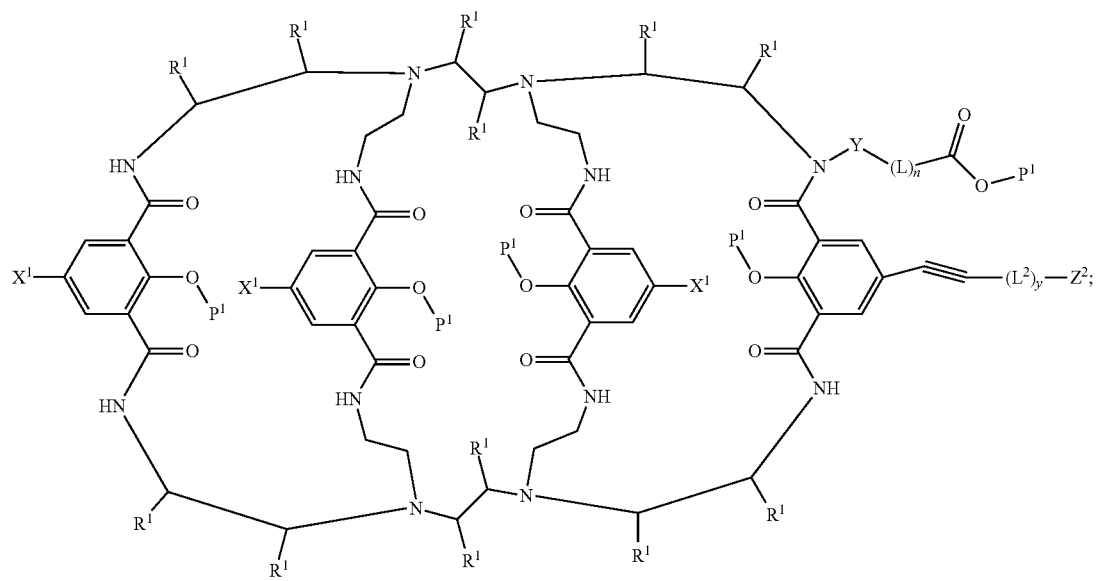
or a salt thereof, the compound of Formula (IVf) has formula:

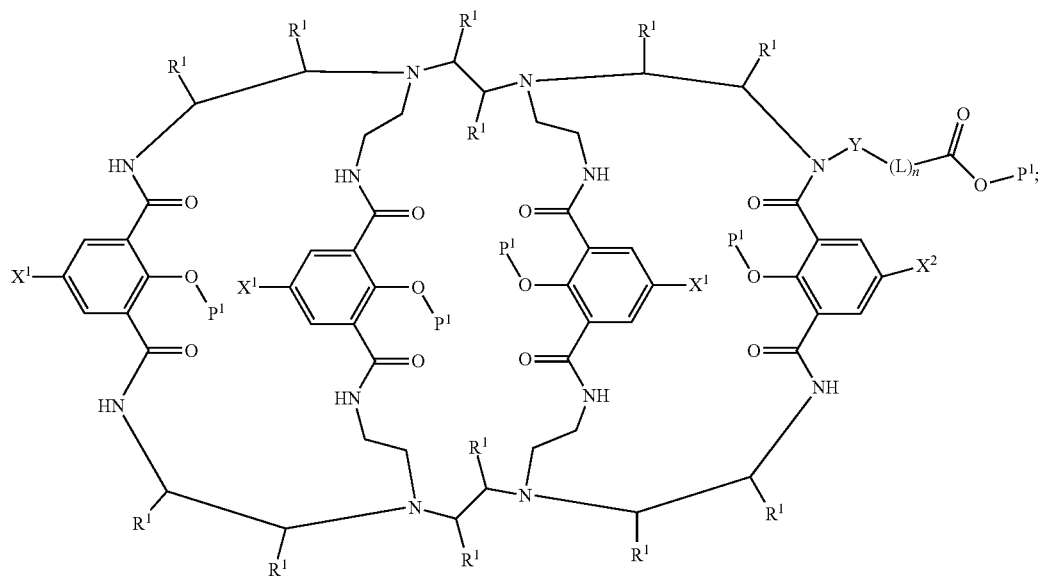

or a salt thereof, the compound of Formula (IVg) has formula:

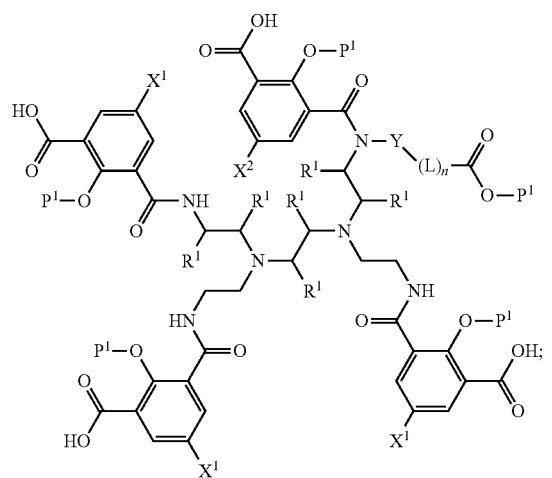

or a salt thereof, the compound of Formula (IVh) has formula:

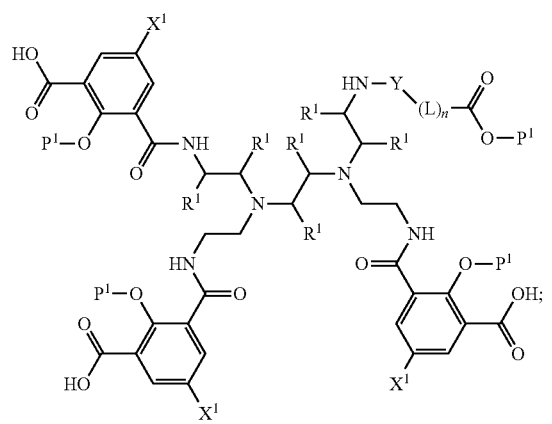

or a salt thereof, the compound of formula (18) has formula:

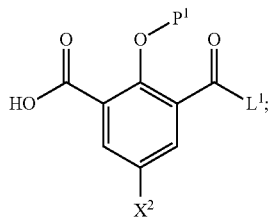

or a salt thereof, and the compound of formula (2) has formula:

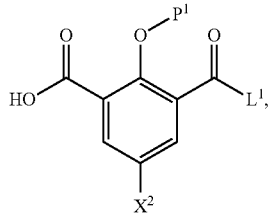

or a salt thereof.

In some embodiments, each $X^1$ is the same.
In some embodiments, each $X^1$ is H.
In some embodiments, Y is $C_{1-3}$ alkylene.
In some embodiments, the $C_{1-3}$ alkylene is methylene.
In some embodiments, at least one of L, $L^1$, and $L^2$ is $CH_2CH_2$—O— or —O—$CH_2CH_2$.
In some embodiments, each $R^1$ is H.
In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, each $Z^1$ or $Z^2$ is independently an activated ester selected from N-hydroxysuccinimide, sulfo-N-hydroxysuccinimide, tetrafluorophenoxy, pentafluorophenoxy, and p-nitrophenoxy.

In some embodiments, each $Z^1$ or $Z^2$ is independently a maleimide.

In some embodiments, each $Z^1$ or $Z^2$ is independently a biorthogonal functional group selected from $N_3$, $C_{2-6}$ alkynyl, a cyclooctynyl, a tetrazine, a transcyclooctene, a oxanorbornadiene, a norbornene, a nitrile oxide, an isocyanide, and a tetrazole.

In some embodiments, each $Z^1$ or $Z^2$ is independently a chemical substrate tag selected from: HaloTag, a SNAPTag, and a CLIPTag.

In some embodiments, each $Z^1$ or $Z^2$ is independently selected from any one of the following groups:

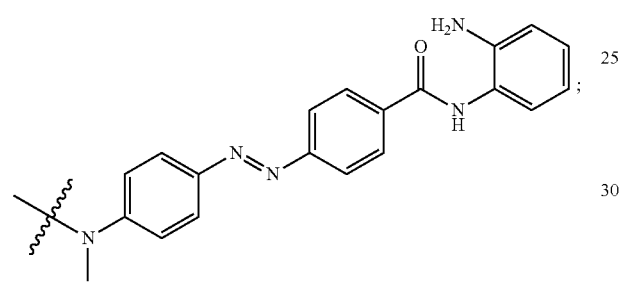

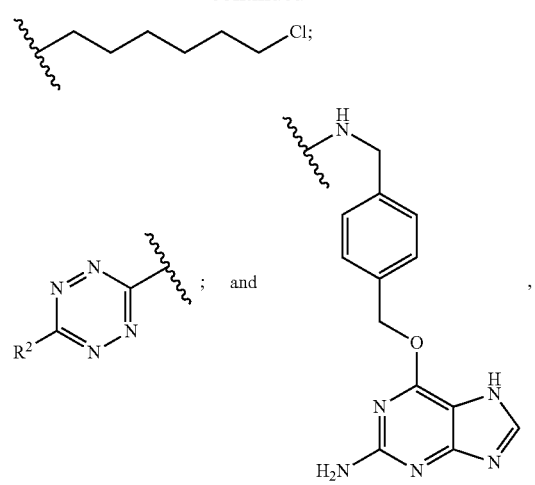

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, each $Z^1$ or $Z^2$ is independently a biomolecule selected from a protein, a peptide, a lipid, a nucleic acid, and a saccharide.

In some embodiments, each $Z^1$ or $Z^2$ is independently a photocrosslinking label selected from an azide, a benzophenone, and an aziridine.

In some embodiments, the present disclosure provides a compound of Formula (V):

(V)

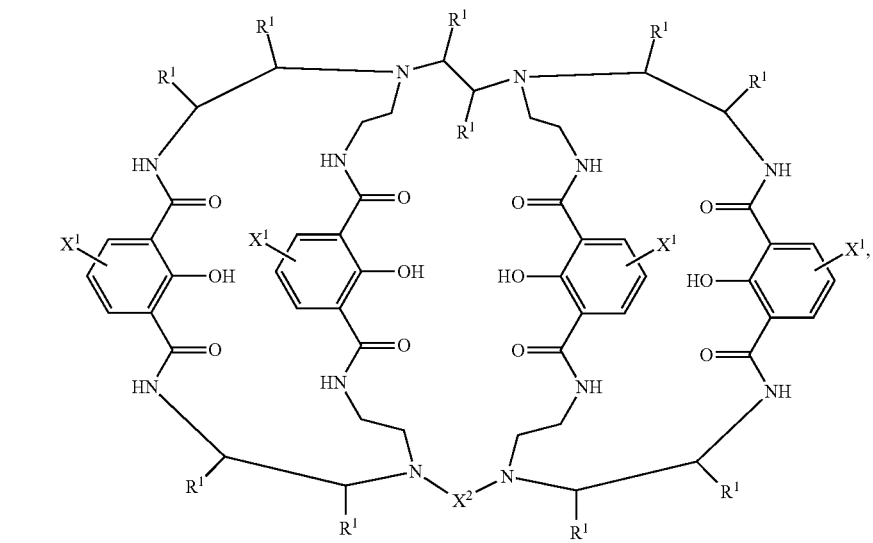

or a pharmaceutically acceptable salt thereof, wherein: $X^2$ is selected from any one of the following groups:

(i)

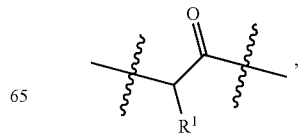

-continued

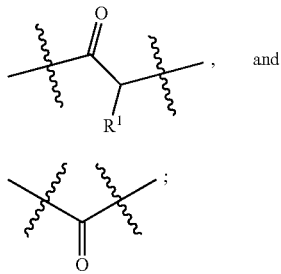

each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, the compound of Formula (V) has formula:

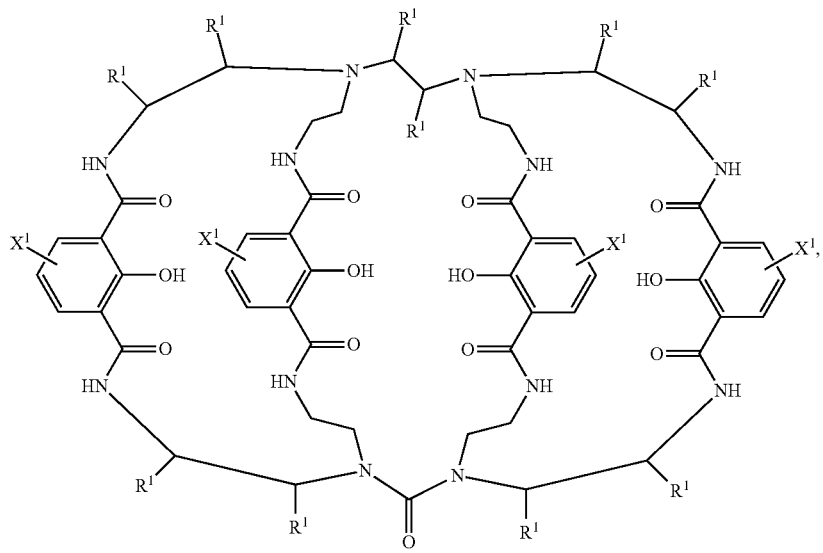

or a pharmaceutically acceptable salt thereof.

In some embodiments, the compound of Formula (V) has formula:

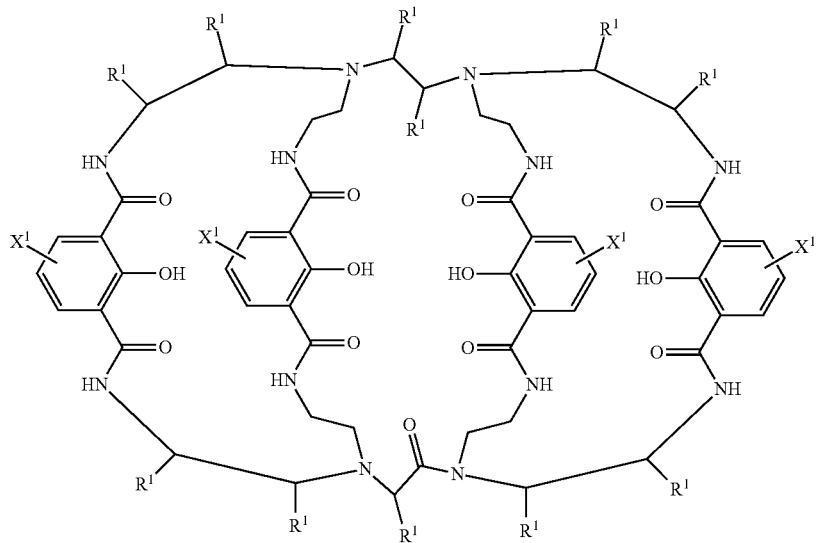

or a pharmaceutically acceptable salt thereof.

In some embodiments, each $X^1$ is independently selected from H, halo, $NO_2$, methyl, and methoxy.

In some embodiments, each $X^1$ is H.

In some embodiments, each $X^1$ is independently a halo.

In some embodiments, each halo is independently selected from Br, Cl, F, and I.

In some embodiments, each $X^1$ is the same.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present disclosure provides a compound of Formula (VI):

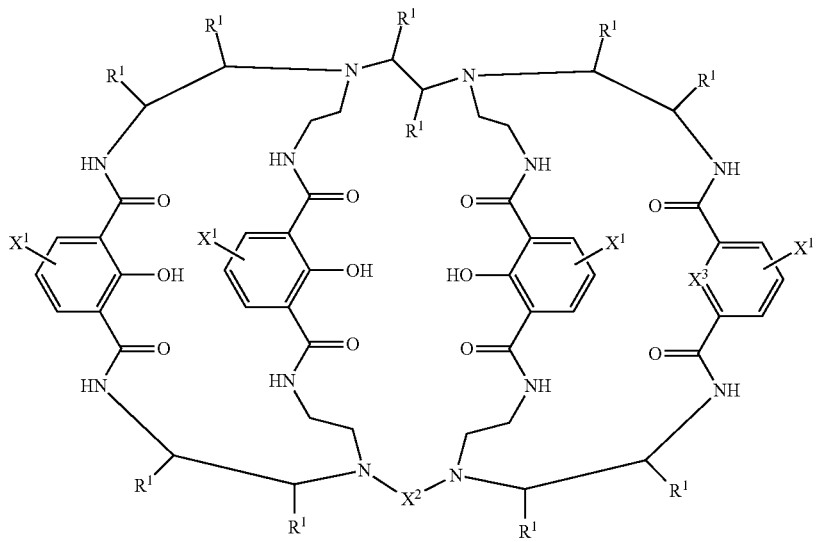

or a pharmaceutically acceptable salt thereof, wherein:

$X^2$ is selected from any one of the following groups:

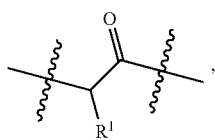 (i)

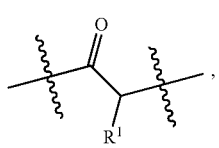 (ii)

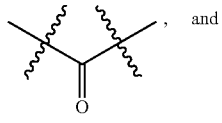, and (iii)

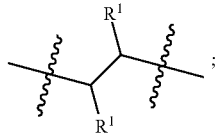 (iv)

$X^3$ is selected from CH, C-Hal, and N;

each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, $X^2$ is group (i).

In some embodiments, $X^2$ is group (ii).

In some embodiments, $X^2$ is group (iii).

In some embodiments, $X^2$ is group (iv).

In some embodiments, $X^3$ is CH.

In some embodiments, $X^3$ is C-Hal.

In some embodiments, Hal is selected from Cl, Br, and I.

In some embodiments, $X^3$ is C—Br.

In some embodiments, $X^3$ is N.

In some embodiments, each $X^1$ is independently selected from H, halo, $NO_2$, methyl, and methoxy.

In some embodiments, each $X^1$ is independently a halo.

In some embodiments, each $X^1$ is H.

In some embodiments, each halo is independently selected from Br, Cl, F, and I.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present disclosure provides a compound of Formula (VII):

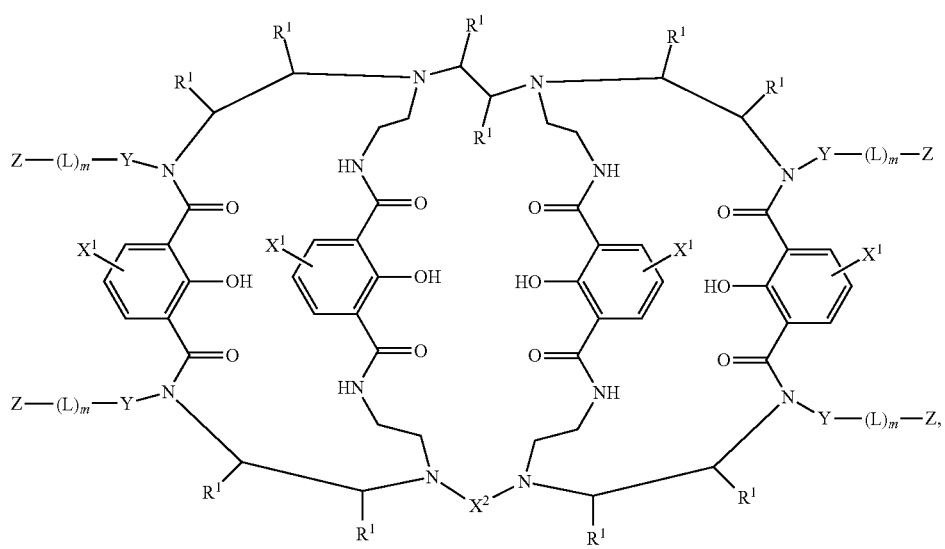

(VII)

or a pharmaceutically acceptable salt thereof, wherein:

$X^2$ is selected from any one of the following groups:

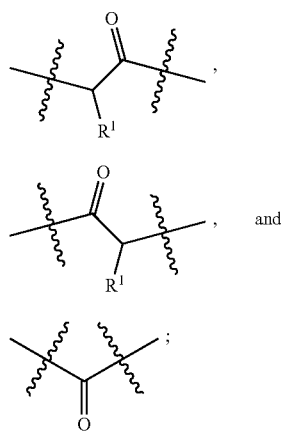

each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each m is an integer from 0 to 100; wherein if m is 0 then L is a bond; and each Z is selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

wherein:

if Y is a bond and m is 0, then Z is H or $C_{1-3}$ alkyl; and at least one m is greater than 0.

In some embodiments, the compound of Formula (VII) has formula:

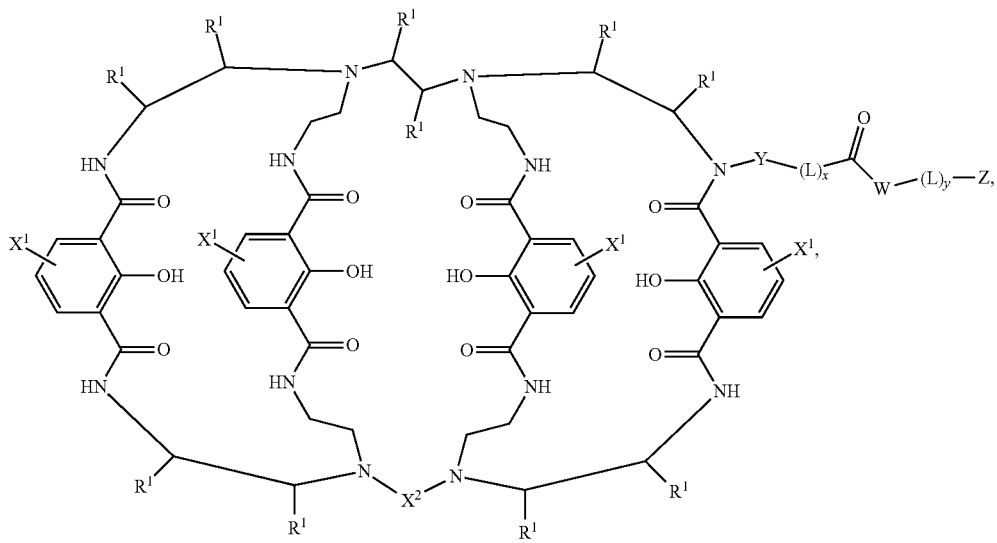

or a pharmaceutically acceptable salt thereof, wherein:

W is selected from NH and O;

the sum of x and y is m, if x is 0 then L is a bond; and if y is 0 then L is a bond and Z is H or $C_{1-3}$ alkyl.

In some embodiments, $X^2$ is group (i).

In some embodiments, $X^2$ is group (ii).

In some embodiments, $X^2$ is group (iii).

In some embodiments, Z is an activated ester selected from N-hydroxysuccinimide, sulfo-N-hydroxysuccinimide, tetrafluorophenoxy, pentafluorophenoxy, and p-nitrophenoxy.

In some embodiments, Z is a maleimide.

In some embodiments, Z is a biorthogonal functional group selected from $N_3$, $C_{2-6}$ alkynyl, a cyclooctynyl, a tetrazine, a transcyclooctene, a oxanorbornadiene, a norbomene, a nitrile oxide, an isocyanide, and a tetrazole.

In some embodiments, Z is a chemical substrate tag selected from: HaloTag, a SNAPTag, and a CLIPTag.

In some embodiments, Z is selected from any one of the following groups:

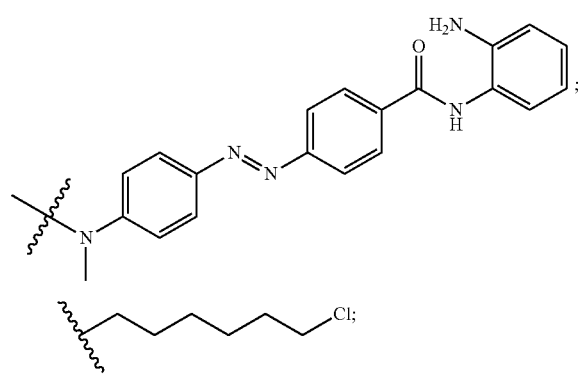

-continued

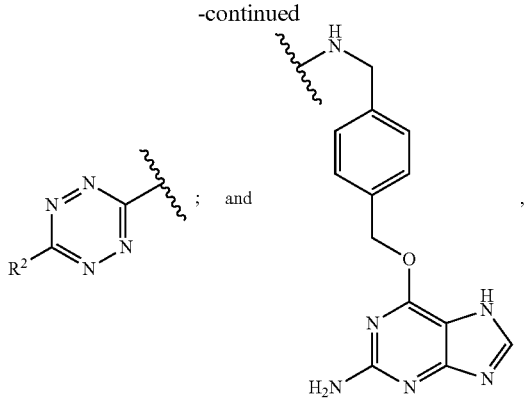

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, Z is a biomolecule selected from a protein, a peptide, a lipid, a nucleic acid, and a saccharide.

In some embodiments, Z is a photocrosslinking label selected from an azide, a benzophenone, and an aziridine.

In some embodiments, m is an integer from 0 to 50.

In some embodiments, m is an integer from 0 to 30.

In some embodiments, Y is methylene or ethylene.

In some embodiments, at least one L is C(O)NH.

In some embodiments, at least one L is $CH_2CH_2$—O— or —O—$CH_2CH_2$.

In some embodiments, each $X^1$ is independently selected from H, halo, $NO_2$, methyl, and methoxy.

In some embodiments, each $X^1$ is independently a halo.

In some embodiments, each halo is independently selected from Br, Cl, F, and I.

In some embodiments, each $X^1$ is H.

In some embodiments, each $X^1$ is Br.

In some embodiments, each $R^1$ is H.

In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the present disclosure provides a compound of Formula (VIII):

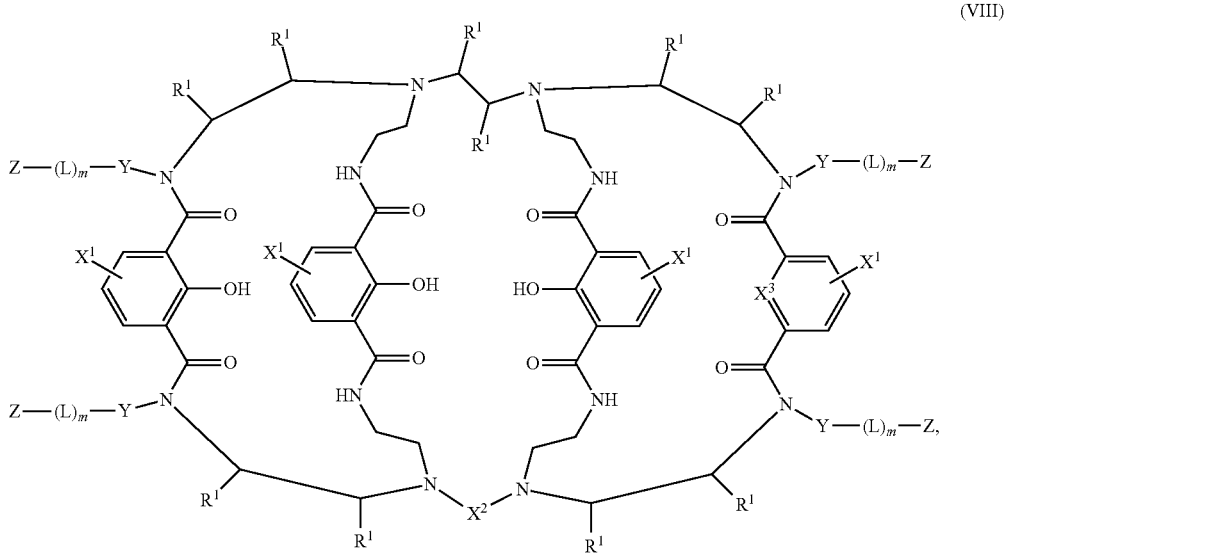

(VIII)

or a pharmaceutically acceptable salt thereof, wherein:

$X^2$ is selected from any one of the following groups:

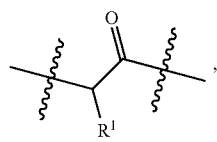

(i)

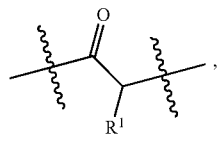

(ii)

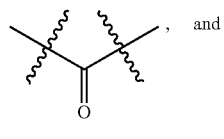

(iii) and

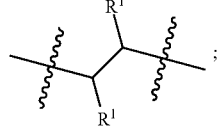

(iv)

$X^3$ is selected from CH, C-Hal, and N;

each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$;

each Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each m is an integer from 0 to 100; wherein if m is 0 then L is a bond; and each Z is selected from H, $C_{1-3}$ alkyl, an activated ester, a biorthogonal functional group, $NH_2$, $C_{1-3}$ alkylamino, di($C_{1-3}$ alkyl)amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

wherein:

if Y is a bond and m is 0, then Z is H or $C_{1-3}$ alkyl; and at least one m is greater than 0.

In some embodiments, the compound of Formula (VIII) has formula:

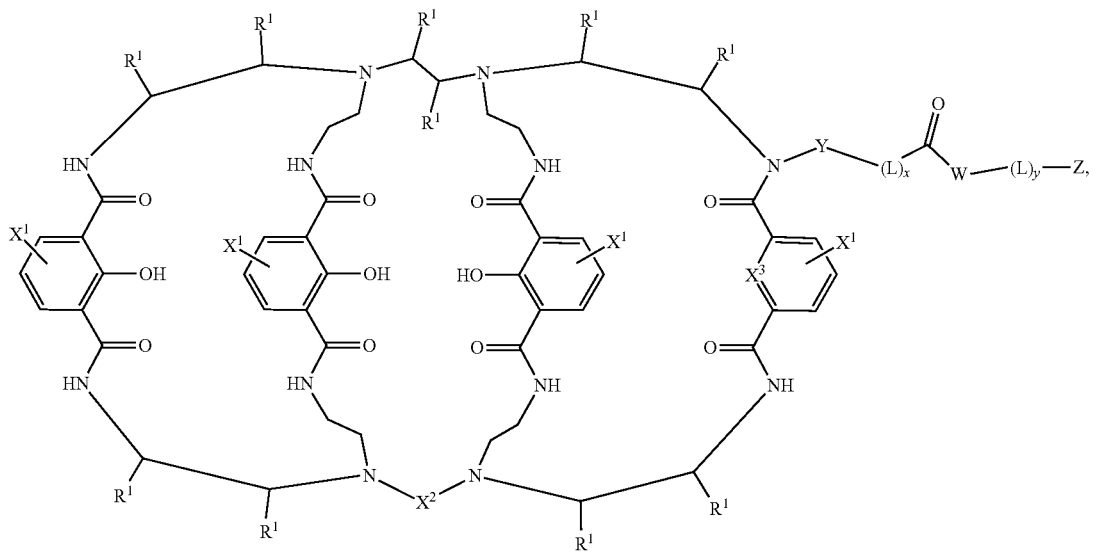

or a pharmaceutically acceptable salt thereof, wherein:
W is selected from NH and O;
the sum of x and y is m,
if x is 0 then L is a bond; and
if y is 0 then L is a bond and Z is H or $C_{1-3}$ alkyl.

In some embodiments, $X^2$ is group (i).
In some embodiments, $X^2$ is group (ii).
In some embodiments, $X^2$ is group (iii).
In some embodiments, $X^2$ is group (iv).
In some embodiments, $X^3$ is CH.
In some embodiments, $X^3$ is C-Hal.
In some embodiments, Hal is selected from Cl, Br, and I.
In some embodiments, $X^3$ is C—Br.
In some embodiments, $X^3$ is N.

In some embodiments, Z is an activated ester selected from N-hydroxysuccinimide, sulfo-N-hydroxysuccinimide, tetrafluorophenoxy, pentafluorophenoxy, and p-nitophenoxy.

In some embodiments, Z is a maleimide.

In some embodiments, Z is a biorthogonal functional group selected from $N_3$, $C_{2-6}$ alkynyl, a cyclooctynyl, a tetrazine, a transcyclooctene, a oxanorbornadiene, a norbornene, a nitrile oxide, an isocyanide, and a tetrazole.

In some embodiments, Z is a chemical substrate tag selected from: HaloTag, a SNAPTag, and a CLIPTag.

In some embodiments, Z is selected from any one of the following groups:

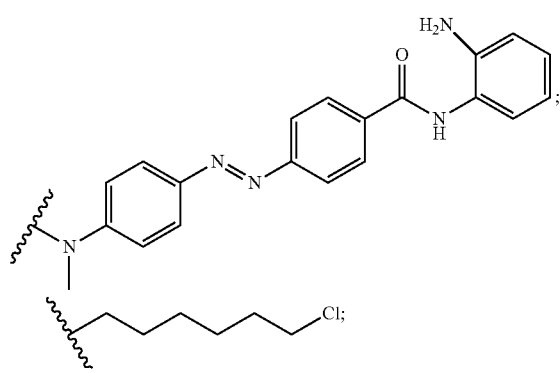

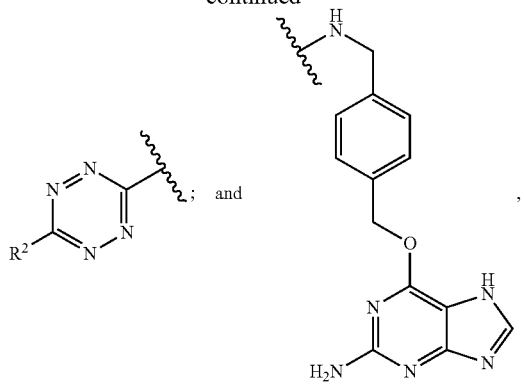

wherein $R^2$ is selected from H, halo, OH, $NH_2$, $C_{1-3}$ alkylamino, di($C_{1-3}$ alkyl)amino, $NO_2$, CN, C(O)OH, $C_{1-3}$ alkyl, $C_{1-3}$ alkoxy, and $C_{1-3}$ haloalkoxy.

In some embodiments, Z is a biomolecule selected from a protein, a peptide, a lipid, a nucleic acid, and a saccharide.

In some embodiments, Z is a photocrosslinking label selected from an azide, a benzophenone, and an aziridine.

In some embodiments, m is an integer from 0 to 50.
In some embodiments, m is an integer from 0 to 30.
In some embodiments, Y is methylene or ethylene.
In some embodiments, at least one L is C(O)NH.
In some embodiments, at least one L is $CH_2CH_2$—O— or —O—$CH_2CH_2$.

In some embodiments, each $X^1$ is independently selected from H, halo, $NO_2$, methyl, and methoxy.
In some embodiments, each $X^1$ is independently a halo.
In some embodiments, each halo is independently selected from Br, Cl, F, and I.
In some embodiments, each $X^1$ is H.
In some embodiments, each $X^1$ is Br.
In some embodiments, each $R^1$ is H.
In some embodiments, at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$.

In some embodiments, one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl)amino, $NO_2$, CN, C(O)OH, $C_{1-3}$ alkoxy, $C_{1-3}$ haloalkoxy, and $N_3$; and the remaining $R^1$ groups are all H.

In some embodiments, the compounds of Formulae (V)-(VIII) can be prepared according the methods analogous to those described herein for Formula (I)-(IV) (e.g., substituting $X^3$ for the C—OH in the formulae as appropriate).

In some embodiments, the present application provides a fluorescent or luminescent complex comprising any one of the compound provided herein, or a pharmaceutically acceptable salt thereof, and a lanthanide metal.

In some embodiments, the lanthanide metal is selected from Tb (terbium), Eu (europium), Sm (samarium), and Dy (dysprosium).

In some embodiments, the lanthanide metal is $Tb^{3+}$.

In some embodiments, the present application provides a fluorescent or luminescent complex comprising a compound of formula:

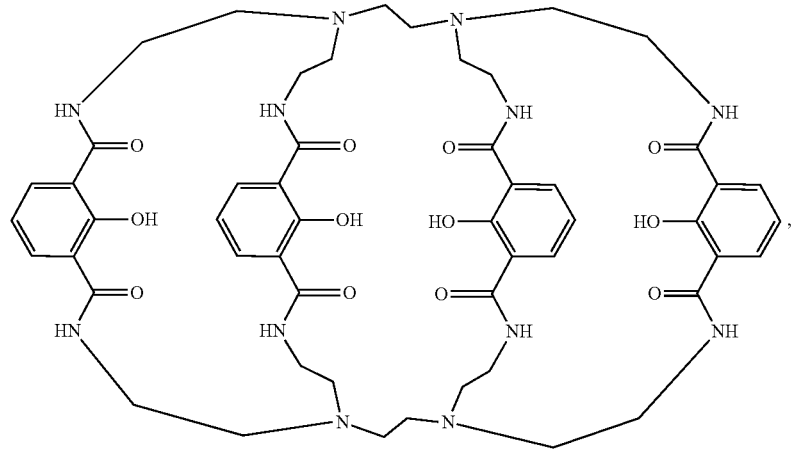 [SMILES: O=C1NCCN2CCNC(=O)c3cccc(c3O)C(=O)NCCN(CCNC(=O)c3cccc1c3O)CCN1CCNC(=O)c3cccc(c3O)C(=O)NCCN(CCNC(=O)c3cccc(c3O)C(=O)NCC1)CC2]

or a pharmaceutically acceptable salt thereof, and a lanthanide metal selected from Eu (europium), Sm (samarium), and Dy (dysprosium).

In some embodiments, the lanthanide metal is Eu (europium).

In some embodiments, the lanthanide metal is Sm (samarium).

In some embodiments, the lanthanide metal is Dy (dysprosium).

In some embodiments, the present application provides a method of using the fluorescent or luminescent complex as described herein as a fluorescent or luminescent donor in a Förster resonance energy transfer (FRET)-based biomedical assay.

In some embodiments, the fluorescent or luminescent complex as described herein comprises a fluorescence or luminescence quencher capable of modulating a lifetime of the complex.

In some embodiments, the complexes of the present application are more easily excitable than the complexes known previously. The excitation of the instant complexes is faster and more efficient. The low-energy excitation sources could be sued to excite the present complexes. This advantageously allows to increase any assay (e.g., biomedical assay) sensitivity by about 100 fold.

Salts and Pharmaceutically Acceptable Salts

In some embodiments, a salt of a compound of any one of Formulae is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form salts (e.g., pharmaceutically acceptable salts) of the compounds of any one of Formulae disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of any one of Formulae disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine Methods of Making Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized R (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "Cn-m" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methylpropan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n\text{-}m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n\text{-}m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n\text{-}m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n\text{-}m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n\text{-}m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, N=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

EXAMPLES

Reagents & Equipment

Reagents were purchased from Chem-Impex International, Aldrich, Fluka, Sigma-Aldrich Co., TCI, and Combi-Blocks and used without further purification unless otherwise noted. Thin layer chromatography was performed with pre-coated aluminum-backed TLC plates (VWR, Aluminum Oxide 60, Neutral F254 & Silica Gel 60, Neutral F254). Visualization of TLC plates was performed with ninhydrin, iodine, KMnO$_4$ or an UVGL-25 Compact UV Lamp 254/365 UV (UVP 115V~60 Hz/0.16 A). Purifications were either performed with aluminum oxide (Brockmann I, Sigma-Aldrich), silica (Silicycle), or on a Biotage Isolera 4 Purification System equipped with a 200-400 nm diode array detector. For flash purifications, Biotage SNAP Flash Chromatography Cartridges were used (KP-C18-Sil & KP-NH). Analytical LC/MS was performed on a Waters 2545 HPLC equipped with a 2998 diode array detector, a 2424 evaporative light scattering detector, a 2475 multichannel fluorescence detector, and a Waters 3100 ESI-MS module, using a XTerraMS C18 5 μm, 4.6×50 mm column at a flow rate of 5 mL/min with a linear gradient (95% A: 5% B to 100% B 90 sec and 30 sec hold at 100% B, solvent A=water+0.1% formic acid, solvent B=acetonitrile+0.1% formic acid). Proton, carbon, and fluorine nuclear magnetic resonance ($^1$H, $^{13}$C, and $^{19}$F NMR spectra) were recorded on a Bruker Avance III 400 spectrometer. Chemical shifts for protons are reported in parts per million (ppm) and are referenced to residual solvent peaks. Data is reported as follows: chemical shift, multiplicity (s=singlet, br s, =broad singlet, d=doublet, t=triplet, q=quartet, p=pentet, m=multiplet), proton coupling constants (J, Hz), and integration.

Synthetic Procedures

N-(2-chloroethyl)-4-methylbenzenesulfonamide (NCP127)

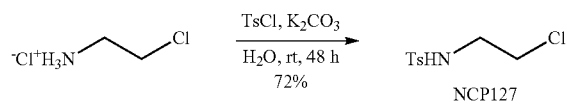

K$_2$CO$_3$ (174 g, 1.26 mol, 3 eq) was dissolved in distilled water (1.7 L). To this solution was added 2-chloroethan-1-aminium chloride (68.1 g, 587 mmol, 1.4 eq) followed by TsCl (80 g, 420 mmol, 1 eq) and the resulting suspension was stirred vigorously at room temperature for 48 h or until the characteristic aromatic TsCl resonances disappeared by $^1$H NMR analysis (CDCl$_3$). The reaction mixture was filtered. The white solid obtained was washed with distilled water and dried in vacuo overnight. Yield=78 g, 72% average yield as a white solid. $^1$H NMR (400 MHz, CDCl$_3$) δ 7.75 (d, J=7.9 Hz, 2H), 7.32 (d, J=7.9 Hz, 2H), 4.95 (s, 1H), 3.55 (t, J=5.8 Hz, 2H), 3.30 (q, J=6.0 Hz, 2H), 2.43 (s, 3H). $^{13}$C NMR (101 MHz, CDCl$_3$) δ 143.99, 136.97, 130.02, 127.17, 44.78, 43.76, 21.69.

1-tosylaziridine (NCP129)

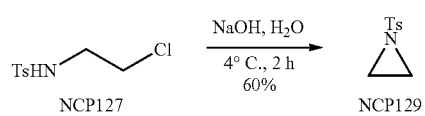

N-(2-chloroethyl)-4-methylbenzenesulfonamide (NCP127, 63.7 g, 273 mmol, 1 eq) was suspended in a pre-chilled (4° C.) solution of 1.4 M NaOH (820 mL, 1.14 mol, 4.2 eq) and the resulting suspension was stirred at 4° C. in an ice bath for 2 h or until the disappearance of the characteristic methylene resonances of NCP127 by $^1$H NMR analysis (CDCl$_3$) was observed. The reaction mixture was allowed to sit at 4° C. overnight to precipitate the product. The solid was filtered, washed with cold distilled water and dried in vacuo overnight. Yield=32.3 g, 60% average yield as a white, crystalline solid. $^1$H NMR (400 MHz, CDCl$_3$) δ 7.84 (d, J=7.9 Hz, 2H), 7.35 (d, J=8.0 Hz, 2H), 2.45 (s, 3H), 2.37 (s, 4H). $^{13}$C NMR (101 MHz, CDCl$_3$) δ 144.81, 135.01, 129.89, 128.15, 27.58, 21.80.

N,N',N'',N'''-((ethane-1,2-diylbis(azanetriyl))tetrakis(ethane-2,1-diyl))tetrakis(4-methylbenzenesulfonamide) (NCP116)

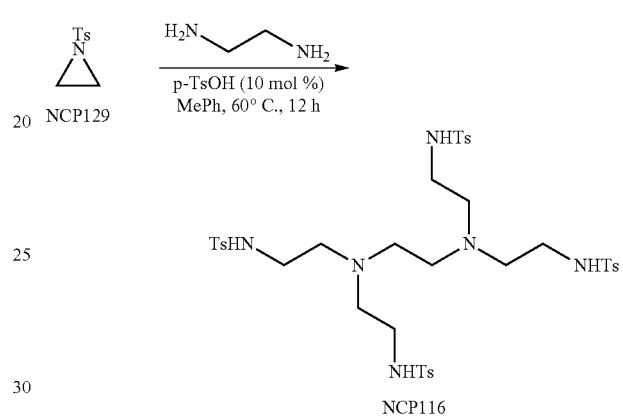

Ethylenediamine (2.56 mL, 38.33 mmol, 1 eq) was dissolved in MePh (125 mL) then p-TsOH (7.7 mL, 0.50 M in ACN, 3.83 mmol, 0.1 eq) was added followed by 1-tosylaziridine (NCP129, 33.3 g, 168.7 mmol, 4.4 eq) and the resulting reaction mixture was equipped with a reflux condenser and heated to 60° C. for 12 h. The reaction mixture was concentrated to dryness in vacuo and the resulting crude solid was suspended in MeOH (100 mL). To this suspension was added triethylamine (1.1 mL, 0.2 eq) and the suspension was stirred for 15 min at room temperature. The solid was filtered, washed with MeOH and dried in vacuo overnight. Yield=29.9 g, 92% average yield as a white, crystalline solid. $^1$H NMR (400 MHz, DMSO-d$_6$) δ 7.65 (d, J=7.9 Hz, 8H), 7.36 (s, 4H), 7.34 (d, 8H), 2.63 (t, J=7.1 Hz, 8H), 2.36 (s, 12H), 2.23 (t, J=6.7 Hz, 8H), 2.09 (s, 4H). $^{13}$C NMR (101 MHz, DMSO-d$_6$) δ 142.58, 137.69, 129.65, 126.49, 53.19, 51.00, 40.51, 20.98. MS (ESI$^{+/-}$) m/z (M+H)$^+$ 849.36, m/z (M−H)$^-$ 847.59, [calculated C$_{38}$H$_{52}$N$_6$O$_8$S$_4$: 848.27].

N1,N1'-(ethane-1,2-diyl)bis(N1-(2-aminoethyl)ethane-1,2-diamine)·6HBr (NCP119)

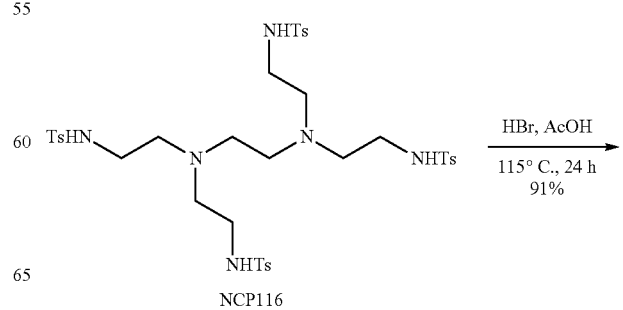

-continued

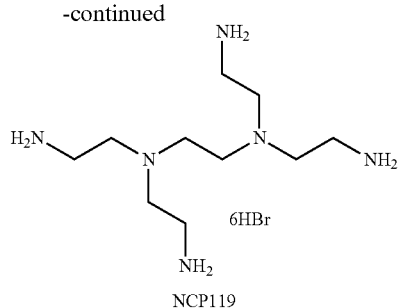

NCP119

N,N',N",N'''-((ethane-1,2-diylbis(azanetriyl))tetrakis(ethane-2,1-diyl))tetrakis(4-methylbenzenesulfonamide) (NCP116, 6.1 g, 7.2 mmol, 1 eq) was suspended in 8 mL of 48% wt aqueous HBr and 5 mL of glacial acetic acid and the resulting suspension was heated to 115° C. under reflux conditions for 24 h. The dark red solution was cooled to room temperature, at which point an off-white solid precipitated. To the reaction mixture was added 20 mL of a 1:1 solution of Et$_2$O/EtOH to further precipitate the desired product. The solid was filtered, washed with the 1:1 Et$_2$O/EtOH solution and dried in vacuo overnight. Yield=4.8 g; 91% average yield as a beige, fluffy solid. $^1$H NMR (400 MHz, D$_2$O) δ 3.17 (t, J=6.8 Hz, 8H), 3.01 (t, J=6.8 Hz, 8H), 2.98 (s, 4H). $^{13}$C NMR (101 MHz, D$_2$O) δ 50.06, 49.02, 35.77. MS (ESI$^+$) m/z (M+H)$^+$233.35, [calculated C$_{10}$H$_{28}$N$_6$: 232.24].

2-methoxyisophthalic acid (NCP123)

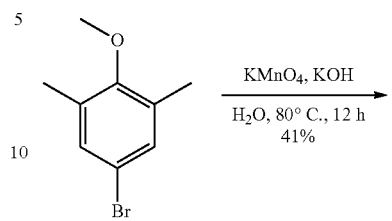

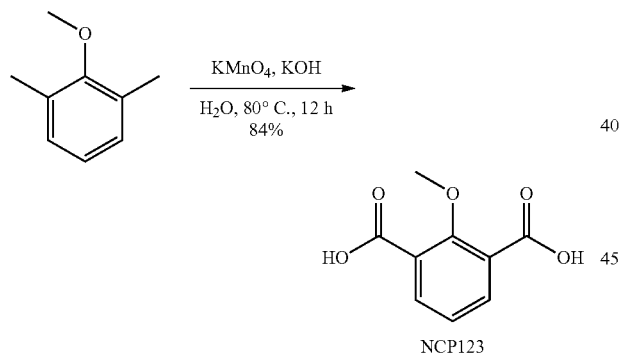

NCP123

Into 450 mL of distilled water was dissolved KOH (13.8 g, 247 mmol, 3.2 eq) then KMnO$_4$ (80.4 g, 509 mmol, 6.6 equivalents) was added, followed by 2,6-dimethylanisole (10.9 mL, 77.1 mmol, 1 eq). The reaction mixture was equipped with a reflux condenser and stirred at 80° C. for 12 h. The reaction mixture was cooled to room temperature and filtered to remove MnO$_2$. The filtrate was acidified to pH 1 with 12 N HCl to precipitate the product as white crystals. The filtrate was cooled to 4° C. overnight to aid in precipitation and the resulting solid was filtered. The solid was washed with distilled water and dried in vacuo overnight. Yield=12.8 g, 84% average yield as a white, crystalline solid. $^1$H NMR (400 MHz, DMSO-d$_6$) δ 13.12 (s, 1H), 7.81 (d, J=7.7 Hz, 2H), 7.25 (t, J=7.7 Hz, 1H), 3.80 (s, 3H). $^{13}$C NMR (101 MHz, DMSO-d$_6$) δ 167.08, 157.78, 133.57, 127.80, 123.66, 63.03. MS (ESI$^-$) m/z (M−H)$^-$ 195.12, [calculated C$_9$H$_8$O$_5$: 196.04].

5-bromo-2-methoxyisophthalic acid (NCP145)

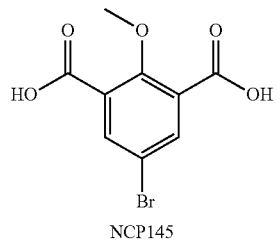

NCP145

The procedure for the synthesis of 2-methoxyisophthalic acid (NCP123) was followed, replacing 2,6-dimethylanisole with 4-bromo-2,6-dimethylanisole where necessary. The reaction was run on a 11.9 mL (74.4 mmol) scale of 4-bromo-2,6-dimethylanisole. Yield=8.5 g, 410% average yield as an off-white, fluffy solid. $^1$H NMR (400 MHz, DMSO-d$_6$) δ 13.48 (s, 2H), 7.94 (s, 2H), 3.80 (s, 3H). $^{13}$C NMR (101 MHz, DMSO-d$_6$) δ 165.65, 156.82, 135.51, 130.03, 115.09, 63.21. MS (ESI$^-$) m/z (M−H)$^-$ 273.15, [calculated C$_9$H$_7$BrO$_5$: 273.95].

2-bromoisophthalic acid (NCP252)

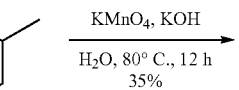

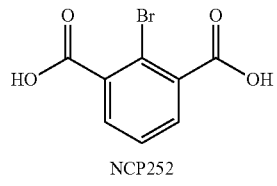

NCP252

The procedure for the synthesis of 2-methoxyisophthalic acid (NCP123) was followed, replacing 2,6-dimethylanisole with 2-bromo-1,3-dimethylbenzene where necessary. The reaction was run on a 6.0 mL (45.0 mmol) scale of 2-bromo-1,3-dimethylbenzene. Yield=3.9 g, 35% average yield as a white, crystalline solid. $^1$H NMR (400 MHz, DMSO-d$_6$) δ 13.61 (s, 2H), 7.70 (d, J=7.6 Hz, 2H), 7.52 (t, J=7.6 Hz, 1H). $^{13}$C NMR (101 MHz, DMSO) δ 167.85, 136.78, 130.81, 127.89, 116.28. MS (ESI$^-$) m/z (M−H)$^-$ 243.14, [calculated C$_8$H$_5$BrO$_4$: 243.94].

2-methoxy-3-((4-nitrophenoxy)carbonyl)benzoic acid (NCP153)

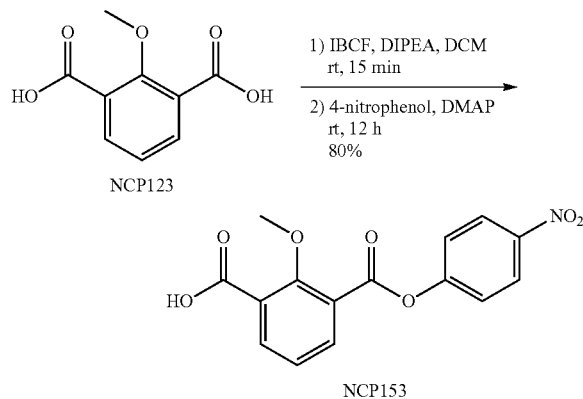

2-methoxyisophthalic acid (NCP123, 3.0 g, 15.3 mmol, 1 eq) and DIPEA (10.7 mL, 61.2 mmol, 4 eq) were dissolved in DCM (100 mL) under an atmosphere of Ar. Isobutyl chloroformate (2.21 mL, 16.8 mmol, 1.1 eq) was added dropwise as a solution in 10 mL DCM over 15 min via a syringe pump. The reaction mixture was stirred for 15 min at room temperature then 4-nitrophenol (2.6 g, 18.4 mmol, 1.2 eq) was added, followed by DMAP (93 mg, 0.8 mmol, 0.05 eq) upon complete dissolution of the 4-nitrophenol. Upon addition of DMAP, vigorous gas evolution occurred. The reaction was stirred at room temperature for 12 h to allow for equilibration. The mixture was diluted into 100 mL DCM and the organic layer was washed 2×200 mL 0.2 N HCl, keeping the pH of the aqueous washes at ~1. The product was extracted with 3×200 mL 0.2 N NaHCO$_3$, with minimal saturated brine solution being added to separate layers if necessary. The combined aqueous layers were slowly acidified to pH 1 with 12 N HCl to precipitate a white, fluffy solid, which was collected via filtration, washed with water then dried in vacuo overnight. Yield=3.8 g, 80% average yield as a white solid. $^1$H NMR (400 MHz, DMSO-d$_6$) δ 13.31 (s, 1H), 8.37 (d, J=9.4 Hz, 2H), 8.16 (d, J=7.8 Hz, 1H), 7.99 (d, J=7.7 Hz, 1H), 7.63 (d, 2H), 7.40 (t, J=7.7 Hz, 1H), 3.89 (s, 3H). $^{13}$C NMR (101 MHz, DMSO-d$_6$) δ 166.70, 162.80, 158.90, 155.27, 145.29, 135.53, 134.68, 128.14, 125.43, 124.48, 124.02, 123.37, 63.40. MS (ESI$^-$) m/z (M–H)$^-$ 316.24, [calculated C$_{15}$H$_{11}$NO$_7$: 317.05].

5-bromo-2-methoxy-3-((4-nitrophenoxy)carbonyl) benzoic acid (NCP255)

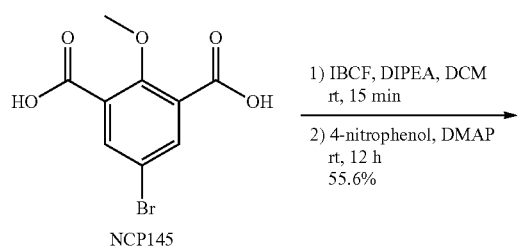
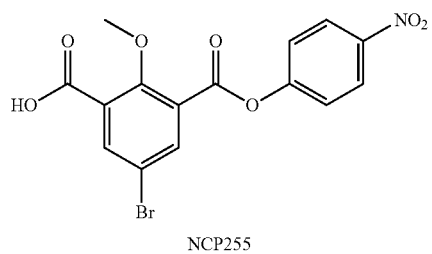

The procedure for the synthesis of 2-methoxy-3-((4-nitrophenoxy)carbonyl)benzoic acid (NCP153) was followed, replacing 2-methoxyisophthalic acid (NCP123) with 5-bromo-2-methoxyisophthalic acid (NCP145) where necessary. The reaction was run on a 750 mg (2.7 mmol) scale of 5-bromo-2-methoxyisophthalic acid (NCP145). Yield=600.5 mg, 55.6% average yield as a white solid. $^1$H NMR (400 MHz, DMSO-d$_6$) δ 13.63 (s, 1H), 8.38 (d, J=8.6 Hz, 2H), 8.33 (s, 1H), 8.11 (s, 1H), 7.66 (d, J=8.6 Hz, 2H), 3.89 (s, 3H). $^{13}$C NMR (101 MHz, DMSO-d$_6$) δ 165.32, 161.51, 157.84, 155.05, 145.39, 137.35, 136.54, 130.24, 126.74, 125.41, 123.37, 115.32, 63.57. MS (ESI$^-$) m/z (M–H)$^-$ 394.20, [calculated C$_{15}$H$_{10}$BrNO$_7$: 394.96].

3-((4-nitrophenoxy)carbonyl)benzoic acid (NCP251)

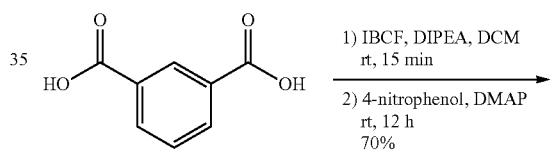

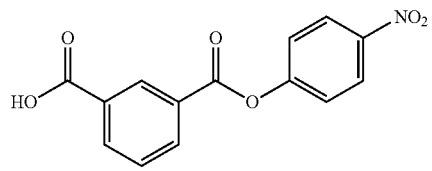

The procedure for the synthesis of 2-methoxy-3-((4-nitrophenoxy)carbonyl)benzoic acid (NCP153) was followed, replacing 2-methoxyisophthalic acid (NCP123) with isophthalic acid where necessary. The reaction was run on a 500 mg (3.0 mmol) scale of isophthalic acid. Yield=600 mg, 70% average yield as a white solid. $^1$H NMR (400 MHz, DMSO-d$_6$) δ 13.46 (s, 1H), 8.65 (s, 1H), 8.41-8.34 (m, 3H), 8.30 (d, J=7.6 Hz, 1H), 7.77 (t, J=7.8 Hz, 1H), 7.66 (d, J=8.7 Hz, 2H). $^{13}$C NMR (101 MHz, DMSO-d$_6$) δ 166.34, 163.35, 155.41, 145.31, 134.75, 134.06, 131.62, 130.55, 129.69, 128.94, 125.36, 123.44, 54.94. MS (ESI$^-$) m/z (M–H)$^-$ 286.22, [calculated C$_{14}$H$_9$NO$_6$: 287.04].

2-bromo-3-((4-nitrophenoxy)carbonyl)benzoic acid (NCP253)

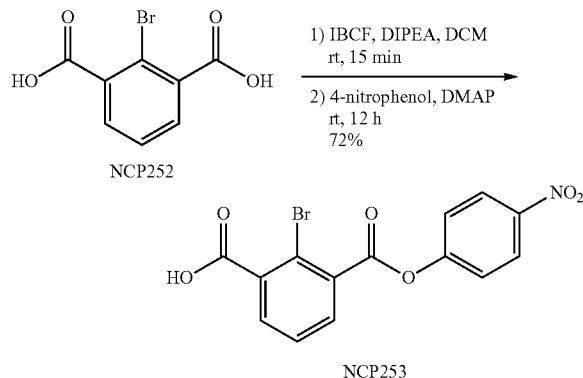

The procedure for the synthesis of 2-methoxy-3-((4-nitrophenoxy)carbonyl)benzoic acid (NCP153) was followed, replacing 2-methoxyisophthalic acid (NCP123) with 2-bromoisophthalic acid (NCP252) where necessary. The reaction was run on a 600 mg (2.5 mmol) scale of 2-bromoisophthalic acid (NCP252). Yield=647 mg, 72% average yield as a white solid. $^1$H NMR (400 MHz, DMSO-d$_6$) δ 13.79 (s, 1H), 8.39 (d, J=8.7 Hz, 2H), 8.11 (d, J=7.6 Hz, 1H), 7.88 (d, J=7.7 Hz, 1H), 7.72-7.64 (m, 3H). $^{13}$C NMR (101 MHz, DMSO-d$_6$) δ 167.51, 163.87, 154.92, 145.52, 137.16, 133.17, 132.56, 132.33, 128.22, 125.54, 123.23, 117.47. MS (ESI$^-$) m/z (M–H)$^-$ 364.16, [calculated C$_{14}$H$_8$BrNO$_6$: 364.95].

6-((4-nitrophenoxy)carbonyl)picolinic acid (NCP256)

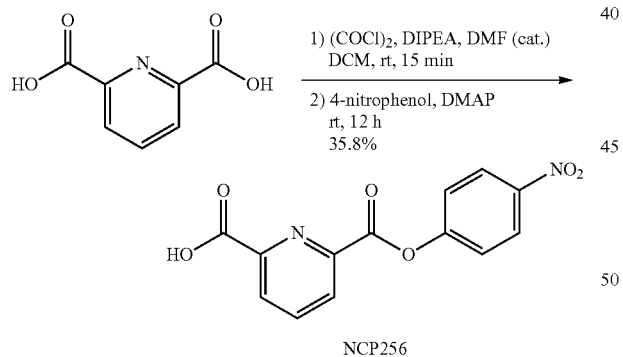

Dipicolinic acid (750 mg, 4.5 mmol, 1 eq) and DIPEA (3.9 mL, 22.4 mmol, 5 eq) were dissolved in DCM (50 mL) and 100 uL catalytic DMF was added. To the reaction mixture was added dropwise over 15 min a solution of oxalyl chloride (471 uL, 5.4 mmol, 1.2 eq) in 5 mL DCM under an atmosphere of Ar with vigorous gas evolution occurring. After 10 min or when gas evolution ceased, 4-nitrophenol (812 mg, 5.8 mmol, 1.3 eq) and, upon complete dissolution of 4-nitrophenol, DMAP (27.4 mg, 224 umol, 0.05 eq) were added and the reaction was stirred at room temperature for 12 h to allow for equilibration. The reaction mixture was diluted into 50 mL DCM and the organic layer was washed 2×100 mL 0.2 N HCl, keeping the pH of the aqueous washes at ~1. The product was extracted with 3×100 mL 0.2 N NaHCO$_3$, with minimal saturated brine solution being added to separate layers if necessary (note: this compound is prone to forming emulsions—allow ample time for layer separation). The combined aqueous layers were slowly acidified to pH 1 with 12 N HCl to precipitate a brown, fluffy solid, which was collected via filtration, washed with water then dried in vacuo overnight. Yield=462.8 mg, 35.8% average yield as a tan solid. $^1$H NMR (400 MHz, DMSO-d$_6$) δ 13.66 (s, 1H), 8.44 (d, J=7.7 Hz, 1H), 8.38 (d, J=8.6 Hz, 2H), 8.35 (d, J=7.8 Hz, 1H), 8.27 (t, J=7.8 Hz, 1H), 7.67 (d, J=8.7 Hz, 2H). $^{13}$C NMR (101 MHz, DMSO-d$_6$) δ 165.52, 162.35, 155.52, 149.14, 146.43, 145.40, 139.39, 128.70, 128.66, 125.45, 123.44. MS (ESI$^{+/-}$) m/z (M+H)$^+$ 289.08, m/z (M–H)$^-$ 287.26, [calculated C$_{13}$H$_8$N$_2$O$_6$: 288.04].

2-methoxy-3-((2,3,5,6-tetrafluorophenoxy)carbonyl)benzoic acid (NCP200)

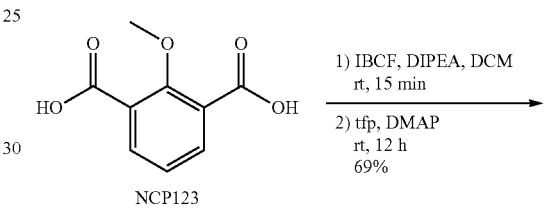

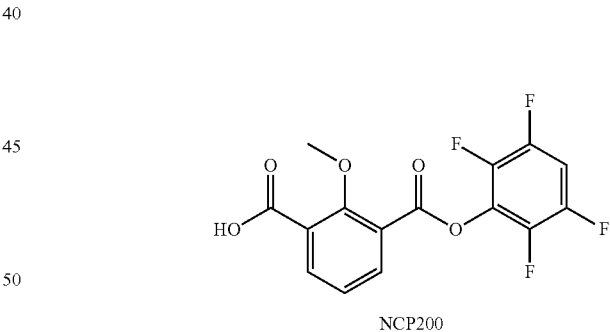

The procedure for the synthesis of 2-methoxy-3-((4-nitrophenoxy)carbonyl)benzoic acid (NCP153) was followed, replacing 4-nitrophenol with 2,3,5,6-tetrafluorophenol (Tfp) where necessary. The reaction was run on a 2.0 g (10.2 mmol) scale of 2-methoxyisophthalic acid (NCP123). Yield=2.4 g, 69% average yield as a white solid. $^1$H NMR (400 MHz, CDCl$_3$) δ 8.39 (d, J=7.8 Hz, 1H), 8.33 (d, J=7.8 Hz, 1H), 7.44 (t, J=7.8 Hz, 1H), 7.10 (p, 1H), 4.10 (s, 3H). $^{13}$C NMR (101 MHz, CDCl$_3$) δ 166.82, 161.13, 160.50, 147.48, 145.05, 142.00, 139.52, 138.68, 137.70, 129.53, 124.95, 124.70, 122.63, 103.86, 64.87. $^{19}$F NMR (377 MHz, CDCl$_3$) δ −138.45, −152.67. MS (ESI$^-$) m/z (M–H)$^-$ 343.23, [calculated C$_{15}$H$_8$F$_4$O$_5$: 344.03].

5-bromo-2-methoxy-3-((2,3,5,6-tetrafluorophenoxy)carbonyl)benzoic acid (NCP216)

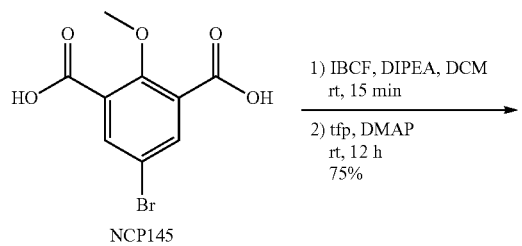

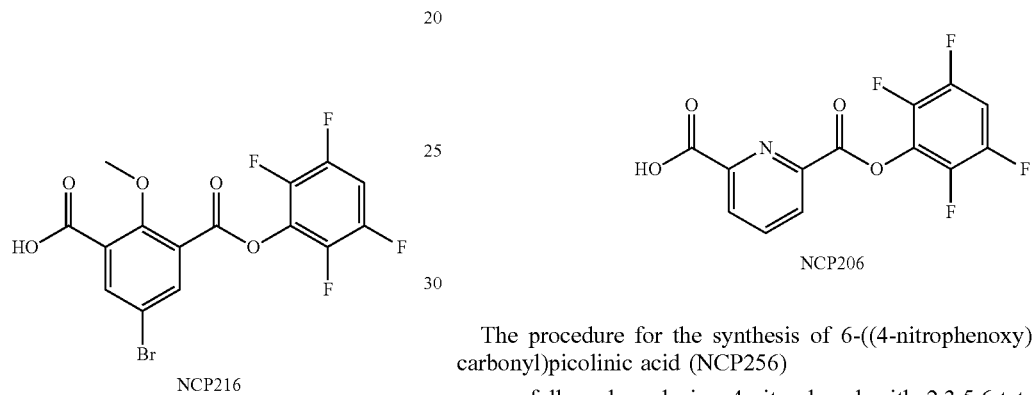

The procedure for the synthesis of 2-methoxy-3-((4-nitrophenoxy)carbonyl)benzoic acid (NCP153) was followed, replacing 4-nitrophenol with 2,3,5,6-tetrafluorophenol (Tfp) and 2-methoxyisophthalic acid (NCP123) with 5-bromo-2-methoxyisophthalic acid (NCP145) where necessary. The reaction was run on a 2.0 g (7.3 mmol) scale of 5-bromo-2-methoxyisophthalic acid (NCP145). Yield=2.3 g, 75% average yield as a white solid. MS (ESI$^-$) m/z (M−H)$^-$ 421.20, [calculated $C_{15}H_7BrF_4O_5$: 421.94].

6-((2,3,5,6-tetrafluorophenoxy)carbonyl)picolinic acid (NCP206)

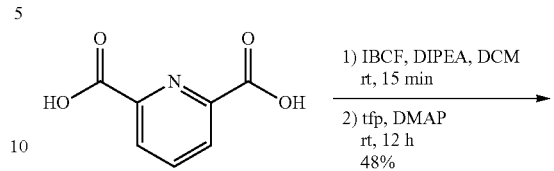

The procedure for the synthesis of 6-((4-nitrophenoxy)carbonyl)picolinic acid (NCP256) was followed, replacing 4-nitrophenol with 2,3,5,6-tetrafluorophenol (Tfp) where necessary. The reaction was run on a 2.0 g (12.0 mmol) scale of dipicolinic acid. Yield=1.8 g, 48% average yield as a tan solid. MS (ESI$^{+/-}$) m/z (M+H)$^+$ 316.17, m/z (M−H)$^-$ 314.23, [calculated $C_{13}H_5F_4NO_4$: 315.02].

3,3',3'',3'''-(5,8-bis(2-formamidoethyl)-2,5,8,11-tetraazadodecanedioyl)tetrakis(2-methoxybenzoic acid) ·2HCl (NCP133)

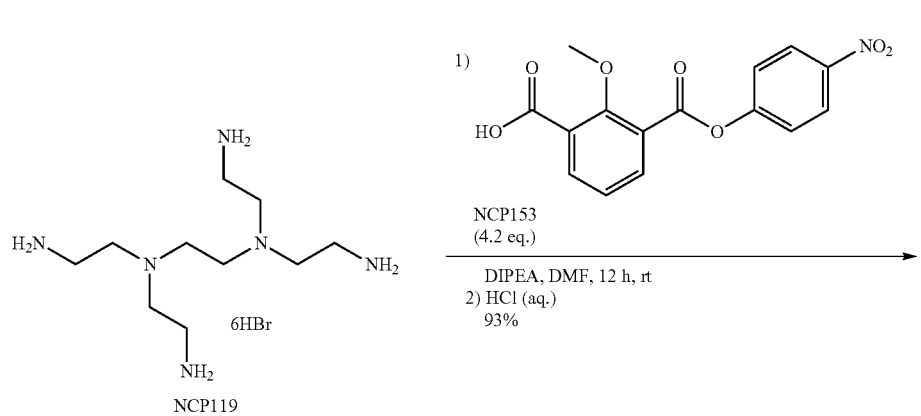

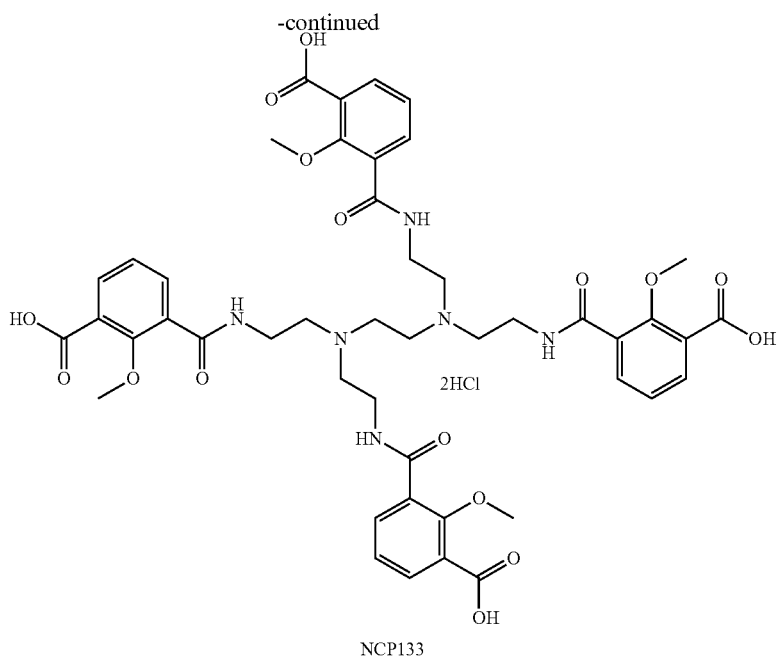

NCP133

N1,N1'-(ethane-1,2-diyl)bis(N1-(2-aminoethyl)ethane-1,2-diamine)-6HBr (NCP119, 150 mg, 209 umol, 1.0 eq) was dissolved in DMF (3 mL) with DIPEA (510 uL, 2.9 mmol, 14 eq) then 2-methoxy-3-((4-nitrophenoxy)carbonyl)benzoic acid (NCP153, 278 mg, 878 umol, 4.2 eq) was added as a solution in 3 mL DMF. The reaction mixture was stirred for 12 h at room temperature then cooled to 4° C. in an ice bath. Once cooled, aqueous HCl (12.0 M, 350 uL, 4.2 mmol, 20 eq) was added. The reaction was allowed to come to room temperature and was stirred for 15 min to ensure complete acidification of all basic species. The reaction mixture was concentrated in vacuo to an oil, which was triturated with ACN (20 mL) to precipitate the desired product as the dihydrochloride salt. The mixture was allowed to settle and the mother liquor was carefully decanted. The solid was briefly dried in vacuo and the trituration process was repeated twice more. Yield=198 mg, 93% average yield as a white, fluffy solid. $^1$H NMR (400 MHz, MeOD) δ 7.90 (d, J=7.7 Hz, 4H), 7.82 (d, J=7.8 Hz, 4H), 7.16 (t, J=7.7 Hz, 4H), 4.13 (s, 4H), 3.96 (br s, 8H), 3.85 (s, 12H), 3.75 (t, 8H). $^{13}$C NMR (101 MHz, MeOD) δ 169.86, 168.67, 159.68, 136.10, 135.62, 128.73, 127.36, 124.94, 64.11, 57.05, 48.90, 36.92. MS (ESI$^{+/-}$) m/z (M+H)$^+$ 945.78, m/z (M−H)$^-$ 943.68, [calculated $C_{46}H_{52}N_6O_{16}$: 944.34].

Me$_4$BH(2,2)IAM (NCP102)

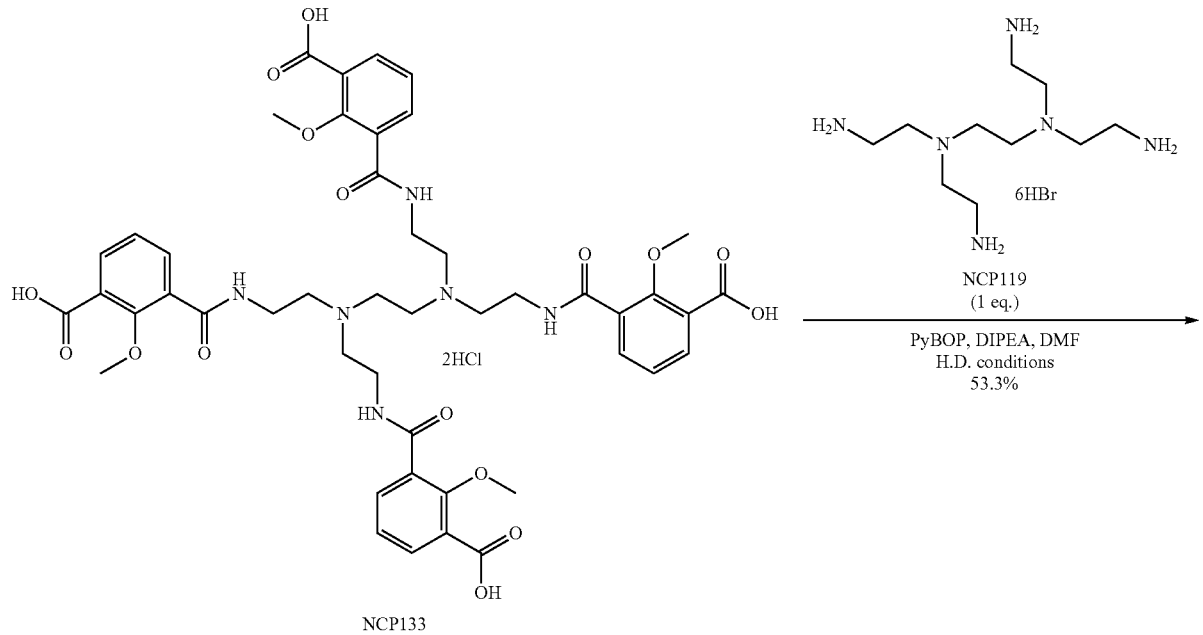

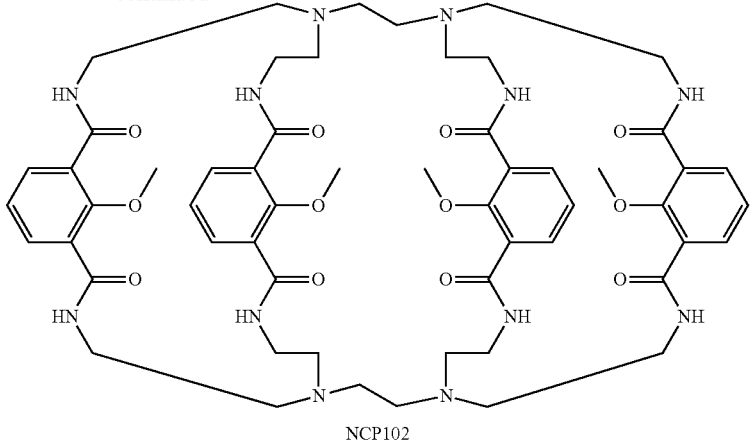

NCP102

PyBOP (43.0 mg, 84 umol, 6.0 eq) and DIPEA (30 uL, 170 umol, 12 eq) were dissolved in DMF (15 mL) in a 50 mL round bottom flask. In separate containers, solutions of the amine portion and acid portion were created. For the amine solution, N1,N1'-(ethane-1,2-diyl)bis(N1-(2-aminoethyl)ethane-1,2-diamine)-6HBr (NCP119, 10.0 mg, 14 umol, 1 eq) and DIPEA (30 uL, 170 umol, 12 eq) were dissolved in 970 uL DMF to create a 1 mL solution of ~14 mM NCP119. For the acid solution, 3,3',3'',3'''-(5,8-bis(2-formamidoethyl)-2,5,8,11-tetraazadodecanedioyl)tetrakis (2-methoxybenzoic acid) (NCP133, 15.8 mg, 15.5 umol, 1.1 eq) and DIPEA (15 uL, 85 uL, 6 eq) were dissolved in 985 uL DMF to create a 1 mL solution of ~15 mM NCP133. At the start of the reaction, half of the NCP133/DIPEA solution (500 uL) was added to the 15 mL solution of PyBOP/DIPEA with good stirring. The solution was stirred for 15 min at room temperature to allow for complete HOBt ester formation. After, 250 uL of the NCP119/DIPEA solution was added dropwise over 10 min (approximately 1 drop every 3 seconds). This amount and order of addition of reagents ensures there is always an excess of HOBt ester-activated NCP133 relative to amine NCP119 in solution, while keeping the maximum effective concentration of reactants at approximately 500 uM. Upon complete addition of the initial 250 uL of NCP119/DIPEA solution, the reaction mixture was stirred for 15 min at room temperature. After 15 min, 250 uL of the NCP133/DIPEA solution was added dropwise over 10 min then stirred for 15 min at room temperature. This process was repeated until both all NCP133/DIPEA and NCP119/DIPEA solutions were added, with the final two additions being two sequential additions of the NCP119/DIPEA solution. Once all reagents were added, the reaction mixture was stirred for 12 h at room temperature. The reaction mixture was concentrated and the crude oil was purified via reverse-phase flash chromatography (C18, 5% ACN/H$_2$O/0.1% FA for 3 CV, 5% ACN to 30% ACN/H$_2$O/0.1% FA over 10 CV, 30% ACN to 100% ACN/H$_2$O/0.1% FA over 1 CV, 100% ACN/0.1% FA for 3 CV). Yield=8.1 mg, 53.3% as a colorless oil. MS (ESI$^{+/-}$) m/z (M+H)$^+$ 1106.11, m/z (M−H)$^-$ 1103.73, [calculated C$_{56}$H$_{72}$N$_{12}$O$_{12}$: 1104.54].

BH(2,2)IAM (NCP134)

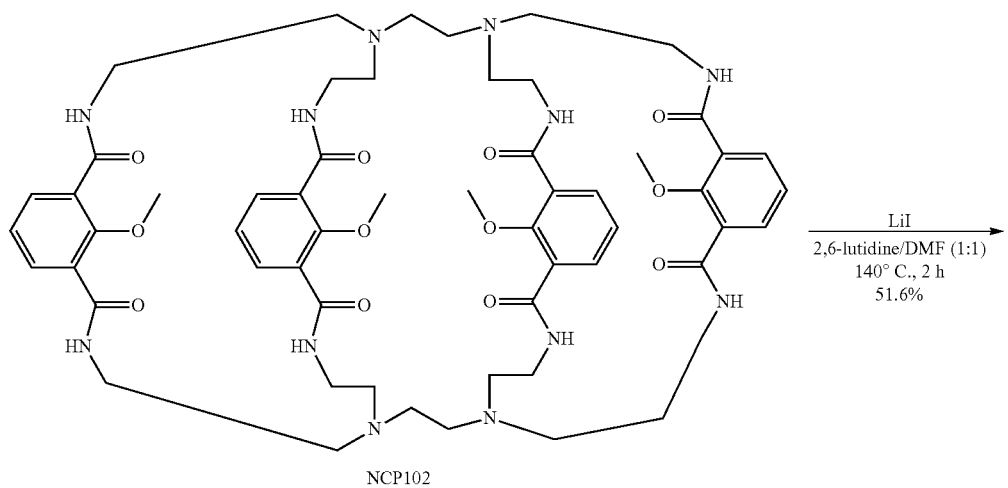

NCP102

$\xrightarrow{\text{LiI}}$ 2,6-lutidine/DMF (1:1) 140° C., 2 h 51.6%

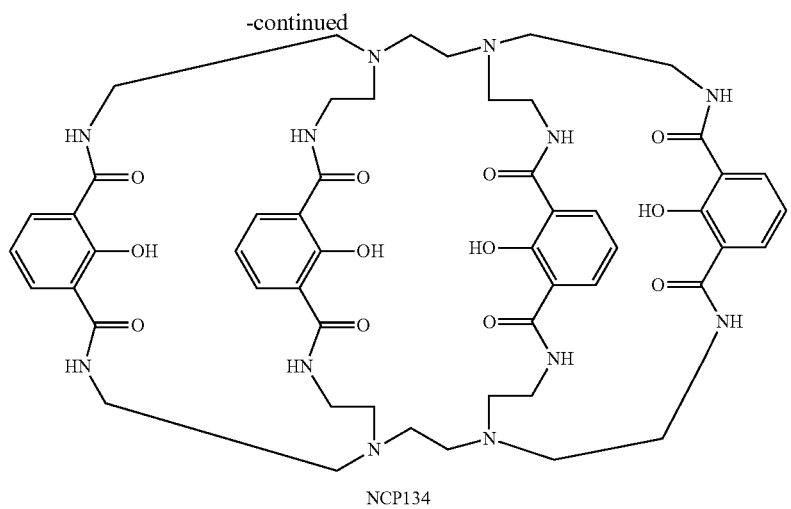

NCP134

Me₄BH(2,2)IAM (NCP102, 10.0 mg, 9.1 umol, 1 eq) was dissolved in 1:1 2,6-lutidine/DMF (1 mL) then LiI (19.5 mg, 146 umol, 16 eq) was added and the reaction was heated to 140° C. for 2 h under reflux conditions. The reaction mixture was concentrated and purified via reverse-phase flash chromatography (5% ACN/H₂O/0.1% FA for 3 CV, 5% ACN to 30% ACN/H₂O/0.1% FA over 10 CV, 30% ACN to 100% ACN/H₂O/0.1% FA over 1 CV, 100% ACN/0.1% FA for 3 CV). Yield=5 mg, 51.6% as a colorless oil. MS (ESI$^{+/-}$) m/z (M+H)$^+$ 1050.00, m/z (M−H)$^-$ 1047.73, [calculated $C_{52}H_{64}N_{12}O_{12}$: 1048.48].

3,3′,3″,3‴-(5,8-bis(2-formamidoethyl)-2,5,8,11-tetraazadodecanedioyl)tetrakis(5-bromo-2-methoxybenzoic acid) (NCP156)

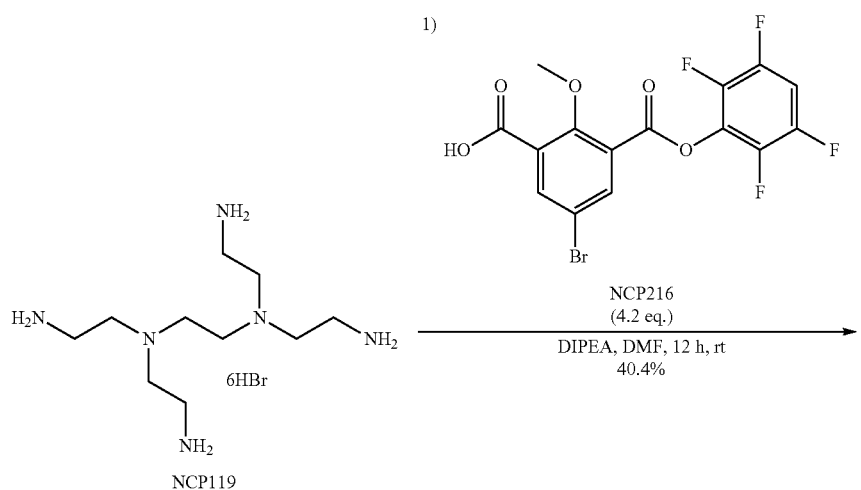

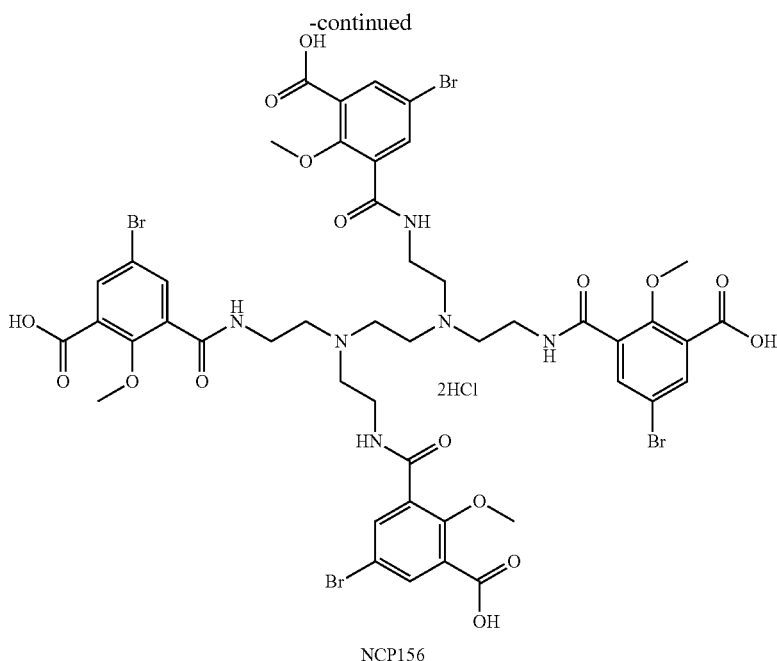

NCP156

The procedure for the synthesis of 3,3',3'',3'''-(5,8-bis(2-formamidoethyl)-2,5,8,11-tetraazadodecanedioyl)tetrakis(2-methoxybenzoic acid) (NCP133) was followed, replacing 2-methoxy-3-((4-nitrophenoxy)carbonyl)benzoic acid (NCP153) with 5-bromo-2-methoxy-3-((2,3,5,6-tetrafluorophenoxy)carbonyl)benzoic acid (NCP216) where necessary. The reaction was run on a 21.0 mg (28 umol) scale of N1,N1'-(ethane-1,2-diyl)bis(N1-(2-aminoethyl)ethane-1,2-diamine)-6HBr (NCP119). The purification gradient used was: (C18, 5% ACN/H$_2$O/0.1% FA for 4 CV, 5% to 100% ACN/H$_2$O/0.1% FA over 10 CV, 100% ACN/0.1% FA for 3 CV). Yield=14.9 mg, 40.4% as a white solid. MS (ESI$^{+/-}$) m/z (M+H)$^+$ 1257.62, m/z (M−H)$^−$ 1255.39, [calculated C$_{46}$H$_{48}$Br$_4$N$_6$O$_{16}$: 1255.99].

Me$_4$Br$_4$BH(2,2)IAM (NCP157)

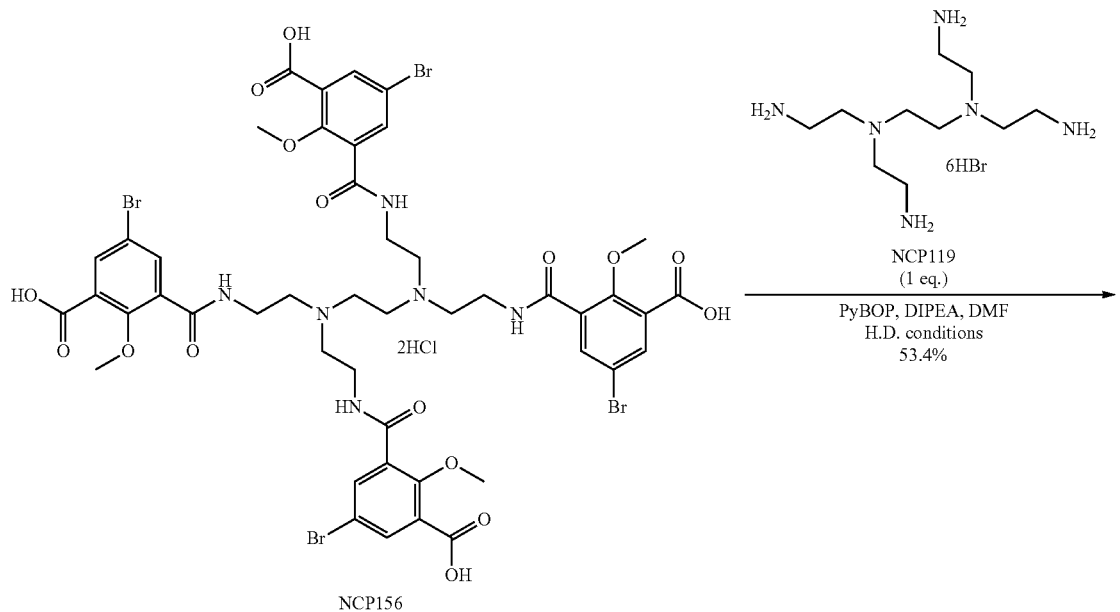

-continued

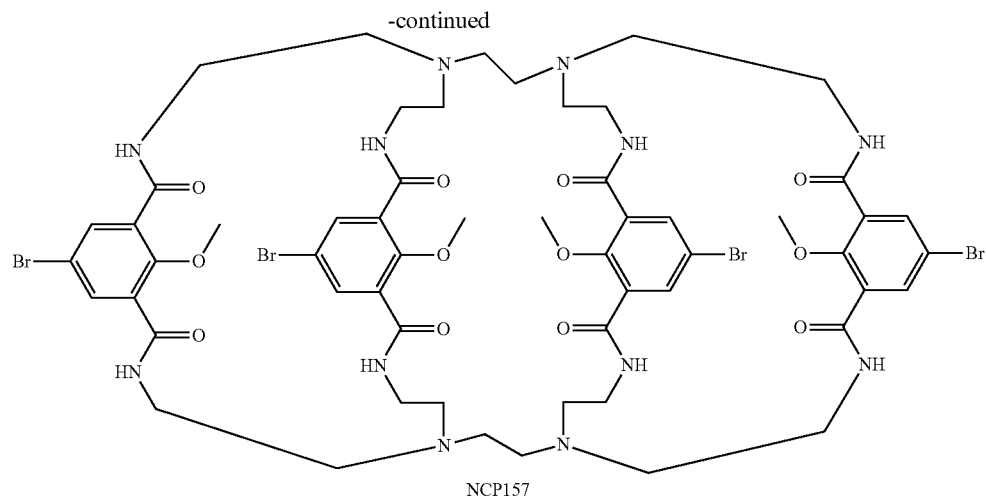

NCP157

The procedure for the synthesis of Me₄BH(2,2)IAM (NCP102) was followed, replacing 3,3',3",3"'-(5,8-bis(2-formamidoethyl)-2,5,8,11-tetraazadodecanedioyl)tetrakis (2-methoxybenzoic acid) (NCP133) with 3,3',3",3"'-(5,8-bis (2-formamidoethyl)-2,5,8,11-tetraazadodecanedioyl) tetrakis(5-bromo-2-methoxybenzoic acid) (NCP156) where necessary. The reaction was run on a 10.2 mg (14 umol) scale of N1,N1'-(ethane-1,2-diyl)bis(N1-(2-aminoethyl)eth-ane-1,2-diamine)-6HBr (NCP119). Yield=9.0 mg, 53.4% as a colorless oil. MS (ESI$^{+/-}$) m/z (M+H)$^+$ 1417.87, m/z (M−H)$^−$ 1415.82, [calculated C$_{56}$H$_{68}$Br$_4$N$_{12}$O$_{12}$: 1416.18].

Br₄BH(2,2)IAM (NCP158)

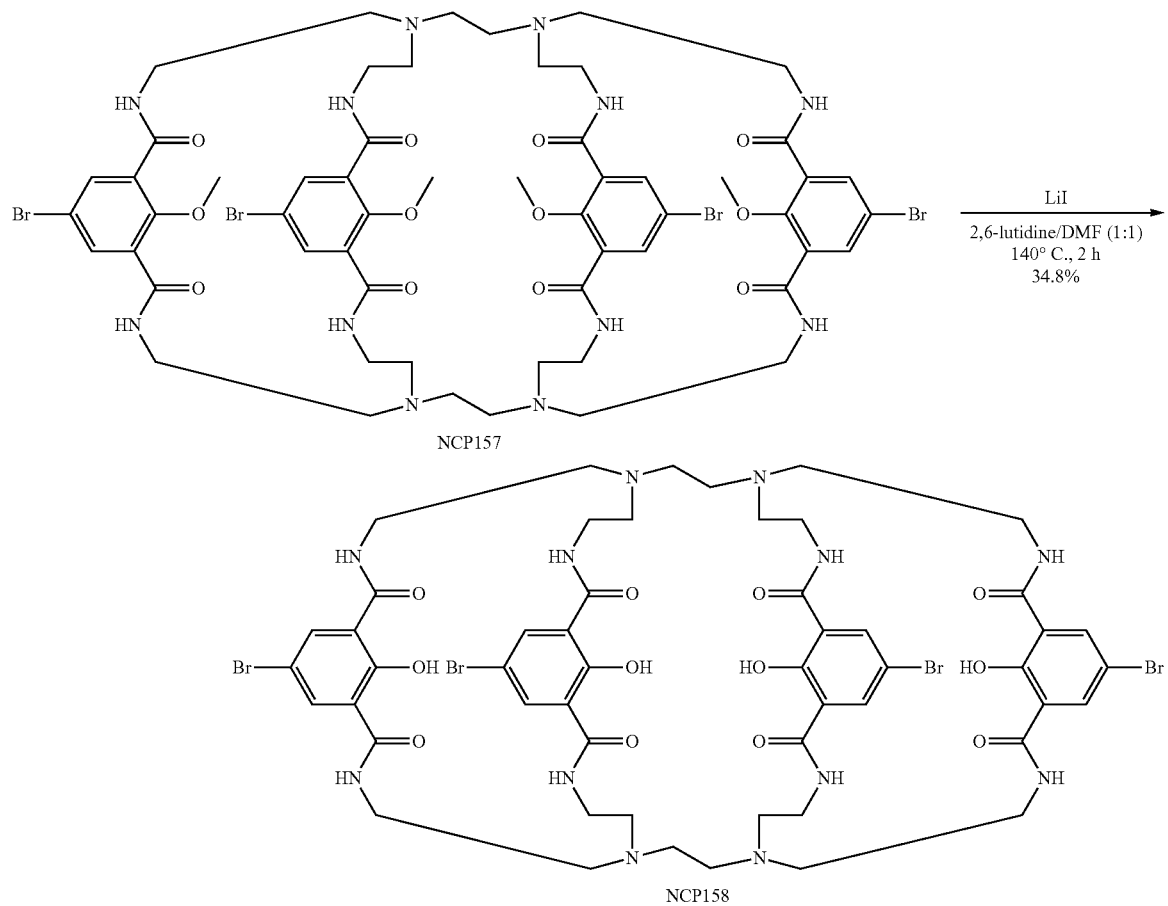

The procedure for the synthesis of BH(2,2)IAM (NCP134) was followed, replacing Me$_4$BH(2,2)IAM (NCP102) with Me$_4$Br$_4$BH(2,2)IAM (NCP157) where necessary. The reaction was run on a 9 mg (6.3 umol) scale of Me$_4$Br$_4$BH(2,2)IAM (NCP157). Yield=3.0 mg, 34.8% as a colorless oil. MS (ESI$^{+/-}$) m/z (M+H)$^+$ 1361.82, m/z (M−H)$^-$ 1359.57, [calculated C$_{52}$H$_{60}$Br$_4$N$_{12}$O$_{12}$: 1360.12].

6-((N-(2-((2-(bis(2-((4-methylphenyl)sulfonamido) ethyl)amino)ethyl)(2-((4-methylphenyl)sulfonamido) ethyl)amino)ethyl)-4-methylphenyl)sulfonamido) hexanoic acid (NCP165)

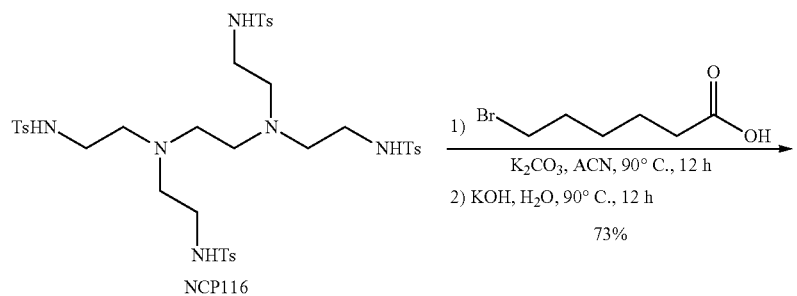

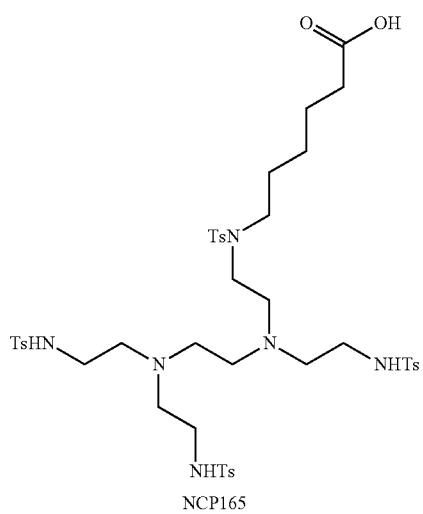

N,N',N'',N'''-((ethane-1,2-diylbis(azanetriyl))tetrakis(ethane-2,1-diyl))tetrakis(4-methylbenzenesulfonamide) (NCP116, 5.0 g, 5.9 mmol, 3.2 eq) and K$_2$CO$_3$ (1.1 g, 7.8 mmol, 4.25 eq) were suspended in ACN (125 mL) then ethyl 6-bromohexanoate (327 uL, 1.8 mmol, 1 eq) was added and the reaction mixture was equipped with a reflux condenser and heated to 90° C. for 12 h. The reaction mixture was filtered while hot to remove carbonate salts. The filtrate was re-heated to 90° C. to dissolve any precipitated starting material then allowed to cool to room temperature before being put at −20° C. overnight to recrystallize unreacted starting material. The solution was filtered and the solid was washed with minimal ACN (2.5 g NCP116 recovered). The filtrate was concentrated to dryness in vacuo then the crude product was suspended in 1 N KOH (100 mL) and heated to 90° C. for 2 h, or until all solid went into solution. The pH was adjusted to 7 with 12 N HCl to precipitate the crude, saponified product as a white, waxy solid. The mother liquor was decanted and the solid was washed with water. The crude solid was suspended in hot MePh, concentrated and dried overnight in vacuo to remove residual water. The crude product was purified via flash chromatography (loading solvent: 1% MeOH/DCM [only soluble material loaded]; k 230 nm, 263 nm; gradient: 100% DCM for 2 CV, 100% DCM to 4% MeOH/DCM over 4 CV, 4% MeOH/DCM for 4 CV, 4% to 10% MeOH/DCM over 2 CV, 10% MeOH/DCM for 3 CV). Additional starting material is also recovered from the column. Yield=1.3 g, 73% average yield as a white solid. Total starting material recovered=3.1 g. $^1$H NMR (400 MHz, CDCl$_3$) δ 7.75 (d, J=7.9 Hz, 2H), 7.71 (d, J=7.9 Hz, 4H), 7.66 (d, J=7.9 Hz, 2H), 7.30 (d, 2H), 7.27 (d, J=8.2 Hz, 6H), 6.23 (s, 3H), 3.13 (t, J=7.3 Hz, 2H), 3.02 (t, J=7.4 Hz, 2H), 2.97 (t, J=5.6 Hz, 2H), 2.89 (t, J=5.3 Hz, 2H), 2.69 (t, J=7.4 Hz, 2H), 2.63 (q, J=7.2, 6.7 Hz, 4H), 2.52-2.44 (m, 6H), 2.41 (s, 3H), 2.39 (s, 6H), 2.38 (s, 3H), 2.35 (t, J=7.0 Hz, 2H), 1.62 (p, J=7.0 Hz, 2H), 1.48 (p, J=7.3 Hz, 2H), 1.30 (p, J=7.7 Hz, 2H). $^{13}$C NMR (101 MHz, CDCl$_3$) δ 178.77, 143.59, 143.49, 136.97, 136.83, 136.81, 136.17, 136.15, 129.94, 129.88, 127.33, 127.28, 127.18, 54.08, 53.69, 53.50, 52.48, 51.56, 49.32, 45.88, 40.61, 34.20, 28.02, 26.03, 24.20, 21.65. MS (ESI$^{+/-}$) m/z (M+H)$^+$ 963.34, m/z (M−H)$^-$ 961.61, [calculated C$_{44}$H$_{62}$N$_6$O$_{10}$S$_4$: 962.34].

Ethyl 6-((2-((2-aminoethyl)(2-(bis(2-aminoethyl)amino)ethyl)amino)ethyl)amino)hexanoate-6HBr (NCP233)

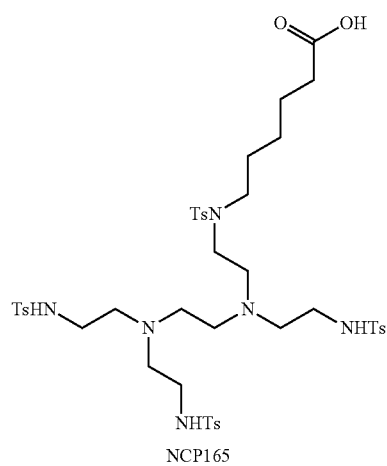

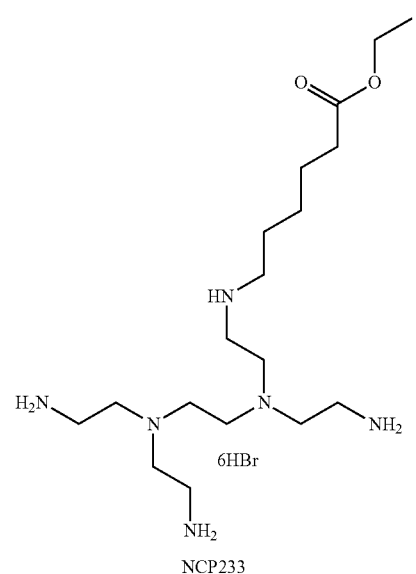

6-((N-(2-((2-(bis(2-((4-methylphenyl)sulfonamido)ethyl)amino)ethyl)(2-((4-methylphenyl)sulfonamido)ethyl)amino)ethyl)-4-methylphenyl)sulfonamido)hexanoic acid (NCP165, 1.03 g, 1.07 mmol) was suspended in 3 mL 48% wt HBr and 2 mL of glacial acetic acid and the resulting suspension was heated to 115° C. under reflux conditions for 48 h. The solution was cooled to room temperature and 15 mL 1:1 EtOH/Et$_2$O solution was added to precipitate the crude product as a waxy solid. The precipitate was allowed to collect in an ice bath for 10 min then the mother liquor was decanted and the solid was washed twice more with the EtOH/Et$_2$O solution and dried in vacuo. Once dried, the crude solid was re-dissolved in 2 mL 48% wt HBr and the precipitation process was repeated to ensure complete removal of acetate/p-TsoH salts. The resulting dried solid was then suspended in EtOH (10 mL) and 48% wt HBr (10 uL, 107 umol, 0.1 eq) was added then the suspension was heated to 85° C. under reflux conditions for 2 h or until all solid went into solution. The reaction mixture was cooled to room temperature then further cooled in an ice bath to precipitate the product, which was collected via centrifugation, washed with cold ethanol and dried overnight in vacuo. Yield=660 mg, 72% average yield as an off-white solid. $^1$H NMR (400 MHz, D$_2$O) δ 4.15 (q, J=7.0 Hz, 2H), 3.40-3.17 (m, 20H), 3.13 (t, J=7.2 Hz, 2H), 2.40 (t, J=7.1 Hz, 2H), 1.74 (p, J=7.0 Hz, 2H), 1.63 (p, J=7.2 Hz, 2H), 1.41 (p, J=7.1 Hz, 2H), 1.24 (t, J=7.0 Hz, 3H). $^{13}$C NMR (101 MHz, D$_2$O) δ 176.92, 61.74, 50.04, 49.35, 49.07, 48.98, 48.09, 43.37, 35.64, 35.38, 33.71, 25.26, 25.20, 23.75, 13.41. MS (ESI$^+$) m/z (M+H)$^+$ 375.51, [calculated C$_{18}$H$_{42}$N$_6$O$_2$: 374.34].

Me₄BH(2,2)IAM-N-hexanoic acid
(NCP240—6-carbon linker)

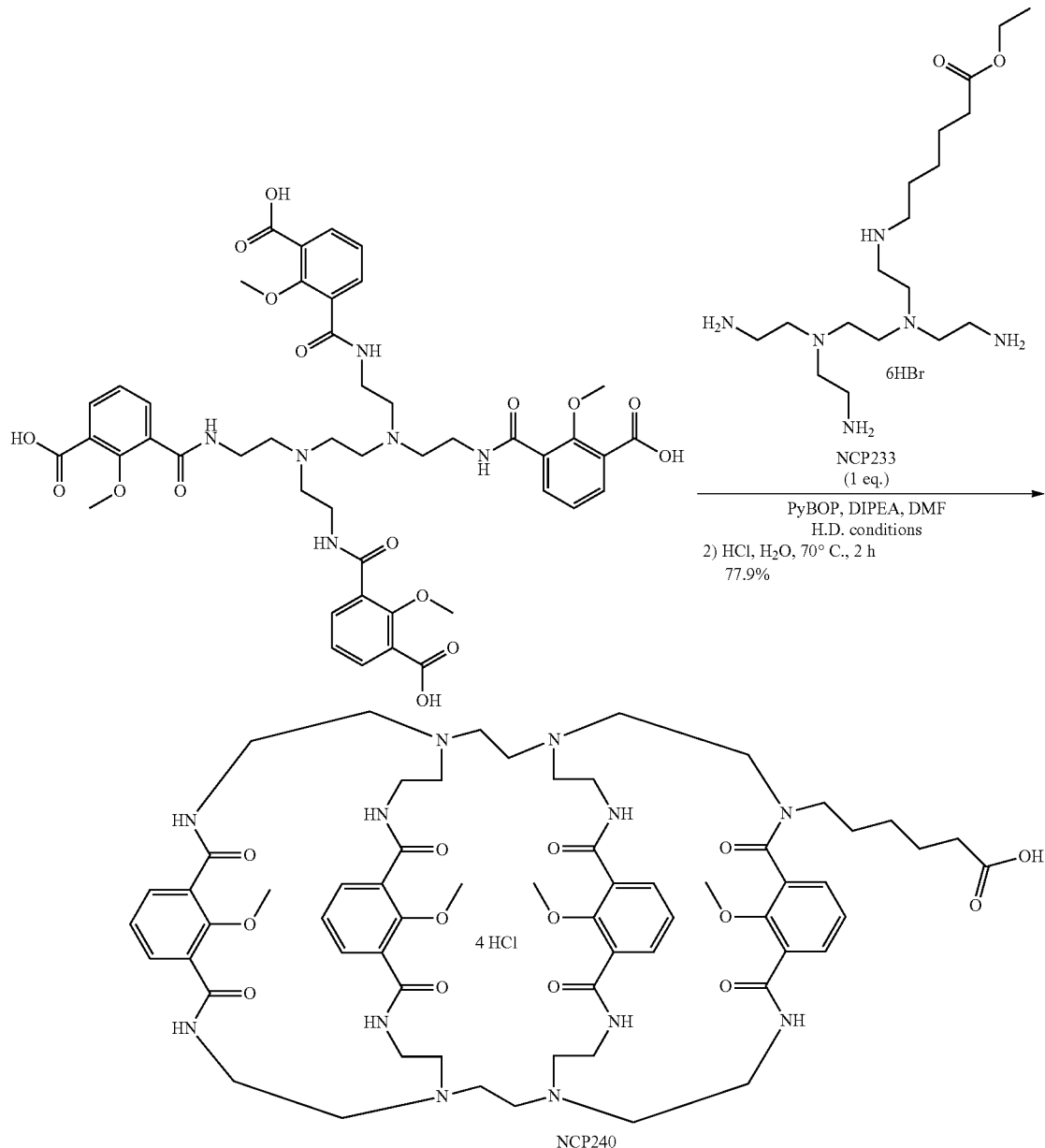

The procedure for the synthesis of Me₄BH(2,2)IAM (NCP102) was followed, replacing N1,N1'-(ethane-1,2-diyl)bis(N1-(2-aminoethyl)ethane-1,2-diamine)-6HBr (NCP119) with ethyl 6-((2-((2-aminoethyl)(2-(bis(2-aminoethyl)amino)ethyl)amino)ethyl)amino)hexanoate-6HBr (NCP233) where necessary. The reaction was run on a 100 mg (116 umol) scale of NCP233. For this reaction, NCP233 and NCP133 were dissolved to a final volume of 6 mL DMF (~20 mM each). At the start, 2 mL NCP133 solution were added, followed by alternating additions of 1 mL of NCP233 and NCP133 until both solutions were completely added. The final two additions were of the NCP233 solution. After complete addition of all reagents and allowing the reaction mixture to stir at room temperature for 12 h, aqueous HCl (12.0 M, 1.0 mL, 11.6 mmol, 100 eq) was added to the reaction mixture. The reaction mixture was concentrated in vacuo to an oil. The crude product was precipitated as the tetrahydrochloride salt via the addition of ~10 mL 1:1 Et₂O/EtOH solution, purified via centrifugation, washed with 10 mL Et₂O, and briefly dried in vacuo. The crude solid was taken up in 1 N HCl (4.0 mL) and heated to 70° C. for 2 h to saponify the ethyl ester and to ensure complete protonation of all basic species. The reaction mixture was concentrated to an oil in vacuo and the product was precipitated via the addition of ~5 mL ACN. The product was purified via centrifugation, washed twice with ACN, and dried in vacuo. Yield=122.2 mg, 77.0% as a tan, fluffy solid. MS (ESI⁺/⁻) m/z (M+H)⁺ 1220.04, m/z (M−H)⁻ 1218.05, [calculated $C_{62}H_{82}N_{12}O_{14}$: 1218.61].

BH(2,2)IAM-N-hexanoic acid (NCP189-6-carbon linker)

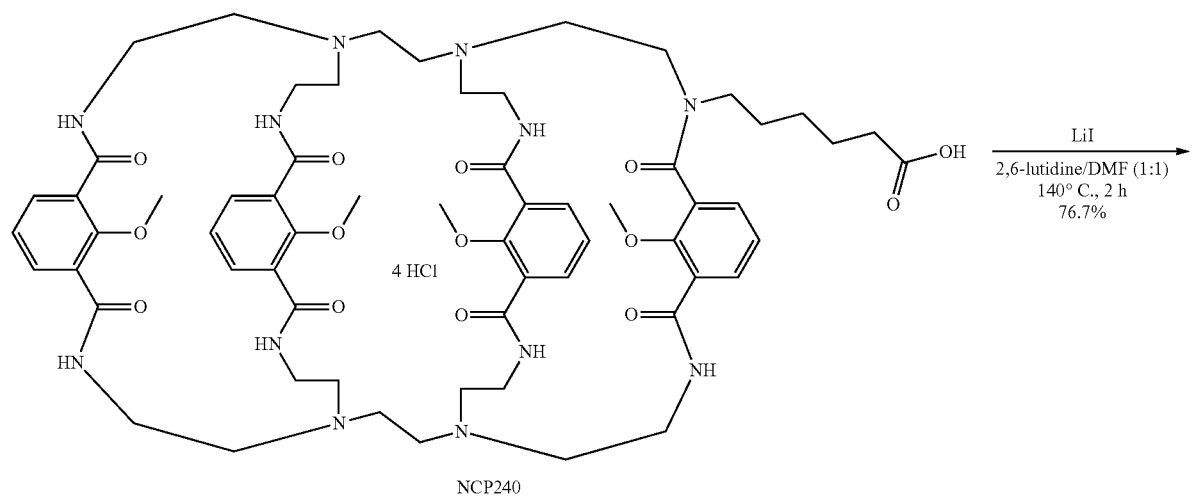

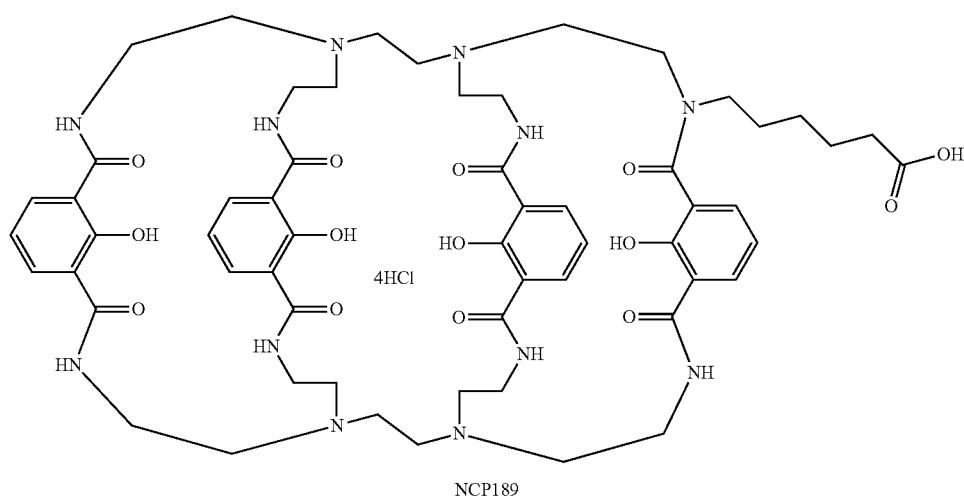

The procedure for the synthesis of BH(2,2)IAM (NCP134) was followed, replacing Me$_4$BH(2,2)IAM (NCP102) with Me$_4$BH(2,2)IAM-N-hexanoic acid (NCP240) where necessary. The reaction was run on a 25.0 mg (18.3 umol) scale of NCP240. After concentrating the reaction mixture to an oil in vacuo, the product was precipitated as the tetrahydrochloride salt via the addition of 1 N HCl (1 mL). The crude product was purified via centrifugation and briefly dried in vacuo. The dried solid was washed twice with ACN and dried in vacuo. Yield=18.4 mg, 76.7% as a tan, fluffy solid. MS (ESI$^{+/-}$) m/z (M+H)$^+$ 1164.03, m/z (M−H)$^-$ 1161.92, [calculated C$_{58}$H$_{74}$N$_{12}$O$_{14}$: 1162.54].

BH(2,2)IAM-N-hexanoic acid-Halotag (NCP190)

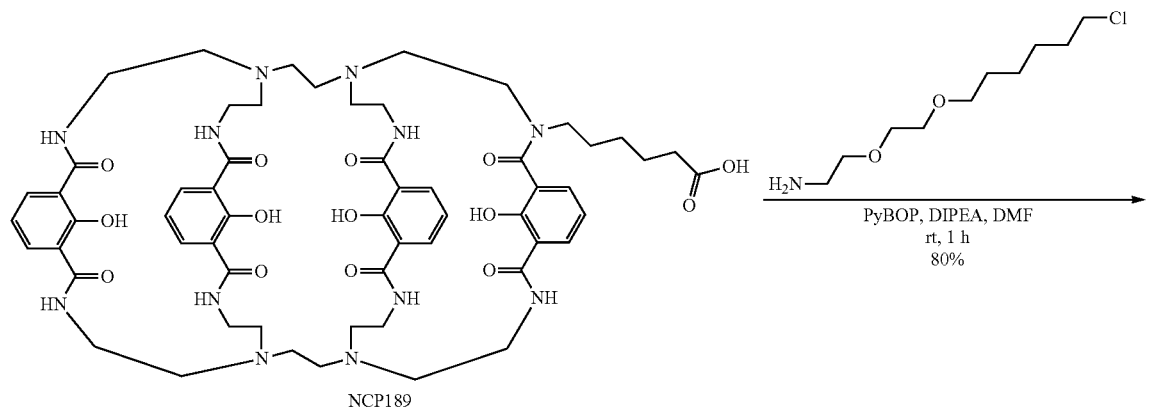

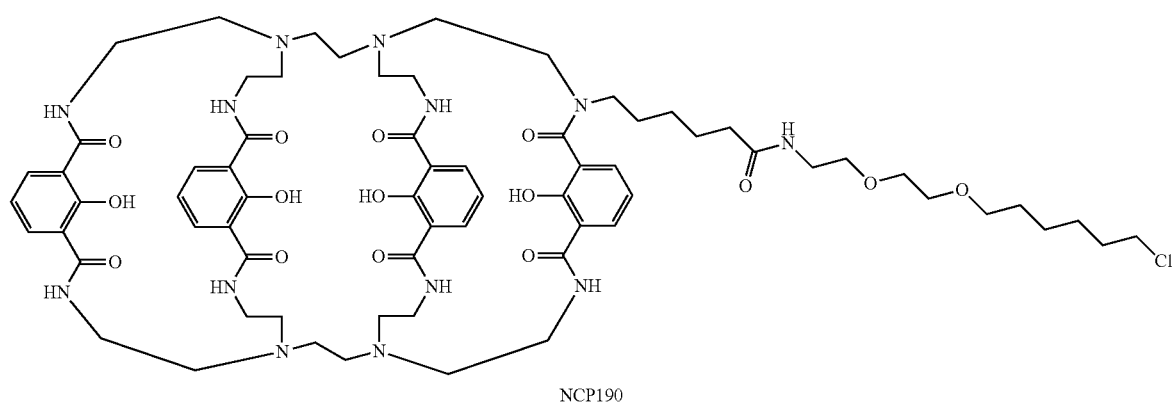

BH(2,2)IAM-N-hexanoic acid (NCP89, 11 mg, 9.5 umol, 1 eq) was dissolved in DMF (4 mL) then DIPEA (33 uL, 190 umol, 20 eq) was added followed by 2-(2-((6-chlorohexyl)oxy)ethoxy)ethan-1-amine (4.2 mg, 19 umol, 2 eq). After, PyBOP (10 mg, 19 umol, 2 eq) was added and the reaction was stirred for 1 h at room temperature. The reaction mixture was concentrated in vacuo and the crude product was triturated with Et$_2$O and purified via centrifugation. Yield=10.2 mg, 80% as a tan solid. MS (ESI$^{+/-}$) m/z (M+H)$^+$ 1369.19, m/z (M–H)$^-$ 1366.88, [calculated C$_{68}$H$_{94}$ClN$_{13}$O$_{15}$: 1367.67].

BH(2,2)IAM-N-hexanoic acid-Snap-tag (NCP191)

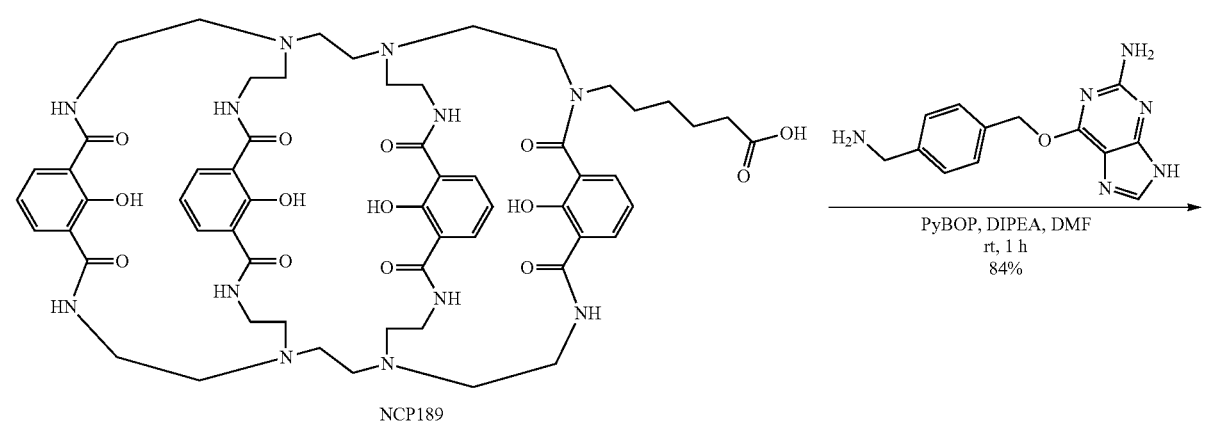

-continued

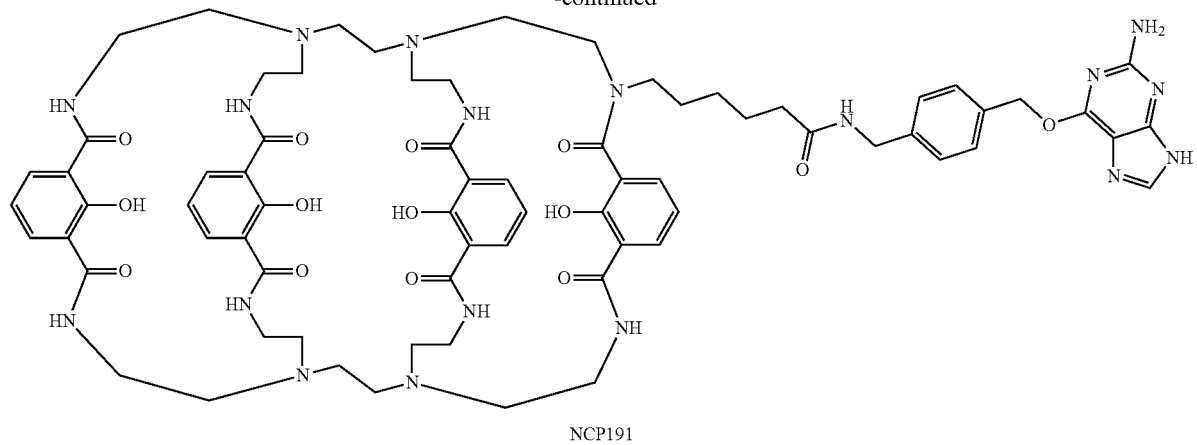

NCP191

The procedure for the synthesis of BH(2,2)IAM-N-hexanoic acid-Halotag (NCP190) was followed, replacing 2-(2-((6-chlorohexyl)oxy)ethoxy)ethan-1-amine with 6-((4-(aminomethyl)benzyl)oxy)-4,5-dihydro-7H-purin-2-amine where necessary. The reaction was run on a 11.5 mg scale of BH(2,2)IAM-N-hexanoic acid (NCP189). Yield=11.8 mg, 84% as a tan solid. MS (ESI$^{+/-}$) m/z (M+H)$^+$ 1416.17, m/z (M−H)$^-$ 1413.79, [calculated $C_{71}H_6N_8O_{14}$: 1414.66].

BH(2,2)IAM-N-hexanoic acid-benzylmethyl-methyltetrazine (NCP192)

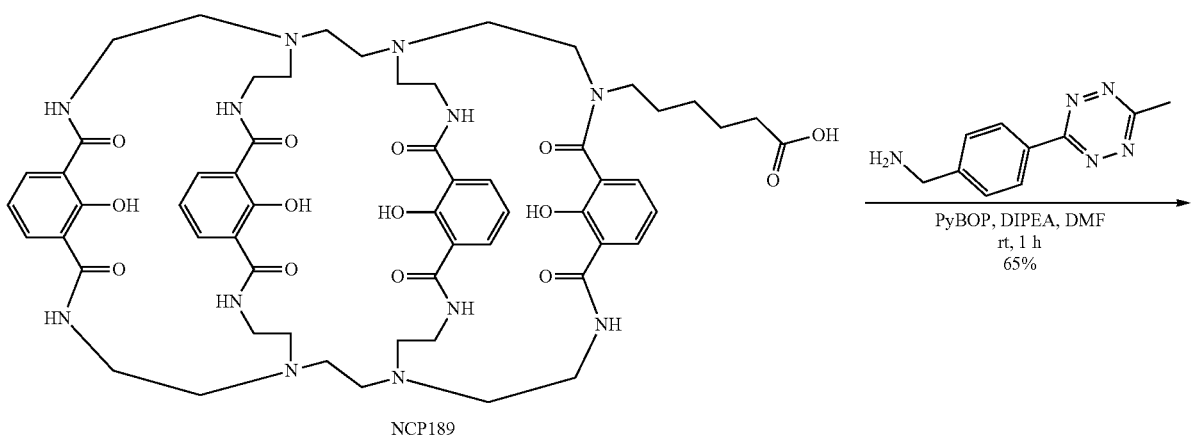

NCP189

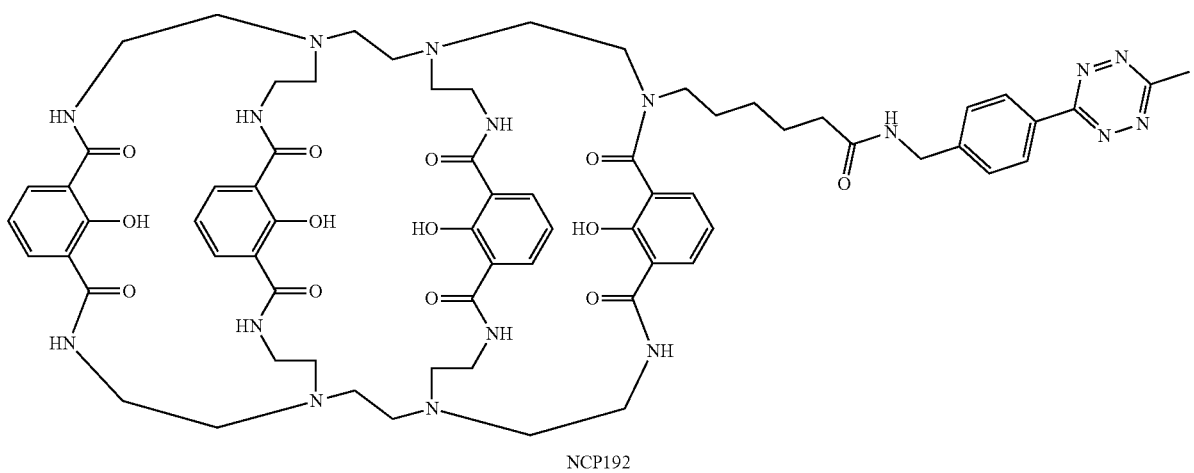

NCP192

The procedure for the synthesis of BH(2,2)IAM-N-hexanoic acid-Halotag (NCP190) was followed, replacing 2-(2-((6-chlorohexyl)oxy)ethoxy)ethan-1-amine with (4-(6-methyl-1,2,4,5-tetrazin-3-yl)phenyl)methanamine where necessary. The reaction was run on an 8.4 mg scale of BH(2,2)IAM-N-hexanoic acid (NCP189). Yield=6.3 mg, 65% as a light pink solid. MS (ESI$^{+/-}$) m/z (M+H)$^+$ 1347.05, m/z (M−H)$^−$ 1344.79, [calculated $C_{68}H_{83}N_{17}O_{13}$: 1345.64].

BH(2,2)IAM-N-hexanoic acid-(E)-N-(2-aminoethyl)-4-((4-(dimethylamino)phenyl)diazenyl)benzamide (NCP197)

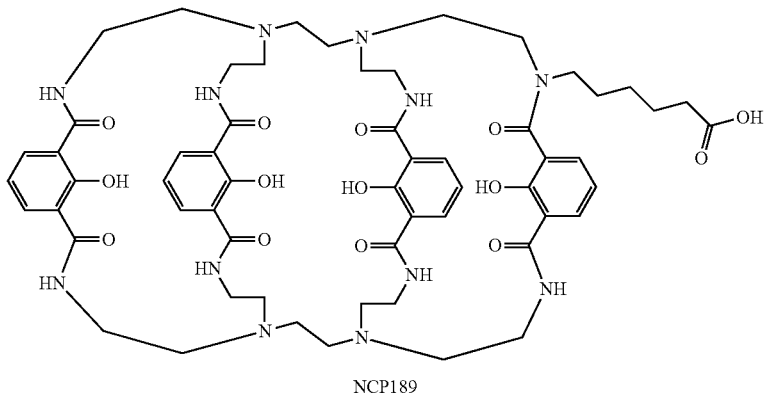

NCP189

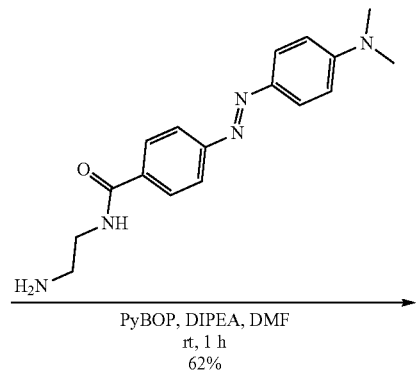

PyBOP, DIPEA, DMF
rt, 1 h
62%

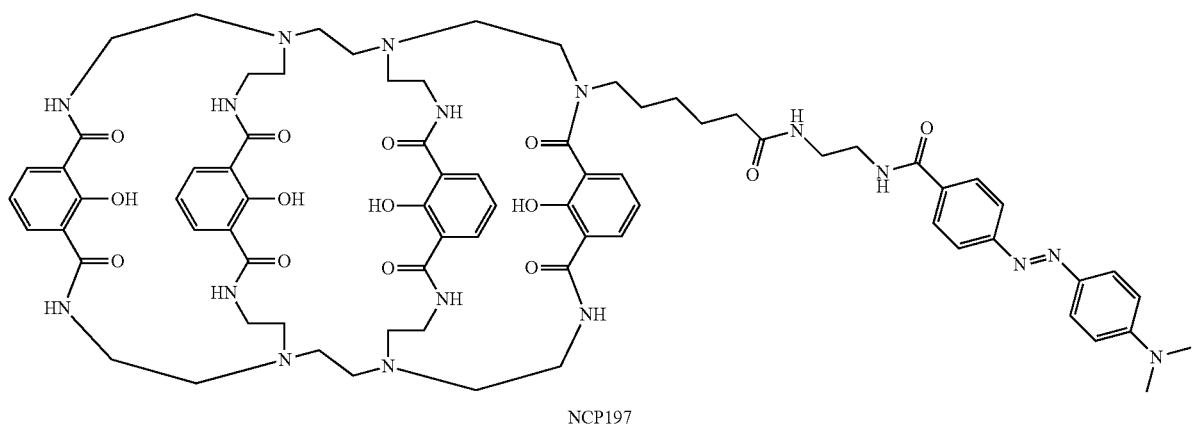

NCP197

The procedure for the synthesis of BH(2,2)IAM-N-hexanoic acid-Halotag (NCP190) was followed, replacing 2-(2-((6-chlorohexyl)oxy)ethoxy)ethan-1-amine with (E)-N-(2-aminoethyl)-4-((4-(dimethylamino)phenyl)diazenyl)benzamide where necessary. The reaction was run on a 9.2 mg scale of BH(2,2)IAM-N-hexanoic acid (NCP189). Yield=7.4 mg, 62% as a red solid. MS (ESI$^{+/-}$) m/z (M+H)$^+$ 1456.46, m/z (M−H)$^−$ 1454.77, [calculated $C_{75}H_{93}N_{17}O_{14}$: 1455.71].

BH(2,2)IAM-N-hexanoic acid-NHS

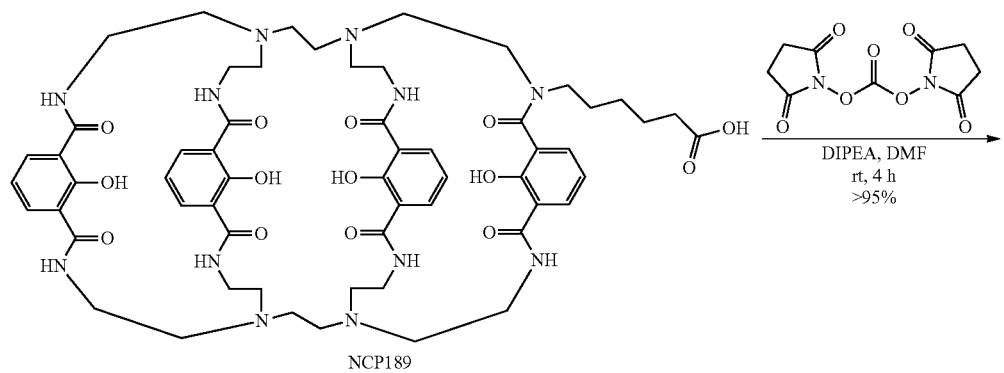

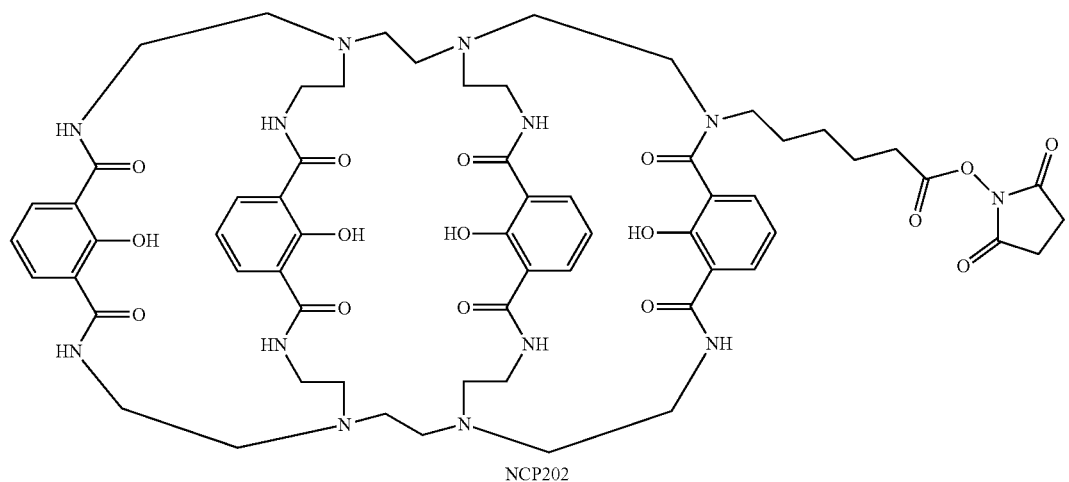

BH(2,2)IAM-N-hexanoic acid (NCP89, 9.1 mg, 7.8 umol, 1 eq) was dissolved in DMF (600 uL) then DIPEA (14 uL, 78 umol, 10 eq) was added followed by DSC (4.0 mg, 16 umol, 2 eq) and the reaction was stirred at room temperature for 4 h. The reaction mixture was concentrated in vacuo and the crude product was triturated with Et$_2$O and purified via centrifugation. Yield=9.5 mg, >95% as a tan solid. MS (ESI$^{+/-}$) m/z (M+H)$^+$ 1260.97, m/z (M−H)$^−$ 1258.87, [calculated C$_{62}$H$_{77}$N$_{13}$O$_{16}$: 1259.56].

6,6′,6″,6‴-(5,8-bis(2-formamidoethyl)-2,5,8,11-tetraazadodecanedioyl)tetrapicolinic acid-2HCl (NCP209)

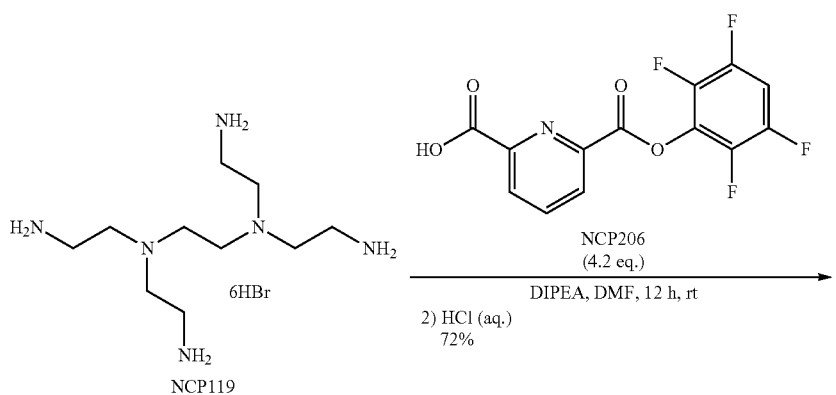

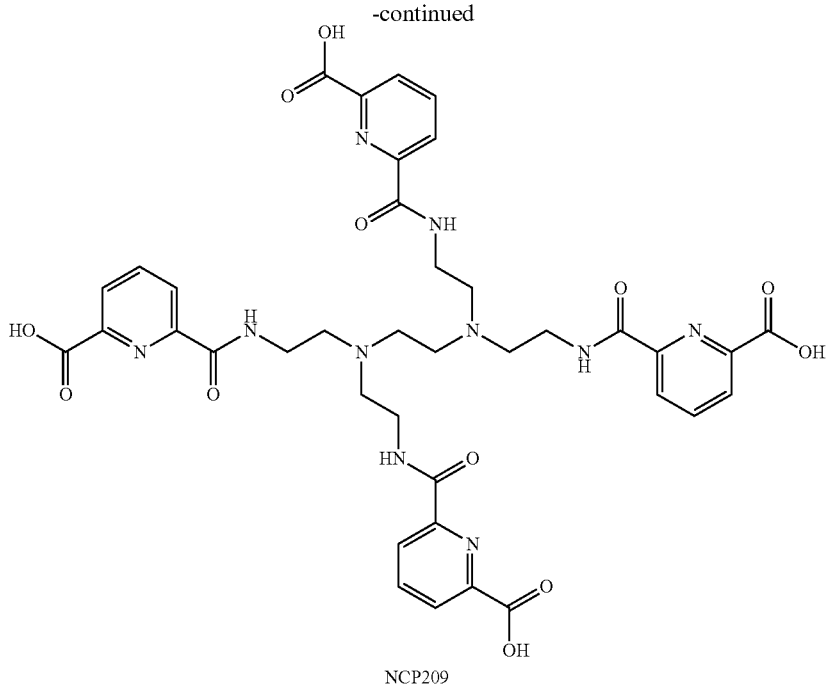

NCP209

The procedure for the synthesis of 3,3',3",3'''-(5,8-bis(2-formamidoethyl)-2,5,8,11-tetraazadodecanedioyl)tetrakis(2-methoxybenzoic acid)-2HCl (NCP133) was followed, replacing 2-methoxy-3-((4-nitrophenoxy)carbonyl)benzoic acid (NCP153) with 6-((2,3,5,6-tetrafluorophenoxy)carbonyl)picolinic acid (NCP206) where necessary. The reaction was run on a 1 g (3.17 mmol) scale of NCP206. Yield=420 mg, 72% as a tan, fluffy solid. $^1$H NMR (400 MHz, MeOD) δ 8.10 (d, J=6.8 Hz, 4H), 7.96 (d, J=7.5 Hz, 4H), 7.91 (t, J=7.6 Hz, 4H), 3.70 (t, 8H), 3.38 (s, 4H), 3.29 (s, 8H). $^{13}$C NMR (101 MHz, MeOD) δ 169.52, 166.82, 151.06, 150.03, 139.78, 128.02, 125.32, 54.50, 52.45, 36.97. MS (ESI$^{+/-}$) m/z (M+H)$^+$ 829.61, m/z (M−H)$^−$ 827.62, [calculated $C_{38}H_{40}N_{10}O_{12}$: 828.28].

BH(2,2)picolinic-N-hexanoic acid (NCP263)

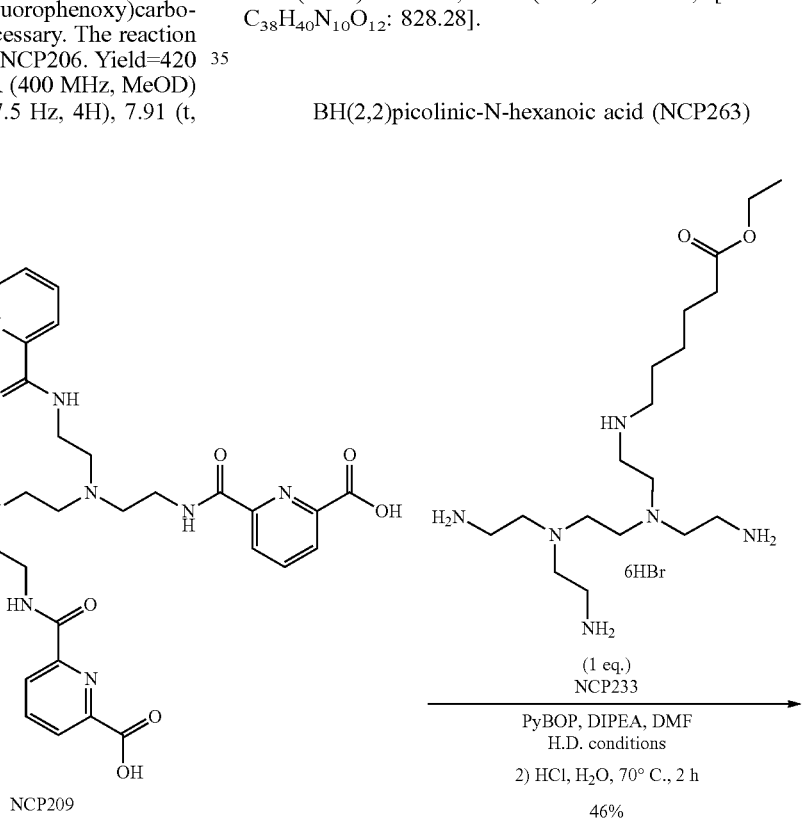

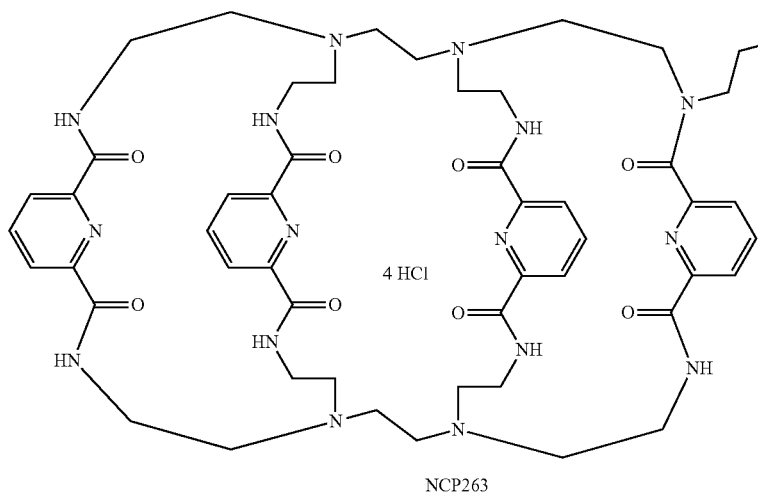

NCP263

The procedure for the synthesis of Me₄BH(2,2)IAM-N-hexanoic acid (NCP240) was followed, replacing 3,3',3",3'''-(5,8-bis(2-formamidoethyl)-2,5,8,11-tetraazadodecane-dioyl)tetrakis(2-methoxybenzoic acid)-2HCl (NCP133) with 6,6',6",6'''-(5,8-bis(2-formamidoethyl)-2,5,8,11-tetraazadodecanedioyl)tetrapicolinic acid-2HCl (NCP209). The reaction was run on a 50 mg (58 umol) scale of NCP233. For this reaction, NCP233 and NCP209 were dissolved to a final volume of 3 mL DMF (~20 mM each). At the start, 2 mL NCP209 solution was added, followed by alternating additions of 1 mL of NCP233 and NCP209 until both solutions were completely added. The final two additions were of the NCP233 solution. Yield=33.7 mg, 46% as a tan, fluffy solid. MS (ESI$^{+/-}$) m/z (M+H)$^+$ 1103.85, m/z (M−H)$^−$ 1101.84, [calculated $C_{54}H_{70}N_{16}O_{10}$: 1102.55].

N-(2-((2-(bis(2-((4-methylphenyl)sulfonamido)ethyl)amino)ethyl)(2-((4-methylphenyl)sulfonamido)ethyl)amino)ethyl)-N-tosylglycine (NCP124)

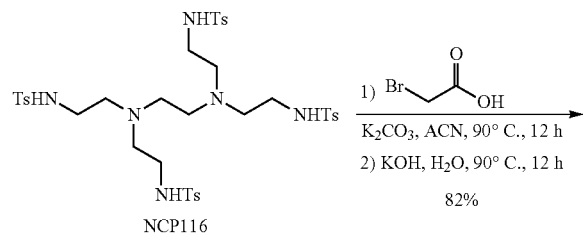

NCP116

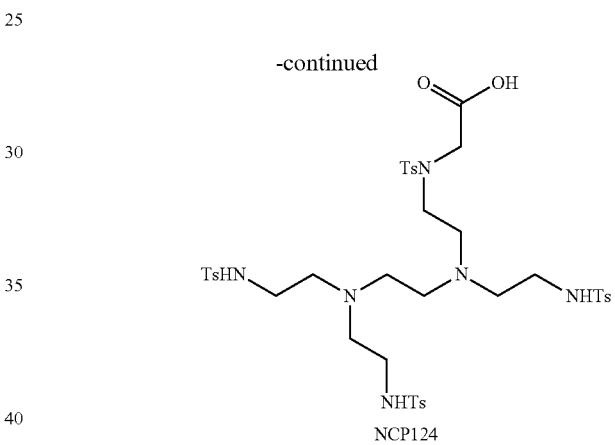

NCP124

The procedure for the synthesis of 6-((N-(2-((2-(bis(2-((4-methylphenyl)sulfonamido)ethyl)amino)ethyl)(2-((4-methylphenyl)sulfonamido)ethyl)amino)ethyl)-4-methylphenyl)sulfonamido)hexanoic acid (NCP165) was followed, replacing ethyl 6-bromohexanoate with tert-butyl bromoacetate where necessary. The reaction was run on 217 uL (1.5 mmol) scale of tert-butyl bromoacetate. Yield=1.1 g, 82% average yield as a white solid. $^1$H NMR (400 MHz, CDCl$_3$) δ 7.74 (d, J=7.8 Hz, 6H), 7.64 (d, J=7.9 Hz, 2H), 7.30-7.23 (m, 5H), 7.17 (d, J=7.9 Hz, 4H), 7.01 (s, 2H), 3.81 (s, 2H), 3.52 (s, 2H), 3.44 (s, 4H), 3.33 (s, 2H), 3.23 (s, 2H), 2.84 (s, 6H), 2.49 (s, 4H), 2.37 (s, 3H), 2.34 (s, 3H), 2.31 (s, 6H). $^{13}$C NMR (101 MHz, CDCl$_3$) δ 174.80, 144.26, 143.45, 143.05, 137.17, 136.28, 133.86, 130.15, 130.05, 129.82, 127.60, 127.43, 127.28, 54.33, 53.78, 53.38, 52.47, 51.18, 48.33, 46.27, 40.60, 38.27, 31.07, 21.66, 21.63, 21.58. MS (ESI$^{+/-}$) m/z (M+H)$^+$ 907.63, m/z (M−H)$^−$ 905.48, [calculated $C_{40}H_{54}N_6O_{10}S_4$: 906.28].

131

Methyl (2-((2-aminoethyl)(2-(bis(2-aminoethyl)amino)ethyl)amino)ethyl)glycinate-6HBr (NCP143)

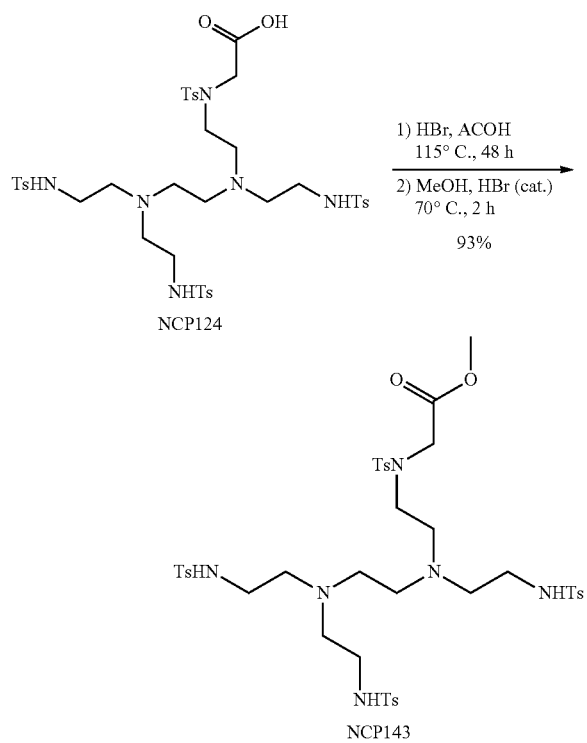

132

The procedure for the synthesis of ethyl 6-((2-((2-aminoethyl)(2-(bis(2-aminoethyl)amino)ethyl)amino)ethyl)amino)hexanoate-6HBr (NCP233) was followed, replacing 6-((N-(2-((2-(bis(2-((4-methylphenyl)sulfonamido)ethyl)amino)ethyl)(2-((4-methylphenyl)sulfonamido)ethyl)amino)ethyl)-4-methylphenyl)sulfonamido)hexanoic acid (NCP165) with N-(2-((2-(bis(2-((4-methylphenyl)sulfonamido)ethyl)amino)ethyl)(2-((4-methylphenyl)sulfonamido)ethyl)amino)ethyl)-N-tosylglycine (NCP124) and EtOH with MeOH where necessary. Heating during the esterification step was conducted at 70° C. instead of 85° C. The reaction was run on a 549 mg (605 umol) scale of NCP124. Yield=444 mg, 93% average yield as an off-white, fluffy solid. $^1$H NMR (400 MHz, MeOD) δ 4.16 (s, 2H), 3.89 (s, 3H), 3.47 (t, J=6.4 Hz, 2H), 3.37 (s, 4H), 3.27 (t, J=6.4 Hz, 4H), 3.24-3.17 (m, 4H), 3.15-3.10 (m, 4H), 3.06 (t, J=6.3 Hz, 2H). MS (ESI$^+$) m/z (M+H)$^+$ 305.52, [calculated $C_{13}H_{32}N_6O_2$: 304.26].

Me$_4$BH(2,2)IAM-N-carboxymethyl methyl ester (NCP148-2-carbon linker)

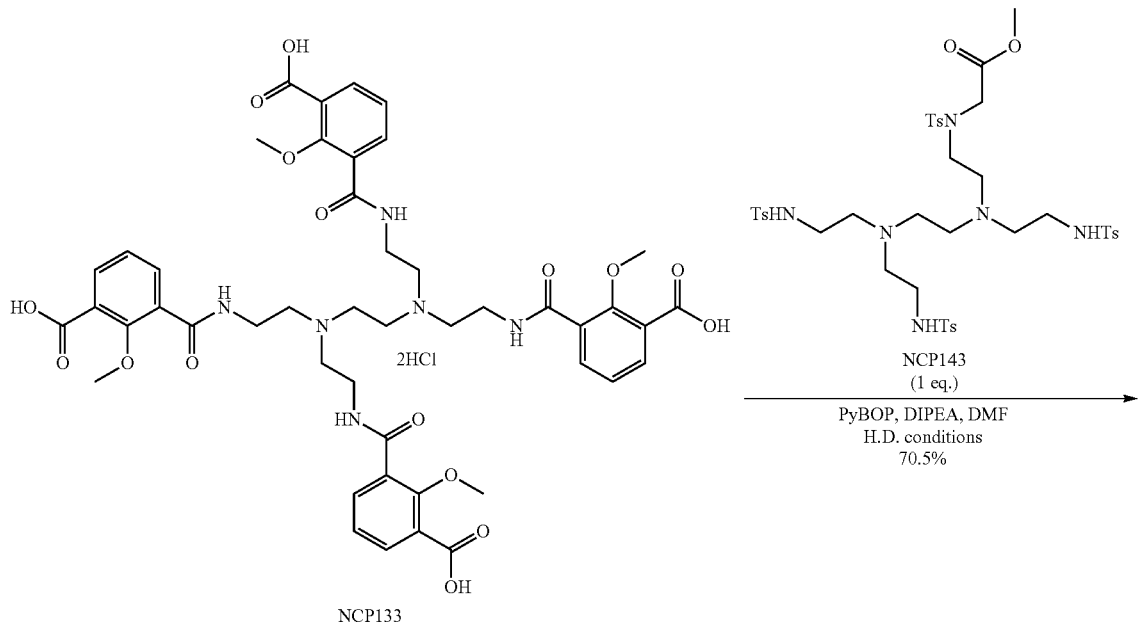

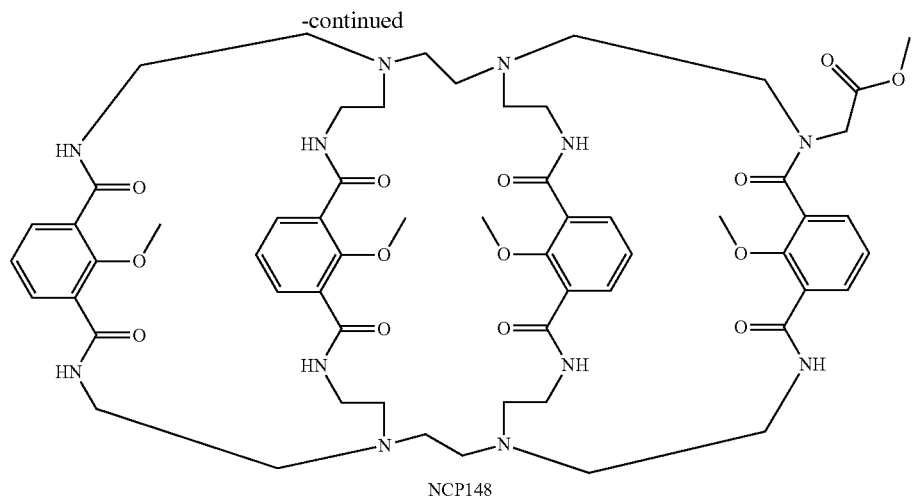

NCP148

The procedure for the synthesis of Me$_4$BH(2,2)IAM (NCP102) was followed, replacing N1,N1'-(ethane-1,2-diyl) bis(N1-(2-aminoethyl)ethane-1,2-diamine)-6HBr (NCP119) with methyl (2-((2-aminoethyl)(2-(bis(2-aminoethyl)amino) ethyl)amino)ethyl)glycinate-6HBr (NCP143) where necessary. The reaction was run on a 181 mg (229 umol) scale of NCP143. For this reaction, NCP143 and NCP133 were dissolved to a final volume of 10 mL DMF (~20 mM each). At the start, 2 mL NCP133 solution were added, followed by alternating additions of 1 mL of NCP143 and NCP133 until both solutions were completely added. The final two additions were of the NCP143 solution. Yield=190 mg, 70.5% as a yellow solid. MS (ESI$^{+/-}$) m/z (M+H)$^+$ 1178.11, m/z (M−H)$^-$ 1176.06, [calculated C$_{59}$H$_{76}$N$_{12}$O$_{14}$: 1176.56].

BH(2,2)IAM-N-carboxymethyl-OH
(NCP144-2-carbon linker)

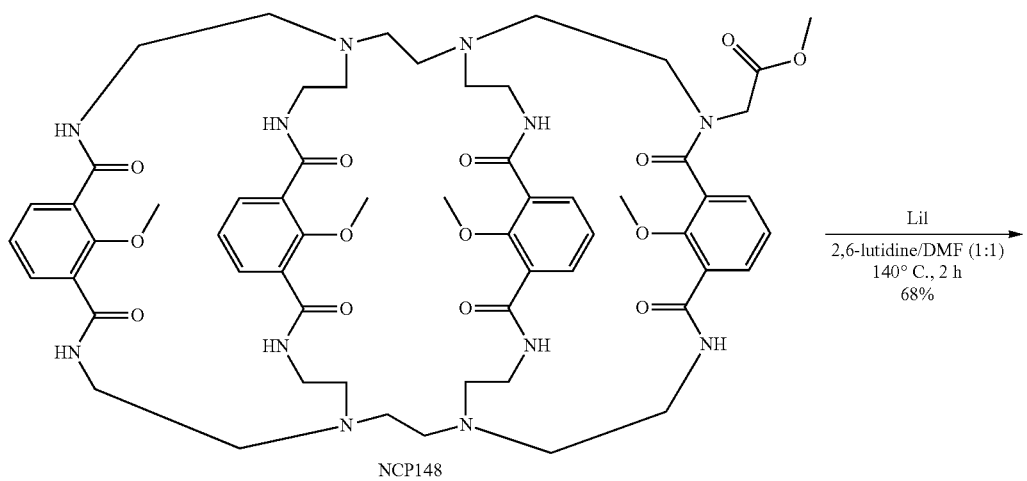

NCP148

LiI
2,6-lutidine/DMF (1:1)
140° C., 2 h
68%

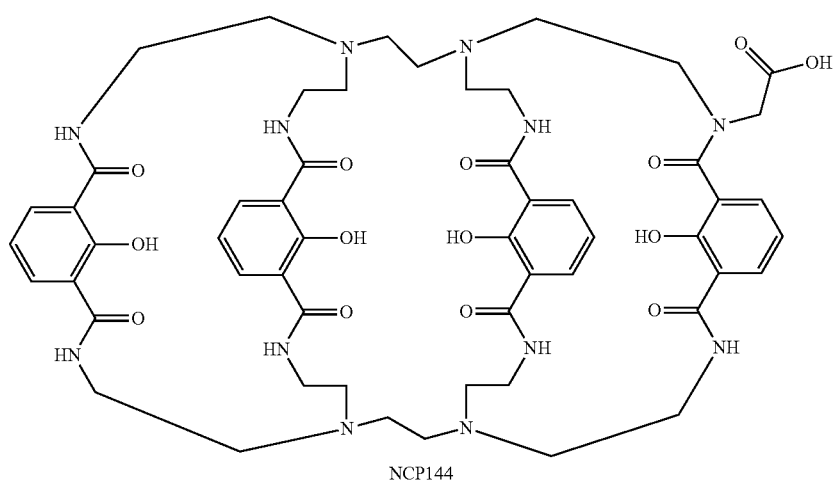
NCP144
The procedure for the synthesis of BH(2,2)IAM (NCP134) was followed, replacing Me₄BH(2,2)IAM (NCP102) with Me₄BH(2,2)IAM-N-carboxymethyl methyl ester (NCP148) where necessary. The reaction was run on a 175 mg (149 umol) scale of NCP148. Yield=112 mg, 68% as a yellow solid. MS (ESI$^{+/-}$) m/z (M+H)$^+$ 1108.00, m/z (M−H)$^-$ 1105.83, [calculated $C_{54}H_{66}N_{12}O_{14}$: 1106.48].
BH(2,2)IAM-N-carboxymethyl-Halotag_(NCP166)
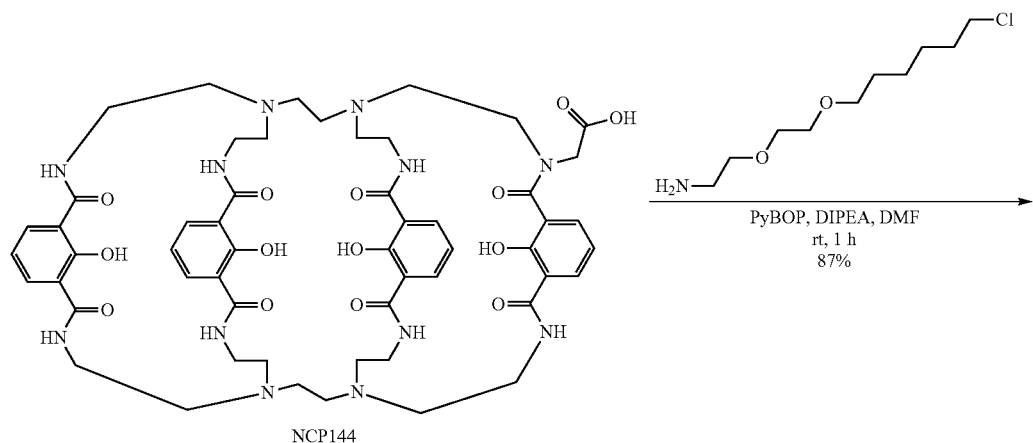
NCP144

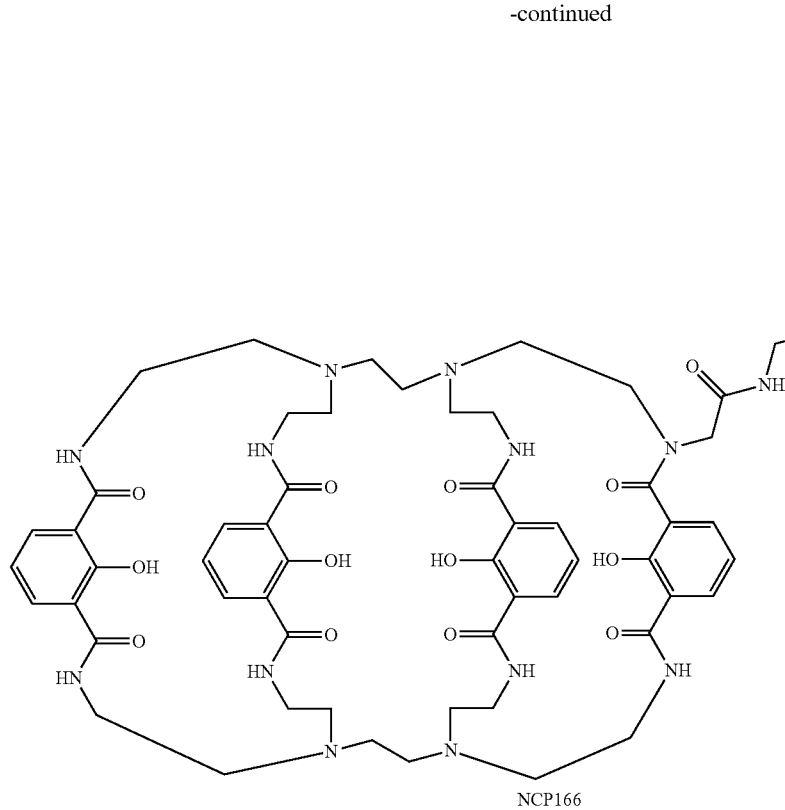

BH(2,2)IAM-N-carboxymethyl-OH (NCP144, 2 mg, 1.8 umol, 1 eq) was dissolved in DMF (1 mL) then DIPEA (3.2 uL, 18 umol, 10 eq) was added followed by 2-(2-((6-chlorohexyl)oxy)ethoxy)ethan-1-amine (1.2 mg, 5.4 umol, 3 eq). After, PyBOP (2.8 mg, 5.4 umol, 3 eq) was added and the reaction was stirred for 1 h at room temperature. The reaction mixture was concentrated in vacuo and the crude product was triturated with Et$_2$O and purified via centrifugation. Yield=2.1 mg, 87.5% as a colorless oil. MS (ESI$^{+/-}$) m/z (M+H)$^+$ 1313.20, m/z (M−H)$^−$ 1311.01, [calculated C$_{64}$H$_{86}$ClN$_{13}$O$_{15}$: 1311.61].

BH(2,2)IAM-N-carboxymethyl-benzylmethyl-methyltetrazine (NCP167)

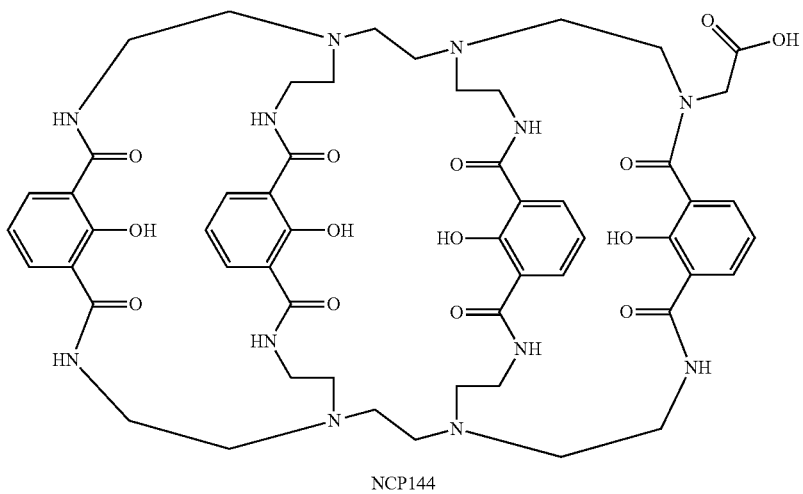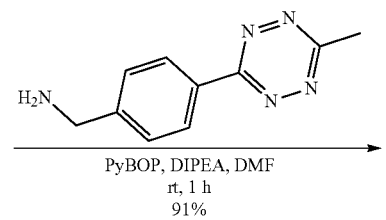

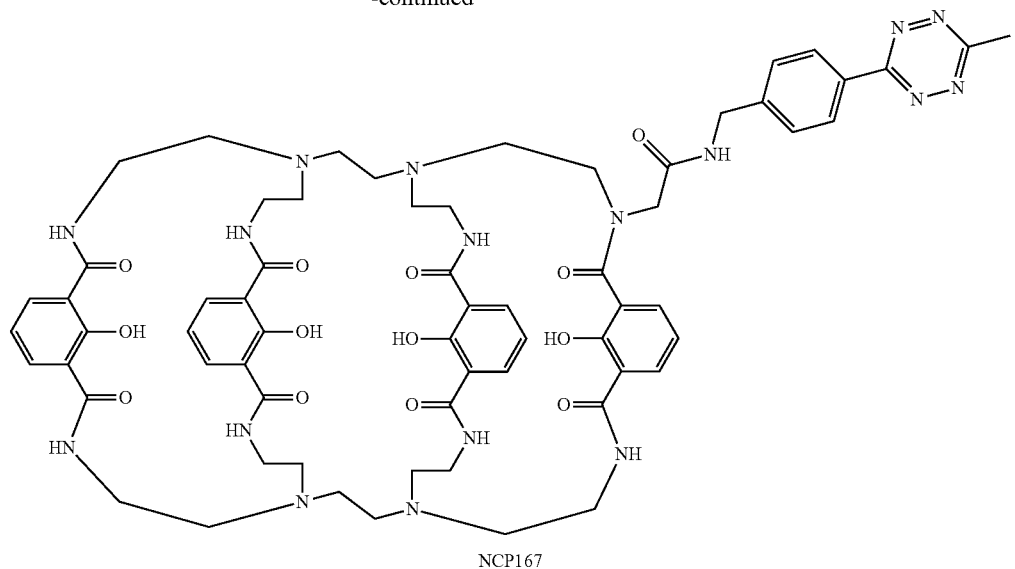

The procedure for the synthesis of BH(2,2)IAM-N-carboxymethyl-Halotag (NCP166) was followed, replacing 2-(2-((6-chlorohexyl)oxy)ethoxy)ethan-1-amine with (4-(6-methyl-1,2,4,5-tetrazin-3-yl)phenyl)methanamine where necessary. The reaction was run on a 0.66 mg scale of BH(2,2)IAM-N-carboxymethyl-OH (NCP144). Yield=0.7 mg, 90.9% as a light pink solid. MS (ESI$^{+/-}$) m/z (M+H)$^+$ 1291.27, m/z (M−H)$^−$ 1288.93, [calculated $C_{64}H_{75}N_{17}O_{13}$: 1289.57].

BH(2,2)IAM-N-carboxymethyl-(E)-4-((4-((2-(2-aminoethoxy)ethyl)(methyl)amino)phenyl)diazenyl)-N-(2-aminophenyl)benzamide (NCP168)

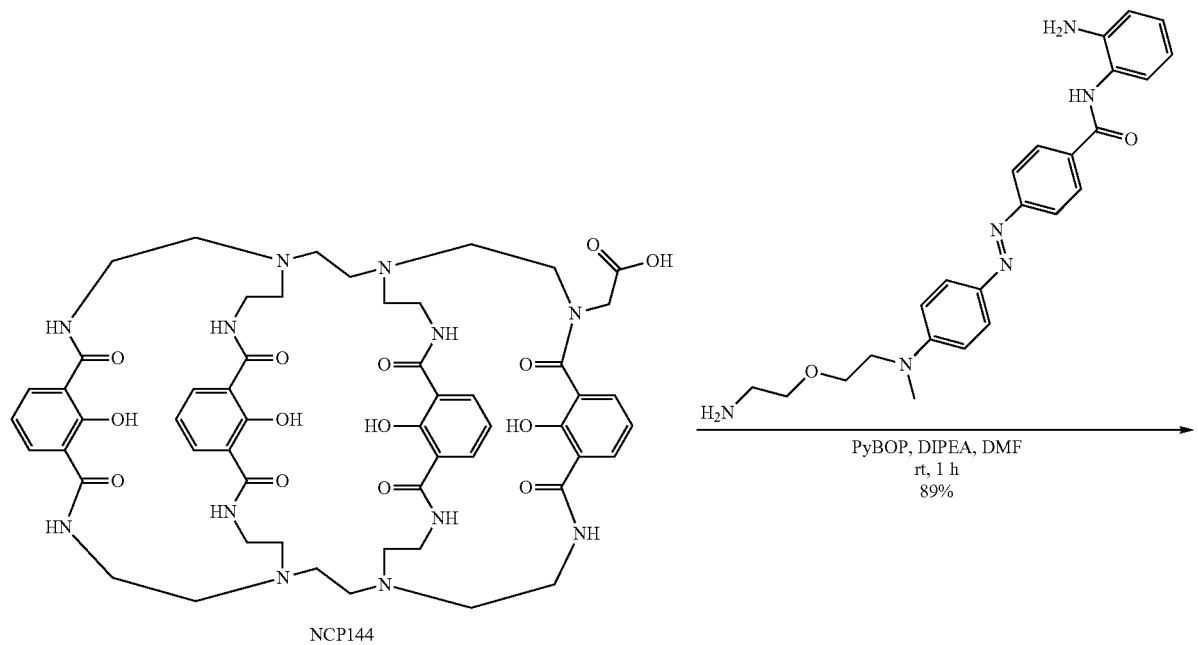

-continued

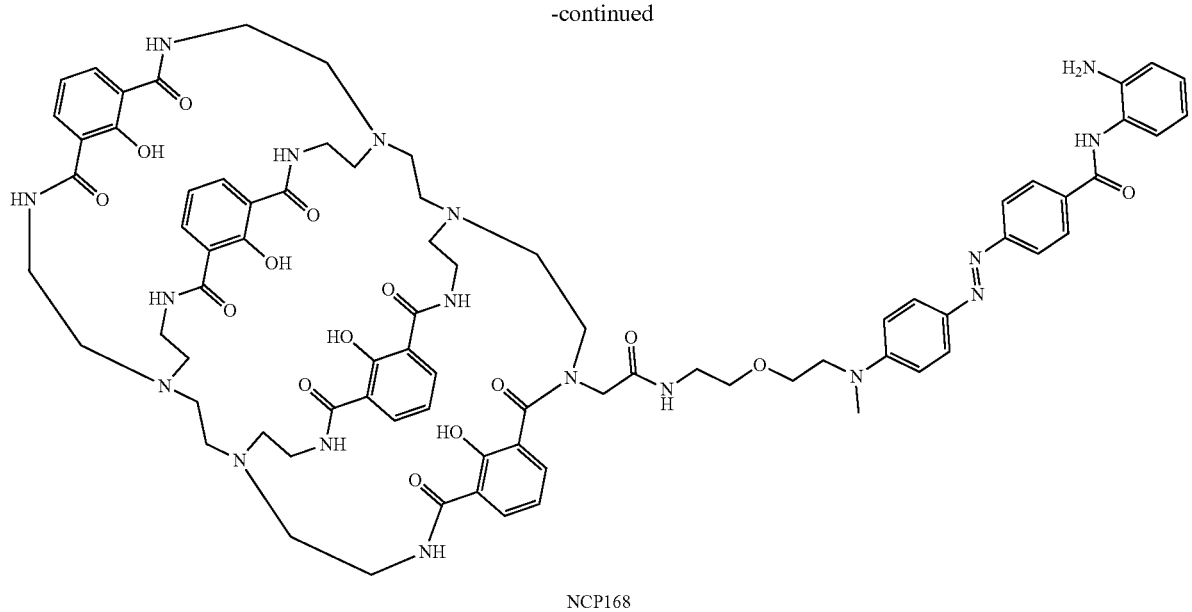

NCP168

The procedure for the synthesis of BH(2,2)IAM-N-carboxymethyl-Halotag (NCP166) was followed, replacing 2-(2-((6-chlorohexyl)oxy)ethoxy)ethan-1-amine with (E)-4-((4-((2-(2-aminoethoxy)ethyl)(methyl)amino)phenyl)diazenyl)-N-(2-aminophenyl)benzamide where necessary. The reaction was run on a 0.66 mg scale of BH(2,2)IAM-N-carboxymethyl-OH (NCP144). Yield=0.81 mg, 89.1% as a red solid. MS (ESI$^{+/-}$) m/z (M+H)$^+$ 1522.32, m/z (M−H)$^-$ 1520.08, [calculated $C_{78}H_{92}N_{18}O_{15}$: 1520.70].

BH(2,2)IAM-N-carboxymethyl-SNAP-tag (NCP169)

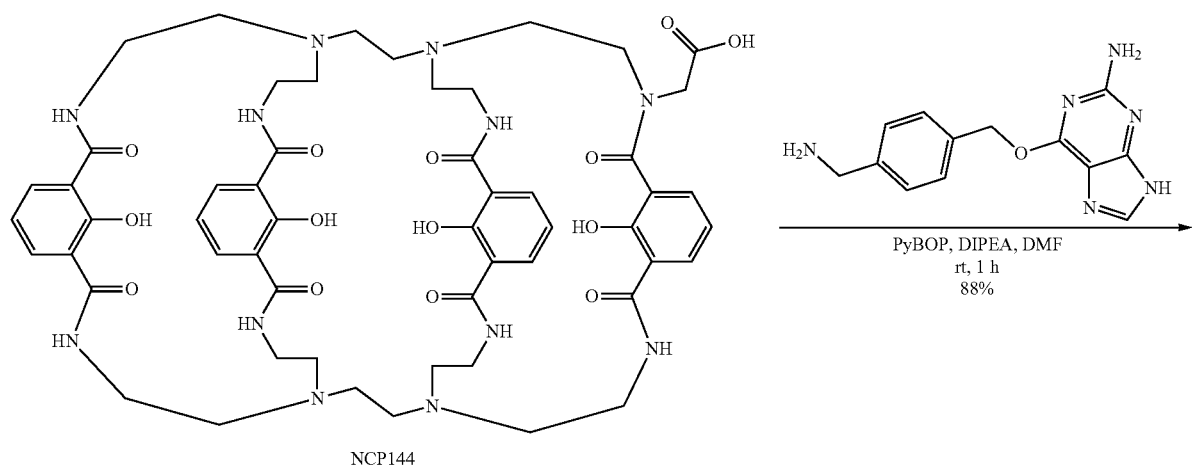

NCP144

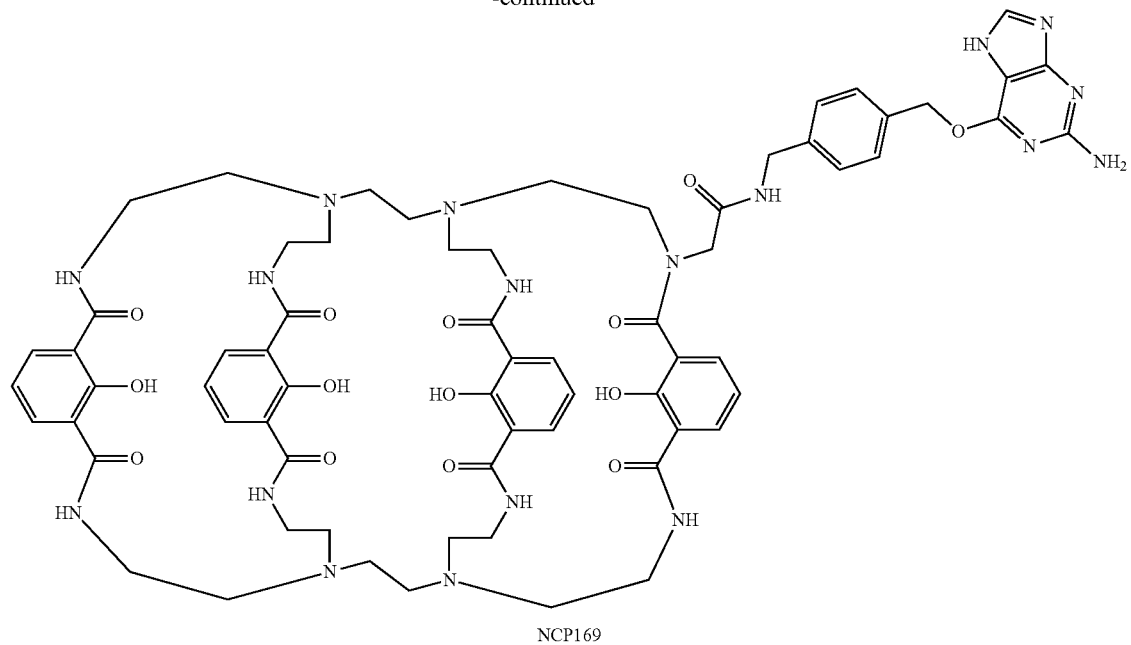

NCP169

The procedure for the synthesis of BH(2,2)IAM-N-carboxymethyl-Halotag (NCP166) was followed, replacing 2-(2-((6-chlorohexyl)oxy)ethoxy)ethan-1-amine with 6-((4-(aminomethyl)benzyl)oxy)-7H-purin-2-amine where necessary. The reaction was run on a 0.66 mg scale of BH(2,2)IAM-N-carboxymethyl-OH (NCP144). Yield=0.75 mg, 88.2% as a white solid. MS (ESI$^{+/-}$) m/z (M+H)$^+$ 1360.24, m/z (M−H)$^-$ 1357.96, [calculated $C_{67}H_{78}N_{18}O_{14}$: 1358.59].

BH(2,2)IAM-N-carboxymethyl-N-(3-(2-(2-(3-aminopropoxy)ethoxy)ethoxy)propyl)-5-(2-oxohexahydro-1H-thieno[3,4-d]imidazol-4-yl)pentanamide (NCP205)

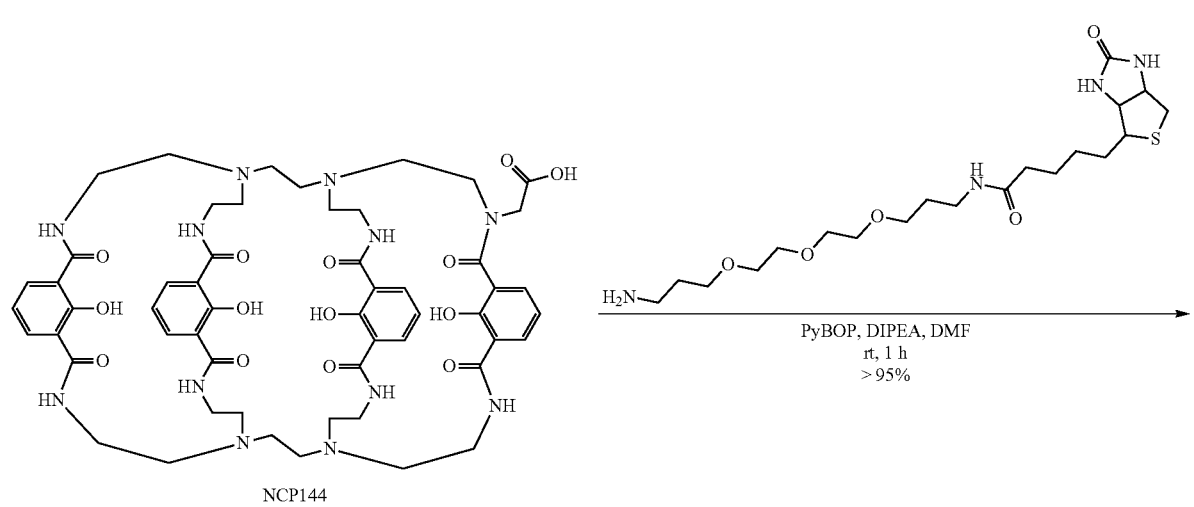

NCP144

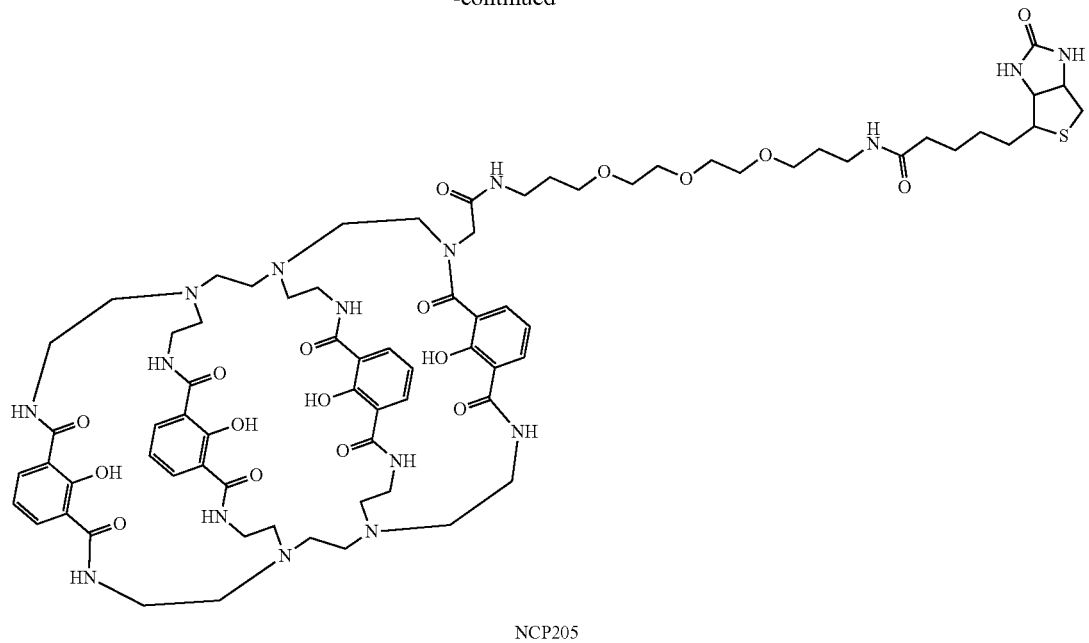

NCP205

The procedure for the synthesis of BH(2,2)IAM-N-carboxymethyl-Halotag (NCP166) was followed, replacing 2-(2-((6-chlorohexyl)oxy)ethoxy)ethan-1-amine with N-(3-(2-(2-(3-aminopropoxy)ethoxy)ethoxy)propyl)-5-(2-oxo-hexahydro-1H-thieno[3,4-d]imidazol-4-yl)pentanamide where necessary. The reaction was run on a 15.0 mg scale of BH(2,2)IAM-N-carboxymethyl-OH (NCP144). Yield=20.4 mg, 88.2% as a yellow oil. MS (ESI$^{+/-}$) m/z (M+H)$^+$ 1535.60, m/z (M−H)$^-$ 1533.79, [calculated $C_{74}H_{102}N_{16}O_{18}S$: 1534.73].

N1,N1,N2-tris(2-(3-carboxy-2-methoxybenzamido)ethyl)-N2-(2-((6-ethoxy-6-oxohexyl)ammonio)ethyl)ethane-1,2-diaminium chloride (NCP236)

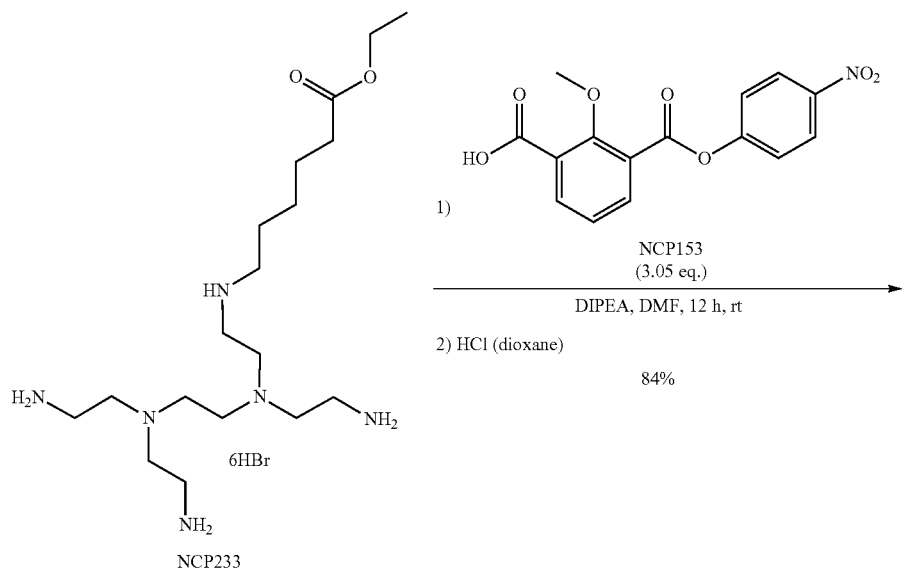

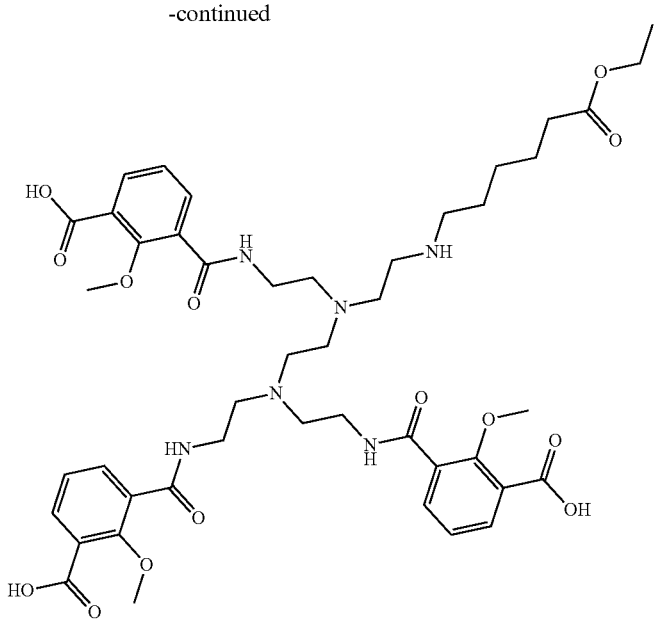

NCP236

Ethyl 6-((2-((2-aminoethyl)(2-(bis(2-aminoethyl)amino) ethyl)amino)ethyl)amino)hexanoate-6HBr (NCP233, 170 mg, 198 umol, 1 eq) and DIPEA (485 uL, 2.8 mmol, 14 eq) were dissolved in DMF (2 mL). In a separate container, 2-methoxy-3-((4-nitrophenoxy)carbonyl)benzoic acid (NCP153, 191.3 mg, 603 umol, 3.05 eq) was dissolved in DMF (3 mL). Over the course of 90 min (30 min intervals) in 1 mL aliquots, the solution of NCP153 was added to the solution of NCP233/DIPEA in DMF with stirring, liberating 4-nitrophenol and generating a deep yellow color. After complete addition, the reaction mixture was stirred at room temperature for 12 h. To the reaction was added HCl/dioxane (4.0 M, 1.5 mL, 5.9 mmol, 30 eq) under an atmosphere of Ar to acidify all basic species. The solution was concentrated to an oil in vacuo. The crude product was precipitated with 15 mL ACN and the precipitate was allowed to settle. The mother liquor was carefully decanted and the solid was briefly dried in vacuo. The ACN trituration process was repeated twice more and the solid dried in vacuo. Yield=169 mg, 84% as an off-white, fluffy solid. $^1$H NMR (400 MHz, D$_2$O) δ 7.87 (d, J=7.6 Hz, 2H), 7.80 (d, J=7.7 Hz, 1H), 7.67 (d, J=7.6 Hz, 1H), 7.63 (d, J=7.7 Hz, 2H), 7.20-7.13 (m, 3H), 4.07 (q, J=7.1 Hz, 2H), 3.83 (t, 4H), 3.76 (s, 9H), 3.61 (t, J=6.1 Hz, 6H), 3.56 (t, J=5.7 Hz, 2H), 3.22 (t, J=6.1 Hz, 2H), 3.16 (t, J=4.9 Hz, 2H), 3.04 (t, J=6.2 Hz, 2H), 2.91 (t, J=7.8 Hz, 4H), 2.18 (t, J=7.4 Hz, 2H), 1.47 (p, J=8.5, 8.0 Hz, 2H), 1.36 (p, J=7.6 Hz, 2H), 1.21-1.13 (m, 5H). $^{13}$C NMR (101 MHz, D$_2$O) δ 176.45, 169.31, 169.08, 169.01, 168.56, 157.40, 156.91, 135.14, 134.45, 134.01, 133.57, 128.46, 126.82, 125.08, 124.89, 124.45, 124.39, 63.27, 61.54, 57.37, 55.13, 52.35, 51.96, 49.19, 48.80, 47.61, 44.30, 37.09, 35.70, 33.44, 25.02, 23.57, 16.72, 13.25. MS (ESI$^{+/-}$) m/z (M+H)$^+$ 909.78, m/z (M−H)$^-$ 907.70, [calculated C$_{45}$H$_{60}$N$_6$O$_{14}$: 908.42].

N1,N1,N2-tris(2-(3-carboxy-2-methoxybenzamido)ethyl)-N2-(2-(3-carboxy-N-(6-ethoxy-6-oxohexyl)benzamido)ethyl)ethane-1,2-diaminium chloride (NCP257)

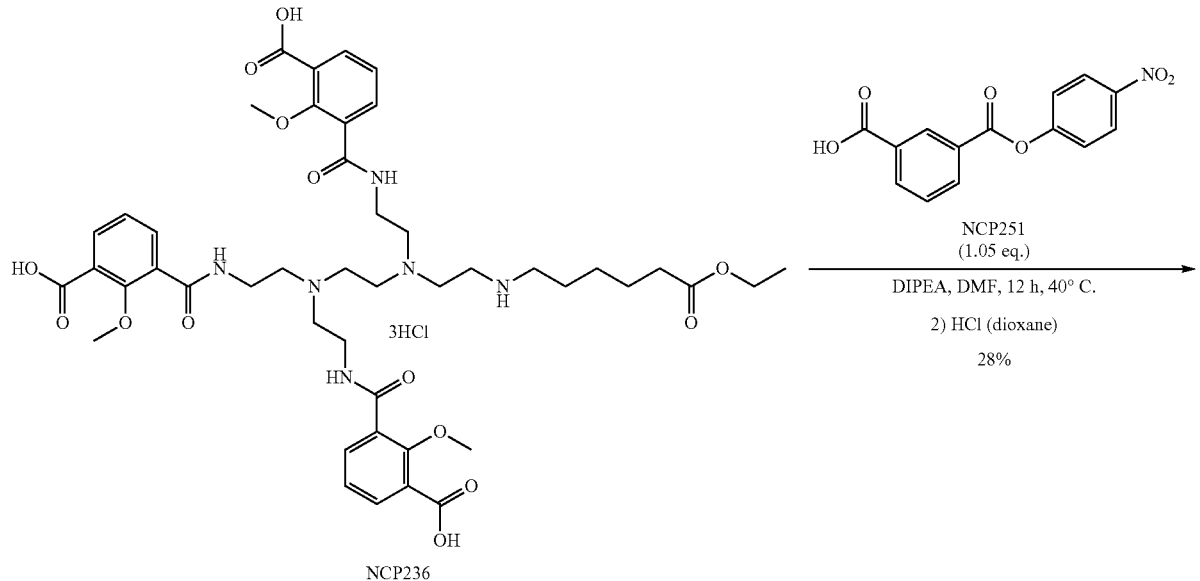

N1,N1,N2-tris(2-(3-carboxy-2-methoxybenzamido)ethyl)-N2-(2-((6-ethoxy-6-oxohexyl)ammonio)ethyl)ethane-1,2-diaminium chloride (NCP236, 100 mg, 98 umol, 1 eq) and DIPEA (170 uL, 982 umol, 10 eq) were dissolved in DMF (2 mL) then 3-((4-nitrophenoxy)carbonyl)benzoic acid (NCP251, 30 mg, 103 umol, 1.05 eq) was added and the reaction was heated to 40° C. for 12 h, at which time LC-MS analysis indicated approximately 30% conversion to the desired product. To the reaction mixture under Ar was added HCl/dioxane (4.0 M, 500 uL, 2 mmol, 20 eq) and the reaction mixture was concentrated to an oil in vacuo. The crude product was precipitated with ~15 mL ACN and the solid was allowed to settle. The mother liquor was carefully decanted and the solid was briefly dried in vacuo. The crude solid was purified via reverse-phase flash chromatography (C18, 5% ACN/H$_2$O/0.1% FA for 3 CV, 5% ACN to 40% ACN/H$_2$O/0.1% FA over 12 CV, 40% ACN to 100% ACN/H$_2$O/0.1% FA over 2 CV, 100% ACN/0.1% FA for 4 CV). The desired fractions were concentrated in vacuo and the product was dissolved in 50 mM HCl and re-concentrated to form the dihydrochloride salt. Yield=27.7 mg, 25% as a white, fluffy solid. MS (ESI$^{+/-}$) m/z (M+H)$^+$ 1057.52, m/z (M−H)$^−$ 1055.70, [calculated C$_{53}$H$_{64}$N$_6$O$_{17}$: 1056.43].

Me₃BH(2,2)IAM-N-hexanoic acid-mono-isophthalic-4HCl (NCP258)

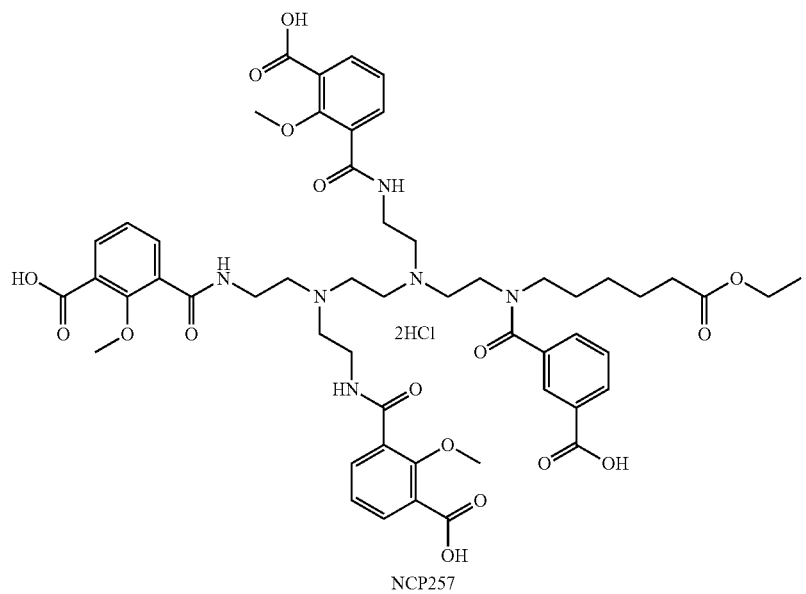

NCP257

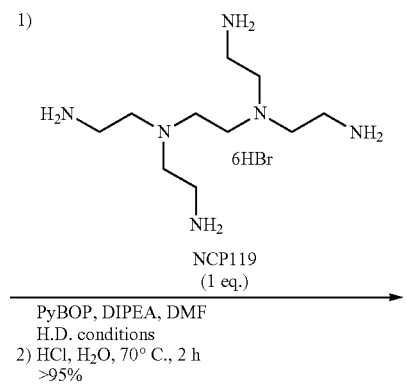

NCP119 (1 eq.)

PyBOP, DIPEA, DMF
H.D. conditions
2) HCl, H₂O, 70° C., 2 h
>95%

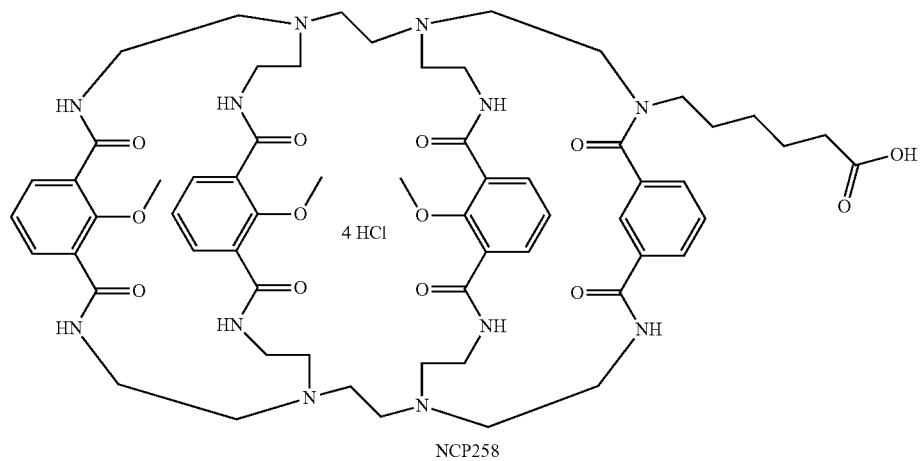

NCP258

The procedure for the synthesis of Me₄BH(2,2)IAM-N-hexanoic acid (NCP240) was followed, replacing ethyl 6-((2-((2-aminoethyl)(2-(bis(2-aminoethyl)amino)ethyl)amino)ethyl)amino)hexanoate-6HBr (NCP233) with N1,N1'-(ethane-1,2-diyl)bis(N1-(2-aminoethyl)ethane-1,2-diamine)-6HBr (NCP119) and 3,3',3'',3'''-(5,8-bis(2-formamidoethyl)-2,5,8,11-tetraazadodecanedioyl)tetrakis(2-methoxybenzoic acid)-2HCl (NCP133) with N1,N1,N2-tris(2-(3-carboxy-2-methoxybenzamido)ethyl)-N2-(2-(3-carboxy-N-(6-ethoxy-6-oxohexyl)benzamido)ethyl)ethane-1,2-diaminium chloride (NCP257) where necessary. The reaction was run on a 11.6 mg (16.1 umol) scale of NCP119. For this reaction, NCP119 and NCP257 were dissolved to a final volume of 1 mL DMF (~16 mM each). At the start, 500 uL NCP257 solution was added, followed by alternating additions of 250 uL of NCP119 and NCP257 until both solutions were completely added. The final two additions were of the NCP119 solution. Yield=21.3 mg, >95% as a tan, fluffy solid. MS (ESI$^{+/-}$) m/z (M+H)$^+$ 1190.07, m/z (M−H)$^-$ 1188.03, [calculated $C_{61}H_{80}N_{12}O_{13}$: 1188.60].

BH(2,2)IAM-N-hexanoic acid-mono-isophthalic-4HCl (NCP259)

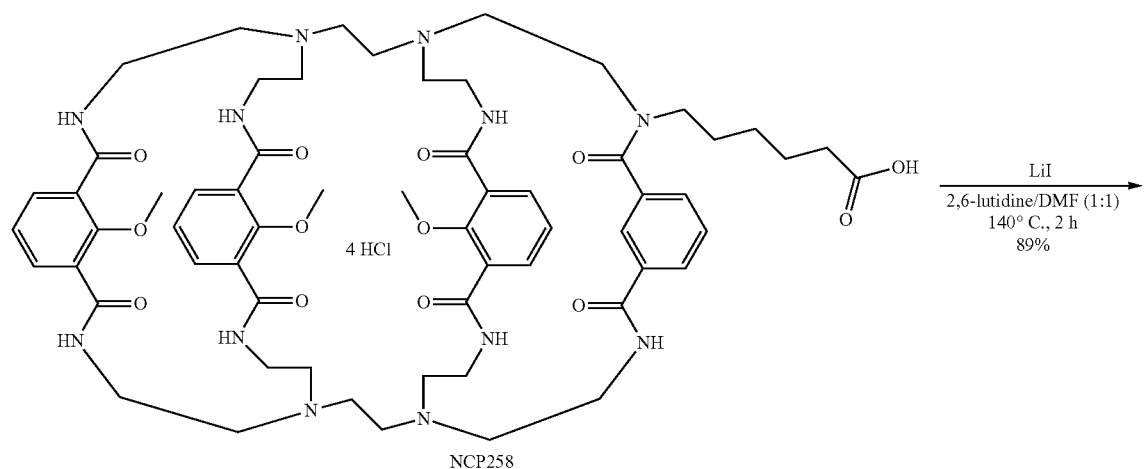

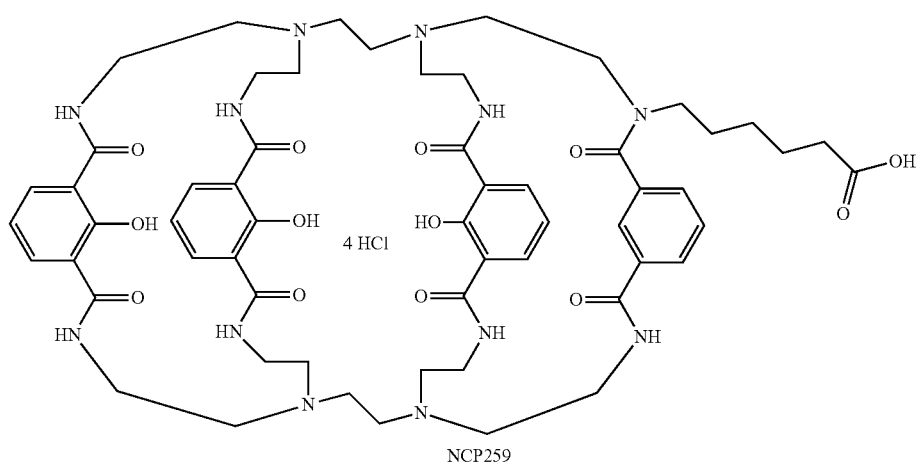

The procedure for the synthesis of BH(2,2)IAM-N-hexanoic acid (NCP189) was followed, replacing Me$_4$BH(2,2)IAM-N-hexanoic acid (NCP240) with Me$_3$BH(2,2)IAM-N-hexanoic acid-mono-isophthalic·4HCl (NCP258) where necessary. The reaction mixture was refluxed at 140° C. for 1 h instead of 2 h. The reaction was run on a 21 mg (15.7 umol) scale of NCP258. Yield=18.0 mg, 89% as a tan, fluffy solid. MS (ESI$^{+/-}$) m/z (M+H)$^+$ 1147.97, m/z (M−H)$^−$ 1145.88, [calculated C$_{58}$H$_{74}$N$_{12}$O$_{13}$: 1146.55].

N1-(2-(5-bromo-3-carboxy-N-(6-ethoxy-6-oxo-hexyl)-2-methoxybenzamido)ethyl)-N1,N2,N2-tris(2-(3-carboxy-2-methoxybenzamido)ethyl)ethane-1,2-diaminium chloride (NCP241)

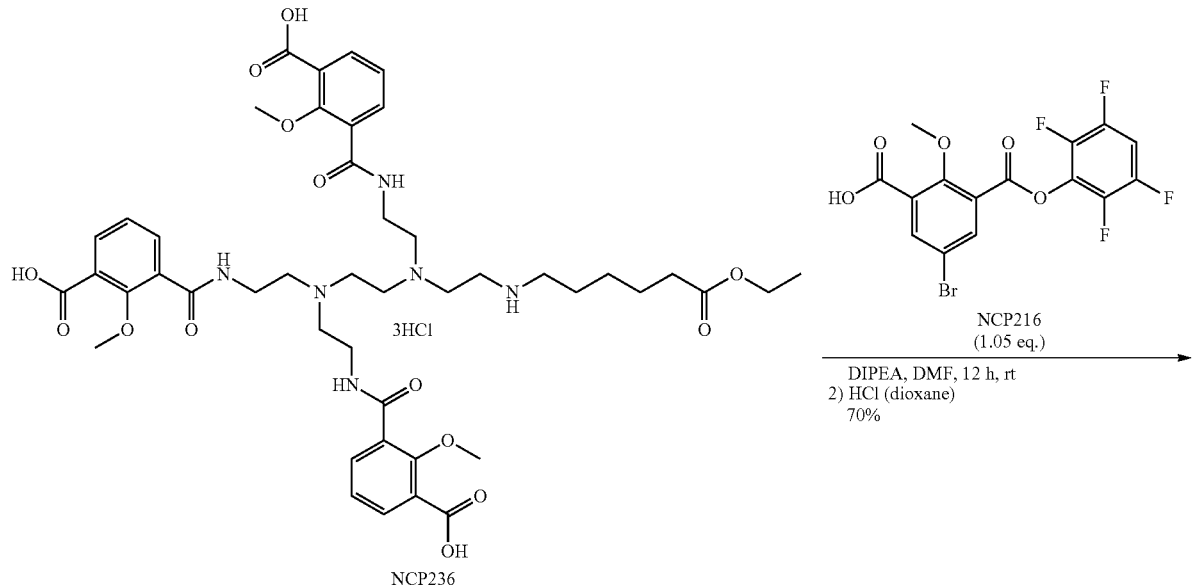

N1,N1,N2-tris(2-(3-carboxy-2-methoxybenzamido)ethyl)-N2-(2-((6-ethoxy-6-oxohexyl)ammonio)ethyl)ethane-1,2-diaminium chloride (NCP236, 75 mg, 74 umol, 1 eq) and DIPEA (130 uL, 736 umol, 10 eq) were dissolved in DMF (1 mL) then 5-bromo-2-methoxy-3-((2,3,5,6-tetrafluorophenoxy)carbonyl)benzoic acid (NCP216, 33 mg, 77 umol, 1.05 eq) was added and the reaction was stirred for 12 h at room temperature. To the reaction mixture under Ar was added HCl/dioxane (4.0 M, 370 uL, 1.47 mmol, 20 eq) and the reaction mixture was concentrated to an oil in vacuo. The product was precipitated with ~15 mL ACN and the solid was allowed to settle. The mother liquor was carefully decanted and the solid was briefly dried in vacuo. The ACN trituration process was repeated twice more and the solid dried in vacuo. Yield=63.9 mg, 70% as an off-white, fluffy solid. MS (ESI$^{+/-}$) m/z (M+H)$^+$ 1165.76, m/z (M-H)$^-$ 1163.70, [calculated $C_{54}H_{65}BrN_6O_{18}$: 1164.35].

N1,N1,N2-tris(2-(3-carboxy-2-methoxybenzamido)ethyl)-N2-(2-(6-carboxy-N-(6-ethoxy-6-oxohexyl)picolinamido)ethyl)ethane-1,2-diaminium chloride (NCP243)

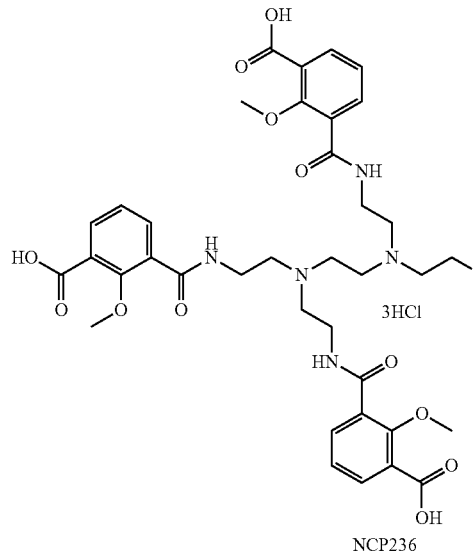

NCP236

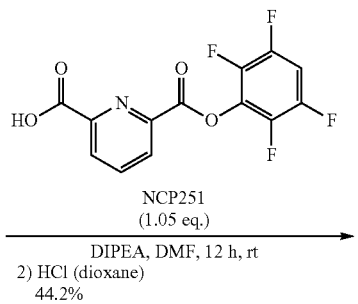

NCP251
(1.05 eq.)
DIPEA, DMF, 12 h, rt
2) HCl (dioxane)
44.2%

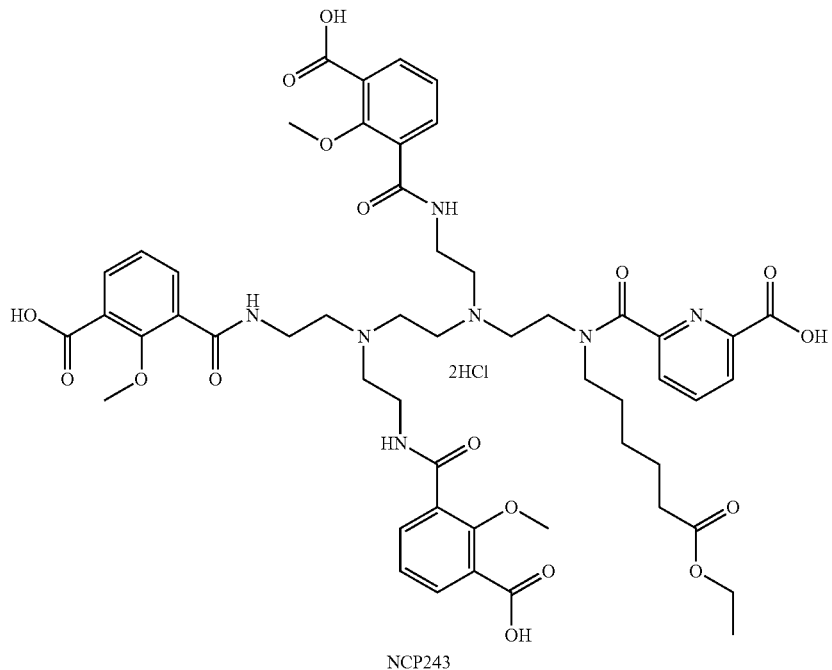

NCP243

N1,N1,N2-tris(2-(3-carboxy-2-methoxybenzamido)ethyl)-N2-(2-(((6-ethoxy-6-oxohexyl)ammonio)ethyl)ethane-1,2-diaminium chloride (NCP236, 75 mg, 74 umol, 1 eq) and DIPEA (130 uL, 736 umol, 10 eq) were dissolved in DMF (2 mL) then 6-((2,3,5,6-tetrafluorophenoxy)carbonyl)picolinic acid (NCP206, 25.5 mg, 81 umol, 1.1 eq) was added and the reaction was stirred for 12 h at room temperature. To the reaction mixture under Ar was added HCl/dioxane (4.0 M, 370 uL, 1.47 mmol, 20 eq) and the reaction mixture was concentrated to an oil in vacuo. The product was precipitated with ~15 mL ACN and the solid was allowed to settle. The mother liquor was carefully decanted and the solid was briefly dried in vacuo. The ACN trituration process was repeated twice more and the solid dried in vacuo. Yield=36.8 mg, 44.2% as an off-white, fluffy solid. MS (ESI$^{+/-}$) m/z (M+H)$^+$ 1058.65, m/z (M−H)$^-$ 1056.69, [calculated $C_{52}H_{63}N_7O_{17}$: 1057.43].

Me₃BH(2,2)IAM-N-hexanoic acid-mono-picolinic-4HCl (NCP244)

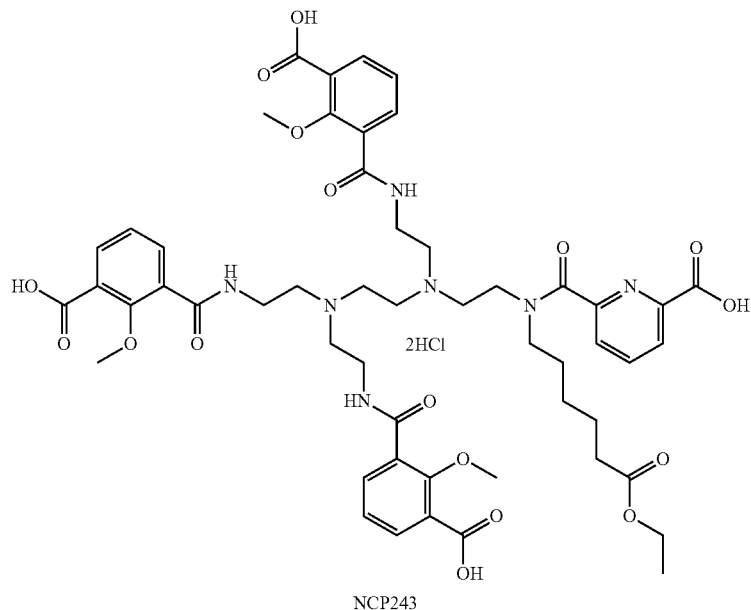

NCP243

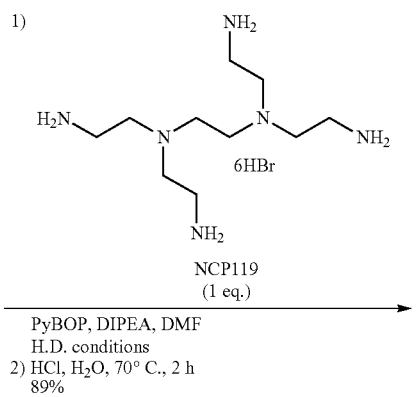

NCP119
(1 eq.)

1) PyBOP, DIPEA, DMF
   H.D. conditions
2) HCl, H₂O, 70° C., 2 h
   89%

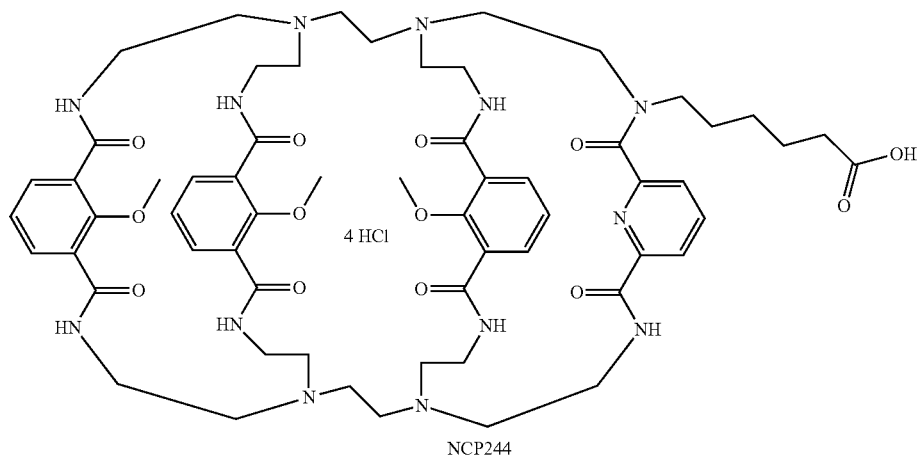

NCP244

The procedure for the synthesis of Me₄BH(2,2)IAM-N-hexanoic acid (NCP240) was followed, replacing ethyl 6-((2-((2-aminoethyl)(2-(bis(2-aminoethyl)amino)ethyl)amino)ethyl)amino)hexanoate-6HBr (NCP233) with N1,N1'-(ethane-1,2-diyl)bis(N1-(2-aminoethyl)ethane-1,2-diamine)-6HBr (NCP119) and 3,3',3'',3'''-(5,8-bis(2-formamidoethyl)-2,5,8,11-tetraazadodecanedioyl)tetrakis(2-methoxybenzoic acid)-2HCl (NCP133) with N1,N1,N2-tris(2-(3-carboxy-2-methoxybenzamido)ethyl)-N2-(2-(6-carboxy-N-(6-ethoxy-6-oxohexyl)picolinamido)ethyl)ethane-1,2-diaminium chloride (NCP243) where necessary. The reaction was run on a 21.3 mg (30 umol) scale of NCP119. For this reaction, NCP119 and NCP243 were dissolved to a final volume of 2 mL DMF (~16 mM each). At the start, 1 mL NCP243 solution was added, followed by alternating additions of 500 uL of NCP119 and NCP243 until both solutions were completely added. The final two additions were of the NCP119 solution. Yield=35.3 mg, 89% as a tan, fluffy solid. MS (ESI$^{+/-}$) m/z (M+H)$^+$ 1190.96, m/z (M−H)$^−$ 1188.94, [calculated $C_{60}H_{79}N_{13}O_{13}$: 1189.59].

BH(2,2)IAM-N-hexanoic acid-mono-picolinic-4HCl
(NCP227)

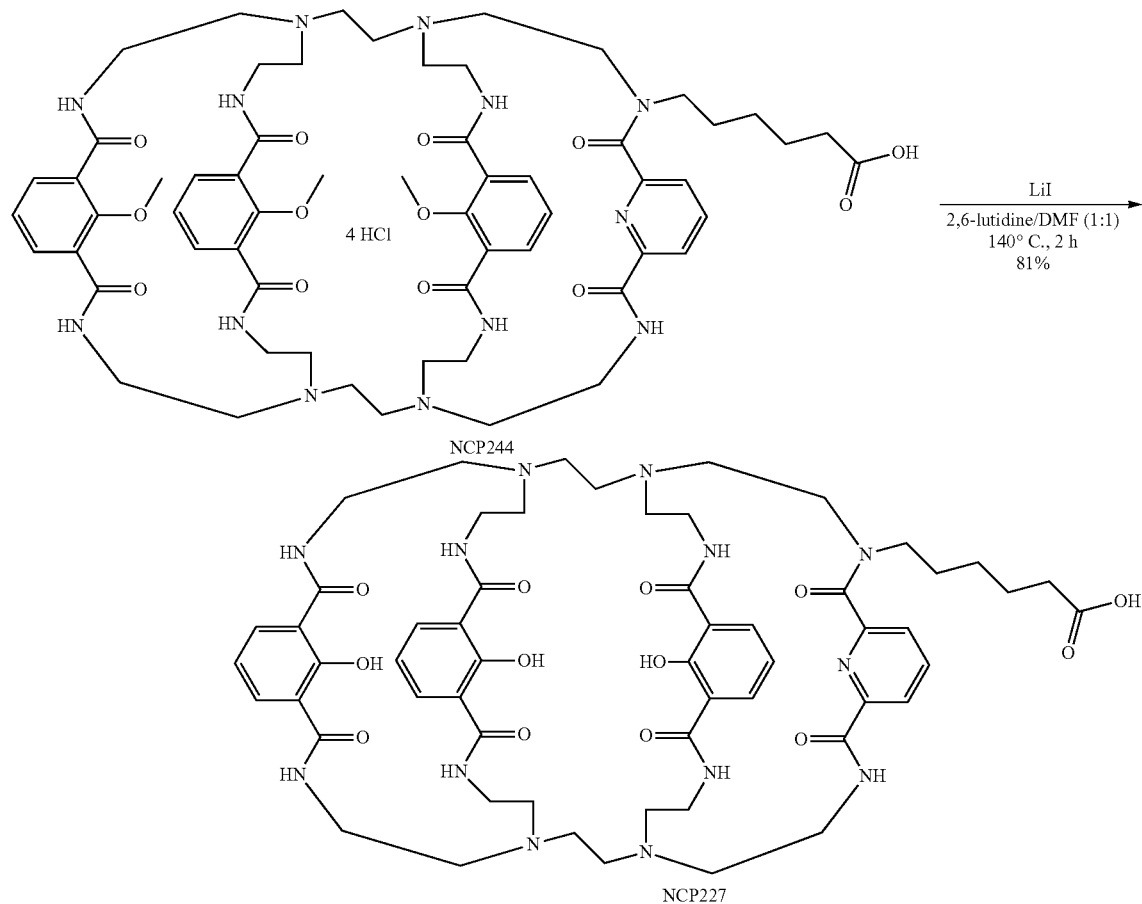

The procedure for the synthesis of BH(2,2)IAM-N-hexanoic acid (NCP189) was followed, replacing Me₄BH(2,2)IAM-N-hexanoic acid (NCP240) with Me₃BH(2,2)IAM-N-hexanoic acid-mono-picolinic·4HCl (NCP244) where necessary. The reaction mixture was refluxed at 140° C. for 1 h instead of 2 h. The reaction was run on a 20 mg (15 umol) scale of NCP244. Yield=15.7 mg, 81% as a tan, fluffy solid. MS (ESI⁺/⁻) m/z (M+H)⁺ 1148.98, m/z (M−H)⁻ 1146.87, [calculated $C_{57}H_{73}N_{13}O_{13}$: 1147.55].

N1-trityl-N₂-(2-(tritylamino)ethyl)ethane-1,2-diamine (NCP234)

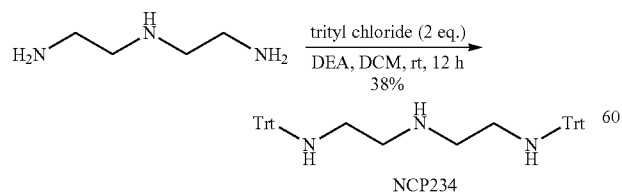

To a solution of diethylenetriamine (750 uL, 6.91 mmol, 1 eq) and diethylamine (DEA, 1.59 mL, 15.2 mmol, 2.2 eq) in DCM (50 mL) was added a solution of trityl chloride (4.0 g, 14.5 mmol, 2.1 eq) in DCM (15 mL) dropwise over 15 min. The reaction was stirred for 12 h at room temperature. The reaction mixture was diluted into 100 mL DCM and the organic layer was washed 2×100 mL H₂O and 1×100 mL saturated brine solution. The organic layer was dried over Na₂SO₄, filtered, and concentrated. The crude product was purified via flash chromatography (loading solvent: DCM); λ 225 nm, 260 nm; gradient: 100% DCM for 2 CV, 100% DCM to 1% MeOH/DCM over 1 CV, 1% MeOH/DCM for 2 CV, 1% to 5% MeOH/DCM over 4 CV, 5% MeOH/DCM for 3 CV). Yield=1.5 g, 38% as a white, fluffy solid. ¹H NMR (400 MHz, CDCl₃) δ 7.51 (d, J=7.8 Hz, 12H), 7.30-7.25 (m, 12H), 7.20 (t, J=7.2 Hz, 6H), 2.68 (t, J=5.7 Hz, 4H), 2.29 (t, J=5.8 Hz, 4H), 1.92 (s, 2H), 1.43 (s, 1H). MS (ESI⁺) m/z (M+H)⁺ 588.74, [calculated $C_{42}H_{41}N_3$: 587.33].

Lithium bis(2-(tritylamino)ethyl)glycinate
(NCP269)

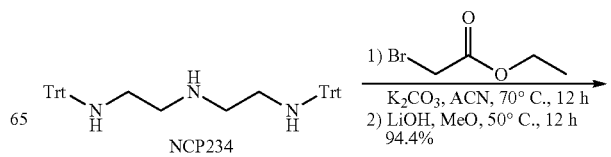

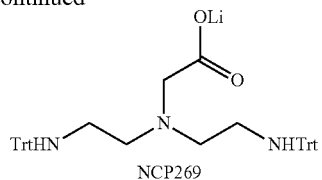

NCP269

N1-trityl-N$_2$-(2-(tritylamino)ethyl)ethane-1,2-diamine (NCP234, 50 mg, 85 umol, 1 eq) and K$_2$CO$_3$ (35 mg, 255 umol, 3 eq) were suspended in ACN (4 mL) then ethyl bromoacetate (10.4 uL, 94 umol, 1.1 eq) was added and the suspension was heated to 70° C. for 12 h. The reaction mixture was cooled to room temperature and the carbonate salts were filtered off. The filtrate was concentrated in vacuo and the resulting yellow solid was dissolved in MeOH (3 mL) and LiOH/MeOH (1.0 M, 850 uL, 850 umol, 10 eq) was added. The reaction mixture was heated to 50° C. for 12 h then concentrated to dryness in vacuo. The resulting solid was triturated with H$_2$O (5 mL) and the solid purified via centrifugation, washed twice more with H$_2$O, and dried in vacuo. Yield=52 mg, 94.4% as an off-white, fluffy powder. MS (ESI$^{+/-}$) m/z (M+H)$^+$ 646.62, m/z (M–H)$^-$ 644.64, [calculated C$_{44}$H$_{43}$N$_3$O$_2$: 645.34].

2-(bis(2-(tritylamino)ethyl)amino)-N,N-bis(2-(tritylamino)ethyl)acetamide (NCP238)

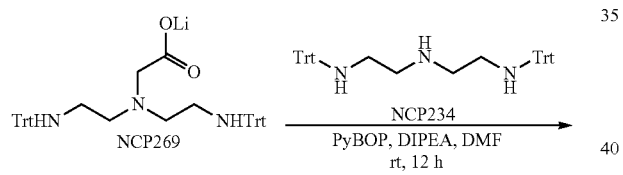

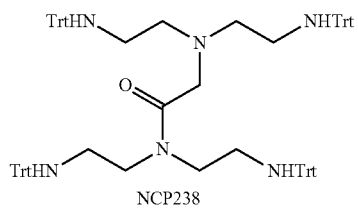

NCP238

Lithium bis(2-(tritylamino)ethyl)glycinate (NCP269, 25.2 mg, 39 umol, 1 eq), DIPEA (20 uL, 116 umol, 3 eq) and N1-trityl-N$_2$-(2-(tritylamino)ethyl)ethane-1,2-diamine (NCP234, 25 mg, 43 umol, 1.1 eq) were dissolved in DMF (1 mL). To the solution was added PyBOP (22.1 mg, 43 umol, 1.1 eq) and the reaction was stirred at room temperature for 12 h. The reaction mixture was diluted into EtOAc (25 mL). The organic layer was washed 1×25 mL H$_2$O, 2×25 mL half saturated NaHCO$_3$ solution, and 1×25 mL saturated brine solution. The organic layer was separated, dried over Na$_2$SO$_4$, filtered, concentrated, and the crude solid was purified via flash chromatography (loading solvent: DCM; k 250 nm, 263 nm; 20% EtOAc/Hex). Yield=40.2 mg, 86% as a white, fluffy solid. MS (ESI$^+$) m/z (M+H)$^+$ 1216.07, [calculated C$_{86}$H$_{82}$N$_6$O: 1214.66].

N,N-bis(2-aminoethyl)-2-(bis(2-aminoethyl)amino)acetamide·5HCl (NCP270)

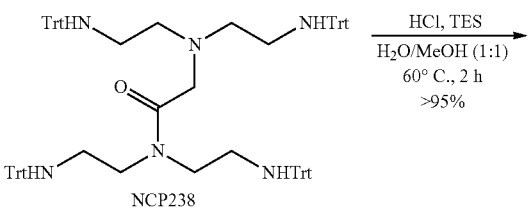

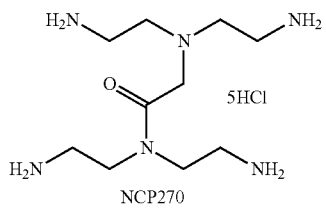

NCP270

2-(bis(2-(tritylamino)ethyl)amino)-N,N-bis(2-(tritylamino)ethyl)acetamide (NCP238, 32 mg, 26 umol, 1 eq) was dissolved in 2 mL of 1 N HCl/MeOH (1:1) then triethylsilane (TES, 34 uL, 211 umol, 8 eq) was added and the reaction mixture was heated to 60° C. for 2 h. Et$_2$O (5 mL) was added to the reaction and the ethereal layer was separated and discarded. The aqueous layer was concentrated in vacuo to an oil and the product was precipitated via the addition of ACN (2 mL). The crude product was purified via centrifugation, washed with ACN, and dried in vacuo. Yield=11 mg, >95% as a white, fluffy solid. MS (ESI$^+$) m/z (M+H)$^+$ 247.26, [calculated C$_{10}$H$_{26}$N$_6$O: 246.22].

Free Cage—Me4-Mono-Glycine Cap-3HCl
(NCP271)

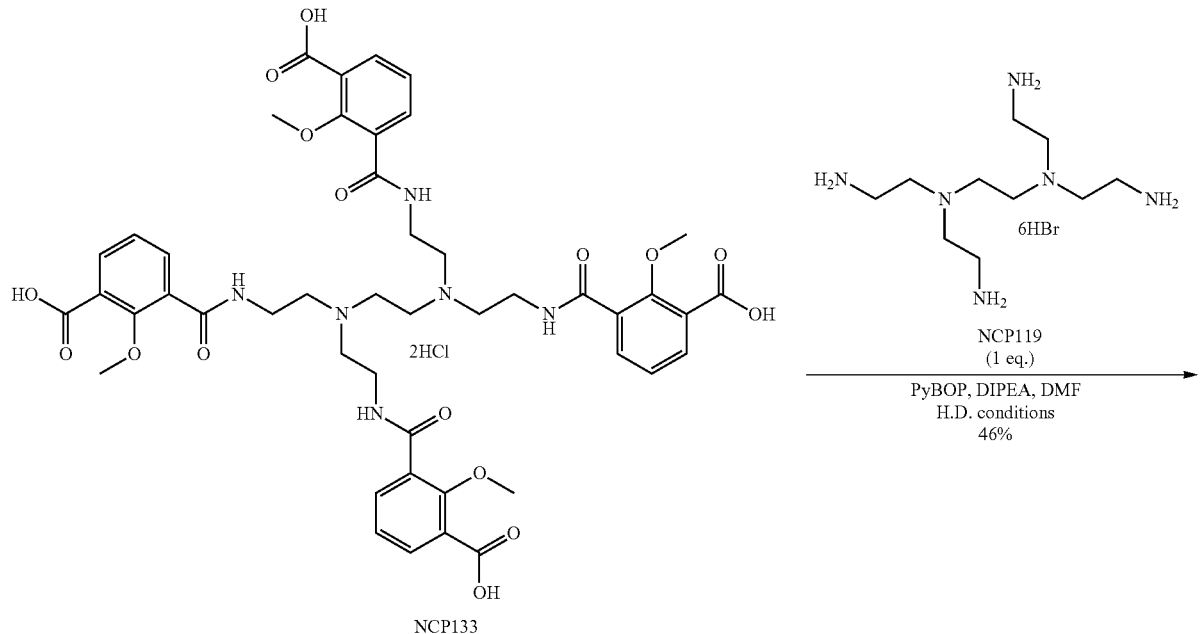

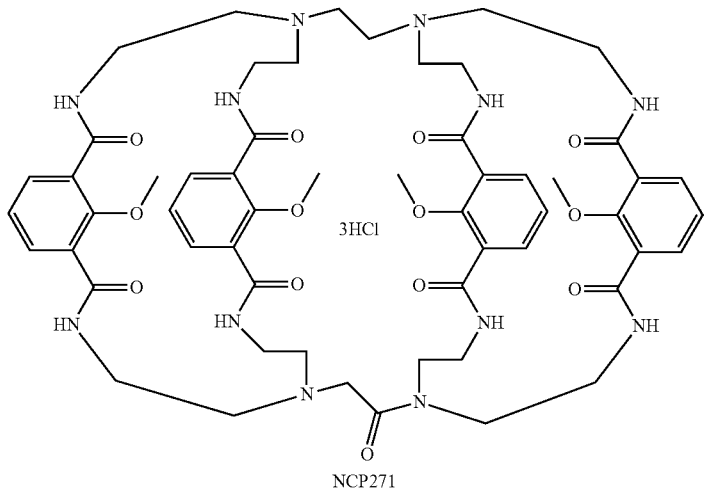

The procedure for the synthesis of Me4BH(2,2)IAM-N-hexanoic acid (NCP240) was followed, replacing ethyl 6-((2-((2-aminoethyl)(2-(bis(2-aminoethyl)amino)ethyl)amino)ethyl)amino)hexanoate-6HBr (NCP233) with N,N-bis(2-aminoethyl)-2-(bis(2-aminoethyl)amino)acetamide-5HCl (NCP270) where necessary. The reaction was run on a 11.3 mg (26 umol) scale of NCP270. For this reaction, NCP270 and NCP133 were dissolved to a final volume of 1.5 mL DMF (19 mM each). At the start, 750 uL NCP133 solution was added, followed by alternating additions of 500 uL of NCP270 and NCP133 until both solutions were completely added. The final addition of NCP133 solution was 250 uL. The final two additions were of the NCP270 solution. Once the crude product was obtained after the Et$_2$O/EtOH and Et$_2$O triturations, the resulting dried solid was suspended in 1 N HCl (1 mL) and purified via centrifugation. The solid was briefly dried in vacuo then triturated twice with ACN, purified via centrifugation, and dried in vacuo. Yield=14.8 mg, 46% as a tan, fluffy solid. MS (ESI$^{+/-}$) m/z (M+H)$^+$ 1119.86, m/z (M−H)$^−$ 1117.49, [calculated C$_{56}$H$_{70}$N$_{12}$O$_{13}$: 1118.52].

Free Cage—Mono-Glycine Cap·3HCl (NCP272)

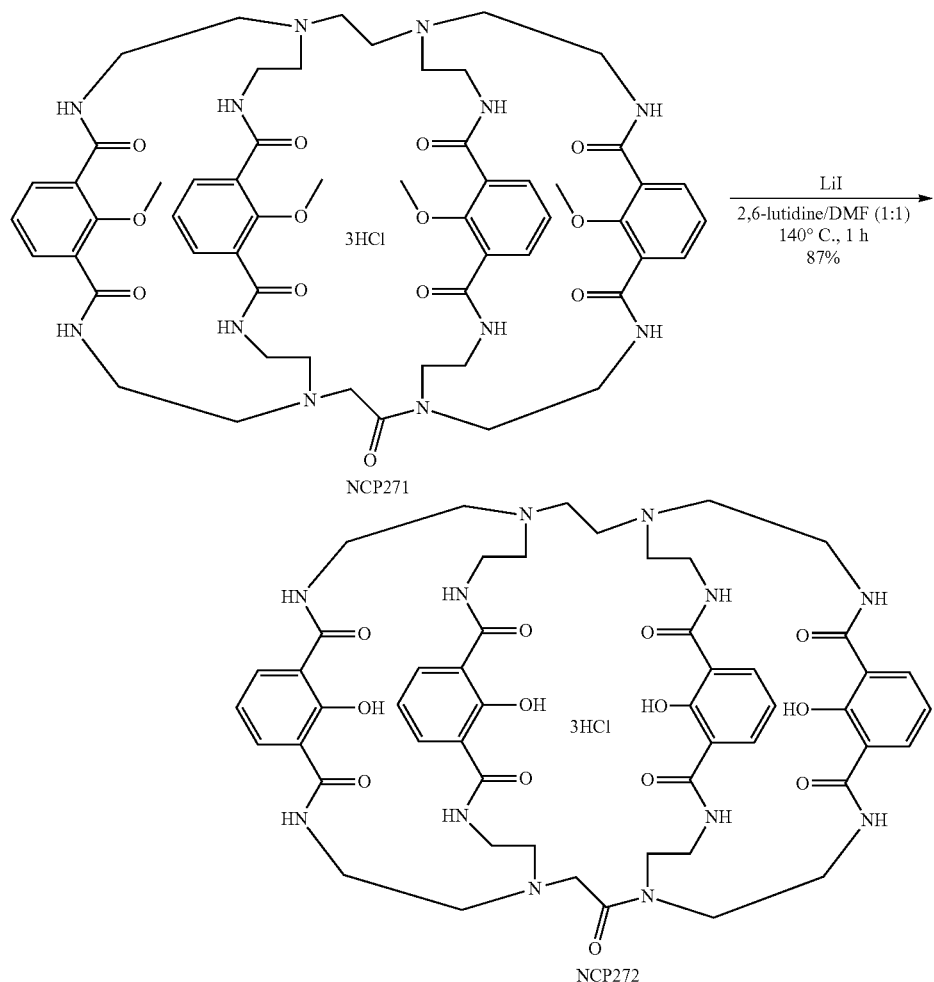

The procedure for the synthesis of BH(2,2)IAM-N-hexanoic acid (NCP189) was followed, replacing Me₄BH (2,2)IAM-N-hexanoic acid (NCP240) with free cage—Me₄-mono-glycine cap·3HCl (NCP271) where necessary. The reaction mixture was refluxed at 140° C. for 1 h instead of 2 h. The reaction was run on a 14.8 mg (12 umol) scale of NCP271. Yield=12.3 mg, 87% as a tan, fluffy solid. MS (ESI$^{+/-}$) m/z (M+H)$^+$ 1063.83, m/z (M−H)$^-$ 1061.79, [calculated $C_{52}H_{62}N_{12}O_{13}$: 1062.46].

2,2'-(azanediylbis(ethane-2,1-diyl))bis(isoindoline-1,3-dione) (NCP230)

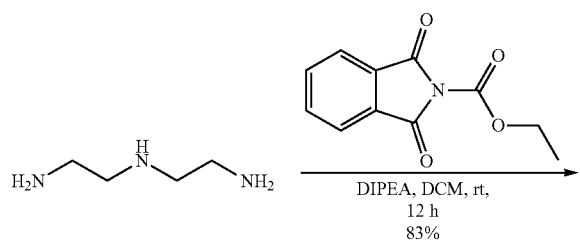

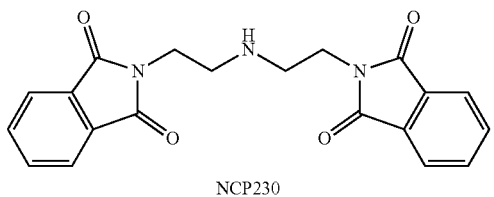

To a solution of diethylenetriamine (790 uL, 7.3 mmol, 1 eq) and DIPEA (6.3 mL, 36.4 mmol, 5 eq) in DCM (50 mL) was added N-carbethoxyphthalimide (3.3 g, 15.3 umol, 2.1 eq). The reaction was stirred for 12 h at room temperature. The reaction mixture was concentrated to dryness in vacuo and the resulting solid was triturated with EtOH (100 mL) and filtered. The solid was washed with EtOH and dried in vacuo overnight. Yield=2.2 g, 83% as a white, fluffy solid. $^1$H NMR (400 MHz, CDCl₃) δ 7.76-7.70 (m, 4H), 7.70-7.64 (m, 4H), 3.77 (t, J=6.0 Hz, 4H), 2.95 (t, J=6.1 Hz, 4H), 1.13 (s, 1H). MS (ESI$^+$) m/z (M+H)$^+$ 364.04, [calculated $C_{20}H_{17}N_3O_4$: 363.12].

1,1,3,3-tetrakis(2-(1,3-dioxoisoindolin-2-yl)ethyl)urea (NCP248)

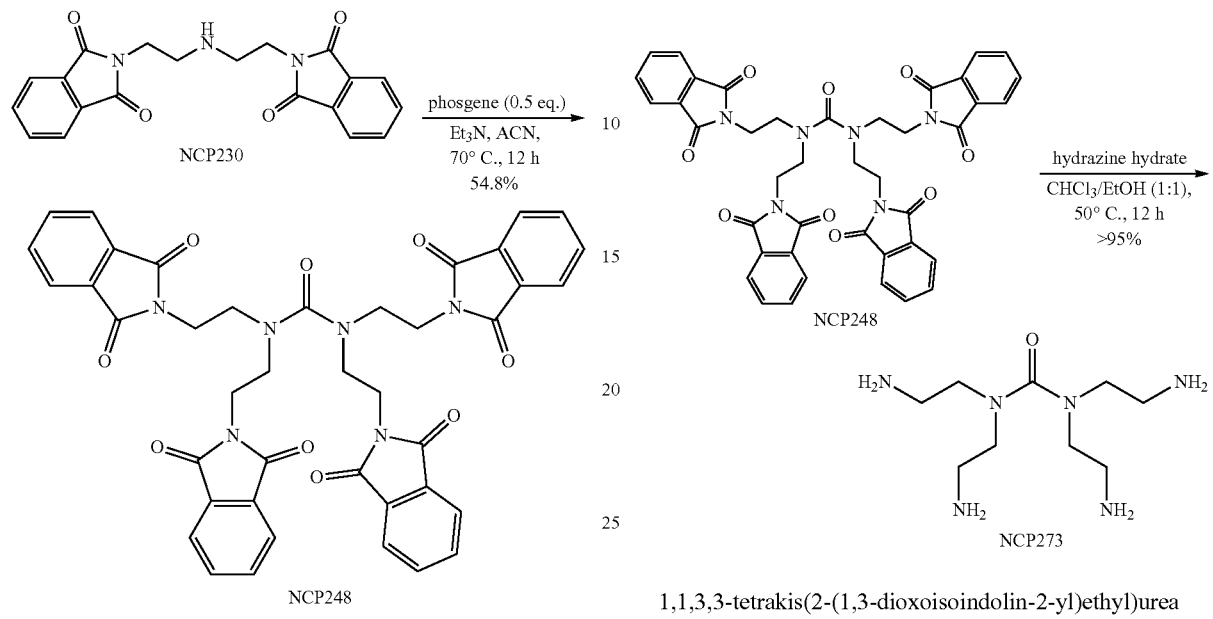

2,2'-(azanediylbis(ethane-2,1-diyl))bis(isoindoline-1,3-dione) (NCP230, 200 mg, 550 umol, 2.05 eq) was suspended in ACN (5 mL) with Et₃N (112 uL, 806 umol, 3 eq) then phosgene (15% w/w in toluene, 192 uL, 269 umol, 1 eq) was added and the reaction mixture was heated to 70° C. for 12 h. The solution was cooled to room temperature to precipitate the product, which was collected by filtration, washed with minimal ACN, and dried in vacuo overnight. Yield=111 mg, 54.8% as a white, crystalline solid. MS (ESI⁺) m/z (M+H)⁺ 753.54, [calculated $C_{41}H_{32}N_6O_9$: 752.22].

1,1,3,3-tetrakis(2-aminoethyl)urea (NCP273)

1,1,3,3-tetrakis(2-(1,3-dioxoisoindolin-2-yl)ethyl)urea (NCP248, 100 mg, 133 umol, 1 eq) was dissolved in 1:1 CHCl₃/EtOH (5 mL) then hydrazine hydrate (50-60%, 260 uL, 2.7 mmol, 20 eq) was added and the reaction mixture was heated to 50° C. for 12 h. The solution was filtered and the filtrate was concentrated, dried in vacuo and used without further purification. Yield=30 mg, >95% as a colorless oil. MS (ESI⁺) m/z (M+H)⁺ 233.33, [calculated $C_9H_{24}N_6O$: 232.20].

Free Cage—Me₄-Mono-Urea Cap-2HCl (NCP274)

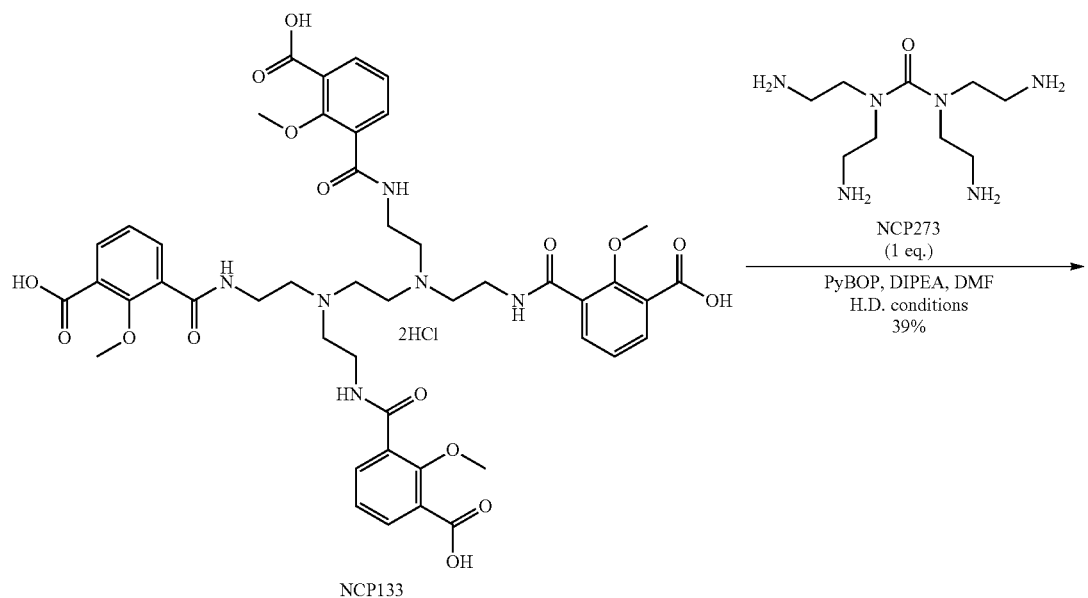

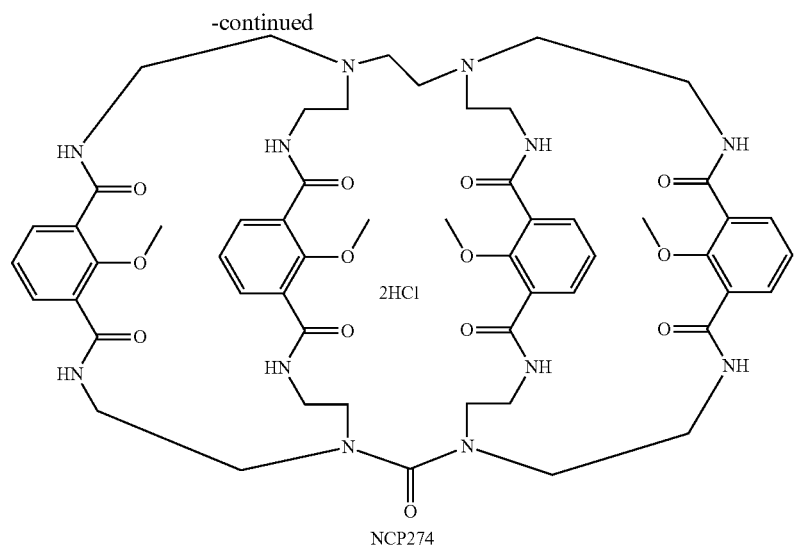

NCP274

The procedure or the synthesis of Me₄BH(2,2)IAM-N-hexanoic acid (NCP240) was followed, replacing ethyl 6-((2-((2-aminoethyl)(2-(bis(2-aminoethyl)amino)ethyl)amino)ethyl)amino)hexanoate-6HBr (NCP233) with 1,1,3,3-tetrakis(2-aminoethyl)urea (NCP273) where necessary. The reaction was run on a 10 mg (43 umol) scale of NCP273. For this reaction, NCP273 and NCP133 were dissolved to a final volume of 2 mL DMF (~20 mM each). At the start, 1 mL NCP133 solution was added, followed by alternating additions of 500 uL of NCP273 and NCP133 until both solutions were completely added. The final two additions were of the NCP273 solution. Once the crude product was obtained after the Et₂O/EtOH and Et₂O triturations, the resulting dried solid was suspended in 1 N HCl (1 mL) and purified via centrifugation. The solid was briefly dried in vacuo then triturated twice with ACN, purified via centrifugation, and dried in vacuo. Yield=20 mg, 39% as a tan, fluffy solid. MS (ESI$^{+/-}$) m/z (M+H)$^+$ 1105.78, m/z (M–H)$^-$ 1103.71, [calculated $C_{55}H_{68}N_{12}O_{13}$: 1104.50].

Free Cage—Mono-Urea Cap-2HCl (NCP275)

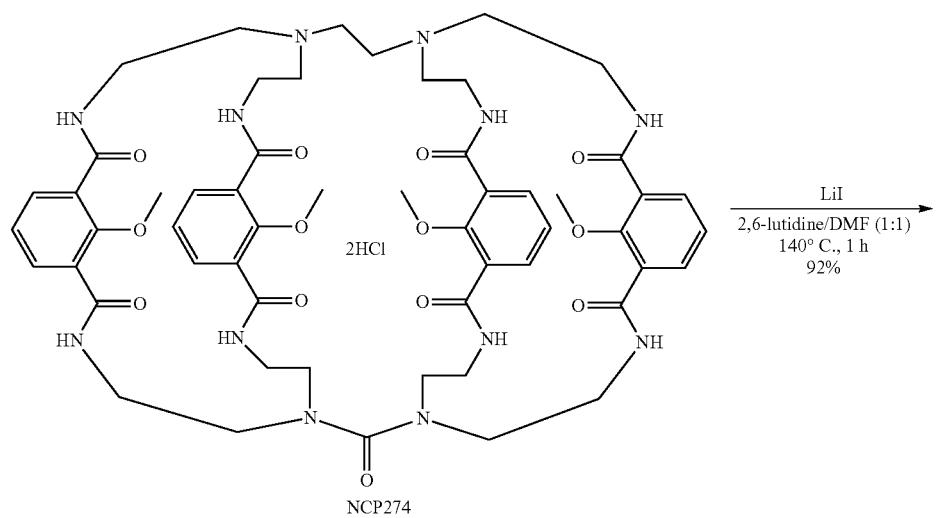

NCP274

-continued

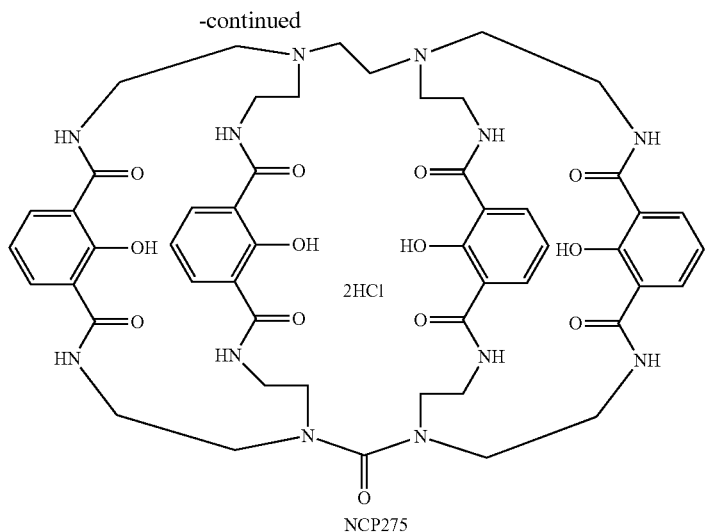

NCP275

The procedure for the synthesis of BH(2,2)IAM-N-hexanoic acid (NCP189) was followed, replacing Me₄BH(2,2)IAM-N-hexanoic acid (NCP240) with free cage—Me₄-mono-urea cap·2HCl (NCP274) where necessary. The reaction mixture was refluxed at 140° C. for 1 h instead of 2 h. The reaction was run on a 20 mg (17 umol) scale of NCP274. Yield=17.5 mg, 92% as a tan, fluffy solid. MS (ESI$^{+/-}$) m/z (M+H)$^+$ 1049.85, m/z (M−H)$^−$ 1047.66, [calculated $C_{51}H_{60}N_{12}O_{13}$: 1048.44].

Tb, Eu, Dy, and Sm Loading

Ligands were loaded with Tb, Eu, Dy, or Sm by dissolving the appropriate compound in MeOH to a concentration of 1 mM with 50 eq of pyridine then adding 1.5 eq of TbCl₃·6H₂O, EuCl₃·6H₂O, DyCl₃·6H₂O, or SmCl₃·6H₂O as a solution in MeOH. The resulting solutions were heated to 50° C. for 30 min and cooled to room temperature. The solutions were concentrated in vacuo and the resulting solids were triturated three times with ACN, purified via centrifugation, and dried in vacuo, resulting in near-quantitative yields.

The terbium complexes were further characterized by LCMS. NCP134-Tb, MS (ESI$^{+/-}$) m/z (M+H)$^+$ 1205.61, m/z (M−H)$^−$ 1203.41, [calculated $C_{52}H_{61}N_{12}O_{12}$Tb: 1204.38]. NCP158-Tb, MS (ESI$^{+/-}$) m/z (M+H)$^+$ 1517.34, m/z (M−H)$^−$ 1515.47, [calculated $C_{52}H_{57}Br_4N_{12}O_{12}$Tb: 1516.02]. NCP144-Tb, MS (ESI$^{+/-}$) m/z (M+H)$^+$ 1263.35, m/z (M−H)$^−$ 1261.75, [calculated $C_{54}H_{63}N_{12}O_{14}$Tb: 1262.38]. NCP166-Tb, MS (ESI$^{+/-}$) m/z (M+H)$^+$ 1468.76, m/z (M−H)$^−$ 1466.59, [calculated $C_{64}H_{83}ClN_{13}O_{15}$Tb: 1467.51]. NCP167-Tb, MS (ESI$^{+/-}$) m/z (M+H)$^+$ 1446.73, m/z (M−H)$^−$ 1444.54, [calculated $C_{64}H_{72}N_{17}O_{13}$Tb: 1445.47]. NCP168-Tb, MS (ESI$^{+/-}$) m/z (M+H)$^+$ 1678.02, m/z (M−H)$^−$ 1676.34, [calculated $C_{78}H_{89}N_{15}O_{15}$Tb: 1676.60]. NCP169-Tb, MS (ESI$^{+/-}$) m/z (M+H)$^+$ 1515.77, m/z (M−H)$^−$ 1513.65, [calculated $C_{67}H_{75}N_{18}O_{14}$Tb: 1514.50]. NCP205-Tb, MS (ESI$^{+/-}$) m/z (M+H)$^+$ 1692.03, m/z (M−H)$^−$ 1689.68, [calculated $C_{74}H_{99}N_{16}O_{18}$STb: 1690.63]. NCP189-Tb, MS (ESI$^{+/-}$) m/z (M+H)$^+$ 1319.89, m/z (M−H)$^−$ 1317.77, [calculated $C_{58}H_{71}N_{12}O_{14}$Tb: 1318.45]. NCP190-Tb, MS (ESI$^{+/-}$) m/z (M+H)$^+$ 1525.07, m/z (M−H)$^−$ 1522.83, [calculated $C_{68}H_{91}ClN_{13}O_{15}$Tb: 1523.57]. NCP191-Tb, MS (ESI$^{+/-}$) m/z (M+H)$^+$ 1572.11, m/z (M−H)$^−$ 1569.77, [calculated $C_{71}H_{83}N_{18}O_{14}$Tb: 1570.56]. NCP192-Tb, MS (ESI$^{+/-}$) m/z (M+H)$^+$ 1503.01, m/z (M−H)$^−$ 1500.71, [calculated $C_{68}H_{80}N_{17}O_{13}$Tb: 1501.54]. NCP197-Tb, MS (ESI$^{+/-}$) m/z (M+H)$^+$ 1613.12, m/z (M−H)$^−$ 1610.90, [calculated $C_{75}H_{90}N_{17}O_{14}$Tb: 1611.61]. NCP202-Tb, MS (ESI$^{+/-}$) m/z (M+H)$^+$ 1416.98, m/z (M−H)$^−$ 1414.90, [calculated $C_{62}H_{74}N_{13}O_{16}$Tb: 1415.46]. NCP227-Tb, MS (ESI$^{+/-}$) m/z (M+H)$^+$ 1304.85, m/z (M−H)$^−$ 1303.93, [calculated $C_{57}H_{70}N_{13}O_{13}$Tb: 1303.45]. NCP259-Tb, MS (ESI$^{+/-}$) m/z (M+H)$^+$ 1303.94, m/z (M−H)$^−$ 1301.79, [calculated $C_{58}H_{71}N_{12}O_{13}$Tb: 1302.45]. NCP272-Tb, MS (ESI$^{+/-}$) m/z (M+H)$^+$ 1219.92, m/z (M−H)$^−$ 1217.15, [calculated $C_{52}H_{59}N_{12}O_{13}$Tb: 1218.36]. NCP275-Tb, MS (ESI$^{+/-}$) m/z (M+H)$^+$ 1205.56, m/z (M−H)$^−$ 1203.49, [calculated $C_{51}H_{57}N_{12}O_{13}$Tb: 1204.34].

The europium complexes were further characterized by LCMS. NCP189-Eu, MS (ESI$^{+/-}$) m/z (M+H)$^+$ 1313.81, m/z (M−H)$^−$ 1311.79, [calculated $C_{58}H_{71}EuN_{12}O_{14}$: 1312.44]. NCP227-Eu, MS (ESI$^{+/-}$) m/z (M+H)$^+$ 1298.71, m/z (M−H)$^−$ 1296.82, [calculated $C_{57}H_{70}EuN_{13}O_{13}$: 1297.44]. NCP259-Eu, MS (ESI$^{+/-}$) m/z (M+H)$^+$ 1297.98, m/z (M−H)$^−$ 1295.69, [calculated $C_{58}H_{71}EuN_{12}O_{13}$: 1296.45]. NCP272-Eu, MS (ESI$^{+/-}$) m/z (M+H)$^+$ 1213.01, m/z (M−H)$^−$ 1211.78, [calculated $C_{52}H_{59}EuN_{12}O_{13}$: 1212.35]. NCP275-Eu, MS (ESI$^{+/-}$) m/z (M+H)$^+$ 1199.98, m/z (M−H)$^−$ 1197.74, [calculated $C_{51}H_{57}EuN_{12}O_{13}$: 1198.34].

The dysprosium complexes were further characterized by LCMS. NCP189-Dy, MS (ESI$^{+/-}$) m/z (M+H)$^+$ 1324.94, m/z (M−H)$^−$ 1322.78, [calculated $C_{58}H_{71}DyN_{12}O_{14}$: 1323.45].

The samarium complexes were further characterized by LCMS. NCP189-Sm, MS (ESI$^{+/-}$) m/z (M+H)$^+$ 1312.63, m/z (M−H)$^−$ 1310.79, [calculated $C_{58}H_{71}N_{12}O_{14}$Sm: 1311.44].

Fluorescence Lifetimes of Selected Tb Complexes is Summarized in Table 1

TABLE 1

| Ligand Structure | Complex | Lanthanide | Life Time, (ms) |
|---|---|---|---|
| (structure) | NCP 134-Tb | Tb | 2.56 |
| (structure) | NCP 158-Tb | Tb | 0.97 |
| (structure) | NCP 144-Tb | Tb | 2.06 |

TABLE 1-continued

| Ligand Structure | Complex | Lanthanide | Life Time, (ms) |
|---|---|---|---|
| | NCP 166-Tb | Tb | 2.23 |
| | NCP 169-Tb | Tb | 1.99 |
| | NCP 189-Tb | Tb | 1.79 |

TABLE 1-continued

| Ligand Structure | Complex | Lanthanide | Life Time, (ms) |
|---|---|---|---|
| | NCP 190-Tb | Tb | 2.46 |
| | NCP 191-Tb | Tb | 2.11 |
| | NCP 259-Tb | Tb | 1.37 |
| | NCP 227-Tb | Tb | 1.20 |

TABLE 1-continued

| Ligand Structure | Complex | Lanthanide | Life Time, (ms) |
|---|---|---|---|
| (structure) | NCP 272-Tb | Tb | 1.53 |
| (structure) | NCP 275-Tb | Tb | 1.39 |

Fluorescence Lifetimes of Selected Eu Complexes is Summarized in Table 2

TABLE 2

| Ligand Structure | Complex | Lanthanide | Life Time, (ms) |
|---|---|---|---|
| (structure) | NCP 189-Eu | Eu | 598 |

TABLE 2-continued

| Ligand Structure | Complex | Lanthanide | Life Time, (ms) |
|---|---|---|---|
| (structure) | NCP 259-Eu | Eu | 657 |
| (structure) | NCP 227-Eu | Eu | 651 |
| (structure) | NCP 272-Eu | Eu | 609 |

TABLE 2-continued

| Ligand Structure | Complex | Lanthanide | Life Time, (ms) |
|---|---|---|---|
| *[macrocyclic ligand structure]* | NCP 275-Eu | Eu | 505 |

Fluorescence lifetimes of NCP189-Dy and NCP189-Sm complexes is in Table 3

TABLE 3

| Ligand Structure | Complex | Lanthanide | Life Time (ms) |
|---|---|---|---|
| *[macrocyclic ligand structure with pendant carboxylic acid]* | NCP 189-Dy | Dy | 22.7 |
| *[macrocyclic ligand structure with pendant carboxylic acid]* | NCP 189-Sm | Sm | 28.1 |

Example A—TR-FRET Assay with HaloSnap Fusion Protein (HSFP)

Figure 4:
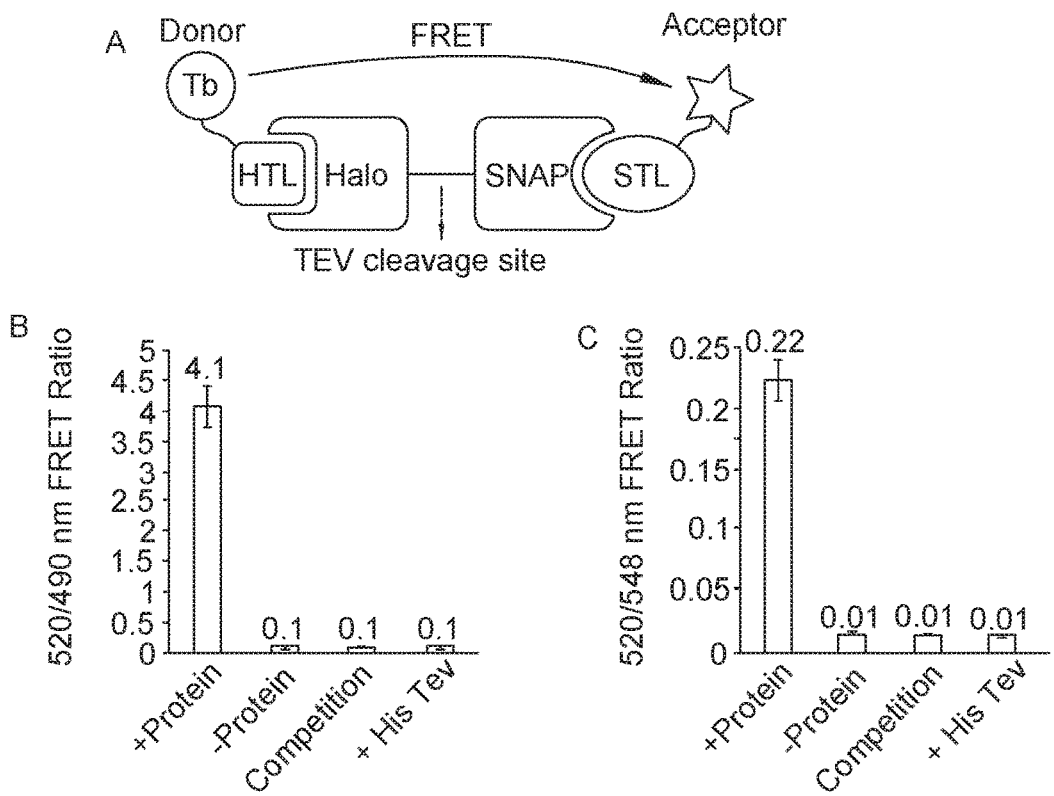
FIG. 4 shows: (A) Scheme depicting Halotag-Snaptag fusion protein (HSFP) labeled with a Halotag-Tb ligand (NCP190-Tb) and a Snaptag-acceptor dye. (B) TR-FRET ratios obtained with Snaptag-BODIPY. (C) TR-FRET ratios obtained with Snaptag-TAMRA.

Recombinant Halotag-Snaptag fusion protein (HSFP) with TEV cleaveage site in between the two domains (5 uM) was labeled with 0.5 eq NCP190-Tb and 2 eq of either Snaptag-BODIPY or Snaptag-TAMRA in 25 mMv Tris buffer, pH 7.4 with 1 mM DTT and 0.05%0 TWEEN-20 detergent for 1 h at room temperature and then 4° C. for 12 h. The labeled protein was diluted to a final assay concentration of 10 nM. For protein labeled with Snaptag-BODIPY, the TR-FRET ratio was obtained from 520 nm (BODIPY) emission and 490 nm (Tb) emission. For protein labeled with Snaptag-TAMRA, the TR-FRET ratio was obtained from 570 nm (TAMRA) emission and 548 nm (Tb) emission. Control experiments were performed in the absence of protein, with protein pre-labeled with a non-fluorescent Halotag ligand, and with protein that had been cleaved with HisTev after labeling. See FIG. 4.

Example B—TR-FRET Assay with Halotag-EGFP Fusion Protein (HaloEGFP)

Figure 5:
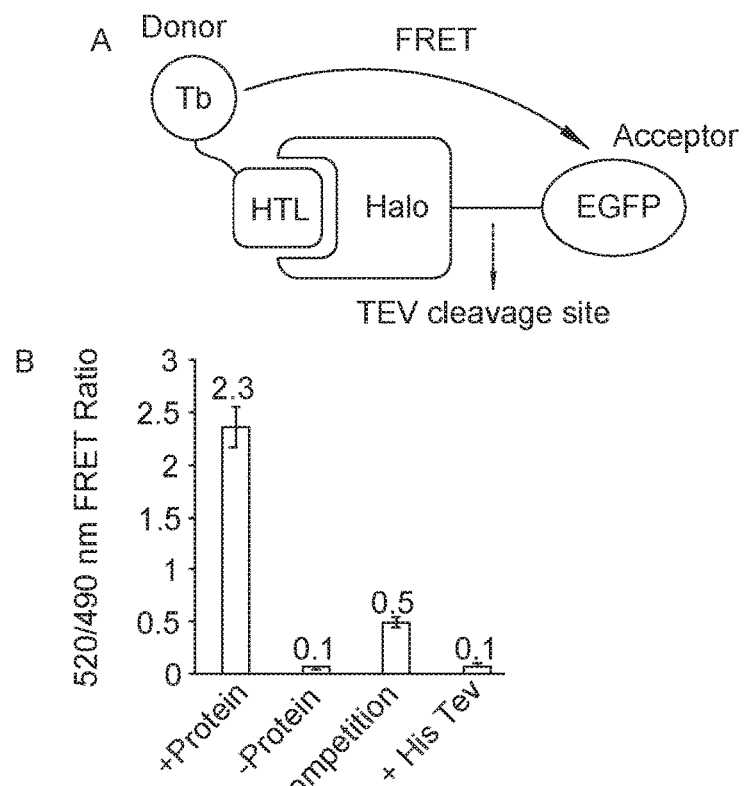
FIG. 5 shows: (A) Scheme depicting Halotag-enhanced green fluorescent protein (HaloEGFP) labeled with a Halotag-Tb ligand (NCP190-Tb). (B) TR-FRET ratios obtained.

Recombinant Halotag-enhanced green fluorescent protein fusion protein (HaloEGFP) with TEV cleaveage site in between the two domains (5 uM) was labeled with 0.5 eq NCP190-Tb in 25 mM Tris buffer, pH 7.4 with 1 mM DTT and 0.05% TWEEN-20 detergent for 1 h at room temperature and then 4° C. for 12 h. The labeled protein was diluted to a final assay concentration of 10 nM. The TR-FRET ratio was obtained from 520 nm (EGFP) emission and 490 nm (Tb) emission. Control experiments were performed in the absence of protein, with protein pre-labeled with a non-fluorescent Halotag ligand, and with protein that had been cleaved with HisTev after labeling. See FIG. 5.

Example C—TR-FRET Assay with Acceptor-Labeled Streptavidin

Figure 6:
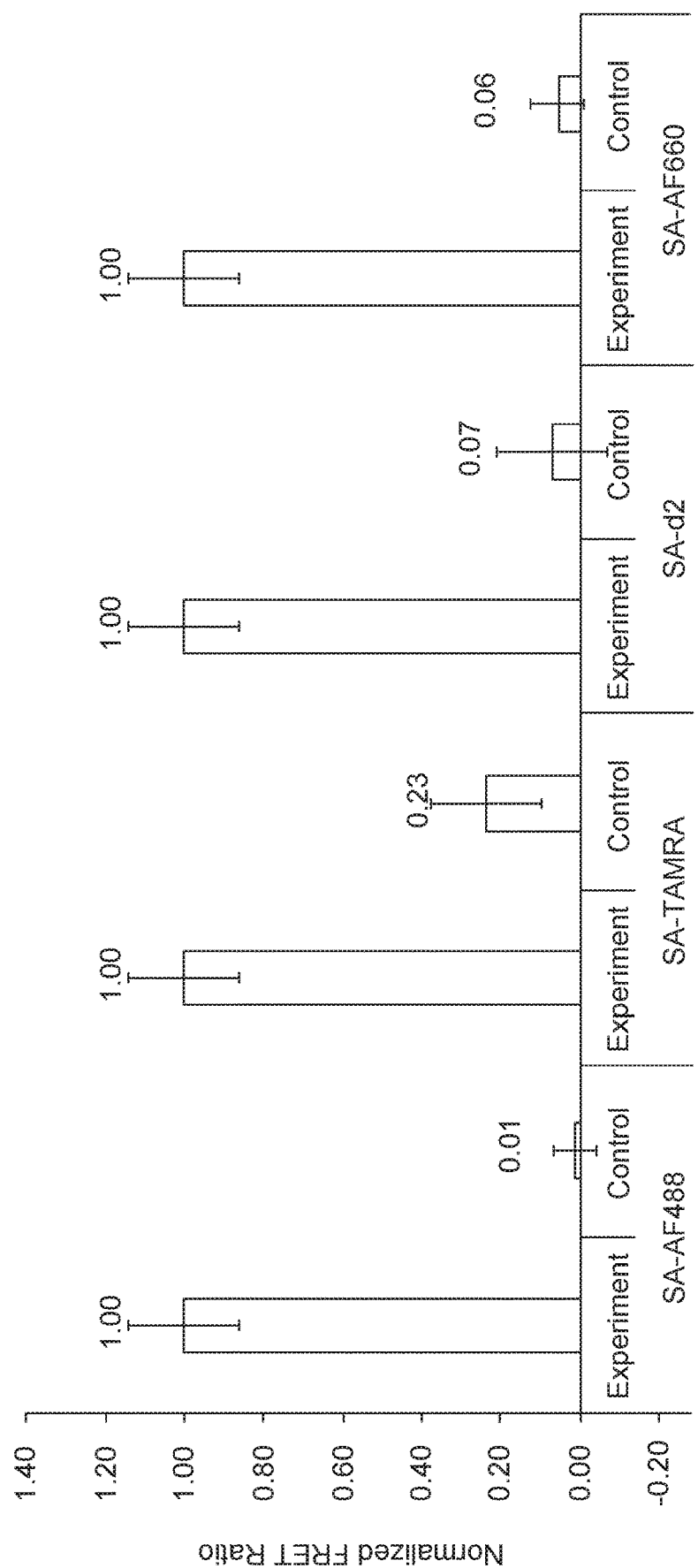
FIG. 6 shows Normalized TR-FRET ratios obtained for NCP205-Tb after incubation with various different streptavidin-acceptor conjugates.

Commercial acceptor-labeled streptavidin conjugates (100 nM) were incubated with 10 nm NCP205-Tb in 25 mM Tris buffer, pH 7.4 with 1 mM DTT and 0.05% TWEEN-20 detergent for 1 h at room temperature. Control experiments were performed in the absence of protein. For Streptavidin-AlexaFluor 488 (SA-AF488), the TR-FRET ratio was obtained from 520 nm (AF488) emission and 490 nm (Tb) emission. For Streptavidin-TAMRA (SA-TAMRA), the TR-FRET ratio was obtained from 570 nm (TAMRA) emission and 548 nm (Tb) emission. For Streptavidin-d2 (SA-d2), the TR-FRET ratio was obtained from 665 nm (d2) emission and 620 nm (Tb) emission. For Streptavidin-AlexaFluor 660 (SA-AF660), the TR-FRET ratio was obtained from 690 nm (AF660) emission and 620 nm (Tb) emission. See FIG. 6.

Example D—NCP190-Tb Stability Data

Figure 7:
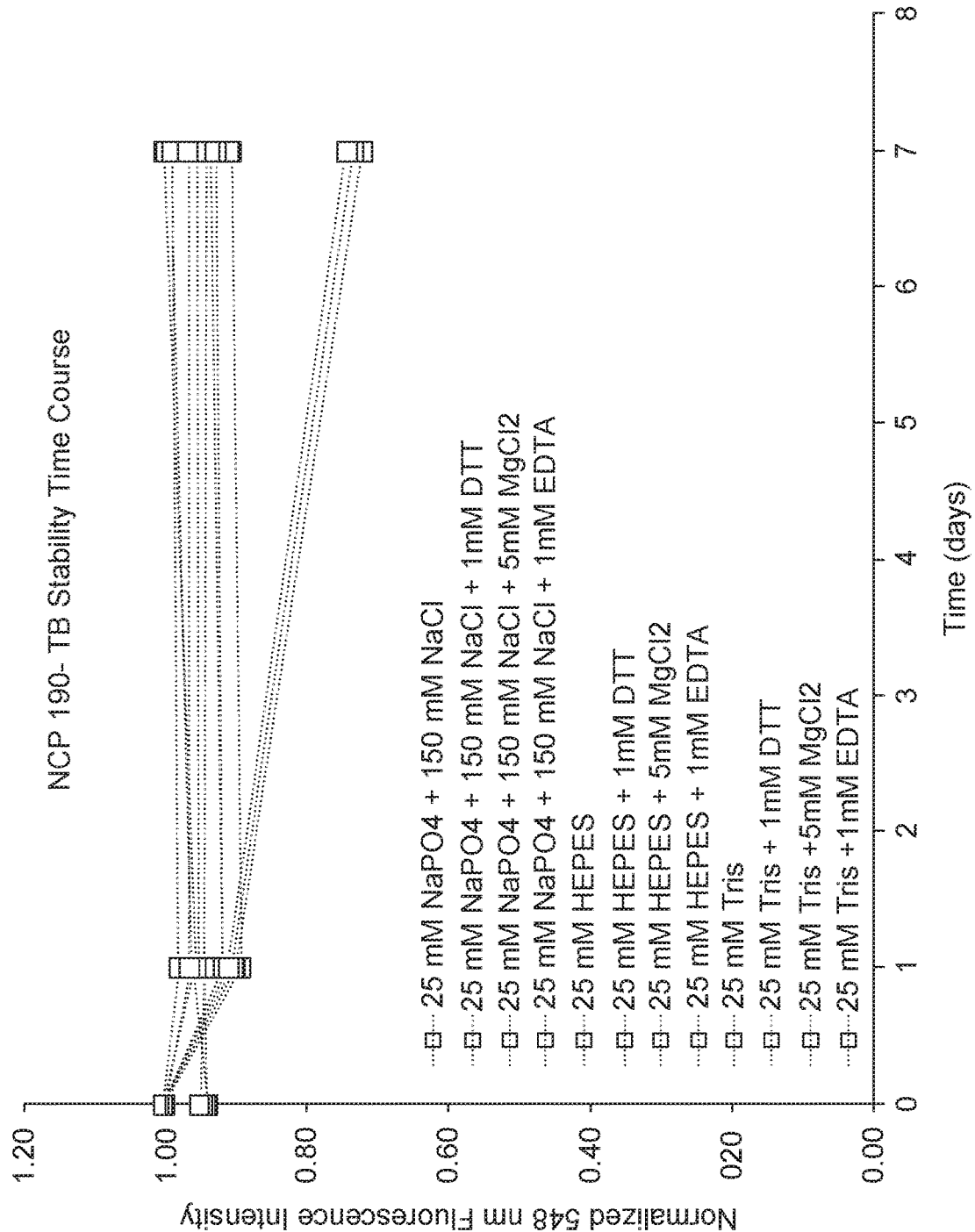
FIG. 7 shows Stability data obtained for NCP190-Tb (10 nM). The complex is only significantly destabilized by EDTA.

The stability of NCP190-Tb (10 nM) was measured over the course of 7 days in various different buffers. All buffers contained 0.05% TWEEN-20 detergent. See FIG. 7.

Example E—NCP134-Tb Stability Data

Figure 8:
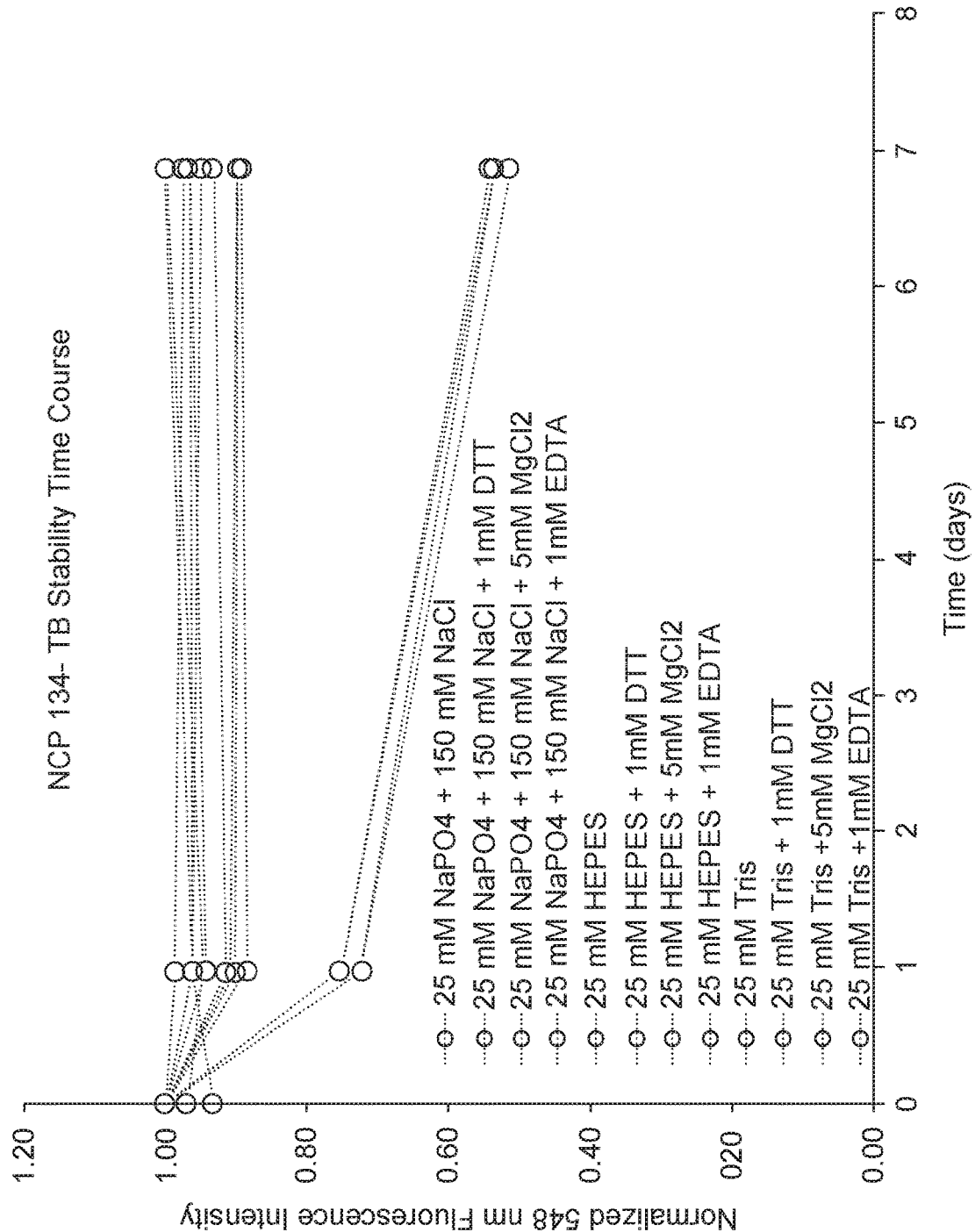
FIG. 8 shows Stability data obtained for NCP134-Tb (10 nM). The complex is only significantly destabilized by EDTA, however to a greater extent relative to NCP190-Tb.

The stability of NCP134-Tb (10 nM) was measured over the course of 7 days in various different buffers. All buffers contained 0.05% TWEEN-20 detergent. See FIG. 8.

Example F—Fluorescence Turn-on with NCP167-Tb and Trans-Cyclooctene (TCO)

Figure 9:
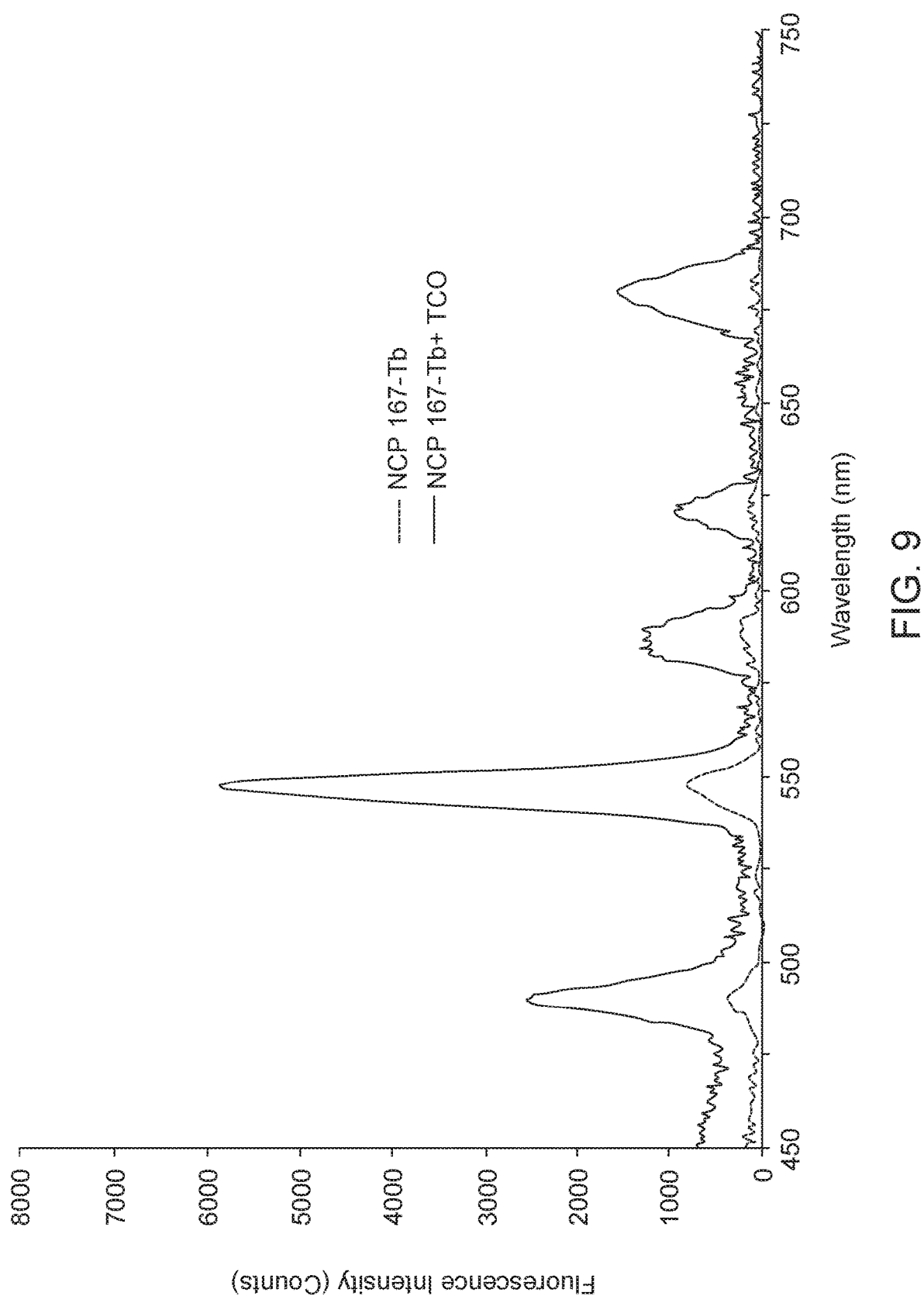
FIG. 9 shows Fluorescence turn-on of NCP167-Tb with TCO (trans-cyclo-octene).
Figure 10:
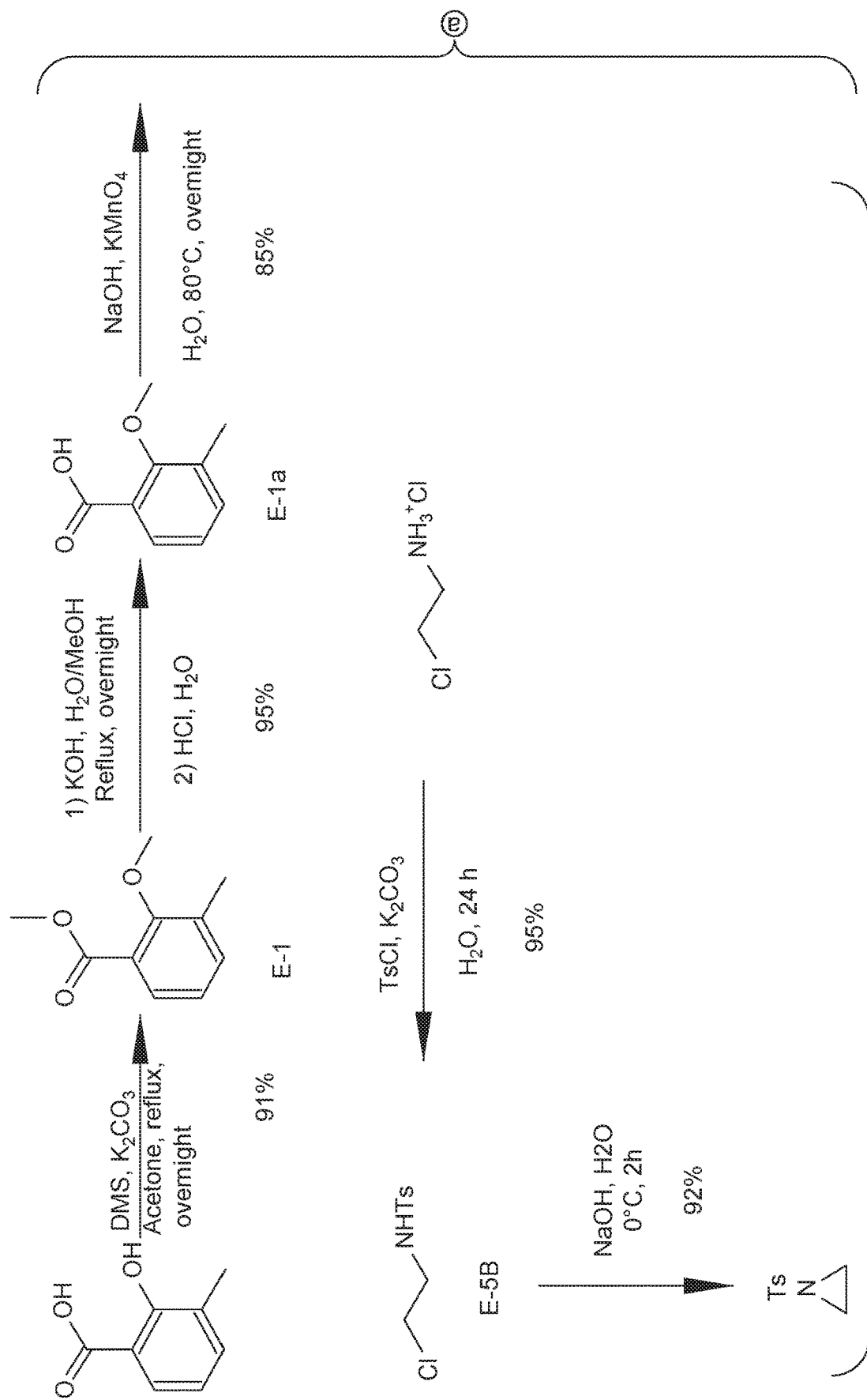
FIG. 10 shows prior synthesis of Lumi4Tb ligand (yields as reported in respective patents).
Figure 11:
FIG. 11 shows Divergent synthesis to access common intermediate 3, which serves as precursor for building blocks 4, 12 and 15. Y refers to aliphatic, aromatic moieties
Figure 12:
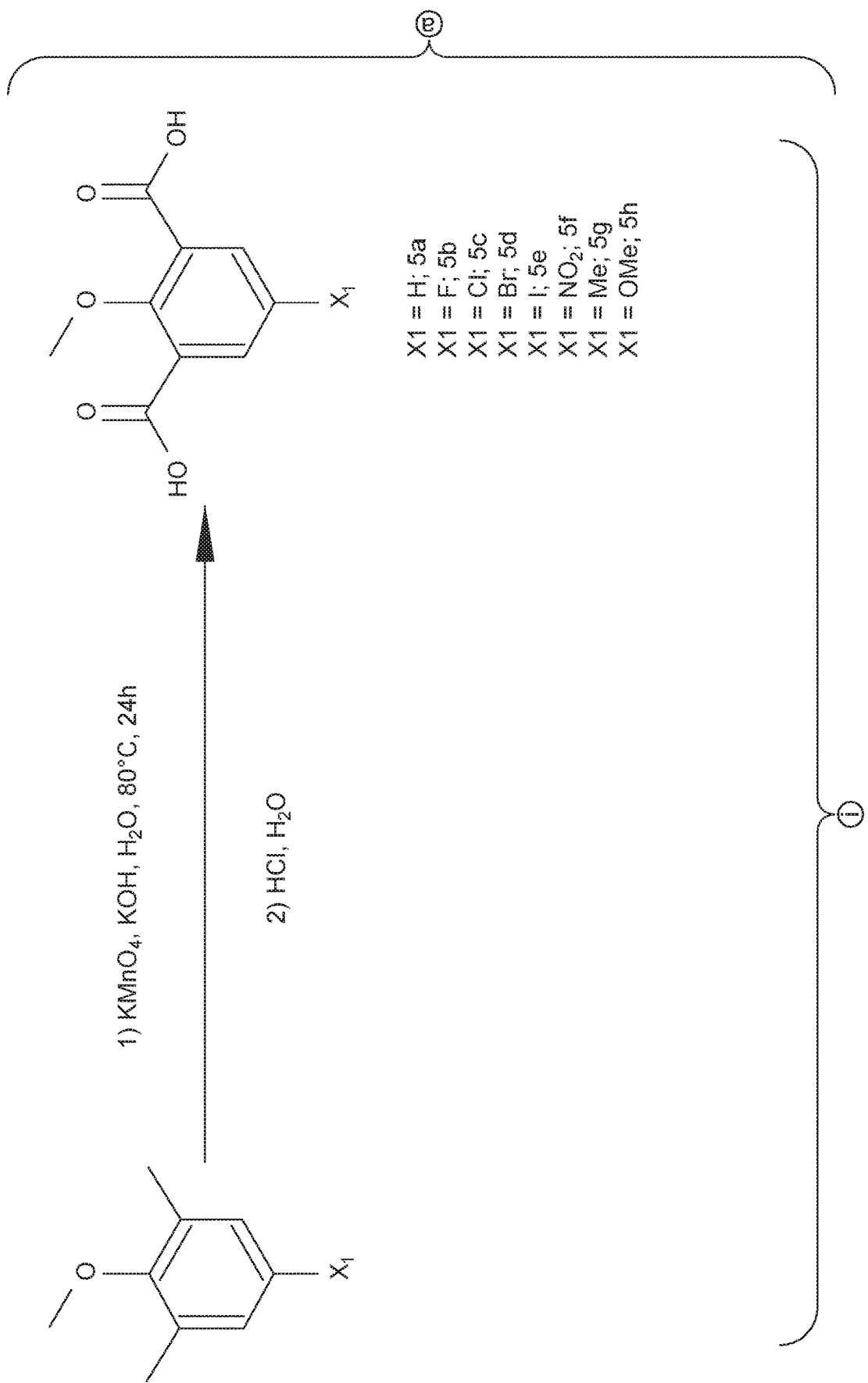
FIG. 12 shows Synthesis to access building block 6 and 9.
Figure 13:
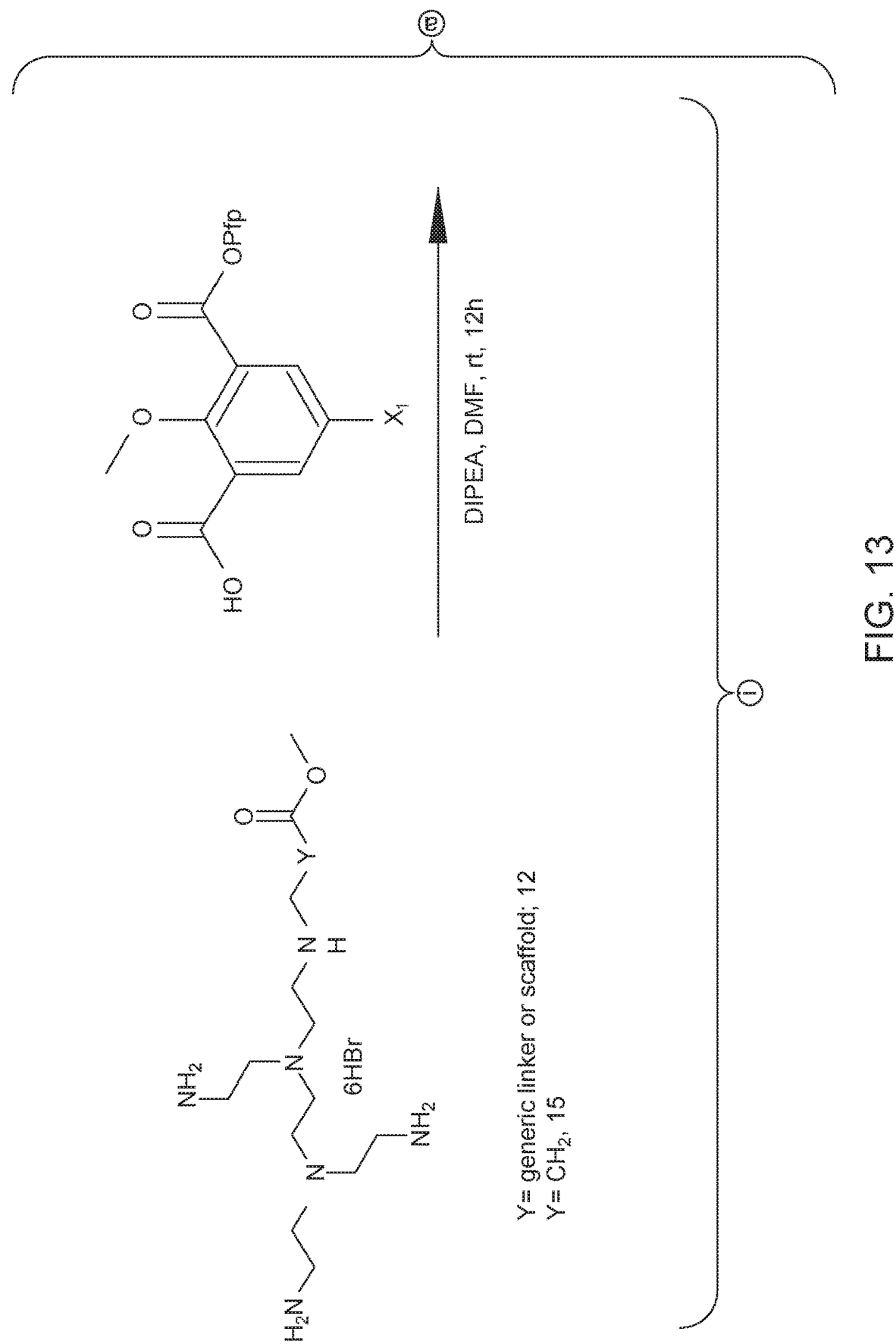
FIG. 13 shows Synthesis of linker modified cage ligands 18.
Figure 14:
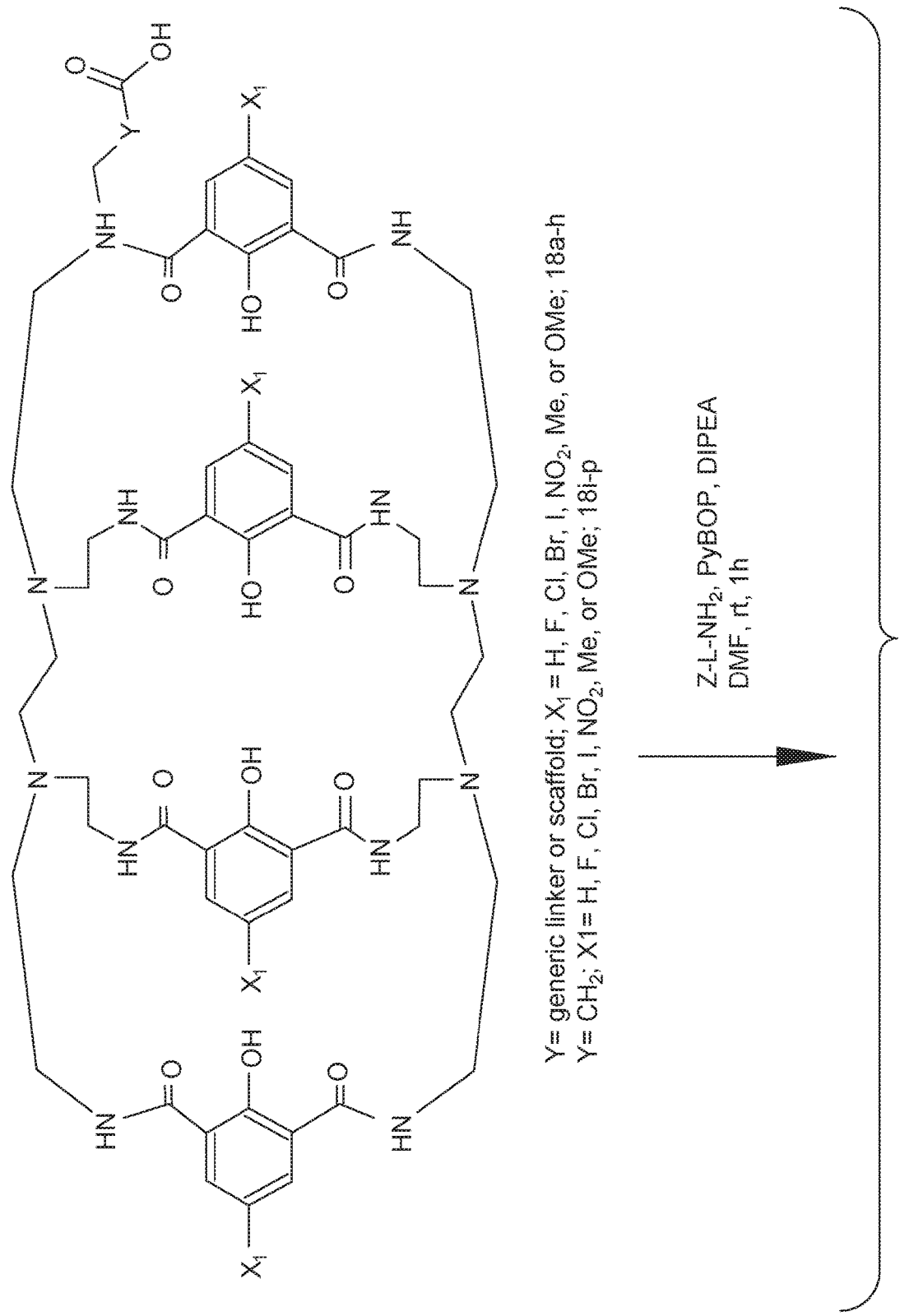
FIG. 14 shows Further modification of 18 to yield functionalized cage ligands 19.
Figure 15:
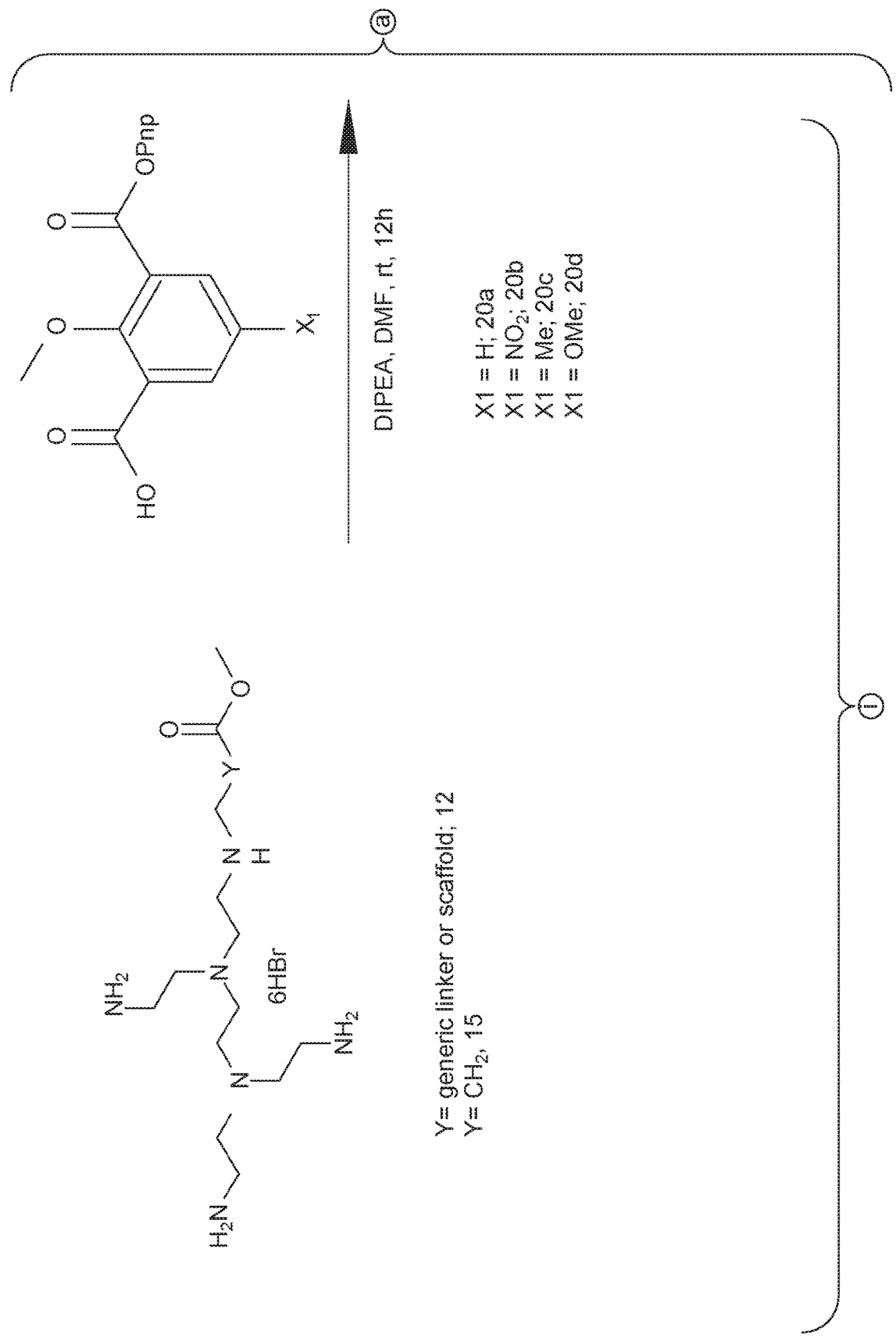
FIG. 15 shows Synthesis of bifunctional cage ligands 25.
Figure 16:
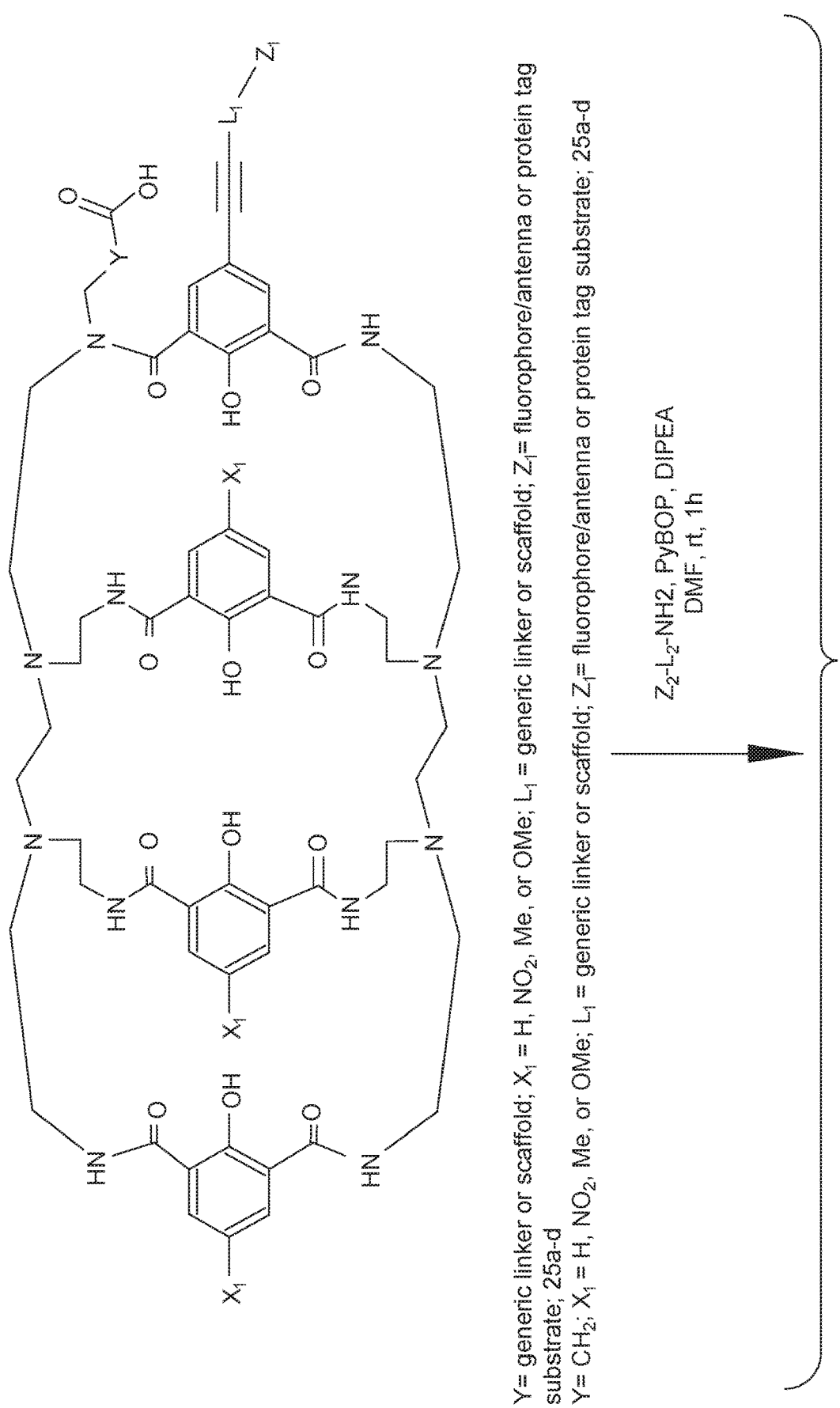
FIG. 16 shows Synthesis of cage ligands 26.
Figure 17:
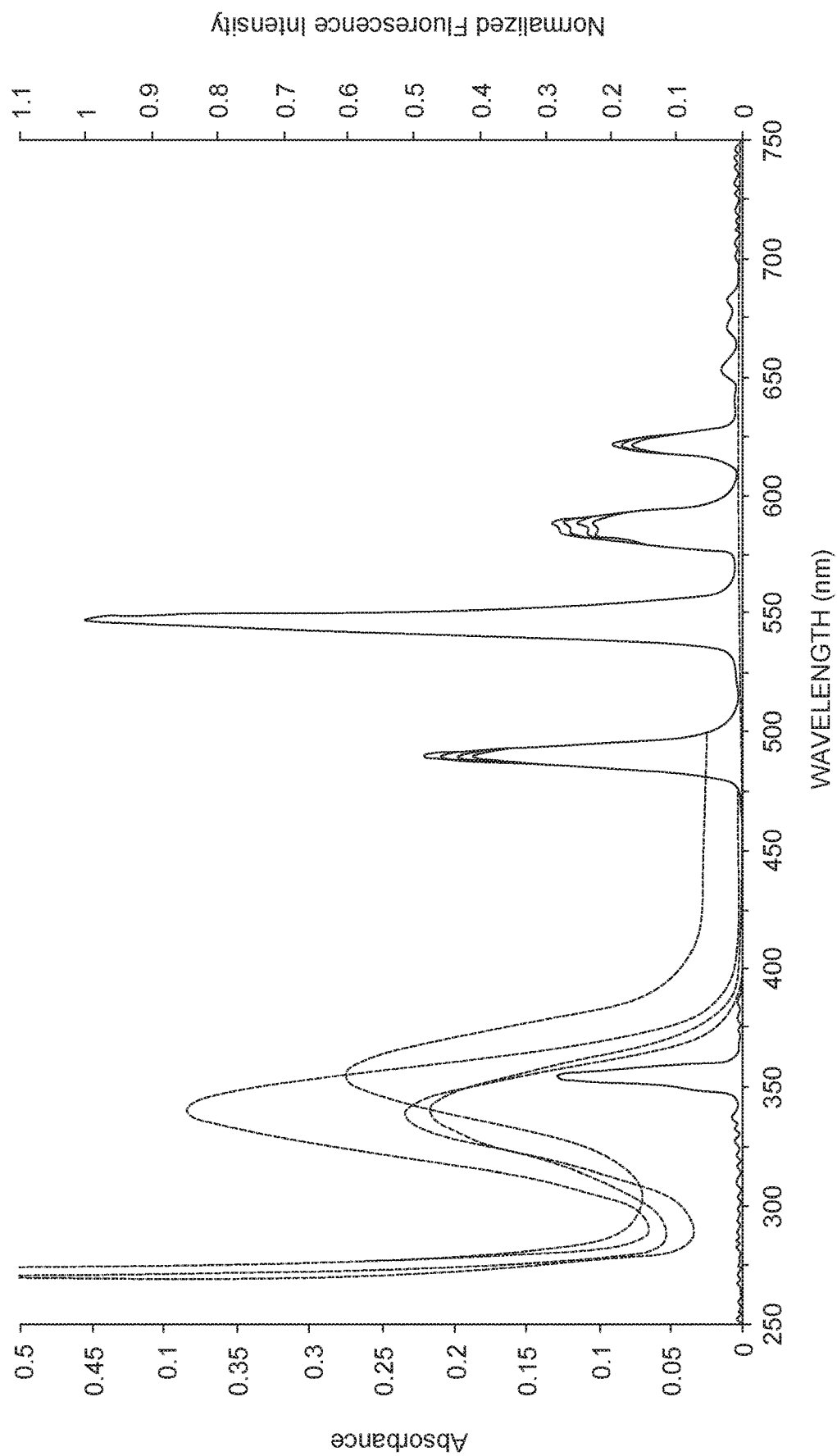
FIG. 17 shows UV/visible absorption spectra (dotted lines, left axis) of 20 uM 9a-Tb, 9d-Tb, 18a-Tb (Y is 0), and 19a (Y is 0, L is PEG2, Z is Halotag) in 1×PBS pH 7.4 (blue, red, green, and black, respectively). Emission spectra (solid lines) of the same respective complexes at 4 uM in 1×PBS pH 7.4 are shown on the right axis.
Figure 20:
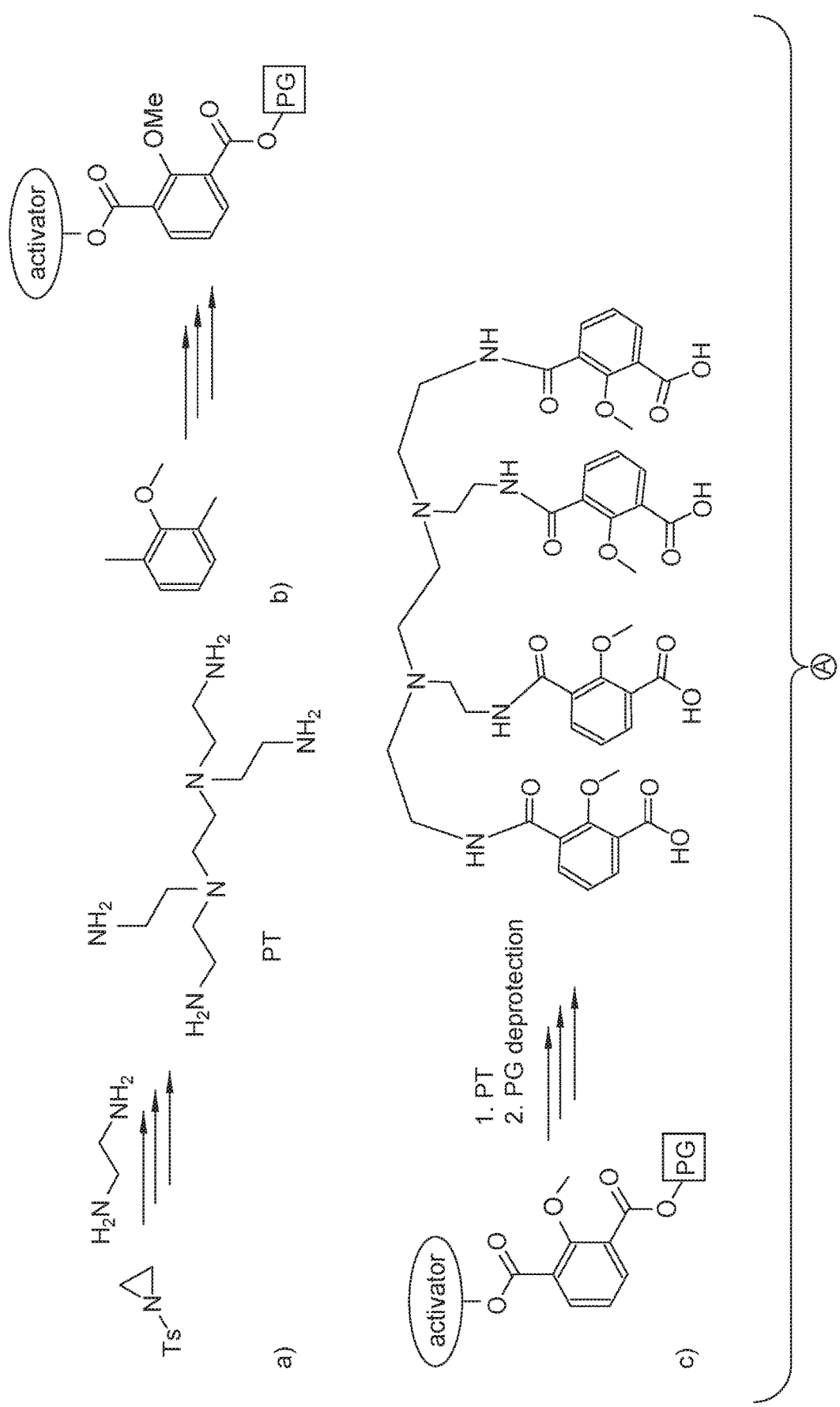
FIG. 20 shows The general scheme for the synthesis of Lumi4Tb® probe without a linker: a) cap synthesis; b) monoactivated cage synthesis; c) monocapped cage synthesis, PG=protecting group; d) bicapped cage synthesis; e) Tb(III) complex synthesis.

NCP167-Tb (1 uM) was reacted with (trans)-cyclooct-4-en-1-yl (2-hydroxyethyl)carbamate (10 uM) in PBS buffer, pH 7.4+0.05% TWEEN-20 detergent for 30 min at room temperature. The figure below shows the fluorescence spectrum of NCP167-Tb before and after addition of the TCO analogue. See FIG. 9.

Example G—Synthesis and Evaluation of Selected Ligands

Compounds depicted in FIGS. 11-16 may be prepared and tested according to any of the following protocols:

N-(2-chloroethyl)-4-methylbenzenesulfonamide (1): 2-chloroethan-1-aminium chloride (38.9 g, 336 mmol, 1.6 equivalents) was dissolved in distilled water (400 mL). To this solution was added $K_2CO_3$ (78.3 g, 567 mmol, 2.7 equivalents) followed by TsCl (40.0 g, 210 mmol, 1.0 equivalent) and the resulting suspension was stirred at room temperature for 48 h or until the disappearance of the characteristic aromatic TsCl resonances disappeared by $^1H$ NMR analysis ($CD_3OD$). The reaction mixture was filtered and the white solid was washed with distilled water and dried in vacuo overnight. Yield=30.0 g, 61.2% as a white solid. $R_f$(20% EtOAc/Hex) 0.65. $^1H$ NMR (400 MHz, $CDCl_3$) δ 7.75 (d, J=7.9 Hz, 2H), 7.32 (d, J=7.9 Hz, 2H), 4.95 (s, 1H), 3.55 (t, J=5.8 Hz, 2H), 3.30 (q, J=6.0 Hz, 2H), 2.43 (s, 3H). $^{13}C$ NMR (101 MHz, $CDCl_3$) δ 143.99, 136.97, 130.02, 127.17, 44.78, 43.76, 21.69.

1-tosylaziridine (2): N-(2-chloroethyl)-4-methylbenzenesulfonamide (1, 8.0 g, 34 mmol, 1.0 equivalent) was suspended in 1.4 M NaOH (100 mL, 140 mmol, 4.2 equivalents) and the resulting suspension was stirred at 4° C. in an ice bath for 4 h or until the disappearance of the characteristic methylene resonances of 1 by $^1H$ NMR analysis ($CD_3OD$) was observed. The reaction mixture was filtered and the white solid was washed with cold distilled water and dried in vacuo overnight. Yield=6.5 g, 95.6% as a white solid. $^1H$ NMR (400 MHz, $CDCl_3$) δ 7.84 (d, J=7.9 Hz, 2H), 7.35 (d, J=8.0 Hz, 2H), 2.45 (s, 3H), 2.37 (s, 4H). $^{13}C$ NMR (101 MHz, $CDCl_3$) δ 144.81, 135.01, 129.89, 128.15, 27.58, 21.80.

N,N',N'',N'''-((ethane-1,2-diylbis(azanetriyl))tetrakis(ethane-2,1-diyl))tetrakis(4-methylbenzenesulfonamide) (3): 1-tosylaziridine (2, 12.4 g, 62.9 mmol, 5.0 equivalents) was dissolved in 50 mL 1:1 toluene/ACN then ethylenediamine (850 uL, 756 mg, 12.6 mmol, 1 equivalent) was added and the reaction was heated to 60° C. for 12 h. The reaction mixture was allowed to cool to room temperature before it was placed in a 4° C. fridge for 4 h to precipitate the product as white crystals. The white crystals were collected by vacuum filtration, washed with minimal ACN and dried in vacuo overnight. Yield=6.3 g, 58.8% as a white, crystalline solid. $^1H$ NMR (400 MHz, $CDCl_3$) δ 7.77 (d, J=7.9 Hz, 8H), 7.28 (d, J=8.2 Hz, 8H), 5.86 (s, 4H), 2.96 (s, 8H), 2.55 (t, J=5.2 Hz, 8H), 2.52 (s, 4H), 2.40 (s, 12H). $^{13}C$ NMR (101 MHz, $CDCl_3$) δ 143.45, 136.99, 129.87, 127.34, 54.13, 53.34, 41.10, 21.68. MS ($ESI^{+/-}$) m/z $(M+H)^+$ 849.62, m/z $(M-H)^-$ 847.46, [calculated $C_{38}H_{52}N_6O_8S_4$: 848.27].

N1,N1'-(ethane-1,2-diyl)bis(N1-(2-aminoethyl)ethane-1,2-diamine)·6HBr (4): N,N',N'',N'''-((ethane-1,2-diylbis(azanetriyl))tetrakis(ethane-2,1-diyl))tetrakis(4-methylbenzenesulfonamide) (4, 1.25 g, 1.47 mmol, 1.0 equivalent) was dissolved in 1.5 mL of 48% wt HBr in $H_2O$ (13.0 mmol, 9.0 equivalents) and 1 mL of glacial acetic acid (20.0 mmol, 10.0 equivalents) and the resulting suspension was heated to 115° C. under reflux conditions for 24 h. The orange solution was cooled to room temperature, at which point an off-white solid precipitated from solution. To the reaction mixture was added 5 mL of a 1:1 solution of $Et_2O/EtOH$ to further precipitate the desired product. The mixture was vacuum filtered and the solid was washed with the 1:1 $Et_2O/EtOH$ solution and dried in vacuo overnight. Yield=864 mg; 81.5% as an off-white solid. $^1$H NMR (400 MHz, $D_2O$) δ 3.17 (t, J=6.8 Hz, 8H), 3.01 (t, J=6.8 Hz, 8H), 2.98 (s, 4H). $^{13}$C NMR (101 MHz, $D_2O$) δ 50.06, 49.02, 35.77. MS (ESI+) m/z (M+H)+ 233.53, [calculated $C_{10}H_{28}N_6$: 232.24].

2-methoxyisophthalic acid (5a): Into 425 mL of distilled water was dissolved KOH (3.2 g, 235.0 mmol, 3.2 equivalents) then $KMnO_4$ (76.58 g, 484.6 mmol, 6.6 equivalents) was added and the resulting suspension was heated to 80° C. with stirring. After, 2,6-dimethylanisole (10.4 mL, 10.0 g, 73.43 mmol, 1.0 equivalent) was added and the reaction mixture was stirred at 80° C. for 12 h. The reaction mixture cooled to room temperature and filtered. The filtrate was acidified to pH 2 with 12 N HCl to precipitate the product as white crystals. The filtrate was cooled to 4° C. for 2 h and filtered. The solid was washed with distilled water and dried in vacuo overnight. Yield=5.9 g, 41.4% as a white, crystalline solid. $^1$H NMR (400 MHz, MeOD) δ 7.94 (d, J=7.7 Hz, 2H), 7.27 (t, J=7.7 Hz, 1H), 3.91 (s, 3H). $^{13}$C NMR (101 MHz, MeOD) δ 168.97, 160.53, 135.82, 128.41, 124.70, 63.96. MS (ESI−) m/z (M−H)− 195.24, [calculated $C_9H_8O_5$: 196.04].

5-bromo-2-methoxyisophthalic acid (5d): The procedure for the synthesis of 2-methoxyisophthalic acid (5a) was followed, substituting 4-bromo-2,6-dimethylanisole for 2,6-dimethylanisole where necessary. The reaction was run on a 11.1 g scale of 4-bromo-2,6-dimethylanisole. Yield=4.9 g, 35% as an off-white, fluffy solid. $^1$H NMR (400 MHz, MeOD) δ 8.03 (s, 2H), 3.90 (s, 3H). $^{13}$C NMR (101 MHz, MeOD) δ 167.43, 159.68, 138.07, 130.58, 116.70, 64.11. MS (ESI−) m/z (M−H)− 273.14, [calculated $C_9H_7BrO_5$: 273.95].

2-methoxy-3-((perfluorophenoxy)carbonyl)benzoic acid (6a): 2-methoxyisophthalic acid (5a, 1.0 g, 5.1 mmol, 1.0 equivalent) and DIPEA (3.6 mL, 2.6 g, 20.0 mmol, 4.0 equivalents) were dissolved in DCM (50 mL) and the resulting solution was cooled to 4° C. in an ice bath. Once cooled, isobutyl chloroformate (670 uL, 0.7 g, 5.1 mmol, 1.0 equivalent) was added dropwise as a solution in 5 mL DCM over 15 min. The mixture was stirred at 4° C. for an additional 15 min once the addition was complete, then pentafluorophenol (1.1 mL, 1.9 g, 10.0 mmol, 2.0 equivalents) was added followed by 4-(dimethylamino)pyridine (DMAP, 62 mg, 0.51 mmol, 0.1 equivalents) and the reaction was allowed to warm to room temperature over 1 h. The reaction mixture was diluted into 200 mL DCM and washed twice with equal volume of a 4:1 solution of saturated brine/1 N HCl (unreacted starting material 5a can be recovered from the aqueous layer by cooling to precipitate as white crystals). The organic layer was dried over $Na_2SO_4$, filtered, and concentrated. The crude product was purified via flash chromatography (10% EtOAc/Hex for 2 CV, 10% EtOAc to 50% EtOAc/Hex over 3 CV, 50% EtOAc/Hex for 3 CV). Yield=0.96 g, 86.6% (relative to recovered starting material) as a white, crystalline solid. $^1$H NMR (400 MHz, $CDCl_3$) δ 8.40 (d, J=6.5 Hz, 1H), 8.31 (d, J=7.8 Hz, 1H), 7.44 (t, J=7.8 Hz, 1H), 4.09 (s, 3H). $^{13}$C NMR (101 MHz, $CDCl_3$) δ 166.02, 161.00, 160.45, 138.88, 137.64, 125.08, 124.79, 122.24, 64.92. $^{19}$F NMR (377 MHz, $CDCl_3$) δ −152.42 (d), −156.96 (t), −161.75 (t). MS (ESI−) m/z (M−H)− 361.13, [calculated $C_{15}H_7F_5O_5$: 362.02].

5-bromo-2-methoxy-3-((perfluorophenoxy)carbonyl) benzoic acid (6d): The procedure for the synthesis of 2-methoxy-3-((perfluorophenoxy)carbonyl)benzoic acid (6a) was followed, substituting 2-methoxyisophthalic acid (6a) for 5-bromo-2-methoxyisophthalic acid (5d) where necessary. The reaction was run on a 200 mg scale of 5-bromo-2-methoxyisophthalic acid (5d). Yield=65 mg, 20.3% as white, crystalline solid. $^1$H NMR (400 MHz, $CDCl_3$) δ 8.38 (s, 1H), 8.32 (s, 1H), 4.04 (s, 3H). $^{19}$F NMR (377 MHz, $CDCl_3$) δ −152.27 (d), −156.72 (t), −161.57 (t). MS (ESI−) m/z (M−H)− 439.02, [calculated $C_{15}H_6BrF_5O_5$: 439.93].

3,3',3'',3'''-(5,8-bis(2-formamidoethyl)-2,5,8,11-tetraazadodecanedioyl)tetrakis(2-methoxybenzoic acid) (7a): N1,N1'-(ethane-1,2-diyl)bis(N1-(2-aminoethyl)ethane-1,2-diamine)-6HBr (4, 109 mg, 152 umol, 1.0 equivalent) and DIPEA (530 uL, 392.5 mg, 3.04 mmol, 20.0 equivalents) were dissolved in DMF (6 mL). To this solution was added 2-methoxy-3-((perfluorophenoxy)carbonyl)benzoic acid (6a, 275 mg, 759 umol, 5.0 equivalents) and the reaction was stirred for 12 h at room temperature. The reaction mixture was concentrated and the resulting crude oil was purified via reverse-phase flash chromatography (C18, 5% $ACN/H_2O$/0.1% FA for 4 CV, 5% to 40% $ACN/H_2O$/0.1% FA over 10 CV, 40% to 100% $ACN/H_2O$/0.1% FA over 1 CV, 100% ACN/0.1% FA for 3 CV). Yield=77.4 mg, 54% as a colorless oil. $^1$H NMR (400 MHz, MeOD) δ 7.90 (d, 4H), 7.82 (d, J=7.8 Hz, 4H), 7.16 (t, J=7.7 Hz, 4H), 4.13 (s, 4H), 3.96 (br s, 8H), 3.85 (s, 12H), 3.75 (s, 8H). $^{13}$C NMR (101 MHz, MeOD) δ 169.86, 168.67, 159.68, 136.10, 135.62, 128.73, 127.36, 124.94, 64.11, 57.05, 48.90, 36.92. MS (ESI+/−) m/z (M+H)+ 945.72, m/z (M−H)− 943.51, [calculated $C_{46}H_{52}N_6O_{16}$: 944.34].

3,3',3'',3'''-(5,8-bis(2-formamidoethyl)-2,5,8,11-tetraazadodecanedioyl)tetrakis(5-bromo-2-methoxybenzoic acid) (7d): The procedure for the synthesis of 3,3',3'',3'''-(5,8-bis(2-formamidoethyl)-2,5,8,11-tetraazadodecanedioyl) tetrakis(2-methoxybenzoic acid) (7a) was followed, substituting 2-methoxy-3-((perfluorophenoxy)carbonyl)benzoic acid (6a) for 5-bromo-2-methoxy-3-((perfluorophenoxy) carbonyl)benzoic acid (6d) where necessary. The reaction was run on a 21.0 mg scale of N1,N1'-(ethane-1,2-diyl)bis (N1-(2-aminoethyl)ethane-1,2-diamine)-6HBr (4). The purification gradient used was: (C18, 5% $ACN/H_2O$/0.1% FA for 4 CV, 5% to 100% $ACN/H_2O$/0.1% FA over 10 CV, 100% ACN/0.1% FA for 3 CV). Yield=14.9 mg, 40.4%. MS (ESI+/−) m/z (M+H)+ 1257.62, m/z (M−H)− 1255.39, [calculated $C_{46}H_{48}Br_4N_6O_{16}$: 1255.99].

$Me_4BH(2,2)IAM$ (8a): PyBOP (43 mg, 84 umol, 6.0 equivalents) and DIPEA (200 uL, 150 mg, 1.1 mmol, 82 equivalents) were dissolved in 14 mL DMF. In separate containers, N1,N1'-(ethane-1,2-diyl)bis(N1-(2-aminoethyl) ethane-1,2-diamine)-6HBr (4, 10 mg, 14 umol, 1.1 equivalents) and 3,3',3'',3'''-(5,8-bis(2-formamidoethyl)-2,5,8,11-tetraazadodecanedioyl)tetrakis(2-methoxybenzoic acid) (7a, 12 mg, 12 umol, 1.0 equivalent) were dissolved in 1 mL DMF each. To the solution of 4 was added 50 uL DIPEA (37.5 mg, 275 umol, 20.5 equivalents) to ensure complete dissolution. In 100 uL portions over 1 h, the solutions of 7a and 4 were added to the stirred solution of PyBOP and DIPEA until all 1 mL of each had been added. The solution of 7a was always added first before the solution of 4 to promote pre-activation of the carboxylic acid moieties. Once the additions were complete, the reaction was stirred for 1 h at room temperature. The reaction mixture was concentrated and the crude oil was purified via reverse-phase flash chromatography (C18, 5% ACN/H$_2$O/0.1% FA for 3 CV, 5% ACN to 30% ACN/H$_2$O/0.1% FA over 10 CV, 30% ACN to 100% ACN/H$_2$O/0.1% FA over 1 CV, 100% ACN/0.1% FA for 3 CV). Yield=8 mg, 53.3% as a colorless oil. MS (ESI$^{+/-}$) m/z (M+H)$^+$ 1106.11, m/z (M–H)$^-$ 1104.73, [calculated C$_{56}$H$_{72}$N$_{12}$O$_{12}$: 1104.54].

Me$_4$Br$_4$BH(2,2)IAM (8d): The procedure for the synthesis of Me$_4$BH(2,2)IAM (8a) was followed, substituting 3,3',3'',3'''-(5,8-bis(2-formamidoethyl)-2,5,8,11-tetraazadodecanedioyl)tetrakis(2-methoxybenzoic acid) (7a) for 3,3',3'',3'''-(5,8-bis(2-formamidoethyl)-2,5,8,11-tetraazadodecanedioyl)tetrakis(5-bromo-2-methoxybenzoic acid) (7d) where necessary. The reaction was run on a 10.2 mg scale of N1,N1'-(ethane-1,2-diyl)bis(N1-(2-aminoethyl)ethane-1,2-diamine)·6HBr (4). Yield=9.0 mg, 53.4% as a colorless oil. MS (ESI$^{+/-}$) m/z (M+H)$^+$ 1417.87, m/z (M–H)$^-$ 1416.82, [calculated C$_{56}$H$_{68}$Br$_4$N$_{12}$O$_{12}$: 1416.18].

BH(2,2)IAM (9a): Me$_4$BH(2,2)IAM (8a, 10 mg, 9.1 umol, 1.0 equivalent) was dissolved in 2,6-lutidine (1 mL) then LiI (19 mg, 133 umol, 14.0 equivalents) were added and the reaction was heated to 100° C. for 4 h under reflux conditions. The reaction mixture was concentrated and purified via reverse-phase flash chromatography (5% ACN/H$_2$O/0.1% FA for 3 CV, 5% ACN to 30% ACN/H$_2$O/0.1% FA over 10 CV, 30% ACN to 100% ACN/H$_2$O/0.1% FA over 1 CV, 100% ACN/0.1% FA for 3 CV). Yield=5 mg, 51.6% as a colorless oil. MS (ESI$^{+/-}$) m/z (M+H)$^+$ 1050.00, m/z (M–H)$^-$ 1047.73, [calculated C$_{52}$H$_{64}$N$_{12}$O$_{12}$: 1048.48].

Br$_4$BH(2,2)IAM (9d): The procedure for the synthesis of BH(2,2)IAM (9a) was followed, substituting Me$_4$BH(2,2)IAM (8a) for Me$_4$Br$_4$BH(2,2)IAM (8d) where necessary. The reaction was run on a 9 mg scale of Me$_4$Br$_4$BH(2,2)IAM (8d). Yield=3.0 mg, 34.8% as a colorless oil. MS (ESI$^{+/-}$) m/z (M+H)$^+$ 1361.82, m/z (M–H)$^-$ 1359.57, [calculated C$_{52}$H$_{60}$Br$_4$N$_{12}$O$_{12}$: 1360.12].

N-(2-((2-(bis(2-((4-methylphenyl)sulfonamido)ethyl)amino)ethyl)(2-((4-methylphenyl)sulfonamido)ethyl)amino)ethyl)-N-tosylglycine (10, Y=0): N,N',N'',N'''-((ethane-1,2-diylbis(azanetriyl))tetrakis(ethane-2,1-diyl))tetrakis(4-methylbenzenesulfonamide) (3, 2 g, 2.4 mmol, 1.0 equivalent) was dissolved in 1 N NaOH (60 mL) at 60° C. then bromoacetic acid (3.3 g, 24 mmol, 10.0 equivalents) was added with stirring. The reaction mixture was kept stirring at 60° C. for 12 h then acidified to pH 8 with 12 N HCl to precipitate the crude product. The crude product was purified via flash chromatography (100% DCM for 2 CV, 100% DCM to 2% MeOH/DCM over 2 CV, 2% MeOH/DCM for 2 CV, 2% MeOH/DCM to 5% MeOH/DCM over 3 CV, 5% MeOH/DCM for 3 CV, 5% MeOH/DCM to 10% MeOH/DCM over 3 CV, 10% MeOH/DCM for 3 CV). Starting material 3 can be recovered from the silica column easily as it elutes before the desired product. Yield=504 mg, 82% (relative to recovered starting material) as a white foam. $^1$H NMR (400 MHz, CDCl$_3$) δ 7.74 (d, J=7.8 Hz, 6H), 7.64 (d, J=7.9 Hz, 2H), 7.30-7.23 (m, 5H), 7.17 (d, J=7.9 Hz, 4H), 7.01 (s, 2H), 3.81 (s, 2H), 3.52 (s, 2H), 3.44 (s, 4H), 3.33 (s, 2H), 3.23 (s, 2H), 2.84 (s, 6H), 2.49 (s, 4H), 2.37 (s, 3H), 2.34 (s, 3H), 2.31 (s, 6H). $^{13}$C NMR (101 MHz, CDCl$_3$) δ 174.80, 144.26, 143.45, 143.05, 137.17, 136.28, 133.86, 130.15, 130.05, 129.82, 127.60, 127.43, 127.28, 54.33, 53.78, 53.38, 52.47, 51.18, 48.33, 46.27, 40.60, 38.27, 31.07, 21.66, 21.63, 21.58. MS (ESI$^{+/-}$) m/z (M+H)$^+$ 907.63, m/z (M–H)$^-$ 905.48, [calculated C$_{40}$H$_{54}$N$_6$O$_{10}$S$_4$: 906.28].

3-((N-(2-((2-(bis(2-((4-methylphenyl)sulfonamido)ethyl)amino)ethyl)(2-((4-methylphenyl)sulfonamido)ethyl)amino)ethyl)-4-methylphenyl)sulfonamido)propanoic acid (13): N,N',N'',N'''-((ethane-1,2-diylbis(azanetriyl))tetrakis(ethane-2,1-diyl))tetrakis(4-methylbenzenesulfonamide) (3, 500 mg, 589 umol, 1.0 equivalent) was dissolved in ACN (10 mL) then K$_2$CO$_3$ (488 mg, 3.5 mmol, 6.0 equivalents) was added followed by tert-butyl acrylate (130 uL, 114 mg, 887 umol, 1.5 equivalents) and the reaction mixture was heated to 85° C. under reflux conditions for 1 h. The reaction mixture was concentrated in vacuo and the resulting solid was dissolved in 1 N NaOH (10 mL) then heated to 90° C. under reflux conditions for 3 h to saponify the tert-butyl ester. The solution was acidified to pH 8 with 1 N HCl to precipitate the crude product. The crude product was purified via flash chromatography (100% DCM for 3 CV, 100% DCM to 2% MeOH/DCM over 1 CV, 2% MeOH/DCM for 2 CV, 2% MeOH/DCM to 5% MeOH/DCM over 4 CV, 5% MeOH/DCM for 4 CV, 5% MeOH/DCM to 10% MeOH/DCM over 4 CV, 10% MeOH/DCM for 4 CV). Yield=133.8 mg, 25.5% as a white foam. $^1$H NMR (400 MHz, CDCl$_3$) δ 7.79-7.64 (m, 8H), 7.24 (m, 8H), 3.41 (s, 2H), 3.26 (s, 2H), 3.05 (s, 2H), 2.83 (br s, 9H), 2.57 (br s, 9H), 2.37 (s, 12H). MS (ESI$^{+/-}$) m/z (M+H)$^+$ 921.64, m/z (M–H)$^-$ 919.47, [calculated C$_{41}$H$_{56}$N$_6$O$_{10}$S$_4$: 920.29].

(2-((2-aminoethyl)(2-(bis(2-aminoethyl)amino)ethyl)amino)ethyl)glycine·6HBr (11, Y=0): N-(2-((2-(bis(2-((4-methylphenyl)sulfonamido)ethyl)amino)ethyl)(2-((4-methylphenyl)sulfonamido)ethyl)amino)ethyl)-N-tosylglycine (10, Y=0, 549 mg, 605 umol, 1.0 equivalent) was suspended in 750 uL 48% HBr (6.6 mmol, 11.0 equivalents) and 500 uL glacial acetic acid (8.7 mmol, 14.0 equivalents) and the suspension was heated to 115° C. under reflux conditions for 24 h. The reaction mixture was cooled to room temperature and a waxy solid precipitated. To the reaction mixture was added 5 mL of a 1:1 Et$_2$O/EtOH solution to further precipitate the product. The solution was sonicated for 15 minutes to ensure complete dissolution of impurities. The supernatant was decanted off and the solid was washed twice more with 5 mL of the 1:1 Et$_2$O/EtOH solution (with sonication each time). Yield=460 mg, 98% as an off-white, waxy solid. $^1$H NMR (400 MHz, D$_2$O) δ 3.96 (s, 2H), 3.41-3.33 (m, 6H), 3.33-3.27 (m, 4H), 3.24 (m, 4H), 3.09 (m, 6H). $^{13}$C NMR (101 MHz, D$_2$O) δ 169.39, 50.13, 50.05, 49.76, 49.36, 48.22, 47.70, 44.11, 36.00, 35.09, 20.36. MS (ESI$^{+/-}$) m/z (M+H)$^+$ 291.51, m/z (M–H)$^-$ 289.41, [calculated C$_{12}$H$_{30}$N$_6$O$_2$: 290.24].

Methyl (2-((2-aminoethyl)(2-(bis(2-aminoethyl)amino)ethyl)amino)ethyl)glycinate (12, Y=0): (2-((2-aminoethyl)(2-(bis(2-aminoethyl)amino)ethyl)amino)ethyl)glycine·6HBr (11, Y=0, 263 mg, 339 umol, 1.0 equivalent) was suspended in methanol (6 mL) and H$_2$SO$_4$ (18 uL, 33.2 mg, 339 umol, 1.0 equivalent) was added. The suspension was heated to 65° C. for 48 h under reflux conditions. The solution was cooled to room temperature and 1 mL of toluene was added (to promote removal of water generated during the esterification reaction). The reaction mixture was concentrated in vacuo to yield the product which was used without further purification. Yield=260 mg, 97.4% as an off-white solid. $^1$H NMR (400 MHz, MeOD) δ 4.16 (s, 2H), 3.89 (s, 3H), 3.47 (t, J=6.4 Hz, 2H), 3.37 (s, 4H), 3.27 (t, J=6.4 Hz, 4H), 3.24-3.17 (m, 4H), 3.15-3.10 (m, 4H), 3.06 (t, J=6.3 Hz, 2H). MS (ESI$^+$) m/z (M+H)$^+$ 305.52, [calculated C$_{13}$H$_{32}$N$_6$O$_2$: 304.26].

3,3',3'',3'''-(5,8-bis(2-formamidoethyl)-2,5,8,11-tetraazadodecanedioyl)tetrakis(2-methoxybenzoic acid)-N-carboxymethyl methyl ester (16a, Y=0): The procedure for the synthesis of 3,3',3'',3'''-(5,8-bis(2-formamidoethyl)-2,5,8,11-tetraazadodecanedioyl)tetrakis(2-methoxybenzoic acid) (7a) was followed, substituting N1,N1'-(ethane-1,2-diyl)bis(N1-(2-aminoethyl)ethane-1,2-diamine)-6HBr (4) for methyl (2-((2-aminoethyl)(2-(bis(2-aminoethyl)amino)ethyl)amino)ethyl)glycinate (12, Y=0). The reaction was run on a 200 mg scale of methyl (2-((2-aminoethyl)(2-(bis(2-aminoethyl)amino)ethyl)amino)ethyl)glycinate (12, Y=0). DMAP (3 mg, 0.1 equivalents) was added as a catalyst during the reaction. Yield=122.6 mg, 47.6% as a colorless oil. MS (ESI$^{+/-}$) m/z (M+H)$^+$ 1017.74, m/z (M–H)$^-$ 1015.54, [calculated $C_{49}H_{56}N_6O_{18}$: 1016.37].

Me$_4$BH(2,2)IAM-N-carboxymethyl methyl ester (17a, Y=0): The procedure for the synthesis of Me$_4$BH(2,2)IAM (8a) was followed, substituting 3,3',3'',3'''-(5,8-bis(2-formamidoethyl)-2,5,8,11-tetraazadodecanedioyl)tetrakis(2-methoxybenzoic acid) (7a) for 3,3',3,3'''-(5,8-bis(2-formamidoethyl)-2,5,8,11-tetraazadodecanedioyl)tetrakis(2-methoxybenzoic acid)-N-carboxymethyl methyl ester (16a) where necessary. The reaction was run on a 42.4 mg scale of N1,N1'-(ethane-1,2-diyl)bis(N1-(2-aminoethyl)ethane-1,2-diamine)-6HBr (4). Yield=42.3 mg, 60.9% as a colorless oil. MS (ESI$^{+/-}$) m/z (M+H)$^+$ 1178.11, m/z (M–H)$^-$ 1176.06, [calculated $C_{59}H_{76}N_{12}O_{14}$: 1176.56].

BH(2,2)IAM-N-carboxymethyl-OH (18a, Y=0): The procedure for the synthesis of BH(2,2)IAM (9a) was followed, substituting Me$_4$BH(2,2)IAM (8a) for Me$_4$BH(2,2)IAM-N-carboxymethyl methyl ester (17a) where necessary. The reaction was run on a 9 mg scale of Me$_4$BH(2,2)IAM-N-carboxymethyl methyl ester (17a). Yield=7.0 mg, 83.3% as a colorless oil. MS (ESI$^{+/-}$) m/z (M+H)$^+$ 1108.00, m/z (M–H)$^-$ 1105.83, [calculated $C_{54}H_{66}N_{12}O_{14}$: 1106.48].

BH(2,2)IAM-N-carboxymethyl-PEG2-Halotag (19a, Y=0, L=PEG2, Z=Halotag): BH(2,2)IAM-N-carboxymethyl-OH (18a, 2 mg, 1.8 umol, 1.0 equivalent) was dissolved in DMF (1 mL) then DIPEA (3.2 uL, 2.3 mg, 18 umol, 10.0 equivalents) was added followed by 2-(2-((6-chlorohexyl)oxy)ethoxy)ethan-1-amine (1.2 mg, 5.4 umol, 3.0 equivalents). After, PyBOP (2.8 mg, 5.4 umol, 3.0 equivalents) was added and the reaction was stirred for 1 h at room temperature. The reaction mixture was concentrated in vacuo and the crude product was triturated with Et$_2$O and purified via centrifugation. Yield=2.1 mg, 87.5% as a colorless oil. MS (ESI$^{+/-}$) m/z (M+H)$^+$ 1313.20, m/z (M–H)$^-$ 1311.01, [calculated $C_{64}H_{86}ClN_{13}O_{15}$: 1311.61].

BH(2,2)IAM-N-carboxymethyl-benzylmethyl-methyltetrazine (19b, Y=0, L=benzylmethyl, Z=methyltetrazine): The procedure for the synthesis of BH(2,2)IAM-N-carboxymethyl-PEG2-Halotag (19a, Y=0, L=PEG2, Z=Halotag) was followed, substituting 2-(2-((6-chlorohexyl)oxy)ethoxy)ethan-1-amine for (4-(6-methyl-1,2,4,5-tetrazin-3-yl)phenyl)methanamine where necessary. The reaction was run on a 0.66 mg scale of BH(2,2)IAM-N-carboxymethyl-OH (18a, Y=0). Yield=0.7 mg, 90.9% as a light pink solid. MS (ESI$^{+/-}$) m/z (M+H)$^+$ 1291.27, m/z (M–H)$^-$ 1288.93, [calculated $C_{64}H_{75}N_{17}O_{13}$: 1289.57].

BH(2,2)IAM-N-carboxymethyl-benzylmethyl-methyltetrazine (19c, Y=0, L=CH$_2$CH$_2$OCH$_2$CH$_2$, Z=(E)-N-(2-aminophenyl)-4-((4-(dimethylamino)phenyl)diazenyl)benzamide): The procedure for the synthesis of BH(2,2)IAM-N-carboxymethyl-PEG2-Halotag (19a, Y=0, L=PEG2, Z=Halotag) was followed, substituting 2-(2-((6-chlorohexyl)oxy)ethoxy)ethan-1-amine for (E)-4-((4-((2-(2-aminoethoxy)ethyl)(methyl)amino)phenyl)diazenyl)-N-(2-aminophenyl)benzamide where necessary. The reaction was run on a 0.66 mg scale of BH(2,2)IAM-N-carboxymethyl-OH (18a, Y=0). Yield=0.81 mg, 89.1% as a red solid. MS (ESI$^{+/-}$) m/z (M+H)$^+$ 1522.32, m/z (M–H)$^-$ 1520.08, [calculated $C_{78}H_{92}N_{18}O_{15}$: 1520.70].

BH(2,2)IAM-N-carboxymethyl-benzylmethyl-methyltetrazine (19d, Y=0, L=benzylmethyl, Z=SNAP-Tag): The procedure for the synthesis of BH(2,2)IAM-N-carboxymethyl-PEG2-Halotag (19a, Y=0, L=PEG2, Z=Halotag) was followed, substituting 2-(2-((6-chlorohexyl)oxy)ethoxy)ethan-1-amine for 6-((4-(aminomethyl)benzyl)oxy)-7H-purin-2-amine where necessary. The reaction was run on a 0.66 mg scale of BH(2,2)IAM-N-carboxymethyl-OH (18a, Y=0). Yield=0.75 mg, 88.2% as a white solid. MS (ESI$^{+/-}$) m/z (M+H)$^+$ 1360.24, m/z (M–H)$^-$ 1357.96, [calculated $C_{67}H_{78}N_{18}O_{14}$: 1358.59].

Terbium loading: Ligands were loaded with terbium by dissolving the appropriate compound in MeOH to a concentration of 1 mM then adding 0.95 equivalents of TbCl$_3$·6H$_2$O as a solution in MeOH. The resulting solutions were heated to 50° C. for 30 min then cooled to room temperature and used without further purification.

The terbium complexes were further characterized by LCMS. 9a-Tb, MS (ESI$^{+/-}$) m/z (M+H)$^+$ 1208.02, m/z (M–H)$^-$ 1205.92, [calculated $C_{52}H_{64}N_{12}O_{12}$Tb: 1207.40]. 9d-Tb, MS (ESI$^{+/-}$) m/z (M+H)$^+$ 1519.64, m/z (M–H)$^-$ 1517.49, [calculated $C_{52}H_{60}Br_4N_{12}O_{12}$Tb: 1519.04]. 18a-Tb, MS (ESI$^{+/-}$) m/z (M+H)$^+$ 1266.17, m/z (M–H)$^-$ 1263.77, [calculated $C_{54}H_{66}N_{12}O_{14}$Tb: 1265.41]. 19a-Tb, MS (ESI$^{+/-}$) m/z (M+H)$^+$ 1471.24, m/z (M–H)$^-$ 1469.86, [calculated $C_{64}H_{86}ClN_{13}O_{15}$Tb: 1470.53]. 19b-Tb, MS (ESI$^{+/-}$) m/z (M+H)$^+$ 1449.08, m/z (M–H)$^-$ 1446.89, [calculated $C_{64}H_{75}N_{17}O_{13}$Tb: 1448.50]. 19c-Tb, MS (ESI$^{+/-}$) m/z (M+H)$^+$ 1680.37, m/z (M–H)$^-$ 1677.83, [calculated $C_{78}H_{92}N_{15}O_{15}$Tb: 1679.62]. 19d-Tb, MS (ESI$^{+/-}$) m/z (M+H)$^+$ 1518.19, m/z (M–H)$^-$ 1515.94, [calculated $C_{67}H_{78}N_{18}O_{14}$Tb: 1517.52].

Photophysical measurements: UV/visible and emission spectra were recorded on a Horiba Scientific Dual FL spectrophotometer. Ligands loaded with terbium were diluted into 1×PBS (pH 7.4) to a concentration of 20 uM (for absorbance) or 4 uM (for emission). For emission spectra, the data were normalized to the highest fluorescence signal. The fluorescence lifetime was determined by plotting the ln of the signal decay over time then solving for r in Equation 1:

$$\log(I_t) = \log(\alpha) - \frac{t}{\tau}, \quad (1)$$

where $I_t$ is the intensity at time t, $\alpha$ is a normalization term (the preexponential factor) and $\tau$ is the lifetime.

TABLE A

Summary of the photophysical properties of the tested terbium complexes in 1x PBS pH 7.4

| Complex | $\lambda_{max, Abs}$ (nm) | $\varepsilon_{max}$ (M$^{-1}$cm$^{-1}$) | Emission $\lambda_{max}$ (nm) | $\tau_{PBS}$ (ms) |
|---|---|---|---|---|
| 9a-Tb | 340 | 11,600 | 545 | 2.10 |
| 9d-Tb | 355 | 13,750 | 545 | 0.97 |
| 18a-Tb (Y = 0) | 340 | 19,230 | 545 | 2.06 |
| 19a (Y = 0, L = PEG2, Z = Halotag) | 340 | 10,800 | 545 | 2.23 |

Example H—Synthesis and Evaluation of Selected Ligands

Compounds depicted in FIGS. 18-40 may be prepared and tested according to any of the following procedures The favorable luminescent properties of Ln-based emitters (long lifetimes, narrow luminescent bands, large effective STOKES' shifts) make them unique and irreplaceable as FRET-donors for a variety of biomedical applications. Nowadays, the FRET-assay is becoming a powerful technique for studying molecular interactions inside living cells with improved spatial (angstrom) and temporal (nanosecond) resolution, distance range, sensitivity and a broader range of biological applications. It can be useful, for instance, for the analysis of protein-protein interactions with high spatial and temporal specificity (e.g. clustering), in the study of conformational changes, in the analysis of binding sequences, and in applications such as high-throughput screening.

FRET is the radiation-less energy transfer from an excited fluorescent donor (D) to a nearby (<10 nm) acceptor (A), whose absorption spectrum overlaps with the donor emission spectrum. The changes in a FRET-signal are highly sensitive to distance changes over the length scale of proteins, because the energy-transfer efficiency inversely varies with the sixth power of the separation between the D and the acceptor A. FRET-based biosensors for live-cell imaging often incorporate two differently colored fluorescent proteins, as D and A (usually CFP and YFP), to read out changes in the protein conformation or interaction (FIG. 18a). The imaging of the intermolecular interactions between two labeled proteins may be limited by (i) crosstalk (direct acceptor excitation by light used to excite the donor), (ii) bleed through (partial overlap of donor and acceptor emission wavelengths), and (iii) non-unitary ratios of donor- and acceptor-labeled proteins (FIG. 18b).

The use of lanthanides, especially Tb(III), as FRET donors along with time-gated detection (TGD) (often referred to as lanthanide-based FRET, or LRET) offers distinct advantages over conventional FRET: i) bleed-through is minimized because the narrow emission bands of Tb(III) can be spectrally isolated from sensitized acceptor emission signals (FIG. 18c); ii) crosstalk and autofluorescence background signals are fully eliminated by using TGD, with a microsecond delay (FIG. 18c) due to the long luminescence decay (millisecond range); iii) Tb(III)-based FRET imaging affords the possibility of multiplexed FRET imaging, where Tb(III) can sensitize the emission of two or more differently colored acceptors. To fully implement time-gated FRET microscopy of protein-protein interactions three components are required: i) suitably bright and stable lanthanide complexes, that can be selectively targeted to proteins in living cells; ii) methods to deliver these complexes into specific cellular compartments without unduly perturbing cellular physiology; iii) and a time-gated luminescence microscope.

There are several requirements to the lanthanide complexes to be practically used in such a FRET-based bioassay:
(i) kinetic inertness with respect to metal binding;
(ii) high extinction coefficient (>10000 $M^{-1}$ $cm^{-1}$) and quantum yield (>0.1) of emission;
(iii) long-wavelength (>350 nm) ligand absorption maximum;
(iv) resistance to photobleaching;
(v) one or more functional groups to conjugate with biomolecules or targeting moieties.

While hundreds of luminescent Tb(III) and Eu(III) complexes have been reported, only relatively few meet all of the above-mentioned requirements.

Lumi4Tb® is the most popular FRET-donor, which incorporates all aforementioned properties and is therefore widely used in many biomedical assays. However, these unique properties, as well as the sophisticated synthesis of a Lumi4Tb® probe makes it very expensive and inaccessible for many research purposes. This work demonstrates the optimization of the synthesis of Lumi4Tb® and proposes a novel approach of the linker introduction, so that Lumi4Tb® can be easily attached to biomolecules or targeting moieties.

Synthesis of the macrocyclic ligand: Lumi4Tb® is a Tb(III) complex with a macrocyclic bicapped H(2,2) ligand, bearing a 2 hydroxyisophthalamide (IAM) moiety acting as both, an antenna chromophore and a chelating group (FIG. 19). This predisposes the metal-binding units into an environment ideal for f element cation coordination. Such bicapped macrocyclic complexes retain their exceptional stability and extremely bright photophysical properties under a large variety of solution conditions at nanomolar concentrations and even in the presence of strongly competitive anions and cations, which makes these complexes very applicable in biologically relevant homogeneous assay conditions.

The synthetic route proposed for the synthesis of a Tb(III) complex with the cage-type bicapped macrocyclic ligand contains several important steps:
(i) the synthesis of the caps based on a pentaethylene tetraamine (PT) scaffold (FIG. 20a);
(ii) the synthesis of the monoactivated cages based on a methyl 2-methoxyisophthalate (IAC-OMe) scaffold (FIG. 20b);
(iii) the conjugation of the PT with IAC-OMe, resulting in the formation of a monocapped cage, followed by saponification of methyl ester protecting groups (FIG. 20c);
(iv) conjugation of the monocapped cage with the second cap, following by the deprotection of the methoxy-groups (FIG. 20d);
(v) the synthesis of Tb(III) complexes (FIG. 20e).

Figure 21:
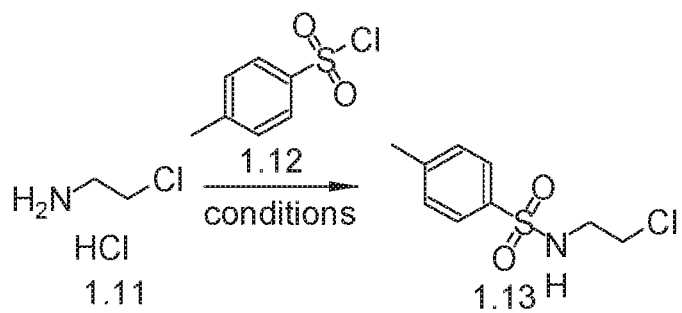
FIG. 21 shows Summary of tested tosylation reactions with 2 chloroethylamine hydrochloride 1.11, the amount of tosyl chloride 1.12 is taken as 1.0 equiv.

The cap 1.17 was synthesized, using an optimized literature procedure based on the original preparation. The synthetic route starts with the protection of 2-chloroethylamine hydrochloride 1.11 with a tosyl-group (FIG. 22, a), using tosyl chloride 1.12 in water and $K_2CO_3$ as a base. The reported conditions for this reaction gave no full consumption of tosyl chloride 1.12, caused by its poor solubility in water and it was isolated together with the product 1.13 (FIG. 21, entry 1). An increase of the reaction time did not result in any further improvement of yield or product purity. Besides, the HCl molecules, generated in the reaction, may prevent the reaction from going further by forming an amine hydrochloride, therefore, basic conditions are required. Alternating the amount of the reactants, the pure product was finally obtained and no further purification was needed (FIG. 21, entry 7).

An increase of the amount of the amine 1.11, ensuring the full consumption of TsCl 1.12, led to the formation of the desired product of decent purity (FIG. 21, entry 6). The optimal reaction conditions, namely 1.4 equiv. of the amine and 2.5 equiv. of $K_2CO_3$, afforded the desired product 1.13 of high purity.

Figure 22:
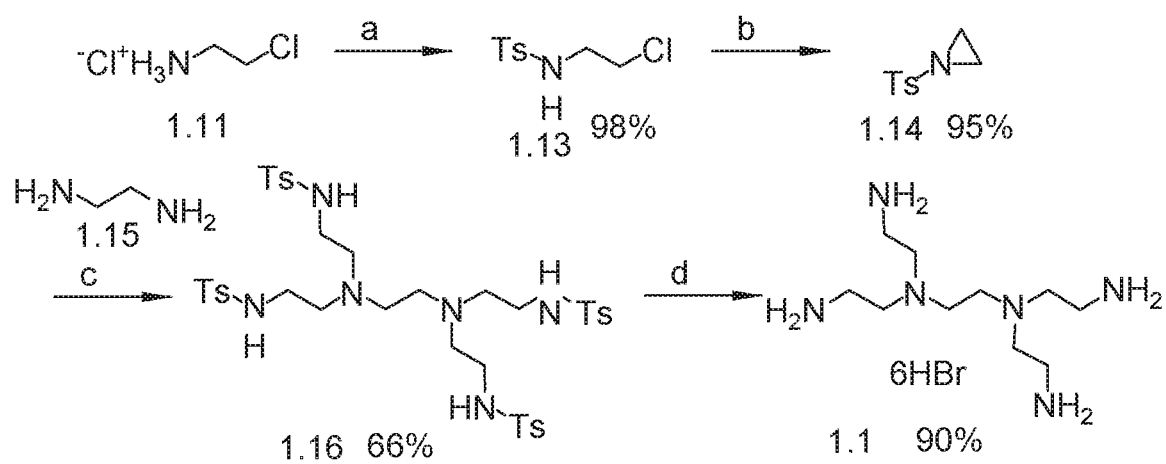
FIG. 22 shows The synthesis of the caps based on the pentaethylene tetraamine scaffold, (a) TsCl (1.12), K2CO3, H2O, ovm; (b) NaOH, H2O, 0-10° C., ovrn; (c) EDA (1.15), benzene, 0° C.-rt, ovm; (d) HBr in AcOH, 48 h, reflux.

The obtained sulfonamide 1.13 was then converted to tosyl-aziridine 1.14 (FIG. 22, b). The subsequent ring-opening during the reaction with ethylene diamine 1.15 (EDA) resulted in the formation of tosyl-protected PT 1.16

(FIG. 22, c). The latter step was performed using benzene as a solvent, as described in the original papers, though the patented protocol of the Lumi4Tb® synthesis suggests to use a toluene/acetonitrile mixture with heating. The slightly higher solubility of tosyl-aziridine 1.14 in benzene in comparison to a toluene/acetonitrile mixture allowed using lower temperatures for this reaction, which decreased the rate of tosyl-aziridine degradation and, eventually, increased the reaction yield (22% using toluene/acetonitrile at 65° C., as described in the patents. 66% using benzene, 0-30° C., as described in. The last step involved the deprotection of tosyl-protecting groups by refluxing 1.16 in 33% HBr solution in acetic acid for 2 days, to afford the compound 1.17. The use of aqueous HBr with acetic acid, as described in the patent, afforded the product in a low yield (46% vs. 90% for non-aqueous HBr, used in this work). The overall yield for the cap synthesis was 55% over 4 steps (FIG. 22).

Figure 23:
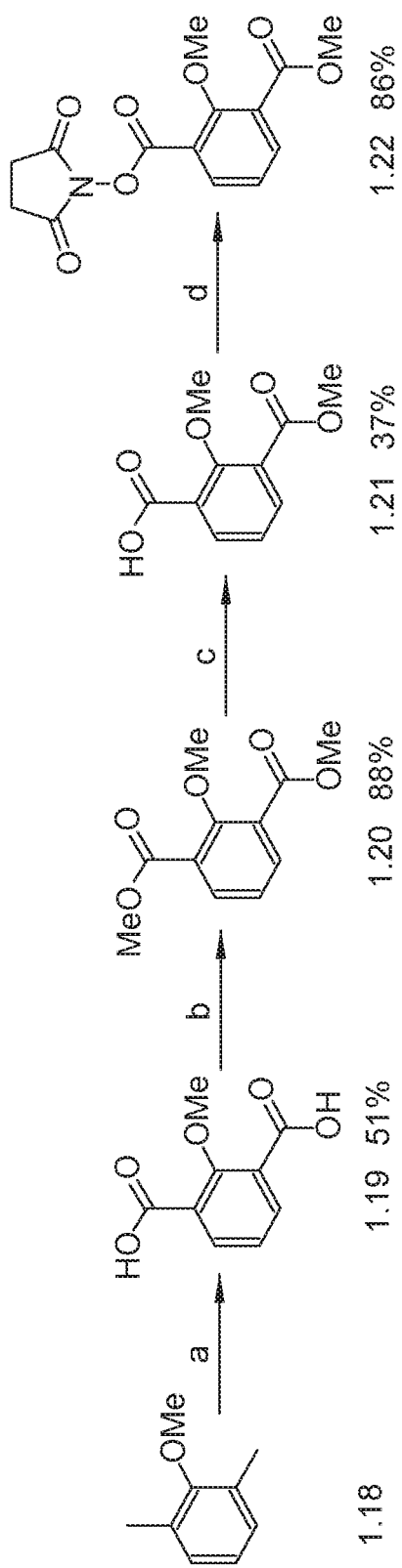
FIG. 23 shows The synthesis of the cages based on the IAC-OMe scaffold (a) 1. KOH, KMnO4, 80° C., ovrn, 2. HCl, H2O; (b) H2SO4, MeOH, 4 h, reflux; (c) 1. KOH (1.00 equiv.), MeOH, 50° C., 4 h, 2. HCl, H2O; (d) NHS, EDC, acetonitrile.
Figure 24:
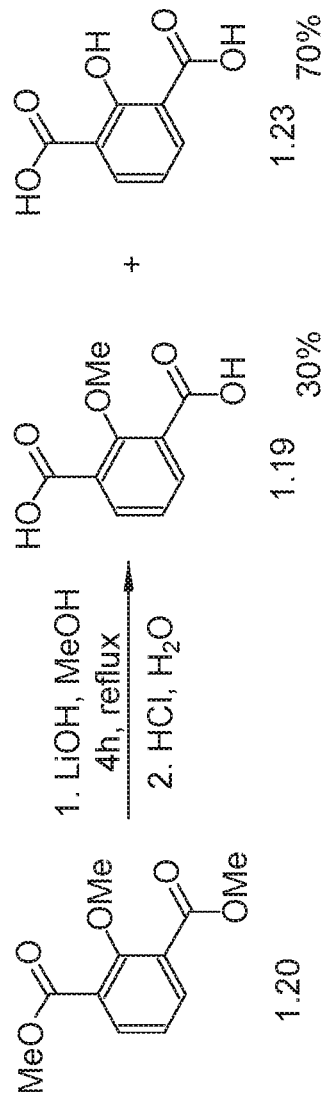
FIG. 24 shows Deprotection of the methyl ether together with methyl esters in ortho-position, refluxing 1.19 with LiOH in MeOH.

The synthesis of the "cages" is shown in the FIG. 23, using the modified procedure from literature. In order to obtain a bicapped ligand, the carboxylic groups of the "cages" should be activated stepwise to prevent the polymerization during the first "cap+cage" coupling (FIG. 20c).

The synthetic route started with the oxidation of 2,6 dimethylanisole 1.18, a cheap and easily available reactant with $KMnO_4$ in water at 80° C., which afforded the dicarboxylic acid 1.19 in 51% yield (FIG. 23, a). The monoprotection of the dicarboxylic acid was performed in two steps, namely i) the protection of both carboxylic groups by the formation of the compound 1.20 with two methyl ester groups using FISCHER esterification with $H_2SO_4$ in MeOH (FIG. 23b); ii) mono deprotection of one carboxylic group to afford compound 1.21 (FIG. 23c) as a result of a mild saponification with 1 equiv. of KOH in MeOH at rt. Since this reaction is not selective, the crude product contained all three possible products: double-, mono- and non-protected 2-methoxyisophthalates (1.20, 1.21 and 1.19, respectively).

Limiting the amount of the byproduct 1.19 by adding only 1.00 equiv. of the base, hydroxides of different alkali metals were tested (FIG. 25). LiOH, which is known to be very effective in saponification reactions, indeed turned out to be more reactive than NaOH and KOH, showing a conversion even at room temperature (FIG. 25, entries 1-2). However, in this case such an efficiency is a drawback, since together with the desired product 1.21, the di-acid 1.19 was formed. Moreover, when the reaction mixture was refluxed with LiOH, the unfavorable deprotection of the ether group was observed, and the reaction resulted in 2 hydroxyisophthalate 1.23 as the major product (FIG. 25, entry 3, FIG. 24) (calculated according to the integration of diode array signals in LC MS). This effect of an unusual deprotection of aromatic ethers in the presence of esters in ortho-position is poorly described in literature, particularly, the deprotection with LiOH has never been reported before.

When NaOH was used as a base, 20% conversion was observed after stirring the reaction mixture for 2 h at rt (FIG. 25, entry 4). Despite the increase of the reaction time, the higher ratio of the desired product (P) 1.21 relatively to the unreacted starting material (SM) 1.20, led to the increase of the amount of the byproduct (BP) 1.19, making these reaction conditions less efficient. Shortening of the reaction time to 1.5 h (FIG. 25, entry 6) led to a sole formation of the BP 1.19.

Potassium hydroxide was found to be more favorable for this reaction. The first 8 h stirring at rt resulted in little conversion (10%) (FIG. 25, entries 7-9) and no byproduct 1.19 was formed. However, after 24 h, the amount of the product 1.21 did not significantly change, while the BP 1.19 started to appear (FIG. 25, entry 10). It was found, that heating of the reaction mixture for at least 2 h at 50° C. led to an improvement of the conversion (FIG. 25, entry 11). On top of that, the yield was slightly higher when water was eliminated, and the reaction was performed in MeOH (FIG. 25, entries 12-14). After explorative research, the optimal reaction time was found to be 4 h (FIG. 25, entry 13).

Due to the limited solubility of potassium benzoates in common organic solvents, the choice of an appropriate solvent might make the product to precipitate, and, hence, increase the overall reaction yield and simplify the purification, e.g. as reported for malonic acid. [Therefore, saponification has been performed in acetonitrile and THF at rt. (FIG. 25, entries 15-16). In both cases, the product 1.21, indeed, was precipitating as the respective potassium salt. However, after reaching the maximum, the amount of precipitate significantly decreased within 2 minutes and only a little amount of the product could be isolated (less than 10% in both cases), resulting in a clear solution still containing all three compounds (SM 1.20, P 1.21, BP 1.19).

Experimentally found optimized reaction conditions are listed in the FIG. 25, entry 13, namely stirring the compound 1.20 with 1.00 equiv. of potassium hydroxide at 50° C. for 4 h, giving 55% of the desired product 1.21, 20% of the di-acid BP 1.19 and 25% of unreacted SM 1.20, according to LC-MS data. The separation of these products was performed by multiple extractions: firstly, the extraction of methyl esters with EtOAc, so that mono- and bis-potassium salts remained in the aqueous layer. Secondly, after the latter was acidified, the mono-protected acid 1.21 was extracted with DCM, while the non-protected dicarboxylic acid 1.19 stayed in the aqueous layer. Thus, the mono-methyl ester 1.21 was isolated in a yield of 37%.

Figure 26:
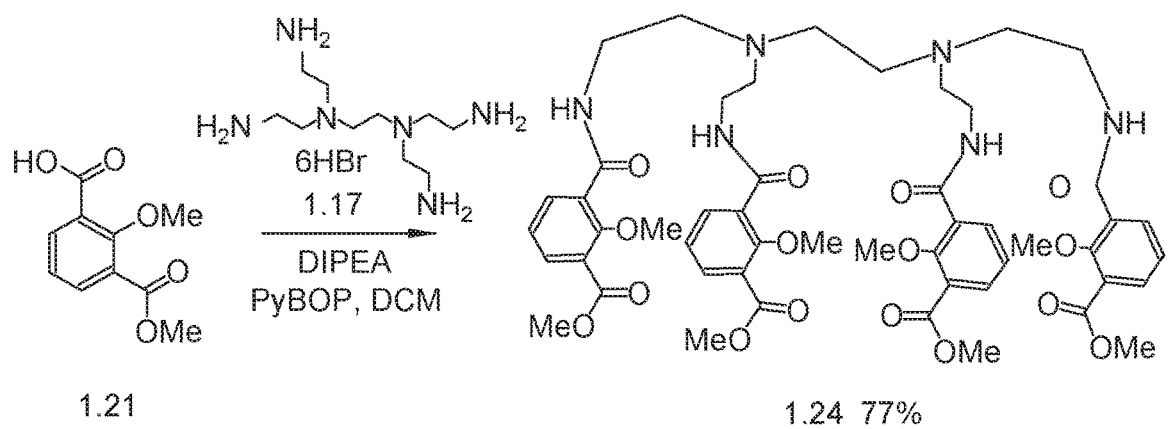
FIG. 26 describes Coupling of the mono-protected acid "cage" 1.21 with PT (1.17), using PyBOP as a coupling agent.
Figure 27:
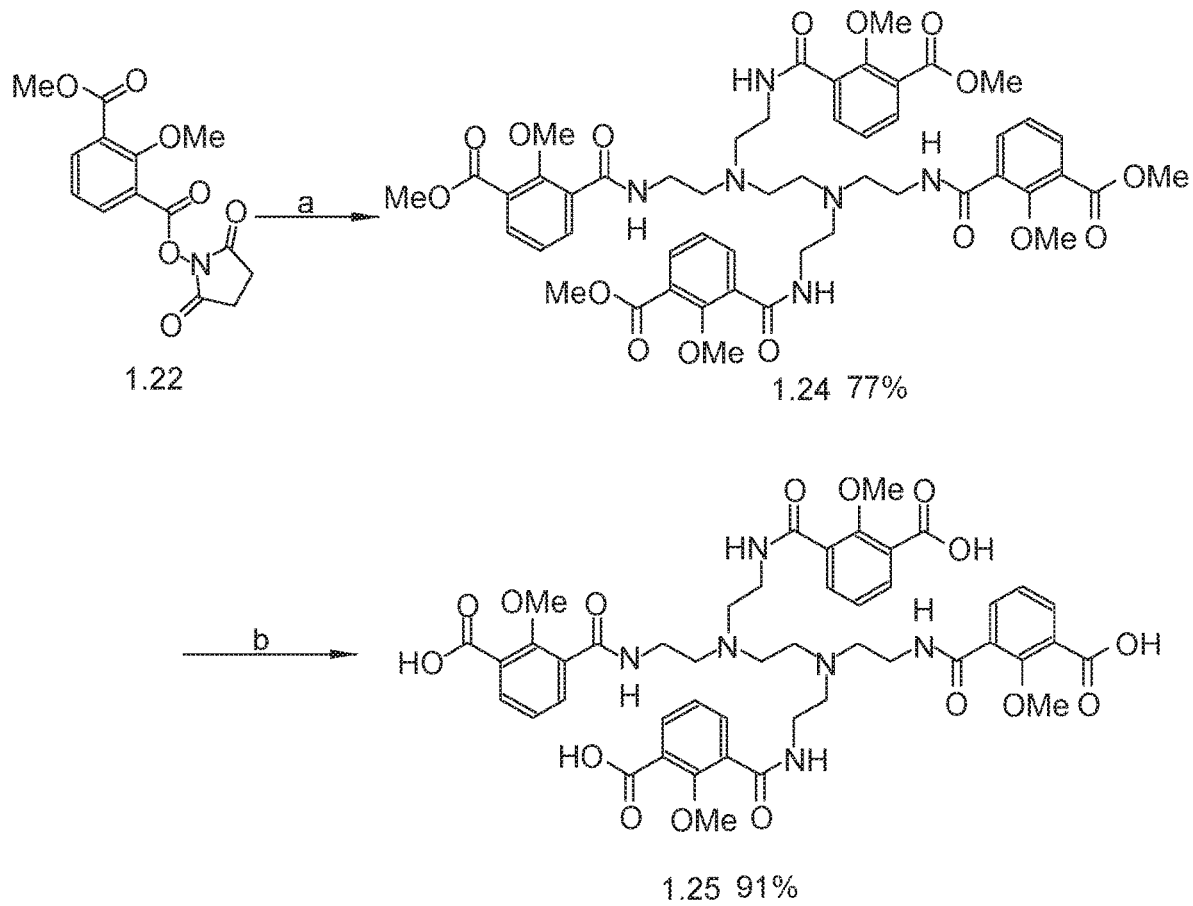
FIG. 27 shows the The coupling of the NHS-preactivated 1.22 with PT (1.17), followed by the deprotection of the methyl esters; a) PT (1.17), DIPEA, DCM; b) 1. KOH, MeOH, 4 h, reflux, 2. HCl.

Compound 1.21 was directly used in the coupling reaction, using PyBOP as coupling agent (FIG. 26). The reaction was completed within 5 minutes, however, the "monocapped" product 1.24 had the same retention time as the PyBOP-related byproduct (phosphine oxide) in hexanes/EtOAc and DCM/MeOH solvent mixtures. Therefore, the attempts to purify the compound via flash column chromatography were not successful.

To conduct the coupling reaction without additional coupling agents, the mono-methyl ester 1.21 had to be preactivated. The activation process consisted of the formation of an N-hydroxysuccinimidyl ester (NHS-ester) by consecutively reacting carboxylic acid with carbodiimide and NHS. The pure NHS-ester 1.22 was recrystallized from methanol in a very good yield (FIG. 23d). The subsequent reaction of the NHS-ester with PT (1.17, FIG. 27a) afforded the monocapped compound 1.24 in 77% yield. The saponification of 1.24 afforded the monocapped compound 1.25, bearing carboxylic acid moieties, ready for the next coupling-step.

The coupling of the mono-capped compound 1.25 with PT is a very delicate reaction, as it should be performed for two compounds with four reactive sites each, leading to numerous byproducts. In order to minimize the amount of byproducts, such reactions are usually performed in high dilution and a very low rate of supply of the starting materials (for instance, dilution 0.25 mmol/L, reaction time 7 days, yield 52%, reported for compound 1.26 or dilution 1.9 mmol/L, reaction time 24 h, yield 46%, reported for an analogous compound. Herein, a new protocol was established, allowing to perform the reaction in 2 h with a lower dilution (5.0 mmol/L).

Figure 28:
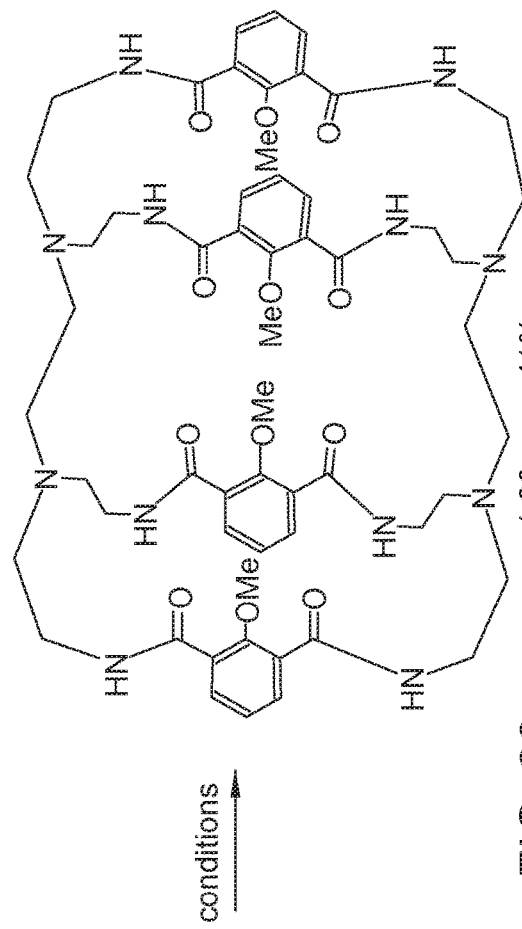
FIG. 28 shows The coupling of the monocapped acid 1.25 with PT (1.17), using PyBOP as a coupling agent to afford the bicapped ligand 1.26; conditions: PT (1.17), PyBOP, DMF, portion wise, 2 h, rt.

Equimolar solutions of the starting materials 1.25 and 1.17 with DIPEA in DMF were added portion wise to a stirred solution of PyBOP, adding a 500 µL portion of each solution simultaneously every 5 min (ten portions in total). After ten portions had been added, the reaction mixture was left stirring for 1 h and then the solvent was evaporated under reduced pressure. The simultaneous addition of two starting materials to a moderately diluted solution of PyBOP ensured the high probability to obtain the desired product 1.26, because of the high rate of amide bond formation using PyBOP activation (FIG. 28).

The next step involved the demethylation of the bicapped cage 1.26, which has been usually done using $BBr_3$ in anhydrous DCM. Since this reaction has been reported to be extremely slow (2-4 days), other conditions were also tested and monitored by LC-MS. The conversion degree was calculated based on the integration of the diode array signals.

Figure 29:
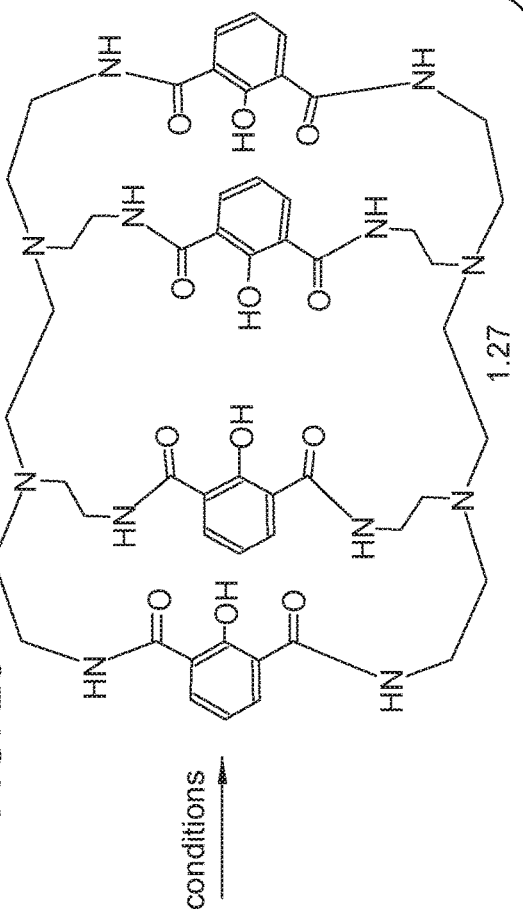
FIG. 29 shows Summary of tested reaction conditions of 1.26 demethylation.
Figure 32:
FIG. 32 shows Comparison of the luminescence intensity under UV-lamp with λex=254 nm for 10 nM aqueous solutions of Tb chloride, Tb-1.27, Tb-1.28 (from left to the right).

The experimental evidence demonstrated the reaction with $BBr_3$ being slow. After 2 days only 18% conversion was detected (FIG. 29, entry 1), whereas an increase of temperature and additional stirring for one day afforded only 26% of the product. ZHU et al. reported, that sodium azide promoted the hydrolysis of the anisole, thus $NaN_3$ in DMF in the presence of 1% water with heating (80° C.), was able to deprotect methyl ethers. Indeed, after 2 h a little conversion was observed (FIG. 29, entry 3). However, after 4 h, neither the starting material 1.26, nor partially deprotected intermediates, nor the product 1.27 were detected on LC-MS. The reaction with LiOH in MeOH, which was shown to deprotect methyl ethers earlier (FIG. 24), also did not afford a product even after 8 h of reflux and in this case the SM 1.26 was fully recovered (FIG. 29, entry 5). Full conversion was, however, achieved by refluxing of 1.26 with LiI in 2,6-lutidine for 4 h (FIG. 29, entry 6). Using the same reaction conditions, compound 1.24, bearing ether and ester groups, was fully deprotected to afford compound 1.28 in 69% yield (FIG. 30). This compound was synthesized for the further complexation with Tb(III) and the investigation if this compound could replace Lumi4Tb®.

Despite high symmetry, $^1H$ and $^{13}C$-NMR spectra of the bicapped ligand 1.27 turned out to be very sophisticated and were difficult to resolve, suggesting the coexistence of several conformers/isomers. Therefore, HPLC, together with mass spectrometry were used for the characterisation of these compounds. In both cases, the HPLC chromatogram of 1.27 showed only one sharp peak, identified by mass spectroscopy as the desired macrotricyclic ligand.

The mild refluxion of the compound 1.27 with a methanol solution of Tb(III) chloride afforded the product Tb-1.27 (Lumi4Tb® probe) in a quantitative yield (FIG. 31).

Figure 33:
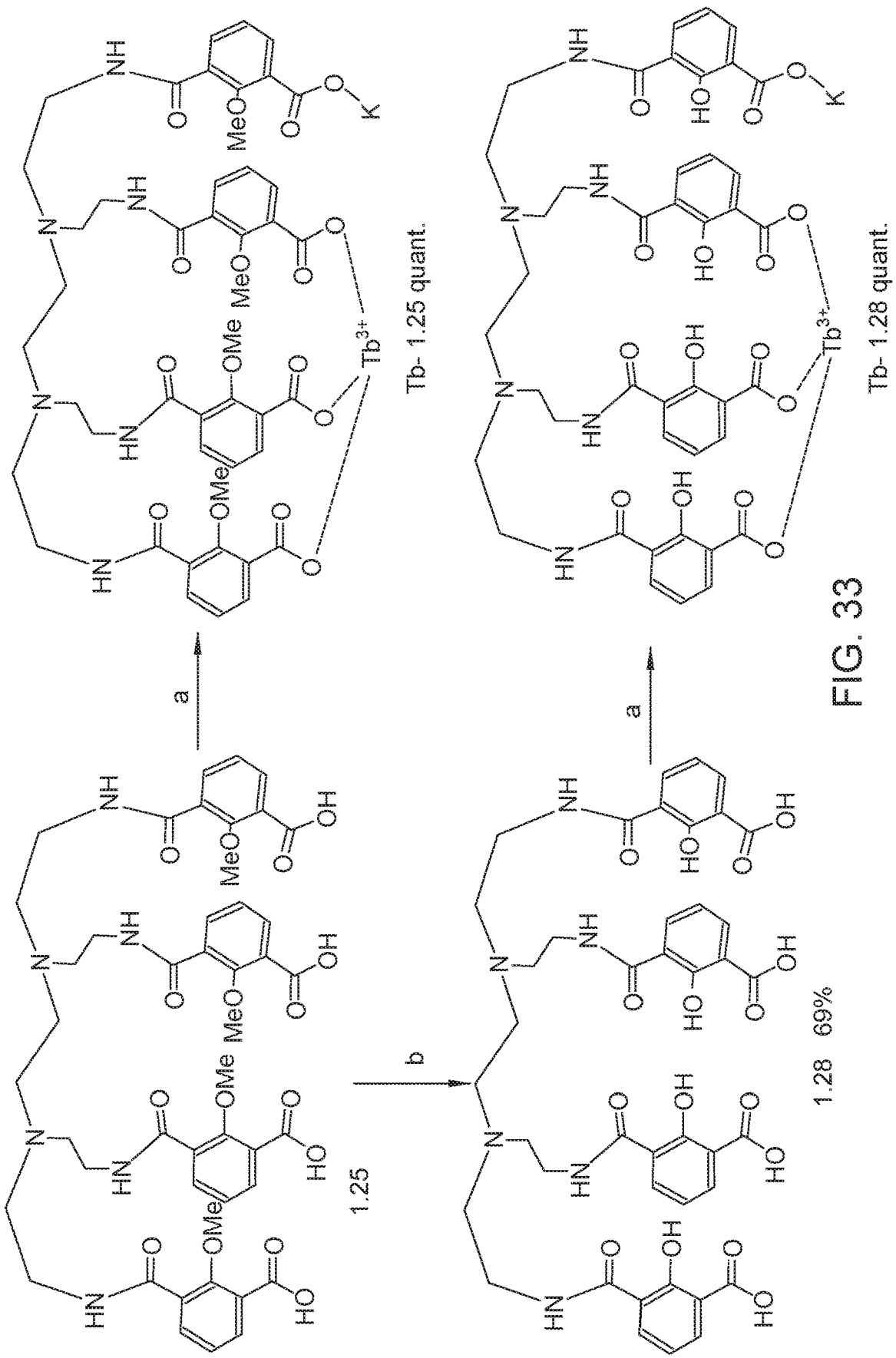
FIG. 33 shows The synthesis of Tb complexes with monocapped carboxylic ligands: a) 1. KOH in MeOH (1.00 equiv.), 2. TbCl3(H2O) in MeOH, reflux; b) LiI, 2,6-lutidine, 4 h, reflux.
Figure 34:
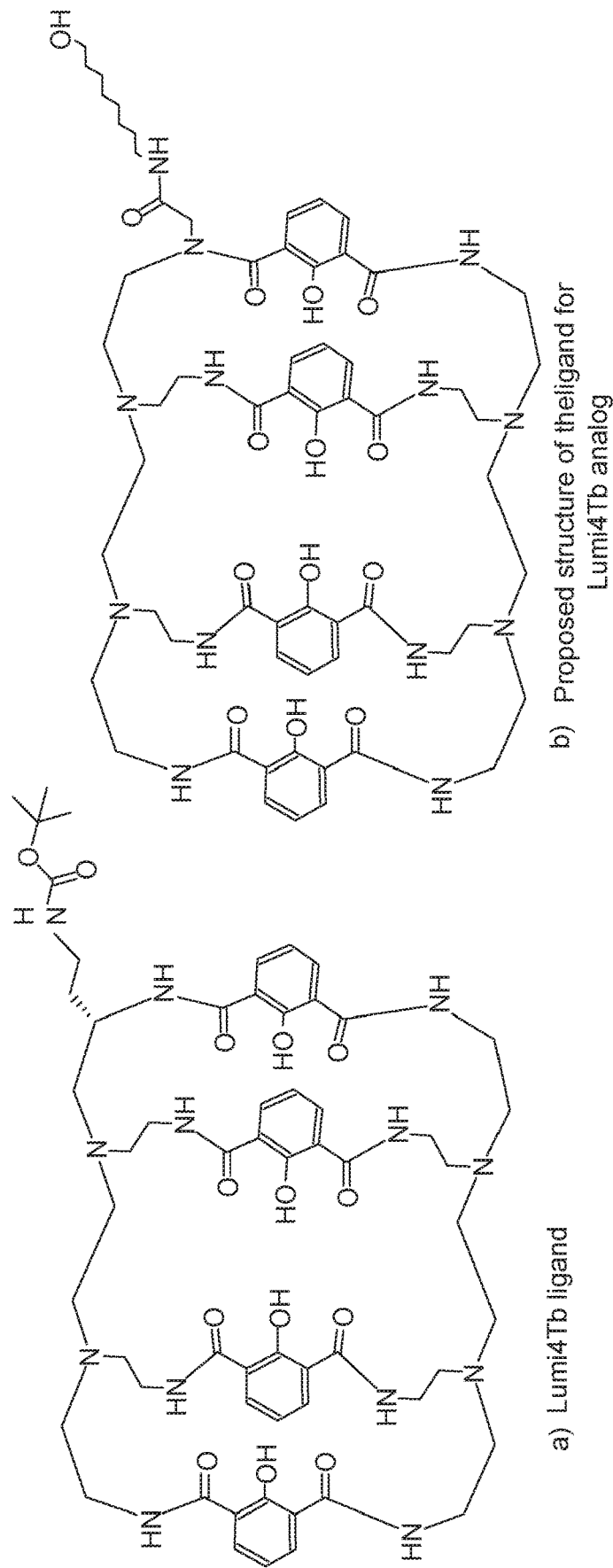
FIG. 34 shows a) Lumi4Tb® ligand structure with an attached linker and b) the bicapped cage structure with a linker, described in this application.

The monocapped ligand 1.25 and its demethylated derivative 1.28 were also used for the complexation with Tb(III). The complexes Tb-1.25 and Tb-1.28 were therefore synthesized using a standard two-step procedure for the synthesis of lanthanide aromatic carboxylates, namely the deprotonation of carboxylates, followed by the addition of terbium chloride. As a result, in the case of Tb-1.28, the slurry precipitated from the MeOH solution, which is due to the lower solubility of this complex in MeOH in comparison to the bicapped complex Tb-1.27. At the same time, complex Tb-1.25 precipitated immediately and turned out to be very poorly soluble, not only in water, but also in most common organic solvents (MeOH, EtOH, toluene, acetonitrile), which is due to the immediate formation of coordination polymers (FIG. 33). This result indicates, that hydroxy groups indeed participate in the coordinative bonding with the Tb(III) ion in the cases of Tb-1.27 and Tb-1.28, making them highly luminescent and soluble (FIG. 32), while in the case of Tb-1.25, Tb(III) coordinates terminal carboxylic groups and did not coordinate donor atoms inside the cage, probably due to steric hindrance.

Figure 35:
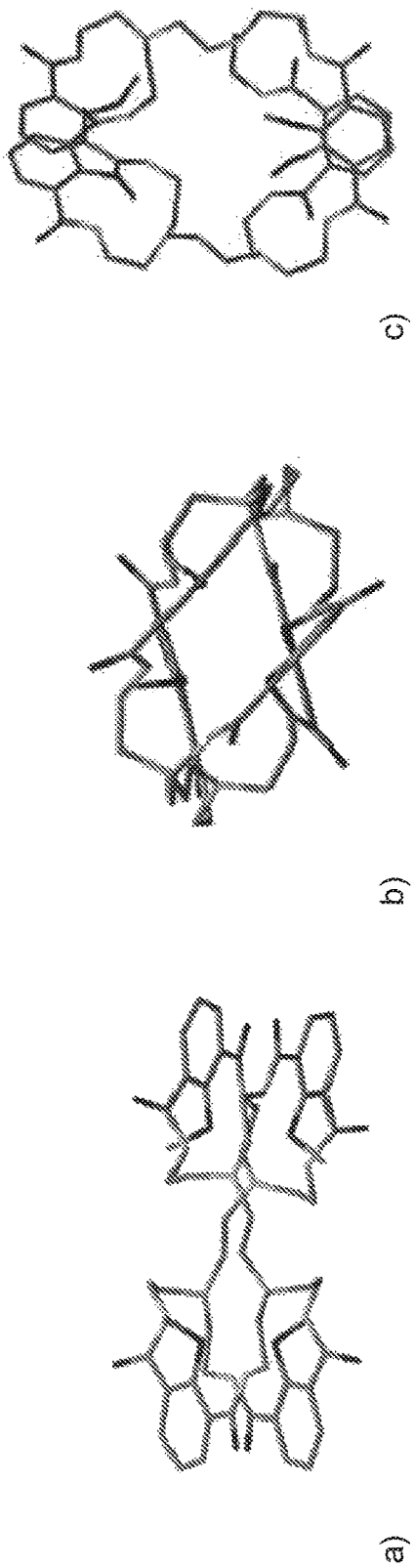
FIG. 35 shows Molecular structure of 1.26 a) front view b) side view c) top view.

Linker introduction and outlook: To make the Lumi4Tb® probe useful for biological assays, it should have a linker that can be used for a conjugation to biomolecules or targeting moieties. In commercially available Lumi4Tb® probes, such a linker is introduced to one of the caps resulting in the formation of an asymmetric, chiral probe (FIG. 34a). The synthesis of this linker is unnecessary complicated, and in this work, we propose to introduce the linker by an amide alkylation (FIG. 34b). According to the crystal structure for compound 1.26, which was refined by RAYMOND et al. (FIG. 35), such an approach should make no difference in the coordination ability of the ligand. The lone pairs of the four tertiary amines on the caps are all directed inwards, while all four methyl groups are directed outwards. The H-bonding network results in a nearly planar structure of the ligand. The four diamido IAM groups adopt an up→down→up→down arrangement with pseudo-symmetry, as shown in FIG. 35a.

As shown in FIG. 35b, four out of eight carbonyl moieties are indeed directed outwards from the cage, which makes them uncapable to coordinate the Tb(III) ion. The neighboring nitrogen atoms are positioned too far away to form a coordination bond with the lanthanide in the center of the cage. Therefore, if one of these positions was modified, it might not affect the geometry of the cage and its coordinating ability.

Figure 36:
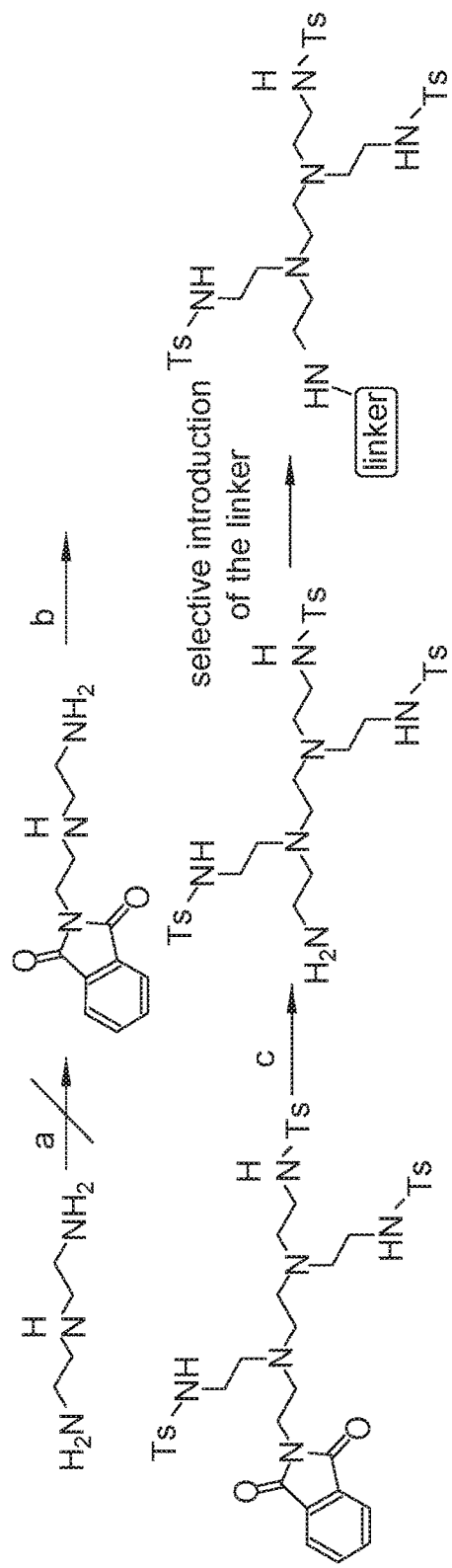
FIG. 36 shows Synthetic route for the synthesis of the cap with the attached linker, proposed in this work: a) phthalic anhydride, solvent, heating b) tosylaziridine, benzene, rt c) 1. H2NNH2·H2O, MeOH, rt, 2. HCl.

The synthetic route, which was proposed for the synthesis of the cap with the attached linker is shown in the FIG. 36. After selective monoprotection of N1-(2-aminoethyl)ethane-1,2-diamine, the ring opening reaction with tosylaziridine and the subsequent phthalimide deprotection affords an asymmetric PT compound, bearing one amino-group, ready for a selective linker introduction (by any reaction, which is more favorable for primary amines vs. sulfonamides).

Unfortunately, the first step of this reaction was not successful, and the desired product has never been isolated, though it was formed in small amounts (<10%), according to LC-MS. The optimization of the reaction conditions by varying the amount of the SM, solvents, temperature and reaction times, however, did not lead to any improvement. Therefore, this approach has never been implemented in this work.

Alternatively, the alkylation of the cap might be performed using the Ts-protected PT compound 1.16. Two synthetic strategies, MITSUNOBU and $SN_2$-reactions, were tested in this work.

Figure 37:
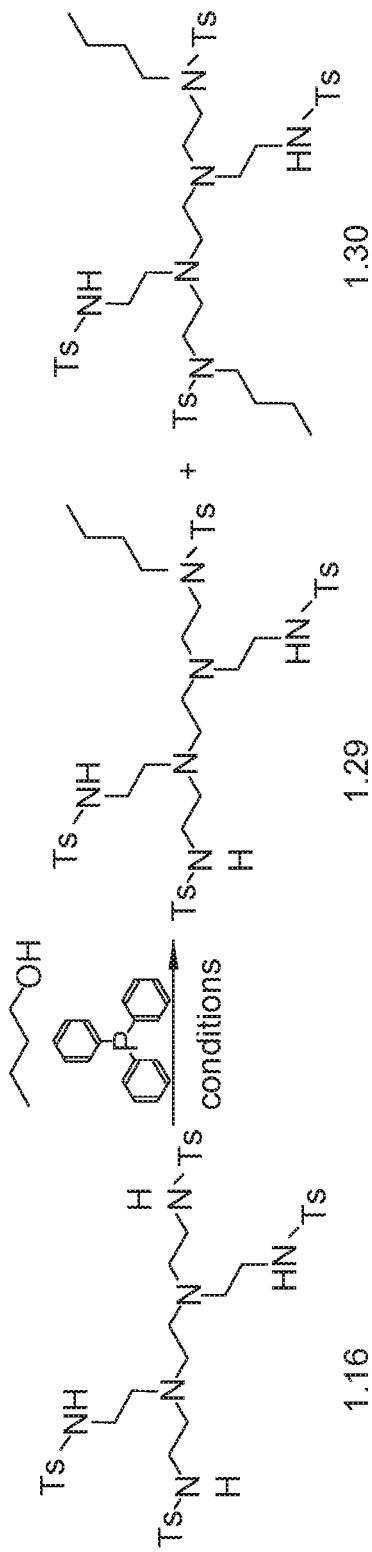
FIG. 37 shows Summary of tested MITSUNOBU reactions with 1.16. The reaction time in all entries was 2 h

To investigate, if MITSUNOBU conditions can be applied to the alkylation of 1.16, a test reaction with 1.00 equiv. of 1-butanol was performed, varying the solvent, the reagent and the temperature. The formation of the products was monitored by LC-MS (FIG. 37).

In a deficiency of 1-butanol, the reaction only gave single and double substituted products (1.29 and 1.30, respectively), and a few, if any amount of triple or quadruple substituted products were detected by LC-MS. Diethyl azodicarboxylate (DEAD) (FIG. 37, entries 4,5,8,9) and diisopropyl azodicarboxylate (DIAD) (FIG. 37, entries 1-3, 6,7) were both tested as reagents for this reaction and both showed quite similar results (FIG. 37). The use of different solvents also made only little difference, probably mostly due to the different solubility of the SM 1.16 in these solvents (FIG. 37, THF, entries 1-5; DMSO, entries 6-9). An increase of the temperature during the reaction indeed accelerated the reaction, however, also caused the formation of more double substituted byproduct 1.30 (FIG. 37, entries 3 and 5).

Figure 38:
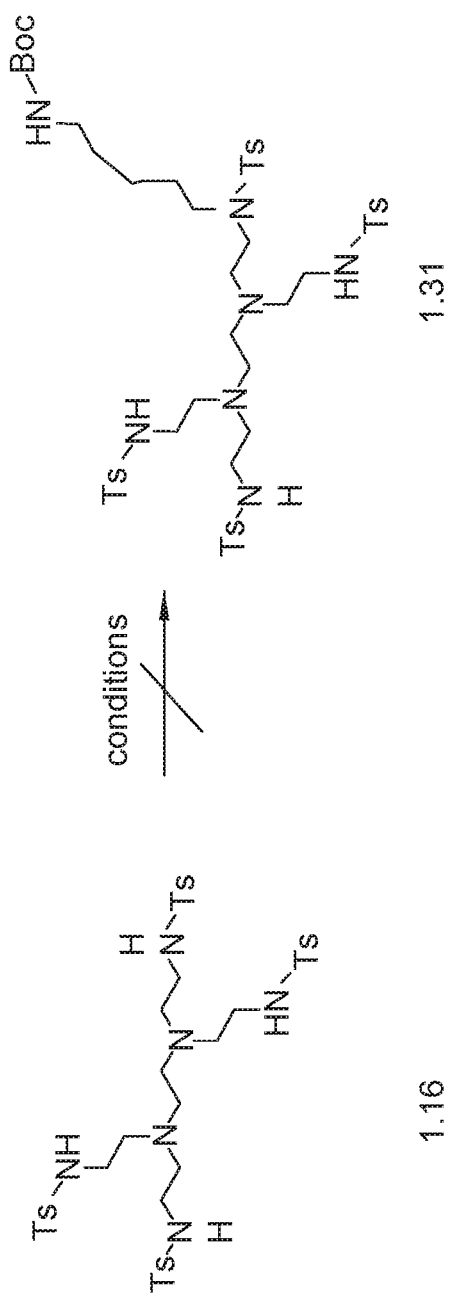
FIG. 38 shows MITSUNOBU reaction with N-Boc-aminohexanol, conditions: N-Boc-aminohexanol, DEAD, TPP, DMSO, 2 h, reflux
Figure 39:
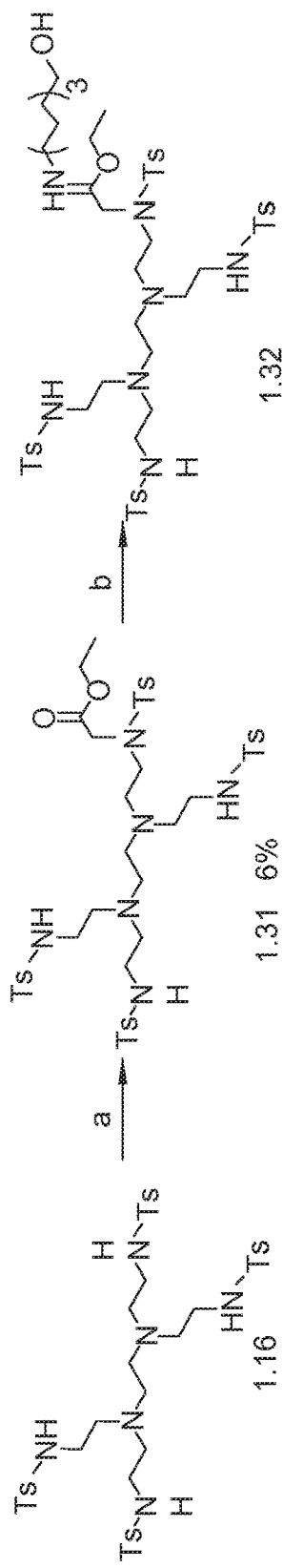
FIG. 39 shows Introduction of the linker using a substitution reaction with subsequent coupling to increase the length of the linker; a) ethyl 2-bromoacetate, acetonitrile, Cs2CO3, 4 h, reflux; b) 1. LiOH, MeOH, 1 h, rt, 2. 8-aminooctanol, PyBOP, DCM.
Figure 40:
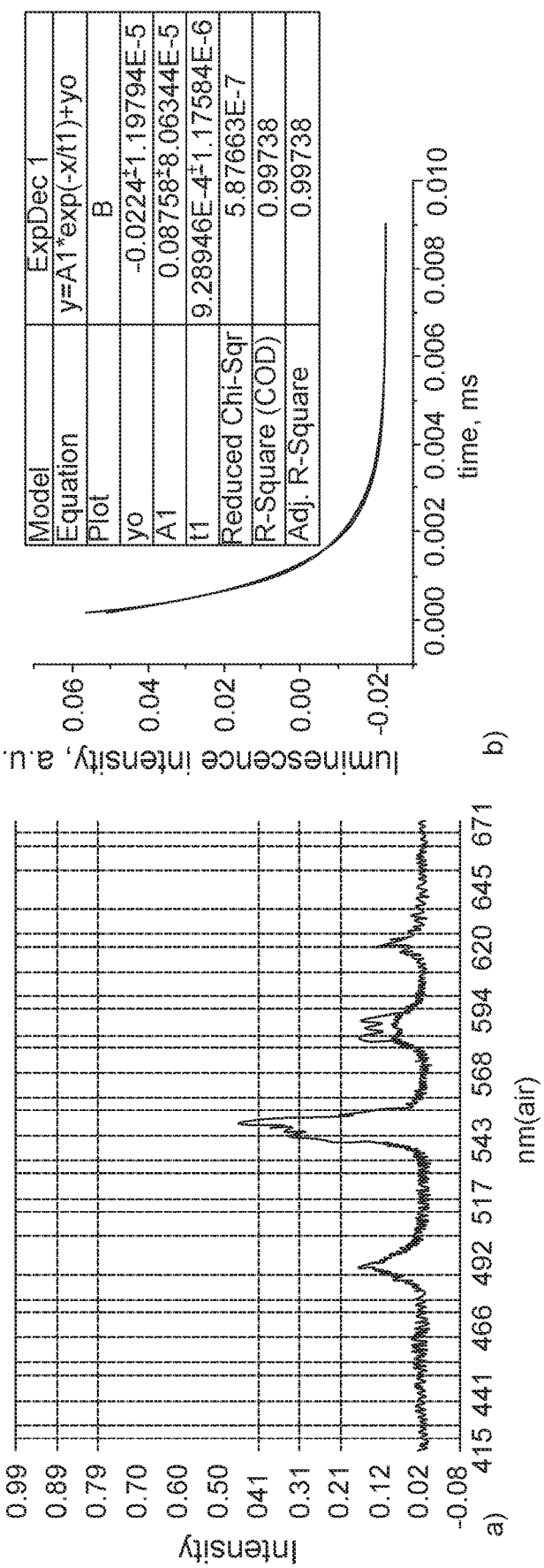
FIG. 40 shows Photophysical measurements for the complex Tb-1.27 in water (blue) and in TBS (green), concentration 0.7 nM, λex=337 nm a) emission spectrum of b) luminescence decay profile, τ=0.93 ms.

Though the possibility to use the MITSUNOBU reaction for the alkylation of compound 1.16 was demonstrated above, only little conversion was observed with N-Boc-aminohexanol, refluxing the latter with 1.16, triphenylphosphine (TPP) and DEAD in DMSO for 2 h (FIG. 38).

Alternatively, the alkylation of the cap can be performed via an $SN_2$-reaction by reflux of 1.16 with 1.00 equiv. of ethyl 2-bromoacetate in acetonitrile for at least 4 h. The long reaction time was chosen due to the poor solubility of the SM 1.16 in acetonitrile. After 4 h, the product 1.31 was isolated together with the doubly alkylated BP, however, this mixture was barely separable. After several attempts to purify the desired product via flash column chromatography, the pure product 1.31 was obtained in a very low yield (6%) (FIG. 39a). Therefore, subsequent reactions were only performed in a very small scale (~2 mg). The formation of compound 1.32 as a result of the PyBOP coupling was demonstrated using LC-MS, a full conversion was achieved within 5 minutes. Though, the synthesis and purification of compound 1.31 still needs to be optimized, the possibility of the introduction of a linker by alkylation of the compound 1.16 was demonstrated.

Photoluminescent properties: The following section describes the investigation of the luminescent properties of the complex Tb-1.27. The luminescence spectra and the lifetime of the excited state were recorded using a custom designed sensing circuit for photophysical measurements, described by S. A. REIS et al. For this purpose, 100 µL of a 0.7 nM solution of Tb-1.27 in tris-buffered saline (TBS) were transferred into a semi-micro 10 mm cuvette. When recording the luminescence, a laser with the excitation of 337 nm was used and the luminescence was detected in a range of 400-700 nm. For luminescence kinetics measurements, ten measurements were made. The signals for all ten runs were then averaged together, filtered through a 100 kHz low-pass filter (5-tap infinite-impulse response BUTTER-WORTH) to remove high frequency noise. As least-squared fit modeling a one-phase decay was used to determine the relaxation half-lives. Values are reported at 95% confidence intervals.

The complex Tb-1.27 exhibited typical Tb(III) based luminescence, demonstrating a similar emission profile, as reported for the Lumi4Tb® probe (FIG. 40a). The lifetime of the excited state was measured to be 0.93 ms, which is, however, different from the reported value of 2.45 ms. This discrepancy probably is due to the use of different solvents for the measurements. The original paper does not specify, which buffer has been used, instead they report to perform the kinetics measurements in "buffered aqueous solution". Nevertheless, the luminescence lifetime value, obtained in this work, lies in a millisecond range, which is rather high and typical for Tb(III) complexes.

Conclusions: Thus, this work optimizes the synthetic strategy to obtain the commercially available FRET-donor Lumi4Tb®, which is a multistep process, containing various bottlenecks from chemical complexity to cost points of view. The proposed synthetic route involves cheap and easily available starting materials and reduces reaction times, maintaining high yields.

The obtained probe possesses a very high luminescence intensity, demonstrating the typical Tb(III) emission profile, similar to those reported by RAYMOND et al. On top of that, the study of the single crystal structure of the bicapped ligand reported previously, allowed to propose a new way of the linker introduction, namely, the amide alkylation, since four nitrogen atoms of the amides are positioned too far away from the center and are not able to form a coordination bond with Tb(III). The synthesis of the alkylated cap has been performed, demonstrating the potential ability of the implementation of the proposed approach.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of making a compound of Formula (II):

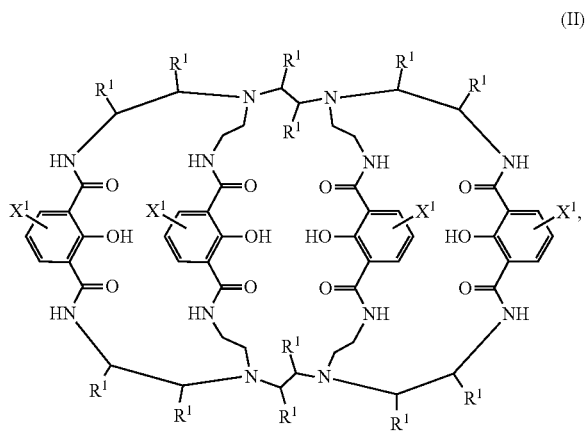

(II)

or a pharmaceutically acceptable salt thereof, wherein:
each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$; and
each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$, the method comprising:

coupling a compound of Formula (IIb):

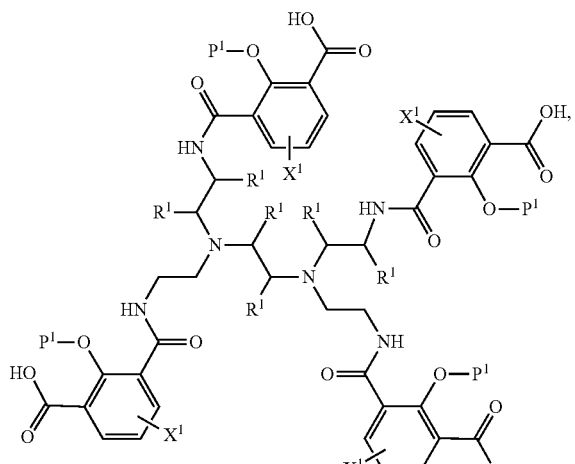
(IIb)

or a salt thereof, with a compound of formula (1):

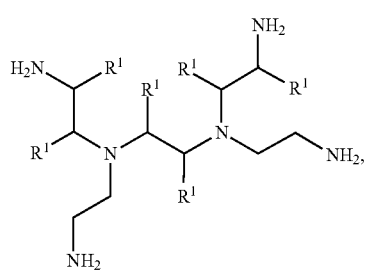
(1)

or a salt thereof, to obtain the compound of Formula (IIa)

(IIa)

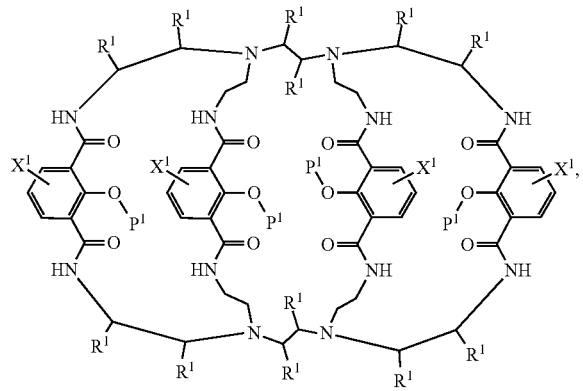

and deprotecting the compound of Formula (IIa) to obtain the compound of Formula (II).

2. The method of claim 1, wherein the deprotecting the compound of Formula (IIa) comprises treating deprotecting the compound of Formula (IIa) with a lithium halide.

3. The method of claim 1, comprising preparing the compound of Formula (IIb) by a method comprising coupling a compound of formula (1), or a salt thereof, with a compound of formula (2):

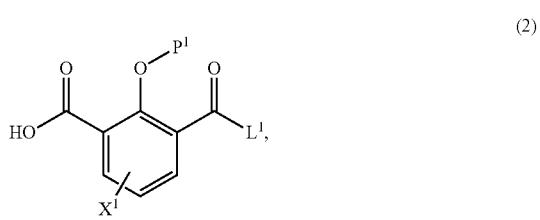
(2)

or a salt thereof, wherein $L^1$ is a leaving group, to obtain the compound of Formula (IIb).

4. The method of claim 3, wherein $L^1$ is an activated ester selected from: N-hydroxysuccinimide, sulfo-N-hydroxysuccinimide, tetrafluorophenoxy, pentafluorophenoxy, and p-nitophenoxy.

5. The method of claim 4, comprising preparing the compound of formula (2) by a method comprising reacting a compound of formula (3):

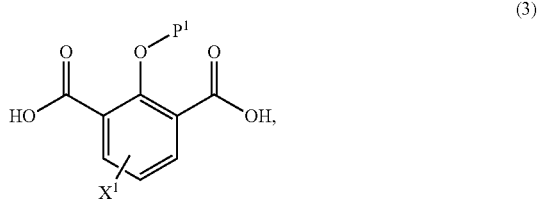
(3)

or a salt thereof, with $L^1H$, to obtain the compound of formula (2).

6. The method of claim 5, comprising preparing the compound of formula (3) by a method comprising oxidizing a compound of formula (4):

(4)

or a salt thereof, to obtain the compound of formula (3).

7. The method of claim 6, wherein:
the compound of Formula (II) has formula:
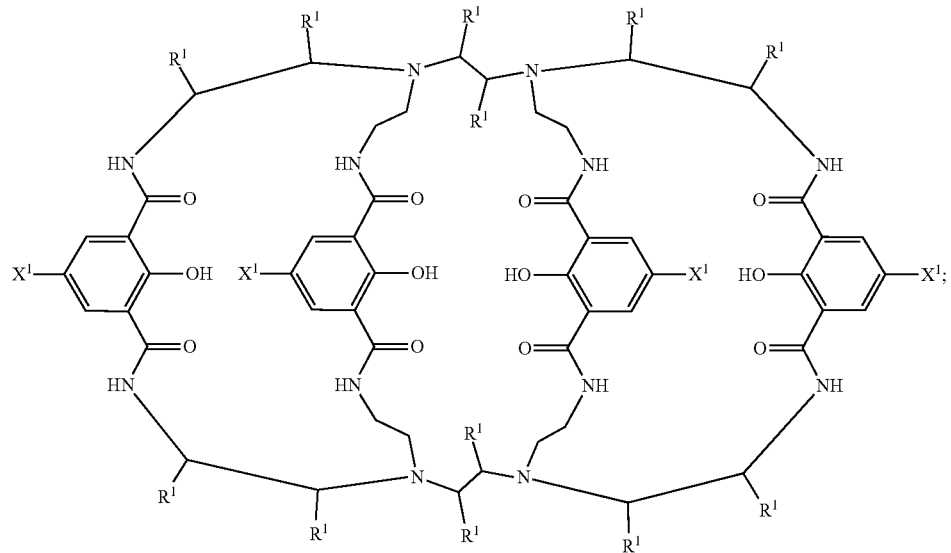
or a salt thereof, the compound of Formula (IIa) has formula:
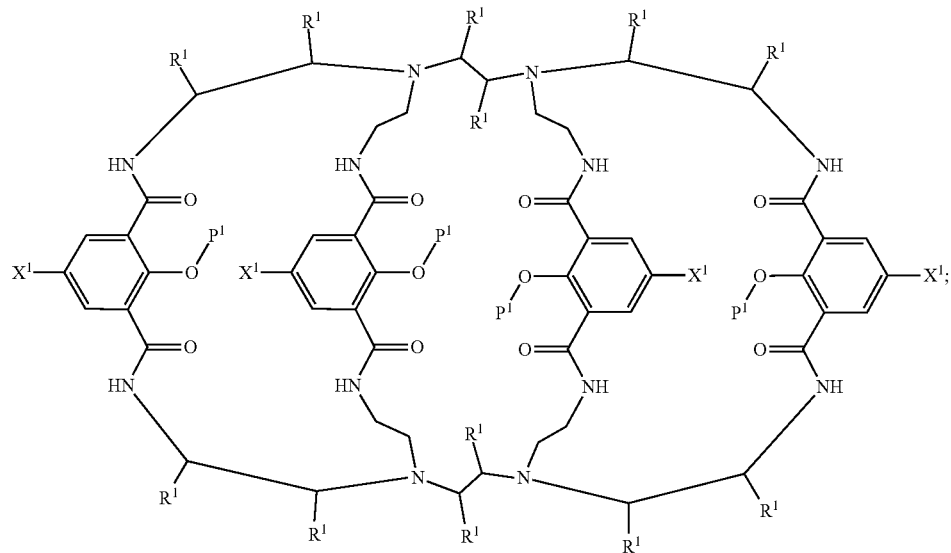

or a salt thereof, the compound of Formula (IIb) has formula:

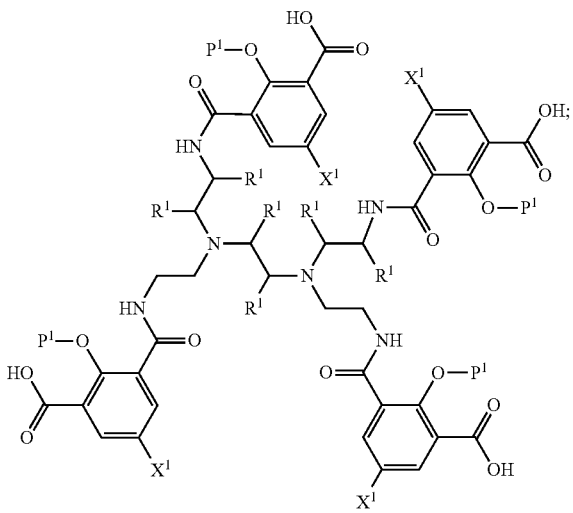

or a salt thereof, the compound of formula (2) has formula:

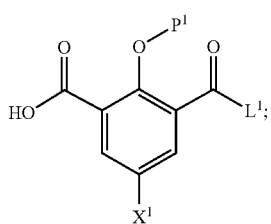

or a salt thereof, the compound of formula (3) has formula:

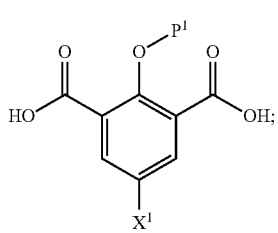

or a salt thereof, and the compound of formula (4) has formula:

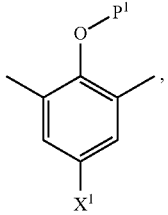

or a salt thereof.

8. The method of claim 1, wherein each $P^1$ is a methyl group.

9. The method of claim 2, wherein the lithium halide LiI.

10. The method of claim 1, wherein each $X^1$ is independently selected from H, halo, $NO_2$, methyl, and methoxy.

11. The method of claim 10, wherein each $X^1$ is independently a halo.

12. The method of claim 1, wherein each $X^1$ is the same.

13. The method of claim 12, wherein each $X^1$ is H or each $X^1$ is Br.

14. The method of claim 1, wherein
each $R^1$ is H, or
at least one $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$, or
one of $R^1$ is selected from $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$; and the remaining $R^1$ groups are all H.

15. A method of making a compound of Formula (IIIf):

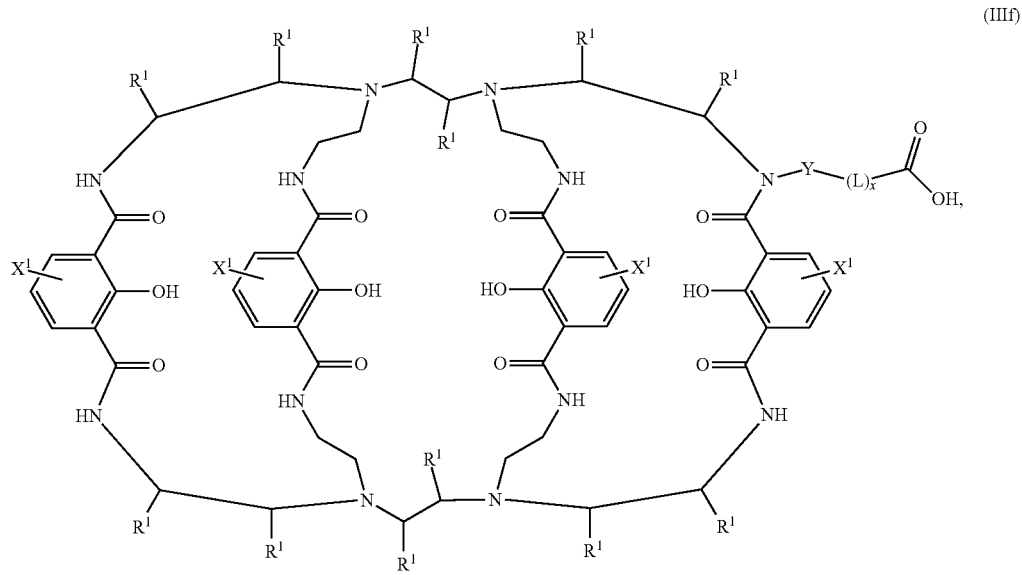

or a pharmaceutically acceptable salt thereof, wherein:

Y is selected from $C_{1-6}$ alkylene, $C_{2-6}$ alkenylene, and $C_{2-6}$ alkynylene;

x is an integer from 0 to 100; wherein if x is 0 then L is a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;

each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;

the method comprising deprotecting a compound of Formula (IIIg):

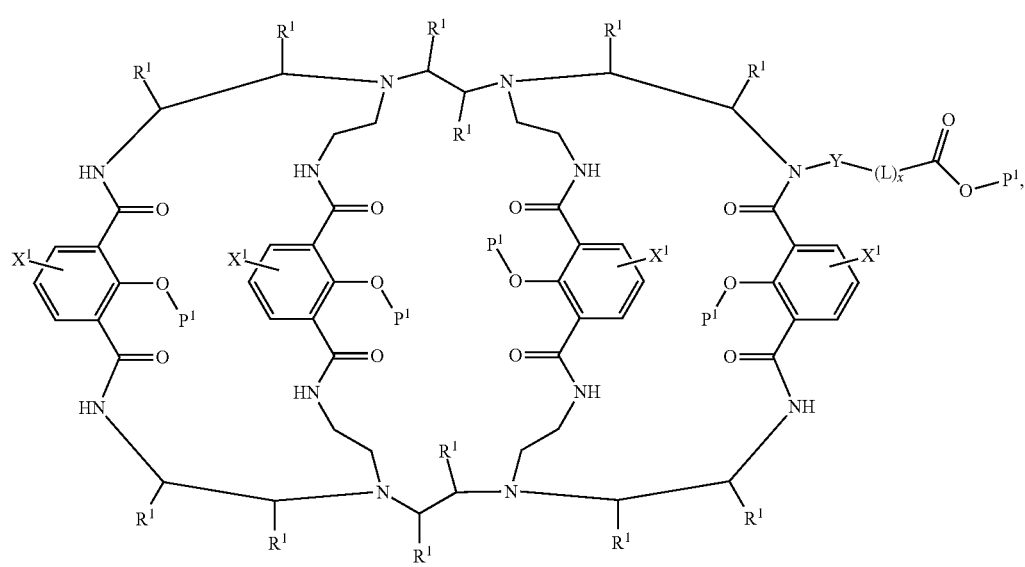

or a salt thereof, wherein each $P^1$ is independently a protecting group,
to obtain the compound of Formula (IIIf).

16. The method of claim 15, wherein the compound of Formula (IIIf) has Formula (IIIc):

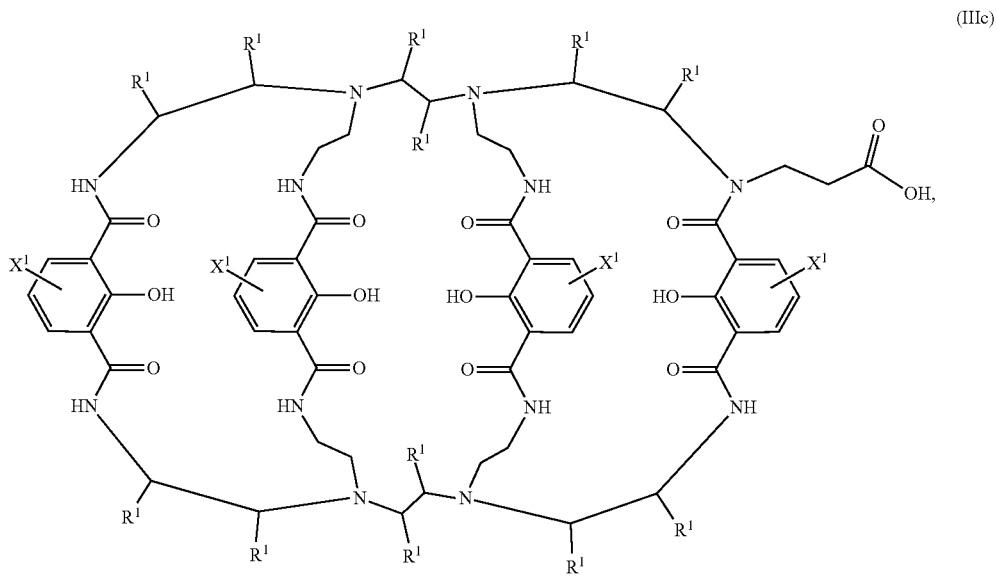

(IIIc)

or a pharmaceutically acceptable salt thereof.

17. A method of making a compound of Formula (IIIi):

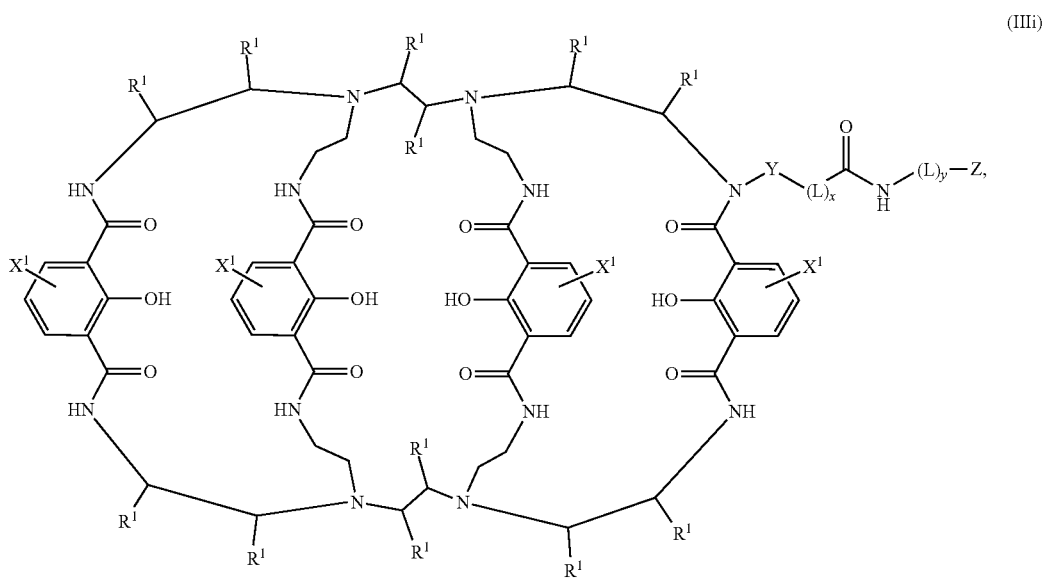

(IIIi)

or a pharmaceutically acceptable salt thereof, wherein:

Y is selected from $C_{1-6}$ alkylene, $C_{2-6}$ alkenylene, and $C_{2-6}$ alkynylene;

x is an integer from 0 to 100; wherein if x is 0 then L is a bond;

y is an integer from 0 to 100, wherein if y is 0 then L is a bond and Z is H or $C_{1-3}$ alkyl;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;

each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, NH$_2$, C$_{1-3}$ alkylamino, di(C$_{1-3}$ alkyl) amino, NO$_2$, CN, C(O)OH, C$_{1-3}$ alkoxy, C$_{1-3}$ haloalkoxy, and N$_3$;

each R$^1$ is independently selected from H, C$_{1-6}$ alkyl, C$_{2-6}$ alkenyl, and C$_{2-6}$ alkynyl, each of which is optionally substituted with 1, 2, or 3 substituents independently selected from halo, OH, SH, NH$_2$, C$_{1-3}$ alkylamino, di(C$_{1-3}$ alkyl) amino, NO$_2$, CN, C(O)OH, C$_{1-3}$ alkoxy, C$_{1-3}$ haloalkoxy, and N$_3$;

each Z is selected from H, C$_{1-3}$ alkyl, an activated ester, a biorthogonal functional group, NH$_2$, C$_{1-3}$ alkylamino, di(C$_{1-3}$ alkyl) amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

the method comprising coupling a compound of Formula (IIIf):

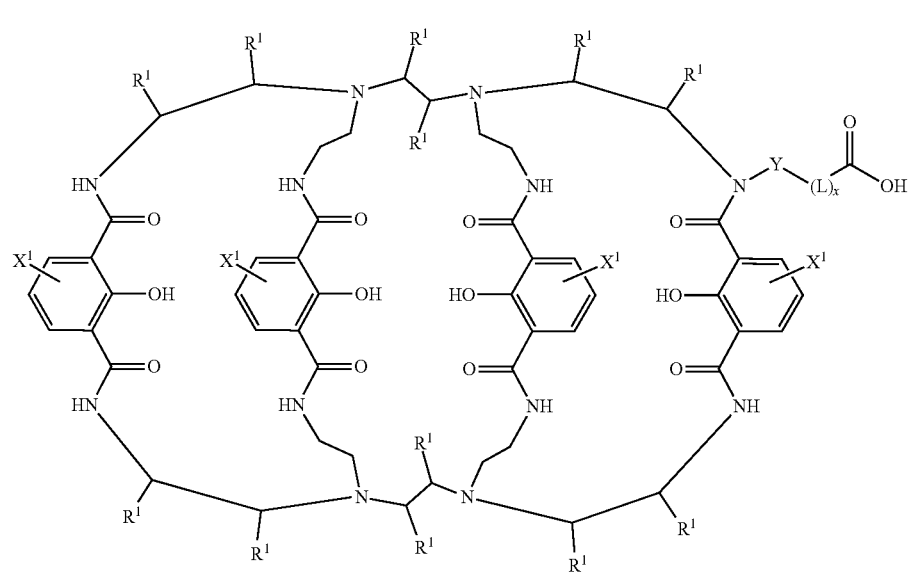

(IIIf)

or a salt thereof, with a compound of formula (15):

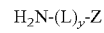

H$_2$N-(L)$_y$-Z    (15), or a salt thereof, to obtain the compound of Formula (IIIi).

18. A method of making a compound of Formula (IVc):

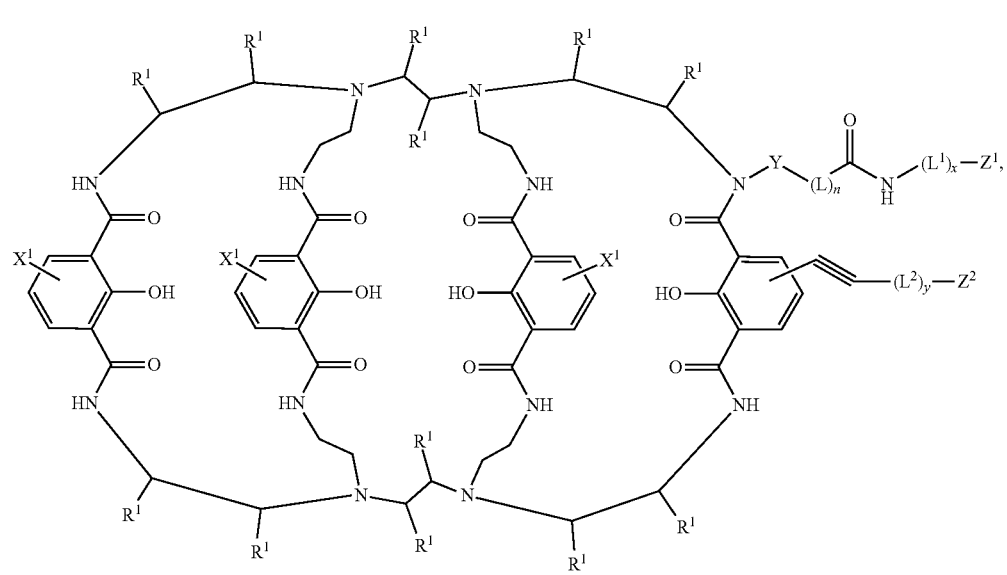

(IVc)

or a pharmaceutically acceptable salt thereof, wherein:

Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each $L^1$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each $L^2$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O)NH—, —NHC(O)—, —C(O)O—, and —OC(O)—;

each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$; and each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;

x is an integer from 0 to 100; wherein if x is 0 then $L^1$ is a bond and $Z^1$ is H or $C_{1-3}$ alkyl;

y is an integer from 0 to 100; wherein if y is 0 then $L^2$ is a bond and $Z^2$ is H or $C_{1-3}$ alkyl;

n is an integer from 0 to 100, wherein if n is o then L is a bond; and $Z^1$ and $Z^2$ are each independently selected from H, $C_{1-3}$ alkyl, an activated ester, a biorthogonal functional group, $NH_2$, $C_{1-3}$ alkylamino, di($C_{1-3}$ alkyl) amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

the method comprising coupling a compound of Formula (IVd):

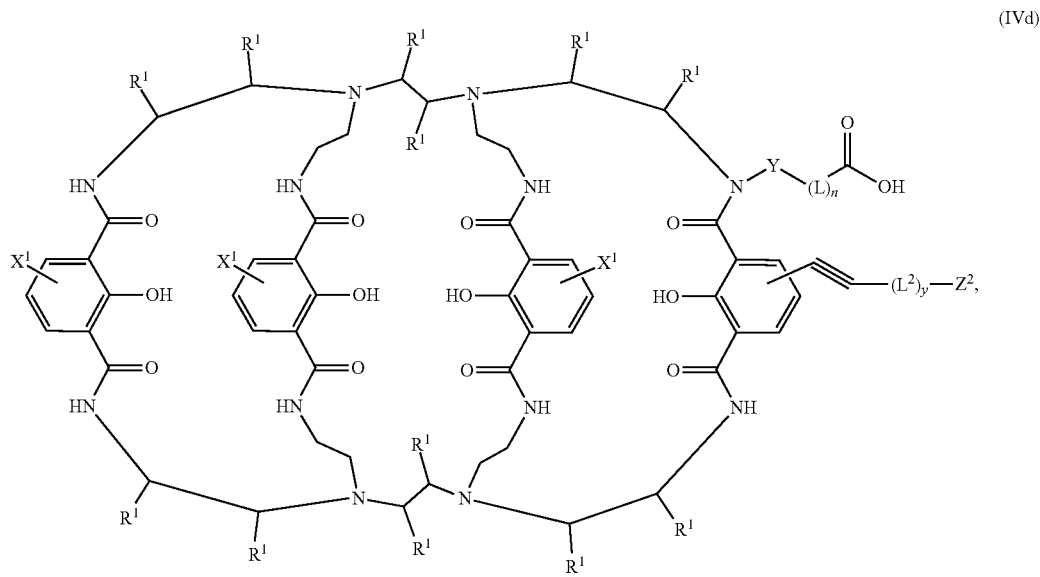

(IVd)

or a salt thereof, with a compound of formula (16):

$H_2N$-$(L^1)_x$-$Z^1$ (16), or a salt thereof, to obtain the compound of Formula (IVc).

19. A compound selected from:

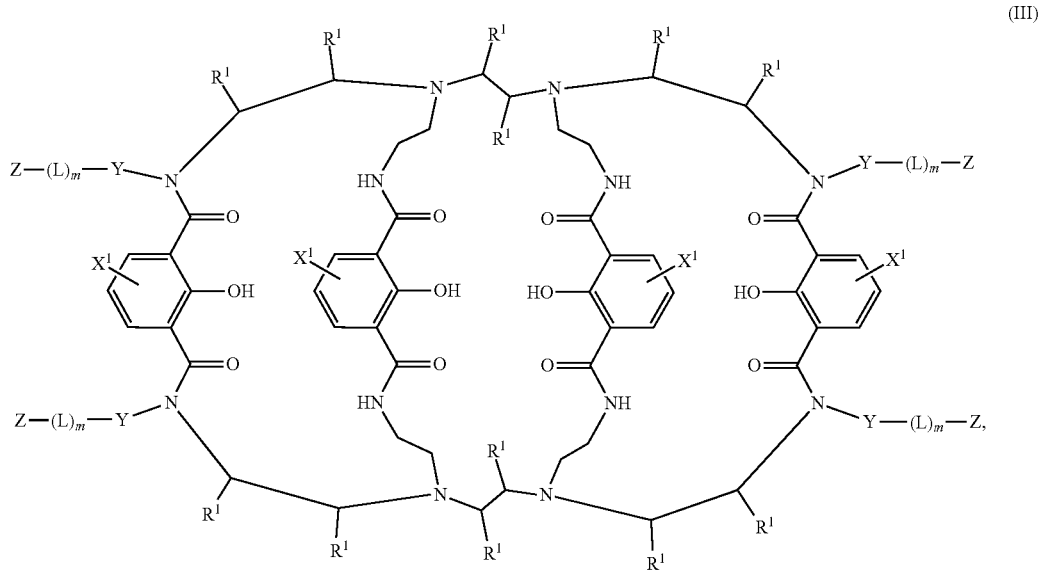

(III)

or a pharmaceutically acceptable salt thereof, wherein:

each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;

each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;

each Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;

each m is an integer from 0 to 100; wherein if m is 0 then L is a bond; and each Z is selected from H, $C_{1-3}$ alkyl, an activated ester, a biorthogonal functional group, $NH_2$, $C_{1-3}$ alkylamino, di($C_{1-3}$ alkyl) amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

wherein:

if Y is a bond and m is 0, then Z is H or $C_{1-3}$ alkyl; and at least one m is greater than 0;

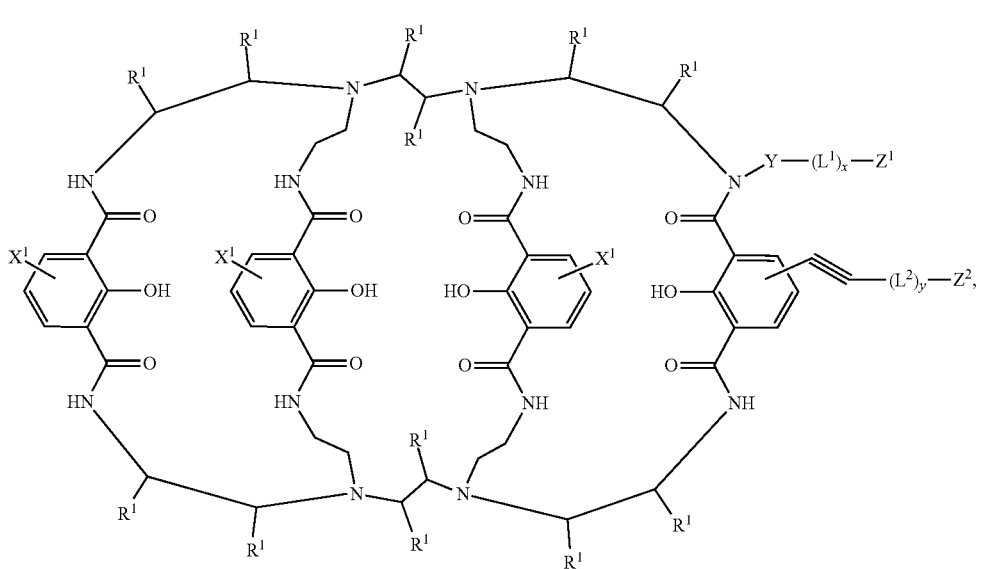

(IV)

or a pharmaceutically acceptable salt thereof, wherein:
  Y is selected from $C_{1-6}$ alkylene, $C_{2-6}$ alkenylene, $C_{2-6}$ alkynylene, and a bond;
  each $L^1$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;
  each $L^2$ is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;
  each $X^1$ is independently selected from halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$; and
  each $R^1$ is independently selected from H, $C_{1-6}$ alkyl, $C_{2-6}$ alkenyl, and $C_{2-6}$ alkynyl, each of which is optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;
  x is an integer from 0 to 100; wherein if x is 0 then $L^1$ is a bond and $Z^1$ is H or $C_{1-3}$ alkyl;
  y is an integer from 0 to 100; wherein if y is 0 then $L^2$ is a bond and $Z^2$ is H or $C_{1-3}$ alkyl;
  $Z^1$ and $Z^2$ are each independently selected from H, $C_{1-3}$ alkyl, an activated ester, a biorthogonal functional group, $NH_2$, $C_{1-3}$ alkylamino, di($C_{1-3}$ alkyl) amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

or a pharmaceutically acceptable salt thereof, wherein:
  $X^2$ is selected from any one of the following groups:

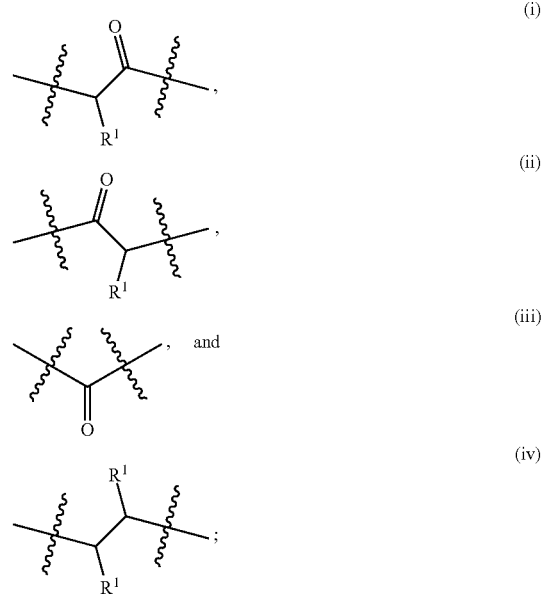

$X^3$ is selected from CH, C-Hal, and N;
  each $X^1$ is independently selected from H, halo, $NO_2$, CN, $N_3$, $C_{1-6}$ alkyl, $C_{1-6}$ alkoxy, $C_{2-6}$ alkenyl, $C_{2-6}$ alkynyl, $C_{6-10}$ aryl, and 5-14 membered heteroaryl, wherein said $C_{1-6}$ alkyl, $C_{2-6}$ alkenyl, $C_{2-6}$ alkynyl, $C_{6-10}$ aryl, and 5-14 membered heteroaryl are each optionally substituted with 1, 2, or 3 substituents independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;
  each $R^1$ is independently selected from H, $C_{1-6}$ alkyl, $C_{2-6}$ alkenyl, and $C_{2-6}$ alkynyl, each of which is optionally substituted with 1, 2, or 3 substituents

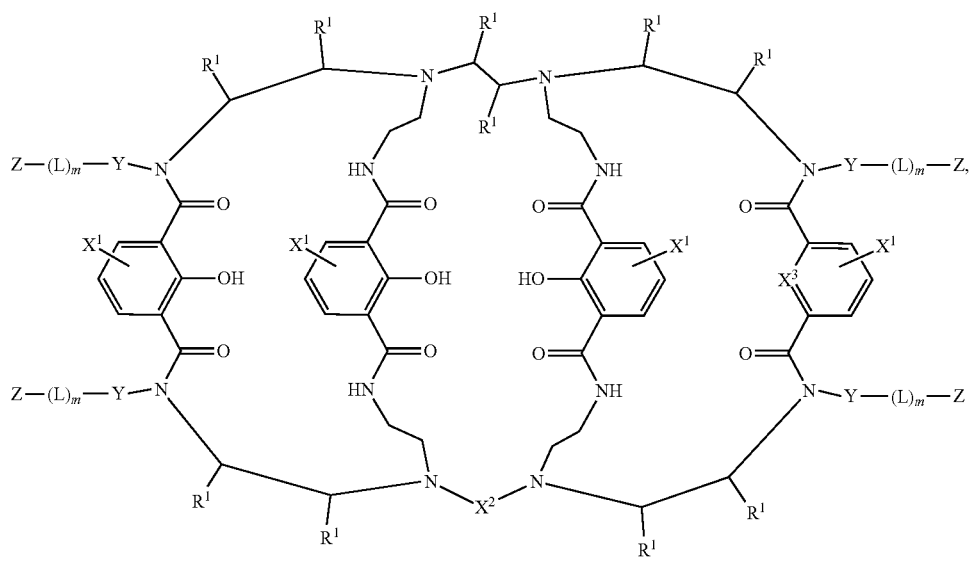

independently selected from halo, OH, SH, $NH_2$, $C_{1-3}$ alkylamino, di($C_{1-3}$ alkyl) amino, $NO_2$, CN, C(O)OH, $C_{1-3}$ alkoxy, $C_{1-3}$ haloalkoxy, and $N_3$;

each Y is selected from $C_{1-6}$ alkylene, $C_{2-6}$ alkenylene, $C_{2-6}$ alkynylene, and a bond;

each L is independently selected from $C_{1-3}$ alkylene, $C_{2-4}$ alkenylene, $C_{2-4}$ alkynylene, $C_{1-3}$ alkylene-O—, —O—$C_{1-3}$ alkylene, phenylene, —C(O) NH—, —NHC(O)—, —C(O)O—, and —OC(O)—;

each m is an integer from 0 to 100; wherein if m is 0 then L is a bond; and each Z is selected from H, $C_{1-3}$ alkyl, an activated ester, a biorthogonal functional group, $NH_2$, $C_{1-3}$ alkylamino, di($C_{1-3}$ alkyl) amino, a maleimide, a fluorophore, a probe, a fluorescent quencher, a chromophore, a nanoparticle, a quantum dot, biotin, desthiobiotin, a chemical substrate tag, a biomolecule, a dye, a photocrosslinking label, and a quencher that can function as a reporter;

wherein:

if Y is a bond and m is 0, then Z is H or $C_{1-3}$ alkyl; and at least one m is greater than 0.

20. A fluorescent or luminescent complex made according to the method of claim 1, the fluorescent or luminescent complex comprising a compound of formula:

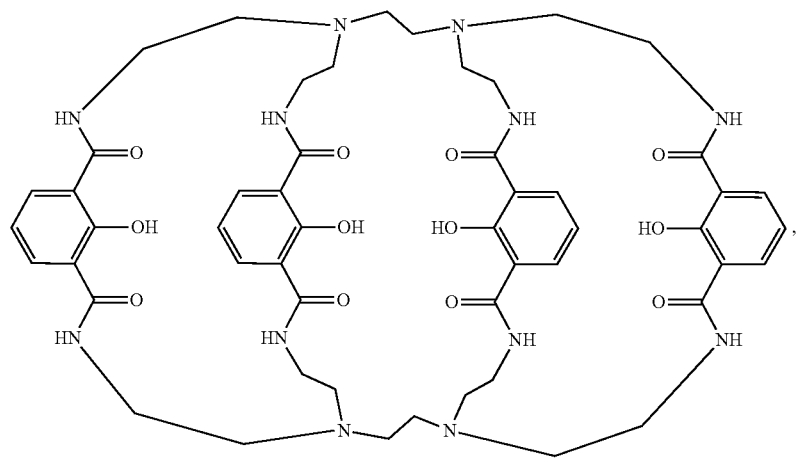 [SMILES: O=C1NCCN2CCNC(=O)c3cccc(c3O)C(=O)NCCN(CCNC(=O)c3cccc1c3O)CCN1CCNC(=O)c3cccc(c3O)C(=O)NCCN(CCNC(=O)c3cccc(c3O)C(=O)NCC1)CC2]

or a pharmaceutically acceptable salt thereof, and a lanthanide metal selected from Eu (europium), Sm (samarium), and Dy (dysprosium).

* * * * *